United States Patent
Gyorkos et al.

(10) Patent No.: US 7,714,009 B2
(45) Date of Patent: May 11, 2010

(54) NITROGEN-CONTAINING FUSED HETEROCYCLIC COMPOUNDS

(75) Inventors: Albert Charles Gyorkos, Westminster, CO (US); Christopher Peter Corrette, Boulder, CO (US); Suk Young Cho, Boulder, CO (US); Timothy Mark Turner, Boulder, CO (US); Scott Alan Pratt, Boulder, CO (US); Kazuyoshi Aso, Osaka (JP); Masakuni Kori, Osaka (JP); Michiyo Gyoten, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 838 days.

(21) Appl. No.: 10/577,334

(22) PCT Filed: Oct. 27, 2004

(86) PCT No.: PCT/US2004/035648
§ 371 (c)(1),
(2), (4) Date: Apr. 28, 2006

(87) PCT Pub. No.: WO2005/044793
PCT Pub. Date: May 19, 2005

(65) Prior Publication Data
US 2007/0135452 A1 Jun. 14, 2007

Related U.S. Application Data
(60) Provisional application No. 60/516,164, filed on Oct. 31, 2003, provisional application No. 60/560,518, filed on Apr. 8, 2004.

(51) Int. Cl.
*A61K 31/4168* (2006.01)
*C07D 403/12* (2006.01)
*C07D 403/14* (2006.01)
*C07D 235/30* (2006.01)
(52) U.S. Cl. .................. 514/388; 548/306.1; 548/307.4
(58) Field of Classification Search ........................ None
See application file for complete search history.

(56) References Cited
U.S. PATENT DOCUMENTS

| | | | |
|---|---|---|---|
| 4,459,296 A | | 7/1984 | Ancher et al. |
| 4,833,142 A | | 5/1989 | Hartog et al. |
| 6,107,301 A | * | 8/2000 | Aldrich et al. ............ 514/261.1 |
| 6,706,720 B2 | | 3/2004 | Atwal et al. |
| 7,531,553 B2 | * | 5/2009 | Di Pietro et al. ............ 514/312 |
| 2003/0216257 A1 | | 11/2003 | Sagasser et al. |
| 2004/0082781 A1 | | 4/2004 | Hibi et al. |

FOREIGN PATENT DOCUMENTS
DE 42 41 658 6/1994
FR 2 851 563 8/2004

(Continued)

OTHER PUBLICATIONS

Ettmayer et al. "Lessons Learned from Marketed and Investigational Prodrugs." J. Med. Chem., (2004), 47(10): 2393-2404.*

(Continued)

*Primary Examiner*—Rei-Tsang Shiao
*Assistant Examiner*—Alicia L Fierro
(74) *Attorney, Agent, or Firm*—Wenderoth, Lind & Ponack, L.L.P.

(57) ABSTRACT

There is provided a CRF receptor antagonist comprising a compound of the formula (I):

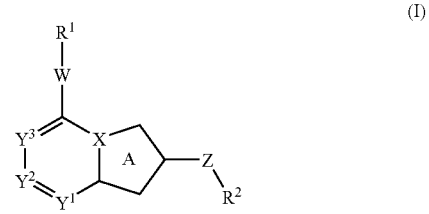

wherein, ring A is a 5-membered ring represented by the formula (A'):

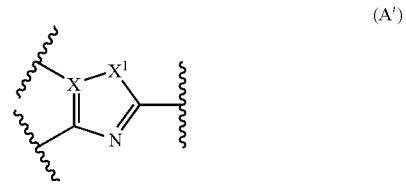

wherein X is a carbon and $X^1$ is an oxygen, a sulfur or —$NR^5$—, or formula (A"):

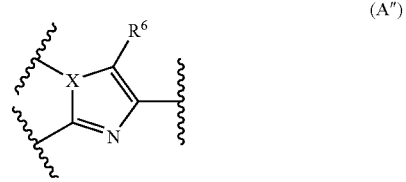

wherein X is a nitrogen and $R^6$ is an optionally substituted hydrocarbyl, $R^1$ is an amino substituted by two optionally substituted hydrocarbyl groups, $R^2$ is an phenyl, $Y^1$ is $CR^{3a}$ or a nitrogen, $Y^2$ is $CR^{3b}$ or a nitrogen and $Y^3$ is $CR^{3c}$ or a nitrogen, provided that one or less of $Y^1$, $Y^2$, and $Y^3$ is nitrogen, W is a bond, —$(CH_2)n$-, and Z is a bond, —$NR^4$—, etc.; or a salt thereof or a prodrug thereof.

7 Claims, No Drawings

FOREIGN PATENT DOCUMENTS

| | | |
|---|---|---|
| WO | WO 98/38188 | 9/1998 |
| WO | WO 01/83472 | 11/2001 |
| WO | WO 02/06233 | 1/2002 |
| WO | WO 02/062800 | 8/2002 |
| WO | WO 03/043634 | 5/2003 |
| WO | WO 03/043636 | 5/2003 |
| WO | WO 03/045385 | 6/2003 |
| WO | WO 03/045386 | 6/2003 |
| WO | WO 03/049741 | 6/2003 |
| WO | WO 03/053946 | 7/2003 |
| WO | 2004/060879 | 7/2004 |

OTHER PUBLICATIONS

Patani et al. "Bioisosterism: A Rational Approach in Drug Design." Chem Rev. 1996 (96) p. 3147-3176.*

Stella, Valentino. "Prodrugs as therapeutics." Expert Opin. Ther. Patents (2004), 14(3): 277-280.*

Testa, Bernard. "Prodrug research: futile or fertile?" Biochemical Pharmacology, 68 (2004): 2097-2106.*

Wolff et al. Burgers Medicinal Chemistry and Drug Discovery. 5th ed. vol. 1: Principles and Practice. pp. 975-977.*

"Corticotropin-releasing factor receptors: Introduction." International Union of Basic and Clinical Pharmacology, Jun. 27, 2006. <http://www.iuphar-db.org/GPCR/IntroductionDisplayForward?chapterID=1321> Accessed Mar. 4, 2009.*

"Depression (major depression): Prevention." MayoClinic.com, Feb. 14, 2008. <http://www.mayoclinic.com/health/depression/DS00175/DSECTION=prevention> Accessed Mar. 4, 2009.*

* cited by examiner

NITROGEN-CONTAINING FUSED HETEROCYCLIC COMPOUNDS

This application claims priority to U.S. Provision Application No. 60/516,164, filed Oct. 31, 2003 and U.S. Provisional Application No. 60/560,518 filed Apr. 8, 2004.

This application is the National Phase filing of International Patent Application No. PCT/US2004/035648, filed Oct. 27, 2004.

BACKGROUND OF THE INVENTION

1. Field of the Invention

The present invention relates to novel nitrogen-containing fused heterocyclic compounds having CRF (corticotropin releasing factor) antagonistic activity and pharmaceutical compositions containing them.

2. Background Art

Corticotropin-releasing factor (hereinafter, abbreviated as "CRF") is a neuropeptide composed of 41 amino acids, and was isolated and purified as a peptide promoting release of adrenocorticotropic hormone (ACTH) from pituitary gland. First, the structure thereof was determined from sheep hypothalamus and, thereafter, the presence thereof was confirmed also in a rat or a human, and the structure thereof was determined [Science, 213, 1394 (1981); Proc. Natl. Acad. Sci. USA, 80, 4851 (1983); EMBO J. 5, 775 (1983)]. An amino acid sequence is the same in a human and a rat, but differed in 7 amino acids in ovine. CRF is synthesized as a carboxyterminal of prepro CRF, cut and secreted. The CRF peptide and a mRNA thereof are present at the largest amount in hypothalamus and pituitary gland, and are widely distributed in a brain such as cerebral cortex, cerebellum, hippocampus and corpus amygdaloideum. In addition, in peripheral tissues, the existence has been confirmed in placenta, adrenal gland, lung, liver, pancreas, skin and digestive tract [J. Clin. Endocrinol. Metab., 65, 176 (1987); J. Clin. Endocrinol. Metab., 67, 768 (1988); Regul. Pept., 18, 173 (1987), Peptides, 5 (Suppl. 1), 71 (1984)]. A CRF receptor is a 7-transmembrane G protein-coupled receptor, and two subtypes of CRF1 and CRF2 are present. It is reported that CRF1 is present mainly in cerebral cortex, cerebellum, olfactory bulb, pituitary gland and tonsil nucleus. On the other hand, the CRF2 receptor has two subtypes of CRF2α and CRF2β. It was made clear that the CRF2α receptor is distributed much in hypothalamus, septal area and choroids plexus, and the CRF2β receptor is present mainly in peripheral tissues such as skeletal muscle and is distributed in a blood vessel in a brain [J. Neurosci. 15, 6340 (1995); Endocrinology, 137, 72 (1996); Biochim. Biophys. Acta, 1352, 129 (1997)]. Since each receptor differs in distribution in a living body, it is suggested that a role thereof is also different [Trends. Pharmacol. Sci. 23, 71 (2002)].

As a physiological action of CRF, the action on the endocrine system is known in which CRF is produced and secreted in response to stress in hypothalamus and acts on pituitary gland to promote the release of ACTH [Recent Prog. Horm. Res., 39, 245 (1983)]. In addition to the action on the endocrine system, CRF acts as a neurotransmitter or a neuroregulating factor in a brain, and integrates electrophysiology, autonomic nerve and conducts to stress [Brain Res. Rev., 15, 71 (1990); Pharmacol. Rev., 43, 425 (1991)]. When CRF is administered in a cerebral ventricle of experimental animal such as a rat, anxiety conduct is observed, and much more anxiety conduct is observed in a CRF-overexpressing mouse as compared with a normal animal [Brain Res., 574, 70 (1992); J. Neurosci., 10, 176 (1992); J. Neurosci., 14, 2579 (1994)]. In addition, α-helical CRF(9-41) of a peptidergic CRF receptor antagonist exerts an anti-anxiety action in an animal model [Brain Res., 509, 80 (1990); J. Neurosci., 14, 2579 (1994)]. A blood pressure, a heart rate and a body temperature of a rat are increased by stress or CRF administration, but the α-helical CRF(9-41) of a peptidergic CRF antagonist inhibits the increase in a blood pressure, a heart rate and a body temperature due to stress [J. Physiol., 460, 221 (1993)]. The α-helical CRF(9-41) of a peptidergic CRF receptor antagonist inhibits abnormal conducts due to withdrawal of a dependent drug such as an alcohol and a cocaine [Psychopharmacology, 103, 227 (1991); Pharmacol. Rev. 53, 209 (2001)]. In addition, it has been reported that learning and memory are promoted by CRF administration in a rat [Nature, 375, 284 (1995); Neuroendocrinology, 57, 1071 (1993); Eur. J. Pharmacol., 405, 225 (2000)].

Since CRF is associated with stress response in a living body, there are clinical reports regarding stress-associated depression or anxiety. The CRF concentration in a cerebrospinal fluid of a depression patient is higher as compared with that of a normal person [Am. J. Psychiatry, 144, 873 (1987)], and the mRNA level of CRF in hypothalamus of a depression patient is increased as compared with that of a normal person [Am. J. Psychiatry, 152, 1372 (1995)]. A CRF binding site of cerebral cortex of a patient who suicided by depression is decreased [Arch. Gen. Psychiatry, 45, 577 (1988)]. The increase in the plasma ACTH concentration due to CRF administration is small in a depression patient [N. Engl. J. Med., 314, 1329 (1986)]. In a patient with panic disorder, the increase of plasma ACTH concentration due to CRF administration is small [Am. J. Psychiatry, 143, 896 (1986)]. The CRF concentration in a cerebrospinal fluid of a patient with anxiety induced by stress such as obsessive-compulsive neurosis, post-psychic trauma stress disorder, Tourette's syndrome and the like is higher as compared with that of a normal person [Arch. Gen. Psychiatry, 51, 794 (1994); Am. J. Psychiatry, 154, 624 (1997); Biol. Psychiatry, 39, 776 (1996)]. The CRF concentration in a cerebrospinal fluid of schizophrenics is higher as compared with that of a normal person [Brain Res., 437, 355 (1987); Neurology, 37, 905 (1987)]. Thus, it has been reported that there is abnormality in the living body response system via CRF in stress-associated mental disease.

The action of CRF on the endocrine system can be presumed by the characteristics of CRF gene-introduced animal and actions in an experimental animal. In a CRF-overexpressing mouse, excessive secretions of ACTH and adrenal cortex steroid occur, and abnormalities analogous to Cushing's syndrome such as atrophy of muscle, alopecia, infertility and the like are observed [Endorcrinology, 130, 3378 (1992)]. CRF inhibits ingestion in an experimental animal such as a rat [Life Sci., 31, 363 (1982); Neurophamacology, 22, 337 (1983)]. In addition, α-helical CRF(9-41) of a peptidergic CRF antagonist inhibited decrease of ingestion due to stress loading in an experimental model [Brain Res. Bull., 17, 285 (1986)]. CRF inhibited weight gain in a hereditary obesity animal [Physiol. Behav., 45, 565 (1989)]. In a nervous orexia inactivity patient, the increase of ACTH in plasma upon CRF administration is small [J. Clin. Endocrinol. Metab., 62, 319 (1986)]. It has been suggested that a low CRF value is associated with obesity syndrome [Endocrinology, 130, 1931 (1992)]. There has been suggested a possibility that ingestion inhibition and weight loss action of a serotonin reuptake inhibiting agent are exerted via release of CRF [Pharmacol. Rev., 43, 425 (1991)].

CRF is centrally or peripherally associated with the digestive tract movement involved in stress or inflammation [Am. J. Physiol. Gastrointest. Liver Physiol. 280, G315 (2001)]. CRF acts centrally or peripherally, weakens the shrinkablity of stomach, and decreases the gastric excreting ability [Regulatory Peptides, 21, 173 (1988); Am. J. Physiol., 253, G241 (1987)]. In addition, α-helical CRF (9-41) of a peptidergic CRF antagonist has a restoring action for hypofunction of stomach by abdominal operation [Am. J. Physiol., 258, G152

(1990)]. CRF inhibits secretion of a bicarbonate ion in stomach, decreases gastric acid secretion and inhibits ulcer due to cold restriction stress [Am. J. Physiol., 258, G152 (1990)]. Furthermore, α-helical CRF (9-41) of a peptidergic CRF antagonist shows the inhibitory action on gastric acid secretion decrease, gastric excretion decrease, small intestinal transport decrease and large intestinal transport enhancement due to restriction stress [Gastroenterology, 95, 1510 (1988)]. In a healthy person, mental stress increases a gas and abdominal pain due to anxiety and intestine dilation, and CRF decreases a threshold of discomfort [Gastroenterology, 109, 1772 (1995); Neurogastroenterol. Mot., 8, 9 [1996]. In a irritable bowel syndrome patient, large intestinal movement is excessively enhanced by CRF administration as compared with a healthy person [Gut, 42, 845 (1998)].

It has been reported from studies on experimental animals and clinical studies that CRF is induced by inflammation and is involved in a inflammatory reaction. In an inflammatory site of an experimental animal and in a joint fluid of a rheumatoid arthritis patient, production of CRF is topically increased [Science, 254, 421 (1991); J. Clin. Invest., 90, 2555 (1992); J. Immunol., 151, 1587 (1993)]. CRF induces degranulation of a mast cell and enhances the blood vessel permeability [Endocrinology, 139, 403 (1998); J. Pharmacol. Exp. Ther., 288, 1349 (1999)]. CRF can be detected also in a thyroid gland of autoimmune thyroiditis patient [Am. J. Pathol. 145, 1159 (1994)]. When CRF is administered to an experimental autoimmune cerebrospinal meningitis rat, the progression of symptom such as paralysis was remarkably inhibited [J. Immunil., 158, 5751 (1997)]. In a rat, the immune response activity such as T-lymphocyte proliferation and the natural killer cell activity is reduced by CRF administration or stress loading [Endocrinology, 128, 1329 (1991)].

From the above-mentioned reports, it is expected that the CRF receptor antagonistic compound would exert an excellent effect for treating or preventing various diseases in which CRF is involved.

As a CRF antagonist, for example, peptide CRF receptor antagonists are reported in which a part of an amino acid sequence of CRF or associated peptides of a human or other mammals is altered or deleted, and they are reported to show a pharmacological action such as ACTH release-inhibiting action and anti-anxiety action [Science, 224, 889 (1984); J. Pharmacol. Exp. Ther., 269, 564 (1994); Brain Res. Rev., 15, 71 (1990)]. However, from a pharmacokinetic point of view such as chemical stability and absorbability for oral administration in a living body, bioavailability and intracerebral transferability, peptide derivatives have a low utility value as a medicine.

SUMMARY OF THE INVENTION

According to the present invention, there is provided:

(1) A compound represented by the formula (I):

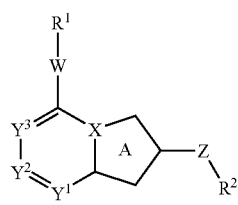

wherein, ring A is a 5-membered ring represented by the formula (A'):

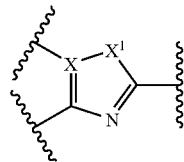

wherein X is a carbon and $X^1$ is an oxygen, a sulfur or —$NR^5$— (wherein $R^5$ is a hydrogen, an optionally substituted hydrocarbyl or an acyl), or formula (A''):

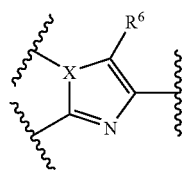

wherein X is a nitrogen and $R^6$ is a hydrogen, an optionally substituted hydrocarbyl or an acyl;

$R^1$ is (1) an amino substituted by two substituents selected from an optionally substituted hydrocarbyl group and an optionally substituted heterocyclic group, or (2) an optionally substituted cyclic amino, provided that the amino nitrogen of said cyclic amino has no carbonyl adjacent to the nitrogen;

$R^2$ is an optionally substituted alkyl, an optionally substituted cycloalkyl, an optionally substituted cycloalkenyl, an optionally substituted aryl or an optionally substituted heterocyclic;

$Y^1$, $Y^2$ and $Y^3$ are each an optionally substituted methyne or a nitrogen, provided that one or less of $Y^1$, $Y^2$ and $Y^3$ is nitrogen;

W is a bond, —$(CH_2)_n$— or —$(CH_2)_m$—CO— (wherein n is an integer of 1 to 4 and m is an integer of 0 to 4);

Z is a bond, —CO—, an oxygen, a sulfur, —SO—, —$SO_2$—, —$NR^4$—, —$NR^4$-alk-, —$CONR^4$— or —$NR^4CO$— (wherein alk is an optionally substituted $C_{1-4}$ alkylene and $R^4$ is a hydrogen, an optionally substituted hydrocarbyl or an acyl);

provided that (i) the compound wherein ring A is the 5-membered ring of the formula A' (wherein X is a carbon and $X^1$ is a sulfur), W is a bond, Z is —NHCO— or —CONH—, and $Y^1$ is $CR^{3a}$ (wherein $R^{3a}$ is a hydrogen, a halogen, or an alkoxy) and (ii) the compound wherein ring A is the 5-membered ring of the formula A' (wherein X is a carbon and $X^1$ is an oxygen, a sulfur, or —NH—), $R^1$ is an optionally substituted 1-piperazinyl, W is a bond, Z is a bond and $R^2$ is an optionally substituted aryl, are excluded;

or a salt thereof;

(2) A prodrug of the compound according to the above-mentioned (1);

(3) The compound according to the above-mentioned (1) wherein $R^1$ is an amino substituted by two optionally substituted $C_{1-4}$ alkyl groups;

(4) The compound according to the above-mentioned (1) wherein $R^1$ is an amino substituted by an optionally substituted $C_{1-4}$ alkyl and an optionally substituted phenyl or optionally substituted heterocyclic;

(5) The compound according to the above-mentioned (1) wherein $R^1$ is a 5- or 6-membered cyclic amino which may be substituted with one or more substituents;

(6) The compound according to claim 1 wherein $Y^1$ is $CR^{3a}$, $Y^2$ is $CR^{3b}$, and $Y^3$ is $CR^{3c}$ (wherein $R^{3a}$, $R^{3b}$ and $R^{3c}$ are independently a hydrogen, a halogen, a nitro, an optionally substituted $C_{1-4}$ hydrocarbyl, an optionally substituted $C_{1-4}$ hydrocarbyloxy, an optionally substituted $C_{1-4}$ hydrocarbylthio, an optionally substituted amino or an acyl containing up to 4 carbon atoms);

(7) The compound according to above-mentioned (1) wherein one of $Y^1$, $Y^2$ and $Y^3$ is nitrogen;

(8) The compound according to the above-mentioned (1) wherein W is a bond;

(9) The compound according to the above-mentioned (1) wherein $R^2$ is an optionally substituted $C_{6-10}$ aryl or an optionally substituted 5- or 10-membered heterocyclic;

(10) The compound according to the above-mentioned (1) wherein $R^2$ is an optionally substituted phenyl or an optionally substituted 5- or 6-membered heterocyclic;

(11) The compound according to the above-mentioned (1) wherein Z is —$NR^4$— (wherein $R^4$ is as defined in the above-mentioned (1));

(12) The compound according to the above-mentioned (1) wherein ring A is a thiazole ring or an imidazole ring represented by the formula (Aa):

(Aa)

wherein $R^{5a}$ is a hydrogen, an optionally substituted $C_{1-4}$ alkyl or an acyl containing up to 4 carbon atoms;

(13) The compound according to the above-mentioned (1) wherein $Y^1$ is $CR^{3a}$, $Y^2$ is $CR^{3b}$, and $Y^3$ is $CR^{3c}$ (wherein $R^{3a}$, $R^{3b}$ and $R^{3c}$ is independently a hydrogen, a halogen or an optionally substituted hydrocarbyl); W is a bond; $R^2$ is an optionally substituted phenyl or an optionally substituted 5- or 6-membered heterocyclic; and Z is —$NR^4$— (wherein $R^4$ is a hydrogen or an optionally substituted hydrocarbyl);

(14) The compound according to the above-mentioned (1) wherein $Y^1$ is $CR^{3a}$, $Y^2$ is $CR^{3b}$ and $Y^3$ is $CR^{3c}$ (wherein $R^{3a}$, $R^{3b}$ and $R^{3c}$ are independently a hydrogen, a halogen, a nitro, an optionally substituted $C_{1-4}$ hydrocarbyl, an optionally substituted $C_{1-4}$ hydrocarbyloxy, an optionally substituted $C_{1-4}$ hydrocarbylthio, an optionally substituted amino or an acyl containing up to 4 carbon atoms); W is a bond; $R^2$ is an optionally substituted $C_{6-10}$ aryl or an optionally substituted 5- or 10-membered heterocyclic; and Z is —$NR^4$— (wherein $R^4$ is a hydrogen or an optionally substituted hydrocarbyl); and ring A is a thiazole ring or an imidazole ring represented by the formula (Aa):

(Aa)

wherein $R^{5a}$ is a hydrogen, an optionally substituted $C_{1-4}$ alkyl, or an acyl containing up to 4 carbon atoms;

(15) A method for treating or preventing a disease wherein a CRF receptor is implicated, which comprises administering to a subject in need thereof an effective amount of a compound represented by the formula (Ia):

(Ia)

wherein ring A is a 5-membered ring represented by the formula (A'):

(A')

wherein X is a carbon and $X^1$ is an oxygen, a sulfur or —$NR^5$— (wherein $R^5$ is a hydrogen, an optionally substituted hydrocarbyl or an acyl), or formula (A"):

(A")

wherein X is a nitrogen and $R^6$ is a hydrogen, an optionally substituted hydrocarbyl or an acyl;

$R^{1a}$ is (1) an amino substituted by two substituents selected from an optionally substituted hydrocarbyl group and an optionally substituted heterocyclic group, or (2) an optionally substituted cyclic amino;

$R^2$ is an optionally substituted alkyl, an optionally substituted cycloalkyl, an optionally substituted cycloalkenyl, an optionally substituted aryl or an optionally substituted heterocyclic;

$Y^1$, $Y^2$ and $Y^3$ are each an optionally substituted methyne or a nitrogen, provided that one or less of $Y^1$, $Y^2$ and $Y^3$ is nitrogen;

W is a bond, —$(CH_2)_n$— or —$(CH_2)_m$—CO—, wherein n is an integer of 1 to 4 and m is an integer of 0 to 4;

Z is a bond, —CO—, an oxygen, a sulfur, —SO—, —$SO_2$—, —$NR^4$—, —$NR^4$-alk-, —$CONR^4$— or —$NR^4CO$— (wherein alk is an optionally substituted $C_{1-4}$ alkylene and $R^4$ is a hydrogen, an optionally substituted hydrocarbyl or an acyl);

provided that the compound wherein ring A is the 5-membered ring of the formula A' (wherein X is a carbon and $X^1$ is a sulfur), W is a bond, Z is —NHCO— or —CONH—, and $Y^1$ is $CR^{3a}$ (wherein $R^{3a}$ is a halogen, or an alkoxy) is excluded;

or a salt thereof;

(16) The method according to the above-mentioned (15) wherein the disease being treated or prevented is selected from affective disorder, depression or anxiety;

(17) Use of the compound (Ia) according to the above-mentioned (15), or a salt thereof for manufacturing a medicament for preventing or treating a disease wherein a CRF receptor is implicated;

(18) Use of the compound (Ia) according to the above-mentioned (15), or a salt thereof for manufacturing a medicament for preventing or treating affective disorder, depression or anxiety;

(19) An agent for preventing or treating a disease wherein a CRF receptor is implicated, which comprises the compound (Ia) according to the above-mentioned (15) or a salt thereof; and

(20) An agent for preventing or treating affective disorder, depression or anxiety which comprises the compound (Ia) according to the above-mentioned (15) or a salt thereof.

DETAILED DESCRIPTION OF THE PREFERRED EMBODIMENTS

In the present specification, the term "hydrocarbyl" means a univalent group containing only carbon and hydrogen.

In the above formulas, ring A of the formulas (I) and (Ia) is a 5-membered ring represented by the following formula A' or A":

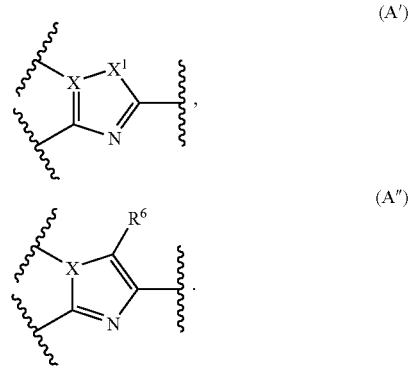

In the formula (A'), X represents a carbon and $X^1$ represents an oxygen, a sulfur or —$NR^5$— (wherein $R^5$ is a hydrogen or an optionally substituted hydrocarbyl or an acyl). That is, examples of the 5-membered ring of the formula (A') include an oxazole ring, a thiazole ring and an imidazole ring.

Examples of the "hydrocarbyl" of "an optionally substituted hydrocarbyl" represented by $R^5$ of the formula: —$NR^5$— include an optionally substituted aliphatic hydrocarbon group, an optionally substituted alicyclic hydrocarbon group, an optionally substituted alicyclic-aliphatic hydrocarbon group, an optionally substituted aromatic hydrocarbon group, an optionally substituted aromatic-aliphatic hydrocarbon group (an aralkyl group), and the like.

Examples of said aliphatic hydrocarbon group include a saturated aliphatic hydrocarbon group having 1-8 carbon atoms (e.g., alkyl group) such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.; and an unsaturated aliphatic hydrocarbon group having 2-8 carbon atoms (e.g., alkenyl group, alkynyl group, alkadienyl group, alkadiynyl group, etc.) such as vinyl, allyl, 1-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 2,4-hexadienyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadiynyl, 1-heptynyl, 1-octynyl, etc.

Examples of said alicyclic hydrocarbon group include a saturated alicyclic hydrocarbon group having 3-7 carbon atoms (e.g., cycloalkyl group, etc.) such as cyclopropyl, cyclobutyl, cyclopentyl, cyclohexyl, cycloheptyl, and the like; an unsaturated alicyclic hydrocarbon group having 3-7 carbon atoms (e.g., cycloalkenyl group, cycloalkadienyl group, etc.) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl, etc.; a partly saturated and fused bicyclic hydrocarbon group [preferably, $C_{9-10}$ partly saturated and fused bicyclic hydrocarbon group, etc. (including those where the benzene ring is combined to 5- or 6-membered non-aromatic cyclic hydrocarbon group)] such as 1-indenyl, 2-indenyl, 1-indanyl, 2-indanyl, 1,2,3,4-tetrahydro-1-naphthyl, 1,2,3,4-tetrahydro-2-naphthyl, 1,2-dihydro-1-naphthyl, 1,2-dihydro-2-naphthyl, 1,4-dihydro-1-naphthyl, 1,4-dihydro-2-naphthyl, 3,4-dihydro-1-naphthyl, 3,4-dihydro-2-naphthyl, etc.; and the like. Said alicyclic hydrocarbon group may be cross-linked.

Examples of said alicyclic-aliphatic hydrocarbon group include those where the above-mentioned alicyclic hydrocarbon group and the above-mentioned aliphatic hydrocarbon group are combined, for example, those having 4-14 carbon atoms such as cyclopropylmethyl, cyclopropylethyl, cyclobutylmethyl, cyclobutylethyl, cyclopentylmethyl, 2-cyclopentenylmethyl, 3-cyclopentenylmethyl, cyclopentylethyl, cyclohexylmethyl, 2-cyclohexenylmethyl, 3-cyclohexenylmethyl, cyclohexylethyl, cycloheptylmethyl, cycloheptylethyl, 2-(3,4-dihydro-2-naphtyl)ethyl, 2-(1,2,3,4-tetrahydro-2-naphtyl)ethyl, 2-(3,4-dihydro-2-naphtyl)ethenyl, etc. (e.g., $C_{3-7}$ cycloalkyl-$C_{1-4}$ alkyl group, $C_{3-7}$ cycloalkenyl-$C_{1-4}$ alkyl group, $C_{3-7}$ cycloalkyl-$C_{2-4}$ alkenyl group, $C_{3-7}$ cycloalkenyl-$C_{2-4}$ alkenyl group, $C_{9-10}$ partly saturated and fused bicyclic hydrocarbon-$C_{1-4}$ alkyl group, $C_{9-10}$ partly saturated and fused bicyclic hydrocarbon-$C_{2-4}$ alkenyl groups, etc.).

Examples of said aromatic hydrocarbon group include an aryl group having 6-10 carbon atoms (including that where a 5- to 6-membered non-aromatic hydrocarbon ring is fused with phenyl group) such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; and the like.

Examples of said aromatic-aliphatic hydrocarbon group include an aralkyl group having 7-14 carbon atoms ($C_{6-10}$ aryl-$C_{1-4}$ alkyl group) such as phenyl-$C_{1-4}$ alkyl group, e.g., benzyl, phenethyl, 1-phenylethyl, 1-phenylpropyl, 2-phenylpropyl, 3-phenylpropyl, etc.; naphthyl-$C_{1-4}$ alkyl group such as α-naphthylmethyl, α-naphthylethyl, β-naphthylmethyl, β-naphthylethyl, etc.; $C_{6-10}$ aryl-$C_{2-4}$ alkenyl group such as phenyl-$C_{2-4}$ alkenyl group, e.g., styryl, cinnamyl, etc.; and the like.

The above-mentioned "hydrocarbyl" group may have a substituent at a substitutable position. Examples of such substituent include a halogen, nitro, cyano, oxo, (1) an optionally substituted heterocyclic group, (2) an optionally substituted sulfinyl group, (3) an optionally substituted sulfonyl group, (4) optionally substituted hydroxyl group, (5) optionally substituted thiol group, (6) an optionally substituted amino group, (7) an acyl group, (8) an optionally esterified or amidated carboxyl group, (9) an optionally substituted phosphoryl group, or the like.

Examples of the substituent of above-mentioned (2) an optionally substituted sulfinyl group, (3) an optionally substituted sulfonyl group, (4) optionally substituted hydroxyl group, (5) optionally substituted thiol group and (6) an optionally substituted amino group include an optionally substituted hydrocarbyl. Examples of "hydrocarbyl" of such optionally substituted hydrocarbyl include those exemplified above. Such hydrocarbyl may be substituted by one or more substituents at a substitutable position. Examples of the substituent group of the optionally substituted hydrocarbyl as a substituent group include halogen, nitro, cyano, hydroxyl, thiol, amino and carboxyl.

As the optionally substituted sulfinyl group of above-mentioned (2), specifically, $C_{1-6}$ alkylsulfinyl (e.g., methylsulfinyl, ethylsulfinyl, propylsulfinyl, butylsulfinyl etc.) and $C_{6-10}$ arylsulfinyl (e.g., phenylsulfinyl, naphthylsulfinyl etc.) are exemplified.

As the optionally substituted sulfonyl group of above-mentioned (3), specifically, $C_{1-6}$ methylsulfonyl, alkylsulfonyl (e.g., ethylsulfonyl, propylsulfonyl, butylsulfonyl etc.) and $C_{6-10}$ arylsulfonyl (e.g., phenylsulfonyl, naphthylsulfonyl etc.) are exemplified.

As the optionally substituted hydroxyl group of above-mentioned (4), specifically, hydroxyl, $C_{1-6}$ alkoxy (e.g., methoxy, ethoxy, n-propoxy, isopropoxy, n-butoxy, isobutoxy, sec-butoxy, tert-butoxy, n-pentyloxy, isopentyloxy, neopentyloxy, etc.) and $C_{6-10}$ aryloxy (e.g., phenoxy, naphthoxy, etc.) are exemplified.

As the optionally substituted thiol group of above-mentioned (5), specifically, thiol, $C_{1-6}$ alkylthio (e.g., methylthio, ethylthio, propylthio, etc.) and $C_{6-10}$ arylthio (e.g., phenylthio, naphthylthio etc.) are exemplified.

As the optionally substituted amino group of above-mentioned (6), specifically, amino, mono-$C_{1-6}$ alkylamino (e.g., methylamino, ethylamino, propylamino, isopropylamino, butylamino etc.), di-$C_{1-6}$ alkylamino (e.g., dimethylamino, diethylamino, ethylmethylamino, dipropylamino, diisopropylamino, dibutylamino etc.), and the like are exemplified.

Examples of the acyl group of above-mentioned (7) include the same group as the acyl for $R^5$.

Examples of the ester group or amide group of the optionally esterified or amidated carboxyl group of above-mentioned (8) include ester group with the same optionally substituted hydrocarbyl as the substituent of optionally substituted hydroxyl group of above-mentioned (4) or amide group with optionally substituted amino group of above-mentioned (6).

As the optionally esterified carboxyl group, specifically, carboxyl, $C_{1-6}$ alkoxy-carbonyl (e.g., methoxycarbonyl, ethoxycarbonyl, propoxycarbonyl, tert-butoxycarbonyl etc.), $C_{6-10}$ aryloxy-carbonyl (e.g., phenoxycarbonyl etc.), $C_{7-16}$ aralkyloxy-carbonyl (e.g., benzyloxycarbonyl, phenetyloxycarbonyl etc.), and the like are exemplified.

As the optionally amidated carboxyl group, specifically, carbamoyl, mono-$C_{1-6}$ alkyl-carbamoyl (e.g., methylcarbamoyl, ethylcarbamoyl etc.), di-$C_{1-6}$ alkyl-carbamoyl (e.g., dimethylcarbamoyl, diethylcarbamoyl, ethylmethylcarbamoyl etc.), $C_{6-10}$ aryl-carbamoyl (e.g., phenylcarbamoyl, 1-naphthylcarbamoyl, 2-naphthylcarbamoyl etc.), 5- to 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.), and the like are exemplified.

Examples of the "acyl" represented by $R^5$ of the formula: —$NR^5$— include a formyl and a group where the carbonyl group is combined with a $C_{1-10}$ alkyl group, a $C_{2-10}$ alkenyl group, a $C_{2-10}$ alkynyl group, a $C_{3-7}$ cycloalkyl group, a $C_{5-7}$ cycloalkenyl group or an aromatic group (e.g., phenyl group, pyridyl group, etc.) (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, etc.) and the like.

$R^5$ is preferably hydrogen, $C_{1-10}$ alkyl, $C_{2-10}$ alkenyl, alkynyl, and more preferably hydrogen, $C_{1-10}$ alkyl.

In the formula (A"), X represents a nitrogen and $R^6$ represents a hydrogen, an optionally substituted hydrocarbyl or an acyl.

Examples of the "optionally substituted hydrocarbyl" and "acyl" represented by $R^6$ include the same groups as those exemplified with respect to the optionally substituted hydrocarbyl and acyl in $R^5$.

$R^6$ is preferably hydrogen, $C_{1-10}$ alkyl, $C_{2-10}$ alkenyl, $C_{2-10}$ alkynyl, and more preferably hydrogen, $C_{1-10}$ alkyl.

$R^1$ and $R^{1a}$ in the formula (I) and (Ia) are (1) an amino substituted by two substituents selected from an optionally substituted hydrocarbyl group and an optionally substituted heterocyclic group, or (2) an optionally substituted cyclic amino, provided that the cyclic amino has no carbonyl adjacent to the nitrogen in the formula (I). Examples of the "optionally substituted hydrocarbyl group" in the "amino substituted by two substituents selected from an optionally substituted hydrocarbyl group and an optionally substituted heterocyclic group" include the same groups as those exemplified with respect to the optionally substituted hydrocarbyl group of $R^5$. Examples of the "optionally substituted heterocyclic group" in the "amino substituted by two substituents selected from an optionally substituted hydrocarbyl group and an optionally substituted heterocyclic group" include the same groups as those exemplified below with respect to the optionally substituted heterocyclic group of $R^2$.

Examples of the "cyclic amino" in the "optionally substituted cyclic amino" include, for example, a 3- to 7-membered cyclic amino group such as aziridino, pyrrolidino, imidazolidino, oxazolidino, thiazolidino, piperidino, 1,2-dihydropyridyl, 1,2,3,6-tetrahydropyridyl, piperazino, morpholino, thiomorpholino and the like. The cyclic amino group may be substituted with 1 to 3 substituents selected from the group consisting of halogen, $C_{1-6}$ alkyl, $C_{2-6}$ alkenyl, $C_{1-6}$ alkoxy-$C_{1-6}$ alkyl, $C_{5-7}$ cycloalkyl, $C_{6-10}$ aryl (said aryl may have 1 or 2 substituents selected from halogen, $C_{1-6}$ alkyl, halogeno $C_{1-6}$ alkyl and $C_{1-6}$ alkoxy), $C_{7-14}$ aralkyl (said aralkyl may have 1 or 2 substituents selected from halogen, $C_{1-6}$ alkyl, halogeno $C_{1-6}$ alkyl and $C_{1-6}$ alkoxy), hydroxy, hydroxy-$C_{1-6}$ alkyl, $C_{6-10}$ aryloxy (said aryloxy may have 1 or 2 substituents selected from halogen, $C_{1-6}$ alkyl, halogeno $C_{1-6}$ alkyl and $C_{1-6}$ alkoxy), $C_{7-14}$ aralkyloxy, $C_{6-10}$ aryl-carbonyl, carboxyl, $C_{1-6}$ alkoxy-carbonyl, carbamoyl, $C_{6-10}$ aryl-carbamoyl, amino, $C_{6-10}$ aryl-carbonylamino, $C_{1-6}$ alkyl-carbonylamino, $C_{1-6}$ alkoxy-carbonylamino, $C_{6-10}$ arylthio, $C_{6-10}$ arylsulfonyl, cyano, 5- to 7-membered heterocyclic group and oxo (provided that the oxo group is not substituted at the position adjacent to the nitrogen bonded to W of formula (I)).

Among these, $R^1$ and $R^{1a}$ in the formula (I) and (Ia) are preferably an amino substituted by two substituents selected from optionally substituted $C_{1-4}$ alkyl and optionally substituted phenyl, more preferably amino substituted by two optionally substituted $C_{1-4}$ alkyl groups. Preferred examples of the optionally substituted $C_{1-4}$ alkyl and optionally substituted phenyl are those unsubstituted or those substituted with a group selected from the group consisting of hydroxy, $C_{1-4}$ alkoxy; amino, mono- or di-$C_{1-4}$ alkyl amino; halogen; and pyridyl.

$R^2$ in the formula (I) and (Ia) are alkyl, an optionally substituted cycloalkyl, an optionally substituted cycloalkenyl, an optionally substituted aryl or an optionally substituted heterocyclic.

Examples of the "alkyl" for $R^2$ include a $C_{1-8}$ alkyl group such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.

Examples of the "cycloalkyl" for "optionally substituted cycloalkyl" of $R^2$ include a $C_{3-7}$ cycloalkyl group such as cyclopropyl, cyclobutyl, cyclopentyl, cyclohexyl, cycloheptyl, and the like.

Examples of the "cycloalkenyl" for the "optionally substituted cycloalkenyl" of $R^2$ include a $C_{3-7}$ cycloalkenyl group such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, etc.

Examples of the "aryl" for the "optionally substituted aryl" of $R^2$ include an aryl group having 6-10 carbon atoms (including that where a 5- to 6-membered non-aromatic hydrocarbon ring is fused with phenyl group) such as phenyl, α-naphthyl, β-naphthyl, 4-indenyl, 5-indenyl, 4-indanyl, 5-indanyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl, etc.; and the like.

Examples of the "heterocyclic" for the "optionally substituted heterocyclic" of $R^2$ include (i) a 5- to 7-membered heterocyclic group containing one sulfur atom, one nitrogen atom or one oxygen atom, (ii) a 5- to 6-membered heterocyclic group containing 2-4 nitrogen atoms, and (iii) a 5- to 6-membered heterocyclic group containing 1-2 nitrogen atoms and one sulfur or oxygen atom, or the like. In addition, each of the heterocyclic groups exemplified in (i) to (iii) may be a saturated or unsaturated heterocyclic group and the unsaturated heterocyclic group may be either aromatic or non-aromatic.

Examples of the heterocyclic for an optionally substituted heterocyclic of $R^2$ include an aromatic monocyclic heterocyclic group and a non-aromatic heterocyclic group.

Specific examples of the heterocyclic for an optionally substituted heterocyclic include (i) an aromatic monocyclic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, etc.) and (ii) a non-aromatic, heterocyclic group (e.g., oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.).

The above-mentioned "cycloalkyl", "cycloalkenyl", "aryl" and "heterocyclic" in $R^2$ may have the same substituent as those exemplified with respect to the optionally substituted hydrocarbyl group of $R^5$ and further may have the same group as optionally substituted hydrocarbyl group of $R^5$ as their substituent.

In addition, two of the substituents of $R^2$ may be combined each other to form a ring. Examples of the ring include, for example, an aromatic fused heterocyclic group such as 8- to 12-membered aromatic fused heterocyclic group (preferably, heterocyclic group consisting of the above-mentioned 5- or 6-membered aromatic monocyclic heterocyclic group fused with a benzene ring or heterocyclic group consisting of the above-mentioned 5- or 6-membered aromatic monocyclic heterocyclic group fused with the same or different above-mentioned 5- or 6-membered aromatic monocyclic heterocyclic group), etc. (e.g. benzofuranyl, isobenzofuranyl, benzothienyl, indolyl, isoindolyl, 1H-indazolyl, benzindazolyl, benzoisooxazolyl, benzoxazolyl, 1,2-benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.); etc.

Among these, $R^2$ is preferably an optionally substituted phenyl or an optionally substituted 5- to 6-membered heterocyclic group.

In the formula (I) and (Ia), $Y^1$ is $CR^{3a}$ or a nitrogen, $Y^2$ is $CR^{3b}$ or a nitrogen, and $Y^3$ is $CR^{3c}$ or a nitrogen (wherein $R^{3a}$, $R^{3b}$ and $R^{3c}$ are independently a hydrogen, a halogen, a nitro, an optionally substituted hydrocarbyl, an optionally substituted hydrocarbyloxy, an optionally substituted hydrocarbylthio, an optionally substituted amino or an acyl), provided that one or less of $Y^1$, $Y^2$, and $Y^3$ is nitrogen.

The 6-membered ring with $Y^1$, $Y^2$ and $Y^3$ of the formula (I) and (Ia) is a ring containing one or less nitrogen atom such as benzene ring and pyridine ring.

Examples of halogen include fluorine, chlorine, bromine, iodine, and the like, preferably, fluorine and chlorine.

Examples of the "optionally substituted hydrocarbyl" in $R^{3a}$, $R^{3b}$ and $R^{3c}$ include the same groups as those exemplified with respect to the optionally substituted hydrocarbyl group of $R^5$.

Examples of the hydrocarbyl for said "optionally substituted hydrocarbyloxy" and "optionally substituted hydrocarbylthio" of $R^{3a}$, $R^{3b}$ and $R^{3c}$ include the same groups as those exemplified with respect to the optionally substituted hydrocarbyl group of $R^5$.

Examples of the "optionally substituted amino" for $R^{3a}$, $R^{3b}$ and $R^{3c}$ include amino group, an N-mono-substituted amino group, and an N,N-di-substituted amino group. Examples of said substituted amino groups include that having one or two substituents of an optionally substituted hydrocarbyl group (e.g., a $C_{1-8}$ alkyl group, a $C_{3-7}$ cycloalkyl group, a $C_{2-8}$ alkenyl group, a $C_{2-8}$ alkynyl group, a $C_{3-7}$ cycloalkenyl group, a $C_{6-10}$ aryl group that may have a $C_{1-4}$ alkyl group, etc.), an optionally substituted heterocyclic group (e.g., the same group as an optionally substituted heterocyclic group of $R^2$), or the formula: —$COR^{3d}$ (wherein $R^{3d}$ represents hydrogen atom or an optionally substituted hydrocarbyl group or an optionally substituted heterocyclic group. As for "the hydrocarbyl group" or "the heterocyclic group" in "an optionally substituted hydrocarbyl group" or "an optionally substituted heterocyclic group" of $R^{3d}$ may have the same substituent as that of "the hydrocarbyl group" or "the heterocyclic group" in "an optionally substituted hydrocarbyl" of $R^5$ or "an optionally substituted heterocyclic" of $R^2$), preferably a $C_{1-10}$ acyl group (e.g., a $C_{2-7}$ alkanoyl, benzoyl, nicotinoyl, etc.). Specific examples thereof include methylamino, dimethylamino, ethylamino, diethylamino, dipropylamino, dibutylamino, diallylamino, cyclohexylamino, phenylamino, N-methyl-N-phenylamino, acetylamino, propionylamino, benzoylamino, nicotinoylamino, and the like.

In addition, the two groups in said substituted amino groups may be combined to form a nitrogen-containing 5- to 7-membered ring (e.g., piperidino, piperazino, morpholino, thiomorpholino, etc.).

Examples of the acyl for $R^{3a}$, $R^{3b}$ and $R^{3c}$ include the same groups as those exemplified with respect to the acyl for $R^5$.

In the formula (I) and (Ia), $Y^1$, $Y^2$ and $Y^3$ are preferably $CR^{3a}$, $CR^{3b}$ and $CR^{3c}$ respectively. $R^{3a}$, $R^{3b}$ and $R^{3c}$ are preferably hydrogen, $C_{1-4}$ alkyl and $C_{1-4}$ alkoxy.

In the formula (I) and (Ia), W is a bond, —$(CH_2)n$- or —$(CH_2)m$-CO—, and n is 1-4 and m is 0-4. Preferably, W is a bond.

In the formula (I) and (Ia), Z is a bond, —CO—, an oxygen, a sulfur, —SO—, —$SO_2$—, —$NR^4$—, —$NR^4$-alk-, —$CONR^4$— or —$NR^4CO$—.

Said alk is an optionally substituted $C_{1-4}$ alkylene such as methylene, ethylene, propylene, butylene and the like.

$R^4$ is a hydrogen, an optionally substituted hydrocarbyl or an acyl. The "optionally substituted hydrocarbyl" and "acyl" for $R^4$ include the same groups as those exemplified with respect to the optionally substituted hydrocarbyl group and acyl for $R^5$.

Preferably, Z is —$NR^4$— (wherein $R^4$ is as defined above). Preferred examples of $R^4$ are hydrogen and $C_{1-4}$ alkyl.

When Z is a bond, the fused ring of the formula (I) is preferably an imidazopyridine ring.

Provided that the compounds wherein ring A is the 5-membered ring of the formula A' (wherein X is a carbon and $X^1$ is a sulfur), W is a bond, Z is —NHCO— or —CONH— and $Y^1$ is $CR^{3a}$ (wherein $R^{3a}$ is a hydrogen, a halogen or an alkoxy) are excluded from the compounds of the formula (I) and (Ia), and further the compounds wherein ring A is the 5-membered ring of the formula A' (wherein X is a carbon and $X^1$ is an oxygen, a sulfur or —NH—), $R^1$ is an optionally substituted 1-piperazinyl, W is a bond, Z is a bond, $R^2$ is an optionally substituted aryl) are excluded from the compounds of the formula (I).

As a preferred compound of the formula (I) and (Ia), a compound wherein $Y^1$ is $CR^{3a}$, $Y^2$ is $CR^{3b}$ and $Y^3$ is $CR^{3c}$ (wherein $R^{3a}$, $R^{3b}$ and $R^{3c}$ are independently a hydrogen, a halogen or an optionally substituted hydrocarbyl); W is a bond; $R^2$ is an optionally substituted phenyl or an optionally substituted 5- or 6-membered heterocyclic; and Z is —$NR^4$— (wherein $R^4$ is a hydrogen or an optionally substituted hydrocarbyl) are exemplified.

Compound (I) or (Ia) may be in the form of a prodrug thereof. The prodrug of Compound (I) or (Ia) refers to a compound that is converted into Compound (I) or (Ia) by a reaction with an enzyme, gastric acid, or the like under a physiological condition in the living body, namely, (i) a compound that is converted into Compound (I) or (Ia) by an enzymatic oxidation, reduction, hydrolysis, or the like, and (ii) a compound that is converted into Compound (I) or (Ia) by hydrolysis with gastric acid or the like. Examples of a prodrug of Compound (I) or (Ia) to be used include a compound or its salt wherein hydroxyl group in Compound (I) or (Ia) is acylated, alkylated, phosphorylated, or converted into borate (e.g., a compound or its salt wherein hydroxyl group in Compound (1) or (Ia) is converted into acetyloxy, palmitoyloxy, propanoyloxy, pivaloyloxy, succinyloxy, fumaryloxy, alanyloxy, dimethylaminomethylcarbonyloxy, etc.), a compound or its salt wherein carboxyl group in Compound (I) or (Ia) is esterified or amidated (e.g., a compound or its salt wherein carboxyl group in Compound (I) or (Ia) is subjected to ethyl esterification, phenyl esterification, carboxyoxymethyl esterification, dimethylaminomethyl esterification, pivaloyloxymethyl esterification, ethoxycarbonyloxyethyl esterification, phthalidyl esterification, (5-methyl-2-oxo-1,3-dioxolan-4-yl)methyl esterification, cyclohexyloxycarbonyl esterification, or conversion into the methyl amide, etc.), or the like. These prodrugs can be produced according to a per se known method or its modified method.

Further, a prodrug of Compound (I) or (Ia) may be a compound or its salt that is converted into Compound (1) or (Ia) under physiological conditions as described in "Development of Drugs", Volume 7, Molecular Design, Hirokawa Shoten, 1990; pages 163-198.

General Synthetic Method

Production of a compound of formula (I) or a salt thereof of the present invention is discussed below. The following examples are given to illustrate the invention and are not intended to be inclusive in any manner. Alternative methods may be employed by one skilled in the art.

A process for preparing compound (I) or a salt thereof of the present invention is shown in the following Methods A to E.

(Method A)

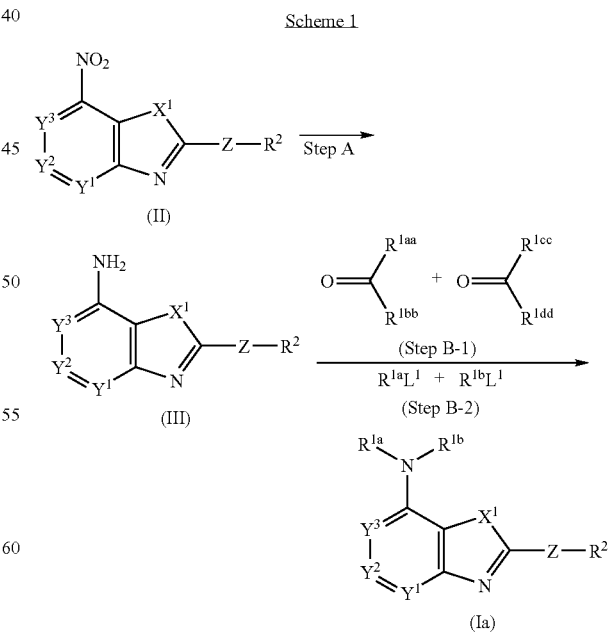

wherein $R^{1a}$, $R^{1b}$ are independently optionally substituted hydrocarbyl groups, or $R^{1a}$ and $R^{1b}$ may be optionally substituted cyclic form, $R^{1aa}$, $R^{1bb}$, $R^{1cc}$ and $R^{1dd}$ are independently hydrogen or optionally substituted hydrocarbyl groups, or $R^{1aa}$ and $R^{1bb}$ or $R^{1cc}$ and $R^{1dd}$ may be optionally substituted cyclic form, $L^1$ is a leaving group (e.g. halogen atom such as chlorine, bromine and iodine, etc, sulfonyloxy group such as p-toluenesulfonyloxy group, methanesulfonyloxy group and trifluoromethanesulfonyloxy group, and acyloxy group such as acetyloxy group and benzoyloxy group) and each of other symbols has a meaning defined above.

In step A, compound (III) or a salt thereof can be prepared by hydrogenation of compound (II) or a salt thereof in the presence of a hydrogenation catalyst, or prepared by a reduction reaction for compound (II) or a salt thereof.

As the catalyst, a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel, Raney nickel are used.

In the present reaction, if needed, any solvents can be used as long as they do not inhibit the reaction. Inter alia, alcohols (e.g. $C_{1-3}$ alcohol such as methanol, ethanol, propanol and the like), ethers (diethyl ether, diisopropyl ether, ethylene glycol dimethyl ether, tetrahydrofuran, dioxane, etc.), or esters (ethyl acetate, etc.) are preferable. These solvents may be used by mixing at an appropriate ratio.

The reaction temperature is 0° C. to 200° C., preferably 20° C. to 100° C. The reaction time is usually 0.5 to 48 hours, preferably 1 to 16 hours. While a reaction is usually performed at atmospheric pressure, it can be performed under pressure (3 to 10 atom) if necessary.

While the amount of a catalyst employed may vary depending on the type of the catalyst employed, it is usually 0.1 to 20% by weight based on an active intermediate or a salt thereof.

Compound (III) or a salt thereof can be also prepared by reduction of compound (II) or a salt thereof. A reducing agent is preferably Fe, Zn, Sn or $SnCl_2$.

This reaction may be performed under acidic conditions. An acid employed in this reduction may for example be an inorganic acid such as hydrochloric acid, sulfuric acid and nitric acid, etc., and an ordinary organic acid such as formic acid, acetic acid, trifluoroacetic acid and methanesulfonic acid, etc. as well as a Lewis acid.

A reaction solvent may for example be alcohols such as methanol and ethanol, etc., ethers such as dioxane and tetrahydrofuran, etc., aromatic hydrocarbons such as benzene, toluene and xylene, etc., esters such as ethyl acetate, etc., halogenated hydrocarbons such as chloroform and dichloromethane, etc., nitriles such as acetonitrile, etc., amides such as N,N-dimethylformamide and N,N-dimethylacetamide, etc. and sulfoxides such as dimethylsulfoxide, etc. These solvents may be used by mixing at an appropriate ratio.

While the reaction temperature may vary depending on the substrate employed as well as other conditions, it is −20 to 200° C., preferably 0 to 100° C. The reaction time is usually 5 minutes to 24 hours, preferably 5 minutes to 10 hours.

Compound (II) or (III) or a salt thereof can be produced by Schemes 2 to 9.

The thus obtained compound (II) or (III) can be isolated and purified by the known isolating and purifying methods, for example, concentration, concentration under reduced pressure, extraction with solvent, crystallization, recrystallization, transfer dissolution and chromatography.

In step B-1, compound (Ia) or a salt thereof, which is encompassed within compound (I) of the invention, can be prepared from compound (III) or a salt thereof and a carbonyl compound $R^{1aa}R^{1bb}C=O$ or $R^{1cc}R^{1dd}C=O$ by in situ production of an imine which is then reduced by an appropriate reducing agent or hydrogenation in the presence of a hydrogenation catalyst. When $R^{1a}$ is equal to $R^{1b}$ in compound (Ia), $R^{1aa}R^{1bb}C=O$ may be used in step B-1. When $R^{1a}$ is not equal to $R^{1b}$ in compound (Ia), the alkylation reactions may be performed stepwise by $R^{1aa}R^{1bb}C=O$ and $R^{1cc}R^{1dd}C=O$ in step B-1.

A reducing agent is preferably sodium borohydride, lithium borohydride, sodium cyanoborohydride and sodium triacetoxyborohydride.

A hydrogenation catalyst is preferably a palladium catalyst such as palladium black, palladium oxide, palladium barium sulfate, palladium on carbon, palladium hydroxide, a platinum catalyst such as platinum black, platinum oxide and platinum on carbon, or nickel catalyst such as reduced nickel, oxidized nickel or Raney nickel. In this reaction, 1 to 10 moles, preferably 1 to 3 moles of the carbonyl compound $R^{1aa}R^{1bb}C=O$, $R^{1cc}C^{1dd}C=O$ and 0.5 to 10 moles, preferably 0.5 to 3 moles of the reducing agent per 1 mole of compound (III) or a salt thereof are used. The reaction solvent may for example be alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

When producing an imine, use of molecular sieves or addition of an acid serves to promote the reaction. An acid employed here is preferably acetic acid and trifluoroacetic acid, etc. While the reaction temperature in this imine production may vary depending on compound (III) or a salt thereof as well as other conditions, it is 0 to 200° C., preferably 0 to 150° C. The reaction time is 30 minutes to hours, preferably 1 hour to 24 hours.

The reaction temperature in the reducing reaction is −20 to 200° C., preferably 0 to 100° C. The reaction time is 30 minutes to 24 hours, preferably 30 minutes to 12 hours.

Compound (Ia) or a salt thereof can be also prepared by reacting compound (III) with $R^{1a}L^1$ or $R^{1b}L^1$. When $R^{1a}$ is equal to $R^{1b}$ in compound (Ia), $R^{1a}L^1$ may be used in step B-2. When $R^{1a}$ is not equal to $R^{1b}$ in compound (Ia), the alkylation reactions may be performed stepwise by $R^{1a}L^1$ and $R^{1b}L^1$ in step B-2.

In step B-2, 1 to 10 moles, preferably 1 to 5 moles of a compound represented by $R^{1a}L^1$ or a salt thereof and 1 to 10 moles, preferably 1 to 3 moles of a base are employed per 1 mole of compound (III) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (III) or a salt thereof employed as well as other reaction conditions, it is −20 to 200° C., preferably 0 to 150° C. The reaction time is 5 minutes to 48 hours, preferably 5 minutes to 24 hours.

Alkylation of compound (III) to prepare compound (Ia) may be performed by combined reactions of steps B-1 and B-2.

The thus obtained compound (Ia) can be isolated and purified by the known isolating and purifying methods, for example, concentration, concentration under reduced pressure, extraction with solvent, crystallization, recrystallization, transfer dissolution and chromatography.

Scheme 2

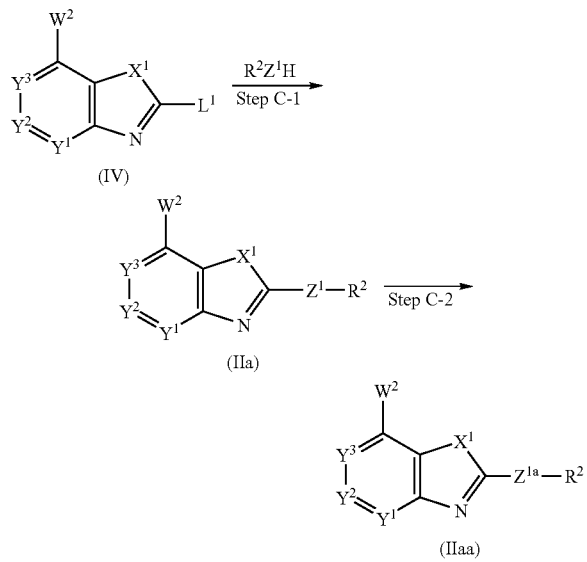

wherein $Z^1$ is oxygen, sulfur, —$NR^4$—, or —$NR^4$-alk-, $Z^{1a}$ is —SO— or —$SO_2$— and $W^2$ is $NO_2$ or $NH_2$, $L^1$ is a leaving groups (e.g. halogen atom such as chlorine, bromine and iodine, etc, sulfonyloxy group such as p-toluenesulfonyloxy group, methanesulfonyloxy group and trifluoromethanesulfonyloxy group, and acyloxy group such as acetyloxy group and benzoyloxy group) and each of other symbols has a meaning defined above.

Compound (IIa) which is encompassed within compound (II) or (III), or a salt thereof can be prepared by reacting compound (IV) with $R^2Z^1H$. Compound (IV) or a salt thereof can be prepared by Schemes 10 or 11 described below.

In step C-1, 1 to 5 moles, preferably 1 to 3 moles of a compound represented by $R^2Z^1H$ or a salt thereof and 1 to 5 moles, preferably 1 to 3 moles of a base are employed per 1 mole of compound (1V) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (IV) or a salt thereof employed as well as other reaction conditions, it is −20 to 200° C., preferably 0 to 150° C. The reaction time is 5 minutes to 48 hours, preferably 5 minutes to 24 hours.

When $Z^1$ is —$NR^4$—, or —$NR^4$-alk- in $R^2Z^1H$, compound (IIa) which is encompassed within compound (II) or (III), or a salt thereof can be also prepared by reacting compound (IV) with $R^2Z^1H$ or a salt thereof in the presence of a palladium catalyst, preferably palladium (II) acetate and a catalytic amount of a phosphine ligand, preferably 2-(dicyclohexylphosphino)biphenyl, according to the procedure of Buchwald et al. (J. Am. Chem. Soc. 1998, 120, 9722) and the modified methods.

When $Z^1$ is sulfur in compound (IIa), compound (IIaa) which is encompassed within compound (II) or (III), or a salt thereof can be prepared by oxidation of compound (IIa) or a salt thereof.

An oxidation agent is preferably hydrogen peroxide, organic peroxides (e.g. 3-chloroperoxybenzoic acid, peroxyacetic acid, etc.), manganese(IV) oxide, sodium metaperiodate.

In step C-2, 1 to 10 moles, preferably 1 to 5 moles of oxidation agent are employed per 1 mole of compound (IIa) or a salt thereof.

This reaction may be performed under acidic conditions. An acid employed in this oxidation may for example be an inorganic acid such as hydrochloric acid, sulfuric acid and nitric acid, etc., and an ordinary organic acid such as formic acid, acetic acid, trifluoroacetic acid and methanesulfonic acid, etc. as well as a Lewis acid.

A reaction solvent may for example be water, alcohols such as methanol and ethanol, etc., ethers such as dioxane and tetrahydrofuran, etc., aromatic hydrocarbons such as benzene, toluene and xylene, etc., esters such as ethyl acetate, etc., halogenated hydrocarbons such as chloroform and dichloromethane, etc., nitriles such as acetonitrile, etc., amides such as N,N-dimethylformamide and N,N-dimethylacetamide, etc. and sulfoxides such as dimethylsulfoxide, etc. These solvents may be used by mixing at an appropriate ratio.

While the reaction temperature may vary depending on the substrate employed as well as other conditions, it is −20 to 200° C., preferably 0 to 100° C. The reaction time is usually 5 minutes to 24 hours, preferably 5 minutes to 10 hours. The thus obtained compound (IIa) and (IIaa) can be isolated and purified by the known isolating and purifying methods, for example, concentration, concentration under reduced pressure, extraction with solvent, crystallization, recrystallization, transfer dissolution and chromatography.

Scheme 3

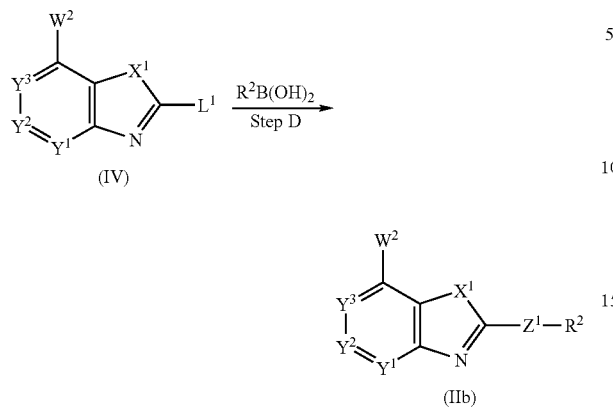

(IIb)

wherein $Z^2$ is bond and each of other symbols has a meaning defined above.

Compound (IIb) which is encompassed within compound (II) or (III), or a salt thereof can be prepared by reacting compound (IV) with a boronic acid $R^2B(OH)_2$ or boronic acid esters or a salt thereof in the presence of a palladium catalyst, preferably tetrakis(triphenylphosphine)palladium (0) and a base according to the procedure of Suzuki coupling (Organic Synthesis via Boranes, vol. 3: Suzuki coupling, A. Suzuki and H. C. Brown, Aldrich, 2002). Compound (IV) or a salt thereof can be prepared by Schemes 10 or 11 described below.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

Examples of solvent having no adverse effect on the reaction include water, alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (IV) or a salt thereof employed as well as other reaction conditions, it is –20 to 200° C., preferably 40 to 150° C. The reaction time is 5 minutes to 48 hours, preferably 1 h to 24 hours.

The thus obtained compound (IIb) can be isolated and purified by the known isolating and purifying methods, for example, concentration, concentration under reduced pressure, extraction with solvent, crystallization, recrystallization, transfer dissolution and chromatography.

Scheme 4

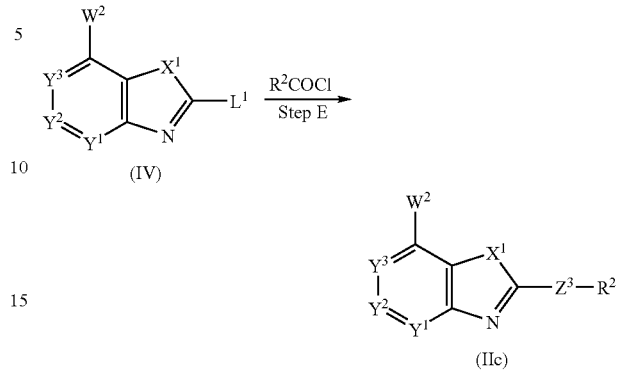

(IIc)

wherein $Z^3$ is C=O and each of other symbols has a meaning defined above.

Compound (IIc) which is encompassed within compound (II) or (III), or a salt thereof can be prepared by reacting compound (IV) with an acid chloride $R^2COCl$ or a salt thereof after treating by an organic metal reagent. Compound (IV) or a salt thereof can be prepared by Schemes 10 or 11 described below.

In step E, an organic metal reagent is employed in an amount of 1 to 5 moles, preferably 1 to 3 moles per 1 mole of compound (IV) or a salt thereof. An organic metal reagent may preferably be organic lithium such as n-BuLi, sec-BuLi, tert-BuLi, etc.

Examples of solvent having no adverse effect on the reaction include ethers such as dioxane and tetrahydrofuran, aromatic hydrocarbons such as benzene, toluene and xylene, amides such as N,N-dimethylformamide and N,N-dimethylacetamide, and sulfoxides such as dimethylsulfoxide. These solvents may be used by mixing at an appropriate ratio.

While the reaction temperature may vary depending on the reagent employed as well as other conditions, it is –100 to 200° C., preferably –78 to 100° C. The reaction time is 5 minutes to 24 hours, preferably 5 minutes to 10 hours.

The thus obtained compound (IIc) can be isolated and purified by the known isolating and purifying methods, for example, concentration, concentration under reduced pressure, extraction with solvent, crystallization, recrystallization, transfer dissolution and chromatography.

Scheme 5

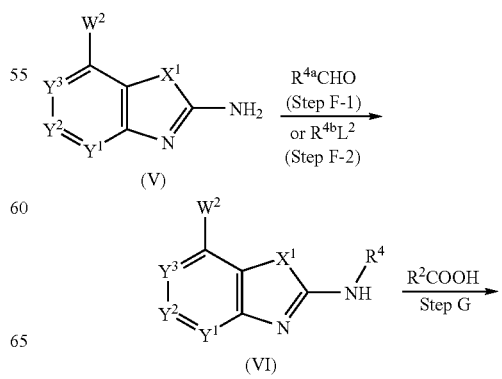

-continued

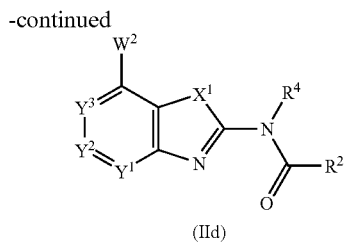

(IId)

wherein R<sup>4a</sup> and R<sup>4b</sup> are independently optionally substituted hydrocarbyl, $L^2$ is leaving groups and each of symbols has a meaning defined above.

In step F-1, compound (VI) or a salt thereof can be prepared from compound (V) or a salt thereof and an aldehyde compound $R^4$CHO by an in situ production of an imine, which is then reduced by an appropriate reducing agent. The reaction can be carried out similar to step B in Scheme 1 to prepare compound (VI). Compound (V) or a salt thereof can be prepared by Scheme 10 described below.

In step F-2, compound (VI) or a salt thereof can be also prepared by reacting (V) with $R^4L^2$ or a salt thereof.

This reaction is carried out in the presence of a base in a solvent having no adverse effect on the reaction according to the conventional method. Specific examples of leaving groups $L^2$ include halogen atom such as chlorine, bromine and iodine, sulfonyloxy group such as p-toluenesulfonyloxy group, methanesulfonyloxy group and trifluoromethanesulfonyloxy group, and acyloxy group such as acetyloxy group and benzoyloxy group.

Example of the base include alkali metal salts such as potassium hydroxide, sodium hydroxide, sodium bicarbonate and potassium carbonate; amines such as pyridine, triethylamine, N,N-dimethylaniline and 1,8-diazabicyclo[5.4.0]undec-7-ene; metal hydrides such as potassium hydride and sodium hydride; and alkali metal alkoxides such as sodium methoxide, sodium ethoxide and potassium t-butoxide.

An amount of these bases to be used is preferably about 1 to about 5 equivalents relative to compound (V).

Examples of solvent having no adverse effect on the reaction include alcohols such as methanol and ethanol, aromatic hydrocarbon such as benzene, toluene and xylene; ethers such as tetrahydrofuran, dioxane and diethyl ether; amides such as N,N-dimethylformamide; and sulfoxides such as dimethyl sulfoxide. These solvents may be used by mixing at an appropriate ratio.

A reaction temperature is usually about −50 to about 150° C., preferably −10° C. to 120° C. A reaction time is usually 0.5 to 20 hours.

The thus obtained compound (VI) can be isolated and purified by the known isolating and purifying methods, for example, concentration, concentration under reduced pressure, extraction with solvent, crystallization, recrystallization, transfer dissolution and chromatography.

In step G, compound (IId) is prepared by reacting a carboxylic acid $R^2$COOH or a reactive derivative at a carboxyl group thereof and compound (VI) or a salt thereof.

Specific examples of the suitable reactive derivative at a carboxyl group of $R^2$COOH include acid halide, acid anhydride, activated amide, activated ester and the like. Examples of the suitable reactive derivative include: acid chloride; acid azide; mixed acid anhydride with an acid such as substituted phosphoric acid such as dialkylphosphoric acid, phenylphosphoric acid, diphenylphosphoric acid, dibenzylphosphoric acid, halogenated phosphoric acid and the like, dialkylphosphorous acid, sulfurous acid, thiosulfuric acid, sulfuric acid, sulfonic acid such as methanesulfonic acid and the like, aliphatic carboxylic acid such as acetic acid, propionic acid, butyric acid, isobutyric acid, pivalic acid, pentanoic acid, isopentanoic acid, trichloroacetic acid and the like or aromatic carboxylic acid such as benzoic acid and the like; symmetric acid anhydride; activated amide with imidazole; 4-substituted imidazole, dimethylpyrazole, triazole or tetrazole; activated ester such as cyanomethylester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxylmethyl thioester, pyranyl ester, pyridyl ester, piperidyl ester, 8-quinolyl thioester and the like, or esters with N-hydroxy compound such as N,N-dimethylhydroxyamine, 1-hydroxy-2-(1H)-pyridone, N-hydroxysuccinimide, N-hydroxyphthalimide, 1-hydroxy-1H-benzotriazole and the like. These reactive derivatives can be arbitrarily selected depending on a kind of compound (VI) to be used.

When $R^2$COOH is used as the form of a free acid or a salt thereof in this reaction, it is desirable that the reaction is carried out in the presence of the normally used condensing agent such as so-called Vilsmeier regent and the like prepared by a reaction of N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide, N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; polyethyl phosphate; polyisopropyl phosphate; phosphorus oxychloride; diphenylphosphorylazide; thionyl chloride; oxalyl chloride; lower alkyl haloformate such as ethyl chloroformate; isopropyl chloroformate and the like; triphenylphosphine; 2-ethyl-7-hydroxybenzisooxazolium salt, 2-ethyl-5-(m-sulfophenyl)isooxazoliumhydroxide internal salt; N-hydroxybenzotriazole; 1-(p-chlorobenzenesulfonyloxy)-6-chloro-1H-benzotriazole; N,N-dimethylformamide with thionyl chloride, phosgene, trichloromethyl chloroformate, phosphorus oxychloride or the like. Alternatively, the reaction may be carried out in the presence of an inorganic base or an organic base such as alkali metal bicarbonate salt, tri(lower)alkylamine, pyridine, N-(lower)alkylmorpholine, N,N-di(lower)alkylbenzylamine and the like. A reaction temperature is not particularly limited, but the reaction is carried out under cooling or under warming.

An amount of $R^2$COOH to be used is 1 to 10 mole equivalent, preferably 1 to 3 equivalent relative compound (VI).

A reaction temperature is usually −30° C. to 100° C.

A reaction time is usually 0.5 to 20 hours.

In addition, when a mixed acid anhydride is used, $R^2$COOH and chlorocarbonic ester (e.g. methyl chlorocarbonate, ethyl chlorocarbonate, isobutyl chlorocarbonate etc.) are reacted in the presence of a base (e.g. triethylamine, N-methylmorpholine, N,N-dimethylaniline, sodium bicarbonate, sodium carbonate, potassium carbonate etc.) and is further reacted with compound (VI).

An amount of $R^2$COOH to be used is usually 1 to 10 mole equivalent, preferably 1 to 3 mole equivalent relative to compound (VI).

A reaction temperature is usually −30° C. to 100° C.

A reaction time is usually 0.5 to 20 hours.

The thus obtained compound (IId) can be isolated and purified by the known isolating and purifying methods, for example, concentration, concentration under reduced pressure, extraction with solvent, crystallization, recrystallization, transfer dissolution and chromatography.

Scheme 6

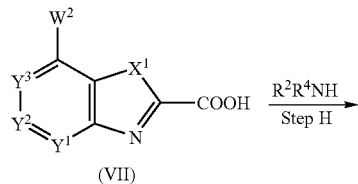

(VII)

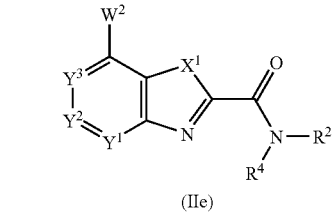

(IIe)

wherein each of symbols has a meaning defined above.

Step H can be carried out similar to step G in Scheme 5 to prepare compound (IIe) which is encompassed within compound (II) or (III), or a salt thereof. Compound (VII) or a salt thereof can be prepared by Scheme 12 described below.

Scheme 7

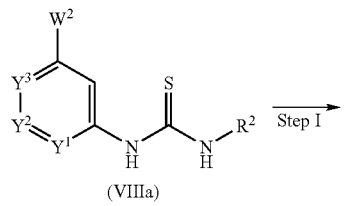

(VIIIa)

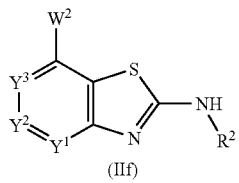

(IIf)

wherein each of symbols has a meaning defined above.

Compound (IIf) which is encompassed within compound (II) or (III), or a salt thereof can be prepared by treatment of compound (VIIIa) with a halogenation agent. Compound (VIIIa) or a salt thereof can be prepared by Schemes 13 or 14 described below.

Examples of the halogenation agent include chlorine, bromine, iodine, thionyl chloride, thionyl bromide, sulfuryl chloride, oxalyl chloride, phosphorus trichloride, phosphorous pentachloride, and phosphorous oxychloride, etc.

In step I, the halogenation agent is employed in an amount of 1 to 10 moles, preferably 1 to 3 moles per 1 mole of compound (VIIIa) or a salt thereof.

Examples of the solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on the reagent employed as well as other conditions, it is $-20$ to $200°$ C., preferably 20 to $100°$ C. The reaction time is 5 minutes to 48 hours, preferably 30 minutes to 24 hours.

The thus obtained compound (IIf) can be isolated and purified by the known isolating and purifying methods, for example, concentration, concentration under reduced pressure, extraction with solvent, crystallization, recrystallization, transfer dissolution and chromatography.

Scheme 8

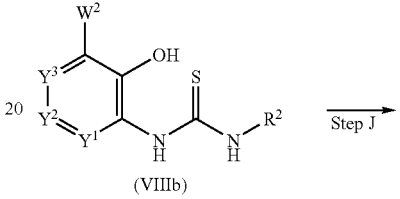

(VIIIb)

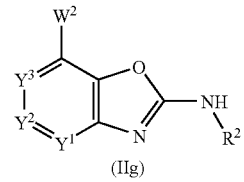

(IIg)

wherein each of symbols has a meaning defined above.

Compound (IIg) which is encompassed within compound (II) or (III), or a salt thereof can be prepared by treatment of compound (VIIIb) with a dehydrothiolation agent. Compound (VIIIb) or a salt thereof can be prepared by Schemes 13 or 14 described below.

Examples of the dehydrothiolation agent include N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, mercury(II) chloride, mercury(II) oxide, copper(II) bromide, copper(II) chloride, silver oxide, silver(I) oxide and silver carbonate, etc.

In step J, the dehydrothiolation agent is employed in an amount of 1 to 10 moles, preferably 1 to 3 moles per 1 mole of compound (VIIIb) or a salt thereof.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

The reaction may be carried out in the presence of an inorganic base or an organic base such as alkali metal salts such as potassium hydroxide, sodium hydroxide, sodium bicarbonate and potassium carbonate; amines such as pyridine, triethylamine, N,N-dimethylaniline and 1,8-diazabicyclo[5.4.0]undec-7-ene; metal hydrides such as potassium hydride and sodium hydride; and alkali metal alkoxides such as sodium methoxide, sodium ethoxide and potassium t-butoxide.

While the reaction temperature may vary depending on the reagent employed as well as other conditions, it is −20 to 150° C., preferably 20 to 100° C. The reaction time is 5 minutes to 10 hours, preferably 5 minutes to 2 hours.

The thus obtained compound (IIg) can be isolated and purified by the known isolating and purifying methods, for example, concentration, concentration under reduced pressure, extraction with solvent, crystallization, recrystallization, transfer dissolution and chromatography.

Scheme 9

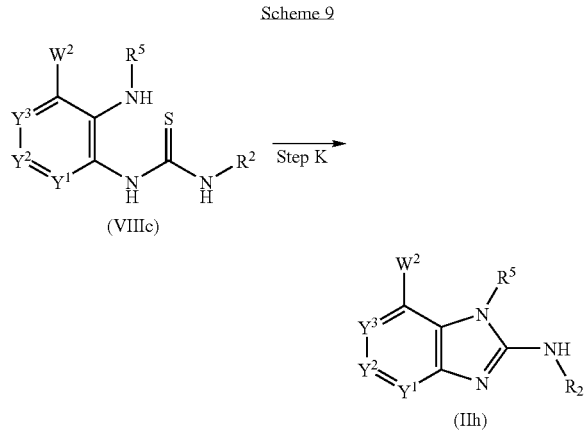

wherein each of symbols has a meaning defined above.

Compound (IIh) which is encompassed within compound (II) or (III), or a salt thereof can be prepared by treatment of compound (VIIIc) with a dehydrothiolation agent. Compound (VIIIc) or a salt thereof can be prepared by Schemes 13 or 14 described below.

Step K can be carried out similar to step J in Scheme 8 to prepare compound (IIh).

Scheme 10

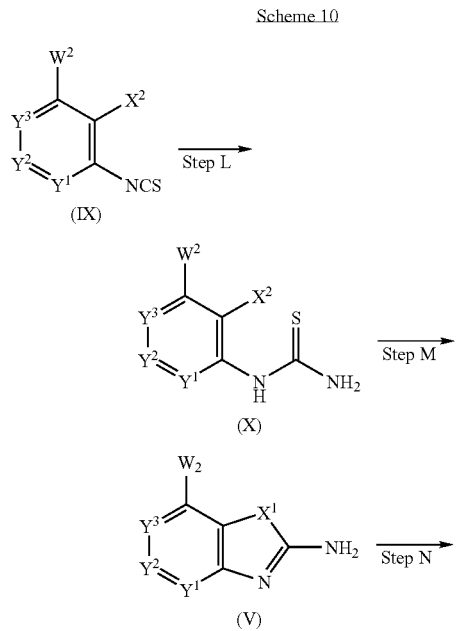

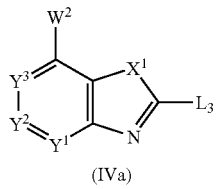

wherein $X^2$ is H, OH or $NHR^5$, $L^3$ is a halogen atom such as chlorine, bromine, and iodine, and each of other symbols has a meaning defined above.

In step L, compound (X) or a salt thereof can be prepared by treatment of compound (IX) with ammonia. Compound (IX) or a salt thereof is mainly commercially available, or can be prepared by reacting thiophosgene with the amino derivatives (XIV) described below (Scheme 13).

Examples of the solvent include water, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxidse such as dimethylsulfoxide. These solvent may be used by mixing at an appropriate ratio.

While the reaction temperature may vary depending on the reagent employed as well as other conditions, it is −20 to 200° C., preferably 20 to 100° C. The reaction time is 5 minutes to 48 hours, preferably 30 minutes to 24 hours.

The thus obtained compound (X) can be isolated and purified by the known isolating and purifying methods, for example, concentration, concentration under reduced pressure, extraction with solvent, crystallization, recrystallization, transfer dissolution and chromatography.

Step M can be carried out according to steps I, J or K in the Schemes 7 to 9 to prepare compound (V).

In step N, an amino group of compound (V) is converted into a diazonium salt, and halogenation agent is reacted thereon, according to the procedure of Sandmeyer reaction, to prepare compound (IVa), which is encompassed within compound (IV). Diazonization in the present method is carried out in the presence of an acid in a solvent having no adverse effect on the reaction according to the conventional method. As the acid, for example, acetic acid and hydrochloric acid are used. As a diazotizing agent, sodium nitrite, alkyl nitrite or sulfated nitrosyl is used.

The thus obtained diazonium salt of compound (V) is reacted with halogenation agent to prepare compound (IV). Examples of the halogenation agent include chlorine, bromine, iodine, copper(I) bromide, copper (II) bromide, copper (I) chloride and copper (II) chloride, etc.

Examples of the solvent include water, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxidse such as dimethylsulfoxide. These solvents may be used by mixing at an appropriate ratio.

A reaction temperature is usually about −50° C. to about 150° C., preferably about −10° C. to about 100° C. A reaction time is usually about 0.5 to about 20 hours.

The thus obtained compound (IVa) can be isolated and purified by the known isolating and purifying methods, for example, concentration, concentration under reduced pressure, extraction with solvent, crystallization, recrystallization, transfer dissolution and chromatography.

Scheme 11

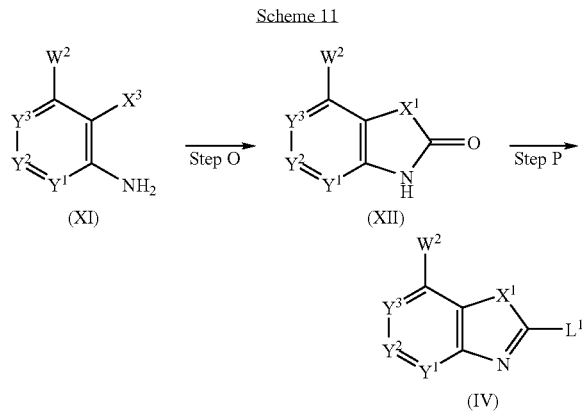

wherein $X^3$ is SH, OH or $NHR^5$ and each of symbols has a meaning defined above.

In step O, compound (XII) or a salt thereof can be prepared by treatment of compound (XI) with 1,1'-carbonyl diimidazole, phosgene, alkyl haloformate such as ethyl chloroformate, phenyl haloformate such as phenyl chloroformate or urea, etc. Compound (XI) or a salt thereof is mainly commercially available or can be prepared from the nitro derivatives corresponded to compound (XI).

Examples of the solvent include ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxidse such as dimethylsulfoxide. These solvents may be used by mixing at an appropriate ratio.

While the reaction temperature may vary depending on the reagent employed as well as other conditions, it is –20 to 200° C., preferably 20 to 100° C. The reaction time is 5 minutes to 48 hours, preferably 30 minutes to 24 hours.

The thus obtained compound (XII) can be isolated and purified by the known isolating and purifying methods, for example, concentration, concentration under reduced pressure, extraction with solvent, crystallization, recrystallization, transfer dissolution and chromatography.

In step P, after base treatment of compound (XII), the resulting moiety may be converted to a leaving group to prepare compound (IV).

Such leaving group may for example be a substituted sulfonyloxy (for example, methanesulfonyloxy and p-toluenesulfonyloxy, etc.), an acyloxy (for example, acetoxy and benzoyloxy, etc.) and an oxy group which is substituted with a heterocyclic or aryl group (such as succinimide, benzotriazole, quinoline and 4-nitrophenyl, etc.), etc.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

In step P, compound (IV) or a salt thereof can be also prepared by treatment of compound (XII) with a halogenation agent.

Examples of the halogenation agent include chlorine, bromine, iodine, thionyl chloride, thionyl bromide, sulfuryl chloride, oxalyl chloride, phosphorus trichloride, phosphorous pentachloride, and phosphorous oxychloride, etc.

The halogenation agent is employed in an amount of 1 to 10 moles, preferably 1 to 3 moles per 1 mole of compound (XII) or a salt thereof.

Examples of the solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on the reagent employed as well as other conditions, it is –20 to 200° C., preferably 20 to 100° C. The reaction time is 5 minutes to 48 hours, preferably 30 minutes to 24 hours.

The thus obtained compound (IV) can be isolated and purified by the known isolating and purifying methods, for example, concentration, concentration under reduced pressure, extraction with solvent, crystallization, recrystallization, transfer dissolution and chromatography.

Scheme 12

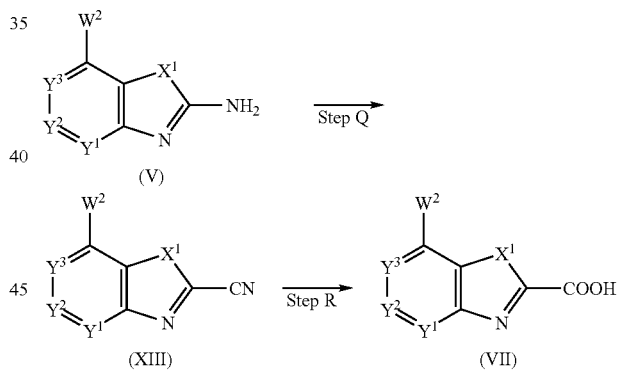

wherein each of symbols has a meaning defined above.

In step Q, an amino group of compound (V) is converted into a diazonium salt, and cyanation agent is reacted thereon to prepare compound (XIII), according to the procedure of Sandmeyer reaction. Diazotization in the present method is carried out in the presence of an acid in a solvent having no adverse effect on the reaction according to the conventional method. As the acid, for example, acetic acid, sulfuric acid and hydrochloric acid are used. As a diazotizing agent, sodium nitrite, alkyl nitrite or sulfated nitrosyl is used.

The thus obtained diazonium salt of compound (V) is reacted with cyanation agent to prepare compound (XIII). Examples of the cyanation agent include copper cyanide, potassium cyanide, sodium cyanide and nickel cyanide, etc.

Examples of the solvent include water, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

A reaction temperature is usually about −50° C. to about 150° C., preferably about −10° C. to about 100° C. A reaction time is usually about 0.5 to about 20 hours.

The thus obtained compound (XIII) can be isolated and purified by the known isolating and purifying methods, for example, concentration, concentration under reduced pressure, extraction with solvent, crystallization, recrystallization, transfer dissolution and chromatography.

In step R, compound (VII) or a salt thereof can be prepared by hydrolysis of compound (XIII) or a salt thereof.

It is preferable that hydrolysis is carried out in the presence of a base or an acid. An acid which may be employed may for example be an inorganic acid such as hydrochloric acid, sulfuric acid and nitric acid, and a base may for example be an inorganic base (alkaline metal hydroxide such as sodium hydroxide and potassium hydroxide, etc., alkaline metal hydrogen carbonate such as sodium hydrogen carbonate and potassium hydrogen carbonate, etc., alkaline metal carbonate such as sodium carbonate and potassium carbonate, etc.).

This reaction is conducted in a 20 to 50 volumes of an aqueous solution of an inorganic acid described above (usually at 10 to 30%) per 1 g of the nitrile compound (XIII), or in an aqueous solution containing 3 to 10 moles of a base described above per 1 mole of the nitrile compound (XIII). In view of the solubility of a compound, the reaction may be performed in an aqueous solution described above which is supplemented with an organic solvent. An organic solvent which may be employed is alcohols such as methanol and ethanol, organic acids such as acetic acid, etc., ethers such as dioxane and tetrahydrofuran, a nitrile such as acetonitrile, amides such as N,N-dimethylformamide and N,N-dimethylacetamide and sulfoxides such as dimethylsulfoxide.

While the reaction temperature may vary depending on the nitrile employed as well as other conditions, it is 0 to 200° C., preferably 20 to 150° C. The reaction time is 30 minutes to 48 hours, preferably 1 to 24 hours.

The thus obtained compound (VII) can be isolated and purified by the known isolating and purifying methods, for example, concentration, concentration under reduced pressure, extraction with solvent, crystallization, recrystallization, transfer dissolution and chromatography.

Scheme 13

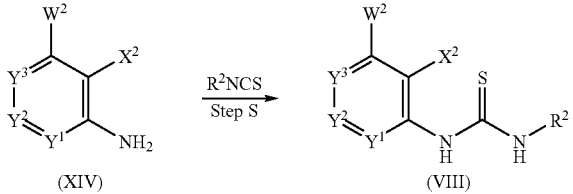

wherein each of symbols has a meaning defined above.

Compound (VIII) or a salt thereof can be prepared by reacting (XIV) with $R^2NCS$ or a salt thereof.

In step S, an isothiocyanate $R^2NCS$ is employed in an amount of 1 to 10 moles, preferably 1 to 3 moles per 1 mole of compound (XIV) or a salt thereof.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XIV) employed as well as other conditions, it is 0 to 200° C., preferably 20 to 150° C. The reaction time is 30 minutes to 48 hours, preferably 1 to 24 hours.

The thus obtained compound (VIII) can be isolated and purified by the known isolating and purifying methods, for example, concentration, concentration under reduced pressure, extraction with solvent, crystallization, recrystallization, transfer dissolution and chromatography.

Scheme 14

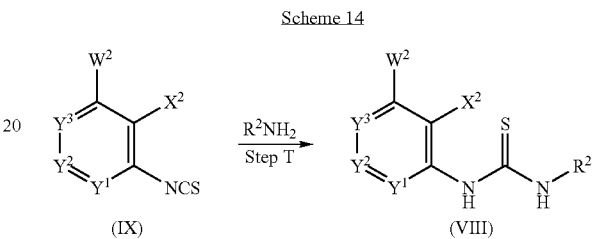

wherein each of symbols has a meaning defined above.

Compound (VIII) or a salt thereof can be also prepared by reacting (IX) with $R^2NH_2$ or a salt thereof.

In step T, compound $R^2NH_2$ is employed in an amount of 1 to 10 moles, preferably 1 to 3 moles per 1 mole of compound (IX) or a salt thereof.

Examples of the solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (IX) employed as well as other conditions, it is 0 to 200° C., preferably 20 to 150° C. The reaction time is 30 minutes to 48 hours, preferably 1 to 24 hours.

The thus obtained compound (VIII) can be isolated and purified by the known isolating and purifying methods, for example, concentration, concentration under reduced pressure, extraction with solvent, crystallization, recrystallization, transfer dissolution and chromatography.

(Method B)

Scheme 15

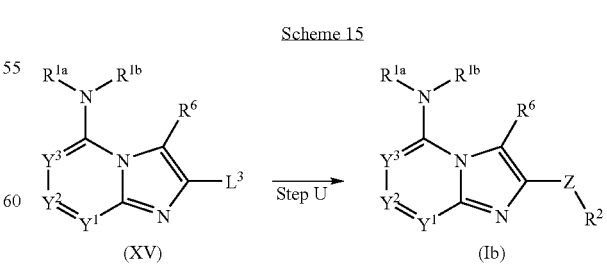

wherein each of symbols has a meaning defined above.

Step U can be carried out similar to step C, D, and E in the Schemes 2 to 4 to prepare compound (Ib) which is encompassed within compound (I). Compound (XV) or a salt thereof can be prepared by Scheme 16 described below.

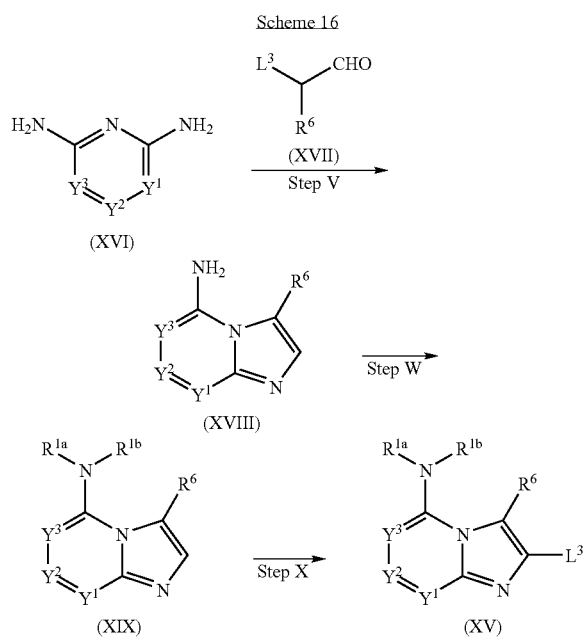

wherein each of symbols has a meaning defined above.

Compound (XVIII) or a salt thereof can be prepared by reacting compound (XVI) with compound (XVII).

In step V, 1 to 5 moles, preferably 1 to 3 moles of compound (XVII) or a salt thereof are employed per 1 mole of compound (XVI) or a salt thereof.

Examples of the solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

This reaction may be performed under basic conditions. A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

While the reaction temperature may vary depending on compound (XVII) or a salt thereof employed as well as other reaction conditions, it is −20 to 200° C., preferably 0 to 150° C. The reaction time is 5 minutes to 48 hours, preferably 5 minutes to 24 hours.

The thus obtained compound (XVIII) can be isolated and purified by the known isolating and purifying methods, for example, concentration, concentration under reduced pressure, extraction with solvent, crystallization, recrystallization, transfer dissolution and chromatography.

Step W can be carried out similar to step B-1 and B-2 in Scheme 1 to prepare compound (XIX).

In step X, compound (XV) or a salt thereof can be prepared by treatment of compound (XIX) with a halogenation agent.

Examples of the halogenation agent include N-chlorosuccinimide, N-bromosuccinimide, chlorine, bromine, iodine, thionyl chloride, thionyl bromide, sulfuryl chloride, oxalyl chloride, phosphorus trichloride, phosphorous pentachloride, and phosphorous oxychloride, etc.

In step X, the halogenation agent is employed in an amount of 1 to 10 moles, preferably 1 to 3 moles per 1 mole of compound (XIX) or a salt thereof.

Examples of the solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as carbon tetrachloride, chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on the reagent employed as well as other conditions, it is −50 to 200° C., preferably 0 to 100° C. The reaction time is 5 minutes to 48 hours, preferably 30 minutes to 24 hours.

The thus obtained compound (XV) can be isolated and purified by the known isolating and purifying methods, for example, concentration, concentration under reduced pressure, extraction with solvent, crystallization, recrystallization, transfer dissolution and chromatography.

(Method C)

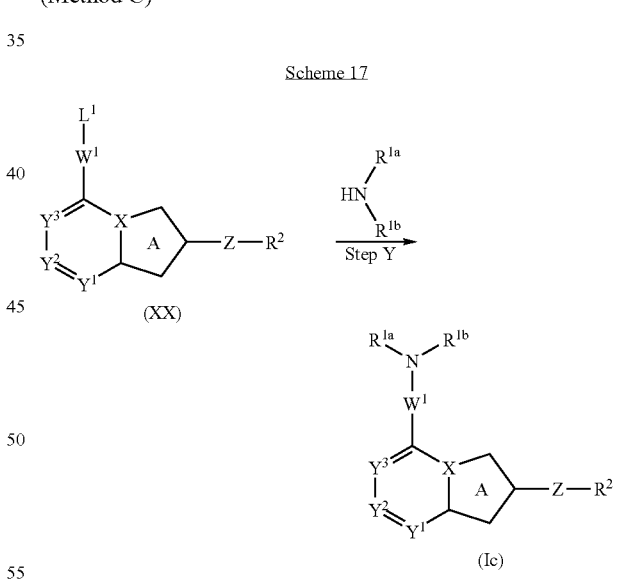

wherein each of symbols has a meaning defined above.

Compound (Ic) which is encompassed within compound (1), or a salt thereof can be prepared by reacting compound (XX) with an amino compound $R^{1a}R^{1b}NH$. Compound (XX) or a salt thereof can be prepared by the procedures described in Methods A and B.

In step Y, 1 to 5 moles, preferably 1 to 3 moles of a compound represented by $R^{1a}R^{1b}NH$ or a salt thereof and 1 to 5 moles, preferably 1 to 3 moles of a base are employed per 1 mole of compound (XX) or a salt thereof.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

Examples of solvent having no adverse effect on the reaction include alcohols such as methanol and ethanol, ethers such as dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XX) or a salt thereof employed as well as other reaction conditions, it is −20 to 200° C., preferably 0 to 150° C. The reaction time is 5 minutes to 48 hours, preferably 5 minutes to 24 hours.

When n is 0 in compound (XX), compound (1c) can be also prepared by reacting compound (XX) with $R^{1a}R^{1b}NH$ or a salt thereof in the presence of a palladium catalyst, preferably palladium (II) acetate and a catalytic amount of a phosphine ligand, preferably 2-(dicyclohexylphosphino)biphenyl, according to the procedure of Buchwald et al. (J. Am. Chem. Soc. 1998, 120, 9722) and the modified methods.

The thus obtained compound (Ic) can be isolated and purified by the known isolating and purifying methods, for example, concentration, concentration under reduced pressure, extraction with solvent, crystallization, recrystallization, transfer dissolution and chromatography.

(Method D)

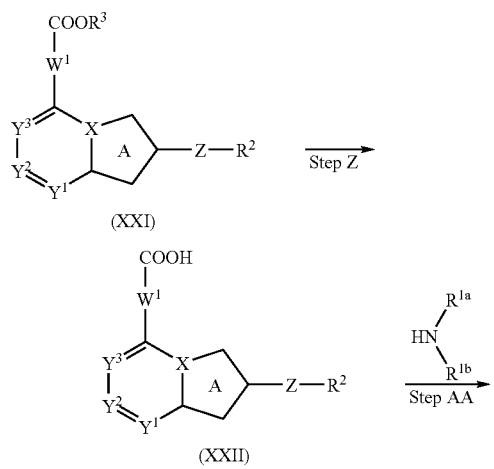

Scheme 18

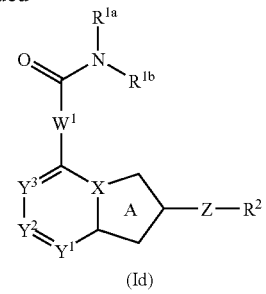

(Id)

wherein $R^3$ is an optionally substituted carbon atom, and each of symbols has a meaning defined above.

In step Z, compound (XXII) is prepared by removing a carboxyl-protecting group. Compound (XXI) or a salt thereof can be prepared by the procedures described in Methods A, B, E and Scheme 19.

All conventional methods used in a reaction for removal of a carboxyl-protecting group, for example, hydrolysis, reduction and elimination using a Lewis acid can be applied to the present reaction. It is preferable that hydrolysis is carried out in the presence of a base or an acid. Examples of the suitable base include inorganic bases such as alkali metal hydroxide (e.g. sodium hydroxide and potassium hydroxide), alkaline earth metal hydroxide (e.g. magnesium hydroxide and calcium hydroxide), alkali metal carbonate (e.g. sodium carbonate and potassium carbonate), alkaline earth metal carbonate (e.g. magnesium carbonate and calcium carbonate), alkali metal bicarbonate (e.g. sodium bicarbonate and potassium bicarbonate), alkali metal acetate (e.g. sodium acetate and potassium acetate), alkaline earth metal phosphate (e.g. magnesium phosphate and calcium phosphate) and alkali metal hydrogen phosphate (e.g. disodium hydrogen phosphate and dipotassium hydrogen phosphate), and organic bases such as trialkylamine (e.g. trimethylamine and triethylamine) picoline, N-methylpyrrolidine, N-methylmorpholine, 1,5-diazabicyclo[4.3.2]non-5-ene, 1,4-diazabicyclo[2.2.2]non-5-ene and 1,8-diazabicyclo[4.3.0]-7-undecene. Hydrolysis using a base is carried out in water or a hydrophilic organic solvent or a mixed solvent in many cases. Examples of a suitable acid include formic acid, hydrochloric acid, hydrobromic acid and sulfuric acid.

The present hydrolysis reaction is usually carried out in an organic solvent, water or a mixed solvent thereof. A reaction temperature is not particularly limited, but is appropriately selected depending on a kind of a carboxyl-protecting group and an elimination method. Elimination using a Lewis acid is carried out by reacting compound (XXI) or a salt thereof with a Lewis acid, for example, trihalogenated boron (e.g. boron trichloride and boron trifluoride), tetrahalogenated titanium (e.g. titanium tetrachloride and titanium tetrabromide), and halogenated aluminium (e.g. aluminium chloride and aluminium bromide), or an organic acid (e.g. trichloroacetic acid and trifluoroacetic acid). This elimination reaction is preferably carried out in the presence of a cation scavenger (e.g. anisole and phenol) and is usually carried out in a solvent such as nitroalkane (e.g. nitromethane and nitroethane), alkylene halide (e.g. methylene chloride and ethylene chloride), diethyl ether, carbon disulfide, and a solvent having no adverse effect on the reaction. These solvents may be used as a mixture thereof.

It is preferable that elimination by reduction is applied to elimination of a protecting group such as halogenated alkyl (e.g. 2-iodoethyl and 2,2,2-trichloroethyl) ester, and aralkyl (e.g. benzyl) ester. Examples of a reduction method using in the present elimination reaction include the conventional catalytic reduction in the presence of a combination of a metal (e.g. zinc and zinc amalgam) or a salt of a chromium compound (e.g. chromate chloride and chromate acetate) and an organic or inorganic acid (e.g. acetic acid, propionic acid and hydrochloric acid); or the conventional metal catalyst (e.g. palladium carbon and Raney nickel). A reaction temperature is not particularly limited, but a reaction is carried out under cooling, at room temperature of under warming.

The thus obtained compound (XXII) can be isolated and purified by the known isolating and purifying methods, for example, concentration, concentration under reduced pressure, extraction with solvent, crystallization, recrystallization, transfer dissolution and chromatography.

In step AA, compound (Id) which is encompassed within compound (I), or a salt thereof is prepared by reacting compound (XXII) or a reactive derivative at a carboxyl group thereof and a salt thereof with the amino compound $R^{1a}R^{1b}NH$ or a reactive derivative at an amino group thereof or a salt thereof.

Step AA can be carried out similar to step G in Scheme to prepare compound (Id) which is encompassed within compound (I).

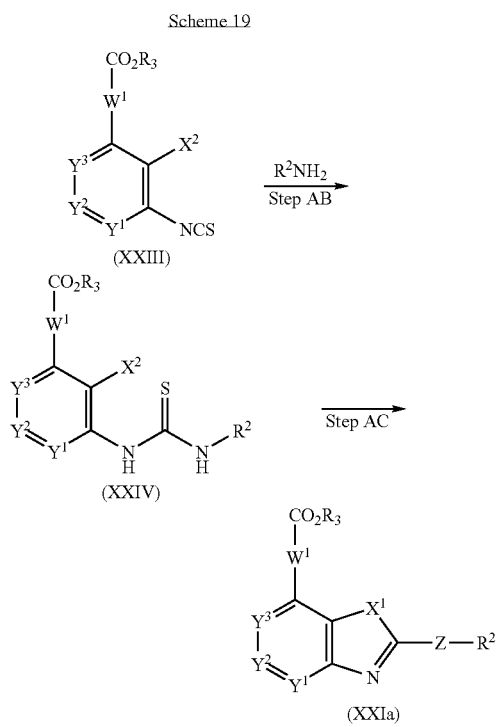

wherein each of symbols has a meaning defined above.

Step AB can be carried out similar to step T in Scheme 14 to prepare compound (XXIV) or a salt thereof. Compound (XXIII) or a salt thereof can be prepared from amino derivatives corresponded to compound (XXIII).

Step AC can be carried out similar to step I in the Scheme 7 to prepare compound (XXIa), which is encompassed within compound (XXI), or a salt thereof.

(Method E)

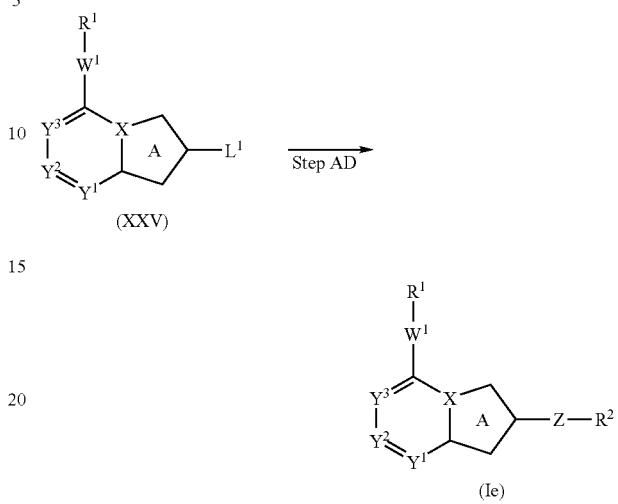

wherein each of symbols has a meaning defined above.

Step AD can be carried out similar to step C, D, and E in the Schemes 2 to 4 to prepare compound (1e) which is encompassed within compound (I). Compound (XXV) or a salt thereof can be prepared by the procedures described in Methods A, B and Scheme 21.

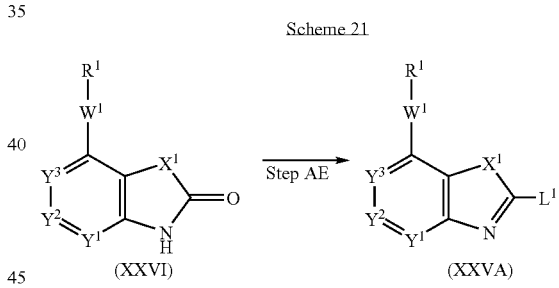

wherein each of symbols has a meaning defined above.

Step AE can be carried out similar to step P in Scheme 11 to prepare compound (XXVa), which is encompassed within compound (XXV). Compound (XXVI) or a salt thereof can be prepared by the procedures in Schemes 22-25 described below.

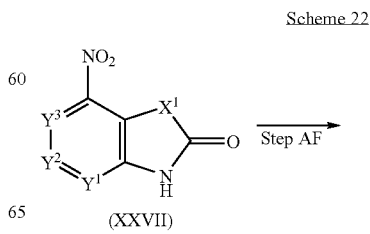

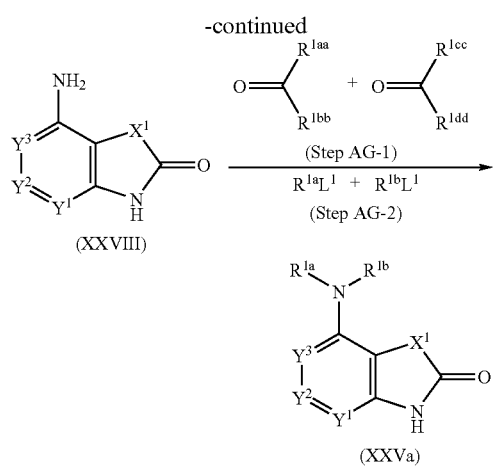

wherein each of symbols has a meaning defined above.

Step AF can be carried out similar to step A in Scheme 1 to prepare compound (XXVIII) or a salt thereof. Compound (XXVII) or a salt thereof can be prepared by the procedures described in step O in Scheme 11.

Step AG can be carried out similar to step B in Scheme 1 to prepare compound (XXVIa), which is encompassed within compound (XXVI), or a salt thereof.

In step AH-2, a palladium catalyst may for example be bis(triphenylphosphine) palladium(II) dichloride, tris(dibenzylidineacetone)dipalladium(0), trans-dichlorobis(tri-o-tolylphosphine)palladium, palladium(II) trifluoroacetate and palladium(II) acetate, preferably tris(dibenzylidineacetone) dipalladium(0). A phosphine ligand may for example be 2,2'-bis(diphenylphosphino)-1,1'-binaphtyl, 2-(di-tert-butylphosphino)biphenyl, 2-(dicyclohexylphosphino)biphenyl, 2-(dicyclohexylphosphino)-2',6'-dimethoxy-1,1'-biphenyl, 2-(dicyclohexylphosphino)-2'-(N,N-dimethylamino)biphenyl, 1,1'-bis(diphenylphosphino)ferrocene, tri-tert-butylphosphine and tricyclohexylphosphine, preferably 2-(dicyclohexylphosphino)biphenyl and 2-(dicyclohexylphosphino)-2',6'-dimethoxy-1,1'-biphenyl. A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide, sodium ethoxide, sodium tert-butoxide and potassium tert-butoxide, etc., an amine such as trimethylamine, triethylamine and diisopropylethylamine, etc., a cyclic amine such as pyridine, etc.

In step AH-2, 1.0 to 5 moles, preferably 1.1 to 2.0 moles of $R^{1e}L^1$, 0.01 to 0.5 moles, preferably 0.05 to 0.2 moles of a Scheme 23

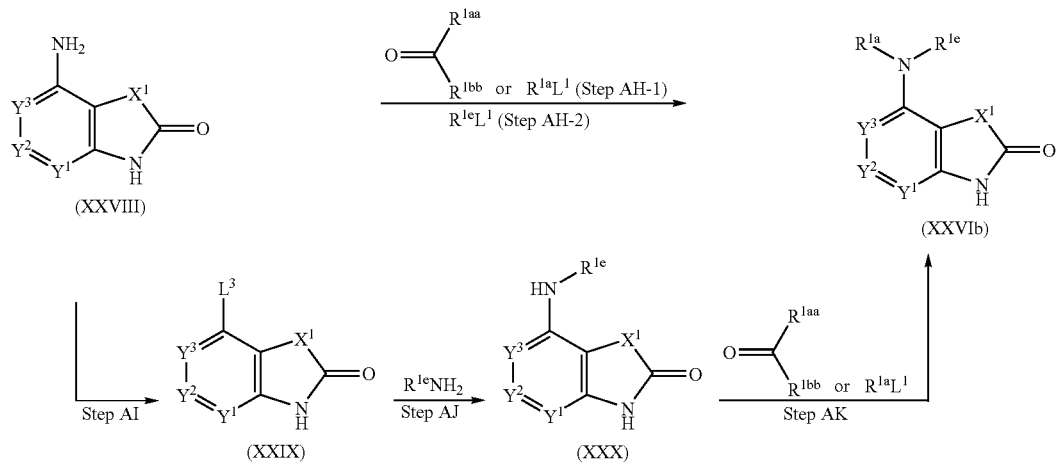

wherein $R^{1e}$ is an optionally substituted aryl or an optionally substituted heteroaryl, and each of the other symbols has a meaning defined above.

Compound (XXVIb), which is encompassed within compound (XXVI), or a salt thereof can be prepared by reacting compound (XXVIII) with $R^{1aa}{}_R{}^{1bb}$=O, $R^{1a}L^1$ or a salt thereof in the similar manner described in step B-1 and B-2 in Scheme 1 and with $R^{1e}L^1$ or a salt thereof in the presence of a palladium catalyst, a phosphine ligand, and a base according to the procedure of Buchwald coupling (Topics in Current Chemistry, 219, 131-209 (2002)) to prepare compound (XXVIb). The order of these two steps, AH-1 and AH-2, may be changed. Compound (XXVIII) or a salt thereof can be prepared by Scheme 22 described above.

palladium catalyst, 0.01 to 0.5 moles, preferably 0.02 to 0.2 moles of a phosphine ligand and 1.0 to 5.0 moles, preferably 1.2 to 3 moles of a base are employed per 1 mole of an amino compound or a salt thereof.

Examples of solvent having no adverse effect on the reaction include ethers such as dioxane, tetrahydrofuran and 1,2-dimethoxyethane, aromatic hydrocarbons such as benzene, toluene and xylene, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XIIa) or a salt thereof employed as well as other reaction conditions, it is 0 to 250° C., preferably 50 to 150° C. The reaction time is 5 minutes to 120 hours, preferably 1 hour to 48 hours.

As an alternative route, compound (XXVIb) or a salt thereof can be prepared via compound (XXIX).

In step AI, compound (XXIX) can be prepared by the similar procedure described in step N in Scheme 10 or reacting compound (XXVIII) with an alkyl nitrite and a metal halide, etc.

In step AI, 1.0 to 5 moles, preferably 1.0 to 2.0 moles of an alkyl nitrite, 0.5 to 3 moles, preferably 0.5 to 2 moles of a metal halide.

Examples of solvent having no adverse effect on the reaction include ethers such as dioxane, tetrahydrofuran and 1,2-dimethoxyethane, aromatic hydrocarbons such as benzene, toluene and xylene, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XXVIII) or a salt thereof employed as well as other reaction conditions, it is −10 to 200° C., preferably 0 to 100° C. The reaction time is 5 minutes to 120 hours, preferably 30 minutes to 24 hours.

The thus obtained compound (XXIX) can be isolated and purified by the known isolating and purifying methods, for example, concentration, concentration under reduced pressure, extraction with solvent, crystallization, recrystallization, transfer dissolution and chromatography.

Step AJ can be carried out similar to step AH-2 to prepare compound (XXX) by reacting with $R^{1e}NH_2$ or a salt thereof.

Step AK can be carried out similar to step B in Scheme 1 to prepare compound (XXVIb).

The thus obtained compound (XXVIb) can be isolated and purified by the known isolating and purifying methods, for example, concentration, concentration under reduced pressure, extraction with solvent, crystallization, recrystallization, transfer dissolution and chromatography.

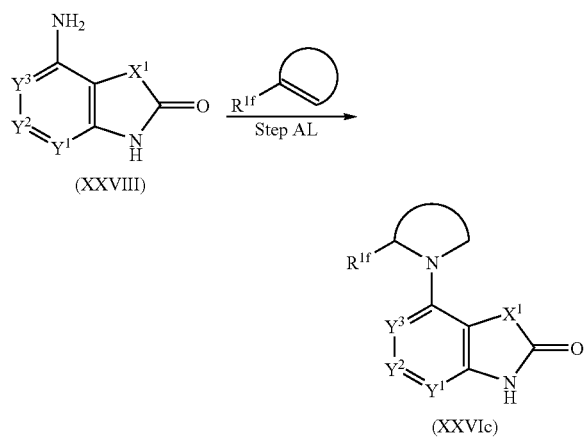

wherein $R^{1f}$ is an optionally substituted alkyl, an optionally substituted carboxyl or an optionally substituted carboxamide, and each of the other symbols has a meaning defined above.

Compound (XXVIc), which is encompassed within compound (XXVI), or a salt thereof can be prepared by oxidation of cycloalkene and next reductive alkylation of compound (XXVIII). Compound (XXVIII) or a salt thereof can be prepared by Scheme 22 described above.

In an oxidation step, an oxidation agent is used and a base or an acid may be used.

An oxidation agent may for example be potassium permanganate, potassium periodate, sodium periodate, sodium dichromate, potassium dichromate, osmium tetroxide, ruthenium tetroxide, oxygen, ozone, hydrogen peroxide, organic peroxide such as 3-chloroperoxybenzoic acid and peroxyacetic acid, etc., preferably ozone. These reagents may be used by mixing at an appropriate ratio.

A base may for example be an alkaline metal hydroxide such as sodium hydroxide and potassium hydroxide, etc., an alkaline metal hydrogen carbonate such as sodium hydrogen carbonate and potassium hydrogen carbonate, etc., an alkaline metal carbonate such as sodium carbonate and potassium carbonate, etc., a cesium salt such as cesium carbonate, etc., an alkaline metal hydride such as sodium hydride and potassium hydride, etc., sodium amide, an alkoxide such as sodium methoxide and sodium ethoxide, etc., an amine such as trimethylamine, triethylamine and diisopropylethylamine, etc., a cyclic amine such as pyridine, etc.

An acid may for example be an inorganic acid such as hydrochloric acid, sulfuric acid and nitric acid, etc., and an ordinary organic acid such as formic acid, acetic acid, trifluoroacetic acid and methanesulfonic acid, etc. as well as a Lewis acid.

In the oxidation reaction, 1 to 10 moles, preferably 1 to 3 moles of the oxidative agent and 0.1 to 10 moles, preferably 0.3 to 2 moles of the base per 1 mole of compound (XXVIII) or a salt thereof are used.

Examples of solvent having no adverse effect on the reaction include alcohols such as methanol and ethanol, ethers such as diethyl ether, dioxane and tetrahydrofuran, aromatic hydrocarbons such as benzene, toluene and xylene, esters such as ethyl acetate, halogenated hydrocarbons such as chloroform and dichloromethane, nitriles such as acetonitrile, amides such as N,N-dimethylformamide and N,N-dimethylacetamide, and sulfoxides such as dimethylsulfoxide. These solvents may be used by mixing at an appropriate ratio.

While the reaction temperature may vary depending on compound (XXVIII) or a salt thereof employed as well as other reaction conditions, it is −100 to 200° C., preferably −100 to 100° C. The reaction time is 1 minute to 48 hours, preferably 1 minute to 24 hours.

The thus obtained oxidant may be isolated and purified by the known isolating and purifying methods, for example, concentration, concentration under reduced pressure, extraction with solvent, crystallization, recrystallization, transfer dissolution and chromatography.

In a reductive alkylation step, the similar manner described in step B-1 in Scheme 1 is used. The thus obtained compound (XXVIc) can be isolated and purified by the known isolating and purifying methods, for example, concentration, concentration under reduced pressure, extraction with solvent, crystallization, recrystallization, transfer dissolution and chromatography.

Scheme 25

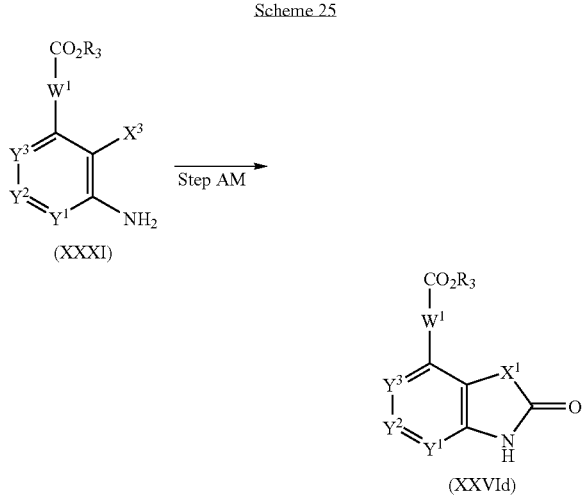

Step AM can be carried out similar to step O in Scheme 11 to prepare compound (XXVId) or a salt thereof. Compound (XXXI) or a salt thereof can be prepared from the nitro derivatives corresponded to compound (XXXI).

Compound (I) obtained by any method described above as a free form may be converted in accordance with a standard procedure for example into a salt with an inorganic acid (for example, hydrochloric acid, sulfuric acid and hydrobromic acid, etc.), an organic acid (for example, methanesulfonic acid, benzenesulfonic acid, toluenesulfonic acid, oxalic acid, fumaric acid, maleic acid and tartaric acid, etc.), an inorganic base (for example, alkaline metal such as sodium and potassium, etc., alkaline earth metal such as calcium and magnesium, etc., aluminum and ammonium, etc.) or an organic base (for example, trimethylamine, triethylamine, pyridine, picoline, ethanolamine, diethanolamine, triethanolamine, dicyclohexylamine and N,N'-dibenzylethylenediamine, etc.), while compound (I) obtained as a salt may be converted into a free form or other salts according to standard procedure.

Compound (I) or a salt thereof thus obtained can be purified and recovered using a separation/purification method known per se (for example, condensation, solvent extraction, column chromatography and recrystallization, etc.).

A starting compound for compound (I) according to the invention may be in a form of a salt, including a salt with an inorganic acid (for example, hydrochloric acid, phosphoric acid, hydrobromic acid and sulfuric acid, etc.) and a salt with an organic acid (for example, acetic acid, formic acid, propionic acid, fumaric acid, maleic acid, succinic acid, tartaric acid, citric acid, malic acid, oxalic acid, benzoic acid, methanesulfonic acid and benzenesulfonic acid, etc.). When any of these compounds carries an acidic group such as —COOH, etc., a salt with an inorganic base (for example, an alkaline metal or an alkaline earth metal such as sodium, potassium, calcium and magnesium, ammonia, etc.) or with an organic base (for example, tri-$C_{1-3}$ alkylamine such as triethylamine, etc.) may be formed.

In each of the reactions described above, when a starting compound carries as a substituent an amino group, an amide group, a urea group, a carboxyl group or a hydroxyl group, then such group may be derivatized with a protective group employed ordinarily in peptide chemistry, which is cleaved after a reaction if desired to yield an intended compound.

A protective group for an amino group, an amide group and a urea group may for example be an optionally substituted $C_{1-6}$ alkylcarbonyl (for example, formyl, methylcarbonyl and ethylcarbonyl, etc.), phenylcarbonyl, a $C_{1-6}$ alkyloxycarbonyl (for example, methoxycarbonyl, ethoxycarbonyl and tert-butylcarbonyl, etc.), phenyloxycarbonyl (for example, benzoxycarbonyl), $C_{7-10}$ aralkylcarbonyl (for example, benzyloxycarbonyl), $C_{7-10}$ aralkyl (for example, benzyl and 4-methoxybenzyl, etc.), trityl, phthaloyl, etc. A substituent on each of the groups listed above may be a halogen atom (for example, fluorine, chlorine, bromine and iodine, etc.), a $C_{1-6}$ alkylcarbonyl (for example, methylcarbonyl, ethylcarbonyl and butylcarbonyl, etc.) and a nitro group, which may occur 1 to about 3 times.

A protective group for a carboxyl group may for example be an optionally substituted $C_{1-6}$ alkyl (for example, methyl, ethyl, n-propyl, i-propyl, n-butyl and t-butyl, etc.), phenyl, trityl and silyl, etc. A substituent on each of the groups listed above may be a halogen atom (for example, fluorine, chlorine, bromine and iodine, etc.), a $C_{1-6}$ alkylcarbonyl (for example, formyl, methylcarbonyl, ethylcarbonyl and butylcarbonyl, etc.) and a nitro group, which may occur 1 to about 3 times.

A protective group for a hydroxyl group may for example be an optionally substituted $C_{1-6}$ alkyl (for example, methyl, ethyl, n-propyl, i-propyl, n-butyl and tert-butyl, etc.), phenyl, a $C_{7-10}$ aralkyl (for example, benzyl, etc.), a $C_{1-6}$ alkylcarbonyl (for example, formyl, methylcarbonyl and ethylcarbonyl, etc.), phenyloxycarbonyl (for example, benzoxycarbonyl, etc.), $C_{7-10}$ aralkylcarbonyl (for example, benzyloxycarbonyl, etc.), pyranyl, furanyl, silyl, etc. A substituent on each of the groups listed above may be a halogen atom (for example, fluorine, chlorine, bromine and iodine, etc.), a $C_{1-6}$ alkyl, phenyl, a $C_{7-10}$ aralkyl, nitro, etc., which may occur 1 to about 4 times.

A method for cleaving a protective group is a method known per se or an analogous method, such as a treatment for example with an acid, a base, a reduction, UV light, hydrazine, phenylhydrazine, sodium N-methyldithiocarbamate, tetrabutylammonium fluoride, palladium acetate, etc.

The pharmaceutical composition containing compound (I) or (Ia) of the present invention is expected to be useful in the treatment and prevention of diseases, in which CRF is involved, such as great depression, postpartum depression, suppression symptom, mania, anxiety, generalized anxiety disorder, panic disorder, phobia, obsessive-compulsive disorder, post psychic trauma stress disorder, Tourette's syndrome, autism, passion disorder, adjustment disorder, dysthymic disorder, sleep disorder, insomnia, bipolar disorder, circulatory disease, neurosis, schizophrenia, digestive ulcer, irritable bowl syndrome, ulcerative colitis, Crohn's disease, diarrhea, constipation, postoperative ileus, gastrointestine dysfunction and nervous vomiting associated with stress, Alzheimer's disease, Alzheimer's type senile dementia, nervous degenerated disease such as Parkinson's disease and Huntington's disease, multi-infarct dementia, senile dementia, nervous orexia inactivity, hyperphagia and other ingestion disorder, obesity, diabetes, alcohol dependency, pharmacophinia, drug withdrawal, migraine, stress headache, tension headache, ischemic nervous disorder, nervous disorder, cerebral paralysis, progressive supranuclear palsy, amyotrophic lateral sclerosis, multiple sclerosis, muscular convulsion, chronic fatigue syndrome, glaucoma, Meniere syndrome, autonomic imbalance, alopecia, hypertension, cardiovascular disorder, tachycardia, congestive heart attack, hyperplea, bronchial asthma, apnea, infant sudden death syndrome, inflammatory disorder, pain, allergic disorder, impotence, menopausal disorder, fertilization disorder, infertility, cancer, immune function abnormality at HIV infection, immune functional abnormality due to stress, cerebrospinal meningitis, acromegaly, incontinence or osteoporosis.

Compound (I) or (Ia) of the present invention can be formulated with a pharmaceutically acceptable carrier and can be orally or parenterally administered as solid formulations such as tablets, capsules, granules, powders, or the like; or liquid formulations such as syrups, injections, or the like. Also, there can be prepared formulations for transdermal administration such as patchings, cataplasms, ointments (including creams), plasters, tapes, lotions, liquids and solutions, suspensions, emulsions, sprays, and the like.

As for a pharmaceutically acceptable carrier, a variety of organic or inorganic carrier substances, which have been conventionally employed as formulation materials, is used and compounded as a bulking agent, a lubricant, a binding agent, and a disintegrator in solid formulations; a vehicle, a solubilizing agent, a suspending agent, an isotonicity agent, a buffering agent, and an analgesic in liquid formulations. If necessary, formulation excipients such as a preservative, an antioxidant, a stabilizer, a coloring agent, a sweetening agent, and the like can be used.

Preferred examples of the bulking agent include lactose, sucrose, D-mannitol, starch, crystalline cellulose, light anhydrous silicic acid, and the like. Preferred examples of the lubricant include magnesium stearate, potassium stearate, talc, colloidal silica, and the like. Preferred examples of the binding agent include crystalline cellulose, α-starch, sucrose, D-mannitol, dextrin, hydroxypropyl cellulose, hydroxypropylmethyl cellulose, polyvinyl pyrrolidone, and the like. Preferred examples of the disintegrator include starch, carboxymethyl cellulose, calcium carboxymethyl cellulose, croscarmellose sodium, sodium carboxymethyl starch, low-substituted hydroxypropyl cellulose, and the like. Preferred examples of the vehicle include water for injection, alcohol, propylene glycol, macrogol, sesame oil, corn oil, and the like.

If necessary, for the purpose of taste masking, enteric coating, or prolonged action, oral formulations can be prepared by coating by a per se known method. Examples of this coating agent include hydroxypropylmethyl cellulose, ethyl cellulose, hydroxymethyl cellulose, hydroxypropyl cellulose, polyoxyethylene glycol, Tween 80, Pluronic F68 [polyoxyethylene (160) polyoxypropylene (30) glycol], cellulose acetate phthalate, hydroxypropylmethyl cellulose phthalate, hydroxymethyl cellulose acetate phthalate, Eudragit (manufactured by Rohm Company, methacrylic acid-acrylic acid copolymer), and the like.

Preferred examples of the solubilizing agent include polyethylene glycol, propylene glycol, benzyl benzoate, ethanol, trisamiomethane, cholesterol, triethanolamine, sodium carbonate, sodium citrate, and the like. Preferred examples of the suspending agent include surface active agents such as stearyltriethanolamine, sodium lauryl sulfate, laurylaminopropionic acid, lecithin, benzalkonium chloride, benzethonium chloride, glycerin monostearate, and the like; hydrophilic, high molecular substances such as polyvinyl alcohol, polyvinyl pyrrolidone, sodium carboxymethyl cellulose, methyl cellulose, hydroxymethyl cellulose, hydroxyethyl cellulose, hydroxypropyl cellulose, and the like; and so on. Preferred examples of the isotonicity agent include sodium chloride, glycerin, D-mannitol, and the like. Preferred examples of the buffering agent include buffer solutions of a phosphate, an acetate, a carbonate, a citrate, or the like. Preferable examples of the analgesic include benzyl alcohol and the like. Preferred examples of the preservative include paraoxybenzoic acid esters, chlorobutanol, benzyl alcohol, phenethyl alcohol, dehydroacetic acid, sorbic acid, and the like. Preferred examples of the antioxidant include sulfites, ascorbic acid, and the like.

The following examples and experiments describe the manner and process of making and using the present invention and are illustrative rather than limiting. It is to be understood that there may be other embodiments which fall within the spirit and scope of the present invention as defined by the claims appended hereto.

Example 1

N-Mesityl-N$^7$,N$^7$-dipropyl-1,3-benzothiazole-2,7-diamine

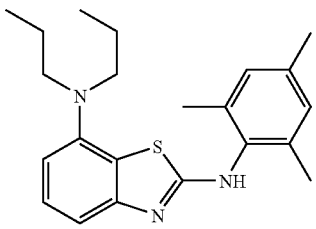

N$^7$-Mesityl-7-nitro-1,3-benzothiazol-2-amine

A mixture of 2.25 g (12.5 mmol) of 3-nitrophenylisothiocyanate and 1.4 mL (10 mmol) of mesityl amine in 10 mL of methanol was stirred at room temperature for 2 h. The resulting precipitate was collected by filtration and dried to give a quantitative yield of 1-(3-nitrophenyl)-3-(mesityl)thiourea. To 1.8 g (5.7 mmol) of the thiourea thus prepared slurried in 20 mL of CCl$_4$ was added 0.35 mL (6.9 mmol) of bromine. The mixture was heated at reflux for 4 h, allowed to cool to room temperature and diluted with dichloromethane. This solution was washed successively with saturated sodium bicarbonate, water and brine before being dried over sodium sulfate. The solution was filtered, concentrated in vacuo and the resulting crude title compound was obtained in quantitative yield and was used without further purification.

MS Calcd.: 313. Found: 314 (M+H).

N$^2$-Mesityl-1,3-benzothiazole-2,7-diamine

To a solution of 1.8 g (5.7 mmol) of N$^2$-mesityl-7-nitro-1,3-benzothiazol-2-amine in 7.2 mL of glacial acetic acid and 25 mL of ethanol was added 1.8 g (32 mmol) of iron powder. The resulting solution was heated at reflux for 18 h before being cooled to room temperature. The slurry was filtered and the filtrate was concentrated to a brown solid. The solid was slurried in water, collected by filtration and purified by flash chromatography eluting with a 33% hexanes/ethyl acetate mixture to give 0.9 g (55%) of the title compound as a tan powder.

MS Calcd.: 283. Found: 284 (M+H).

$N^2$-Mesityl-$N^7$,$N^7$-dipropyl-1,3-benzothiazole-2,7-diamine

To 0.125 g (0.44 mmol) of $N^2$-mesityl-1,3-benzothiazole-2,7-diamine and 0.16 mL (2.2 mmol) of propionaldehyde in 5 mL of dichloroethane was added one drop of glacial acetic acid and 0.28 g (1.3 mmol) of sodium triacetoxyborohydride. The mixture was heated to 50° C. for 1 h and concentrated in vacuo. The crude solid was purified by flash chromatography eluting with a 2% methanol/dichloromethane mixture to give 0.016 g (10%) of the title compound as a tan powder.

$^1$H NMR (CDCl$_3$) δ 0.73 (t, J=7.4 Hz, 6H), 1.31-1.40 (m, 4H), 2.23 (s, 6H), 2.26 (s, 3H), 2.94-2.98 (m, 4H), 6.67 (t, J=2.7 Hz, 1H), 6.92 (s, 2H), 7.14-7.17 (m, 2H).

MS Calcd.: 367. Found: 368 (M+H).

Compounds of Examples 2-6 shown in Table 1, were prepared in a manner similar to that described in Example 1. Compounds 2 and 3 were purified by reverse phase HPLC (CH$_3$CN containing 0.1% TFA/water containing 0.1% TFA) to obtain TFA salts.

TABLE 1

| Example | Structure | Name | Physical Data |
|---------|-----------|------|---------------|
| 2 | 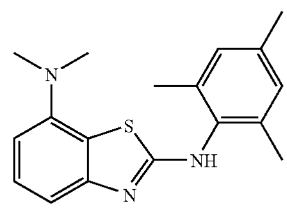 | $N^7$,$N^7$-dimethyl-$N^2$-mesityl-1,3-benzothiazole-2,7-diamine | MS Calcd.: 311; Found: 312 (M + H) |
| 3 | 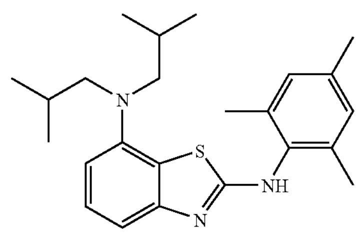 | $N^7$,$N^7$-diisobutyl-$N^2$-mesityl-1,3-benzothiazole-2,7-diamine | MS Calcd.: 395; Found: 396 (M + H) |
| 4 | 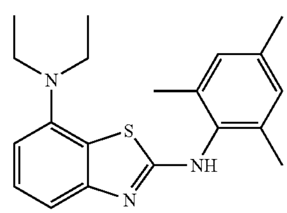 | $N^7$,$N^7$-diethyl-$N^2$-mesityl-1,3-benzothiazole-2,7-diamine | MS Calcd.: 339 Found: 340 (M + H) |
| 5 | 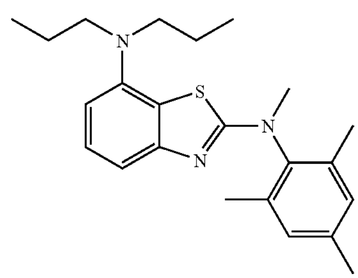 | $N^2$-mesityl-$N^2$-methyl-$N^7$,$N^7$-dipropyl-1,3-benzothiazole-2,7-diamine | MS Calcd.: 381 Found: 382 (M + H) |
| 6 | 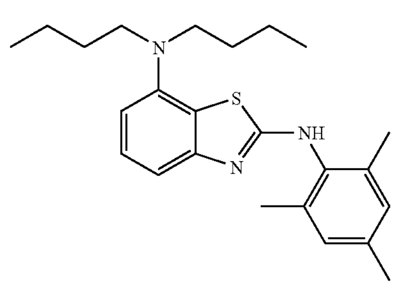 | $N^2$-mesityl-$N^7$,$N^7$-dibutyl-1,3-benzothiazole-2,7-diamine | MS Calcd.: 395 Found: 396 (M + H) |

Example 7

$N^2$-Mesityl-$N^7$,$N^7$-dipropyl[1,3]thiazolo[4,5-b]pyridine-2,7-diamine

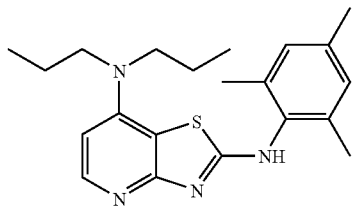

2-Chloro-N,N-dipropylpyridin-4-amine

A mixture of 0.65 g (5.1 mmol) of 4-amino-2-chloropyridine and 1.8 mL (25 mmol) of propionaldehyde in 5 mL of dichloroethane was treated with two drops of glacial acetic acid and 3.2 g (15 mmol) of sodium triacetoxyborohydride. The mixture was heated to 50° C. for 1 h and an additional 0.9 mL (12.5 mmol) of propionaldehyde and 1.6 g (7.5 mmol) of sodium triacetoxyborohydride was added. The mixture was heated at 50° C. for an additional 36 h. The reaction was cooled to room temperature and 0.15 g (4 mmol) of sodium borohydride was added. The reaction was heated to 80° C. for 1 h and cooled to room temperature. The mixture was diluted with dichloromethane and was washed successively with water and brine before being dried over sodium sulfate. The solution was filtered, concentrated in vacuo and the resulting crude oil was purified by flash chromatography eluting with a 80% hexanes/ethyl acetate mixture to give 0.41 g (38%) of the title compound as a colorless oil.

$^1$H NMR (CDCl$_3$) δ 0.91 (t, J=7.4 Hz, 6H), 1.53-1.62 (m, 4H), 3.20 (t, J=7.8 Hz, 4H), 6.32 (dd, J=2.5, 6.0 Hz, 3H), 6.39 (d, J=2.5 Hz, 1H), 7.89 (d, J=6.0 Hz, 1H).

$N^2$-Diphenylmethylene-$N^4$,$N^4$-dipropylpyridine-2,4-diamine

A mixture of 0.52 g (2.4 mmol) of 2-chloro-$N^4$,$N^4$-dipropylpyridin-4-amine, 0.076 g (0.12 mmol) of racemic 2,2'-bis(diphenylphosphino)-1,1'-binaphtyl (BINAP), 0.33 g (3.4 mmol) of sodium tert-butoxide and 0.027 g (0.12 mmol) of palladium (II) acetate in 25 mL of toluene was treated with 0.49 mL (2.9 mmol) of benzophenone imine and heated to 85° C. for 18 h. The crude reaction mixture was diluted with ethyl acetate, filtered through a pad of celite and purified by flash chromatography eluting with a 33% hexanes/ethyl acetate mixture to give 0.65 g (75%) of the title compound as a golden oil.

MS Calcd.: 357. Found: 358 (M+H).

$N^4$,$N^4$-Dipropylpyridine-2,4-diamine

To 0.235 g (0.66 mmol) of $N^2$-diphenylmethylene-$N^4$,$N^4$-dipropylpyridine-2,4-diamine in 9 mL of methanol was added 0.13 g (1.6 mmol) of sodium acetate followed by 0.082 g (1.2 mmol) of hydroxylamine hydrochloride. The resulting clear golden reaction mixture was stirred at room temperature for 45 min and concentrated in vacuo. The crude solids were slurried in dichloromethane, filtered and the filtrate was concentrated. The resulting oil was purified by flash chromatography eluting with a 13% to 20% methanol/dichloromethane gradient containing 2% triethylamine to give 0.106 g (83%) of the title compound as a white solid.

MS Calcd.: 193. Found: 194 (M+H).

1-[4-(Dipropylamino)pyridin-2-yl]-3-mesitylthiourea

To 0.106 g (0.0.55 mmol) of $N^4$,$N^4$-dipropylpyridine-2,4-diamine in 10 mL of methanol was added 0.117 g (0.66 mmol) of mesitylisothiocyanate. The mixture was heated at reflux for 24 h, diluted with water and extracted with ethyl acetate. The organic layer was washed with brine, dried over sodium sulfate, filtered, concentrated in vacuo and the resulting crude solid was purified by flash chromatography eluting with a 85% hexanes/ethyl acetate mixture to give 0.044 g (22%) of the title compound as a white solid.

MS Calcd.: 370. Found: 371 (M+H).

$N^2$-Mesityl-$N^7$,$N^7$-dipropyl[1,3]thiazolo[4,5-b]pyridine-2,7-diamine

To 0.040 g (0.11 mmol) of 1-[4-(Dipropylamino)pyridin-2-yl]-3-mesitylthiourea in 2 mL of glacial acetic acid was added 6.1 μL (0.12 mmol) of bromine. After 30 min at room temperature, an additional 2 μL of bromine was added. The reaction mixture was concentrated after 2 h and washed with ethyl acetate/hexanes. The organics were concentrated and the resulting oil was purified by flash chromatography eluting with a 4% methanol/dichloromethane mixture to give 0.020 g (50%) of the title compound as a light yellow powder.

$^1$H NMR (DMSO-d$_6$) δ 0.84 (t, J=7.2 Hz, 6H), 1.50-1.56 (m, 4H), 2.17 (s, 6H), 2.27 (s, 3H), 3.30 (s, 4H), 6.34 (d, J=5.9 Hz, 1H), 6.98 (s, 2H), 7.88 (d, J=5.9 Hz, 1H), 9.55 (br s, 1H).

MS Calcd.: 368. Found: 369 (M+H).

Example 8

$N^2$-(1-Phenylethyl)-$N^7$,$N^7$-dipropyl-1,3-benzothiazole-2,7-diamine

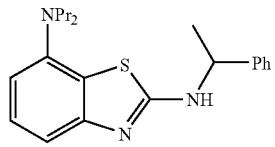

2-Chloro-7-nitro-1,3-benzothiazole

To 0.195 g (1.0 mmol) of 7-nitro-1,3-benzothiazol-2-amine and 0.336 g (2.5 mmol) of cupric chloride in 2 mL of N,N-dimethylformamide (DMF) was added dropwise 0.15 mL (1.25 mmol) of tert-butyl nitrite. The reaction was stirred at room temperature for 24 h, poured into water, and the resulting precipitate was collected and dried to give 0.163 g (76%) of the title compound as a tan powder.

MS Calcd.: 215. Found: 214 (M−H).

7-Nitro-N-(1-phenylethyl)-1,3-benzothiazol-2-amine

To 0.160 g (0.75 mmol) of 2-chloro-7-nitro-1,3-benzothiazole in 2 mL of 1-methyl-2-pyrrolidinone (NMP) was added 0.29 μL (2.2 mmol) of racemic α-methylbenzylamine. The reaction was stirred at room temperature for 18 h, diluted with water and extracted with dichloromethane. The organic layer was concentrated in vacuo and purified by flash chromatography eluting with a 25% ethyl acetate/hexanes mixture to give 0.165 g (74%) of the title compound as a light yellow solid which was used without further analysis in the subsequent step.

N²-(1-Phenylethyl)-1,3-benzothiazole-2,7-diamine

To 0.165 g (0.55 mmol) of 7-nitro-N-(1-phenylethyl)-1,3-benzothiazol-2-amine in 10 mL of DMF was added 0.62 g (2.8 mmol) of stannous chloride dihydrate. The reaction was heated to 80° C. for 48 h and neutralized with saturated sodium bicarbonate. The mixture was filtered through celite and extracted with ethyl acetate. The extracts were dried in vacuo and purified by flash chromatography eluting with a 50-75% ethyl acetate/hexanes gradient mixture to give 0.016 g (11%) of the title compound as a light yellow solid.

MS Calcd.: 269. Found: 270 (M+H).

N²-(1-Phenylethyl)-N⁷,N⁷-dipropyl-1,3-benzothiazole-2,7-diamine

To 0.016 g (0.059 mmol) of N²-(1-phenylethyl)-1,3-benzothiazole-2,7-diamine and 21 µL (0.30 mmol) of propionaldehyde in 2 mL of dichloroethane was added one drop of glacial acetic acid and 0.038 g (0.18 mmol) of sodium triacetoxyborohydride. The mixture was heated to 50° C. for 3 h and concentrated in vacuo. The crude solid was purified by flash chromatography eluting with a 25% ethyl acetate/hexanes mixture to give 0.008 g (38%) of the title compound as a light golden colored oil.

MS Calcd.: 353. Found: 354 (M+H).

Example 9

2-Morpholin-4-yl-N,N-dipropyl-1,3-benzothiazol-7-amine

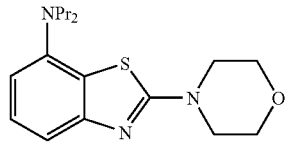

2-Morpholin-4-yl-7-nitro-1,3-benzothiazole

To 0.200 g (0.77 mmol) of 2-bromo-7-nitro-1,3-benzothiazole in 2 mL of DMF was added 0.21 g (1.5 mmol) of potassium carbonate and 81 µL (0.93 mmol) of morpholine. The mixture was stirred at room temperature for 72 h and diluted with water. The precipitate that formed was collected by filtration and purified by flash chromatography eluting with a 33% ethyl acetate/hexanes mixture to give 0.075 g (37%) of the title compound as a cream colored powder.

MS Calcd.: 265. Found: 266 (M+H).

2-Morpholin-4-yl-1,3-benzothiazol-7-amine

To 0.075 g (0.28 mmol) of 2-morpholin-4-yl-7-nitro-1,3-benzothiazole in 6 mL of tetrahydrofuran (THF) was added a pipet tip of Raney nickel. The reaction was kept under a hydrogen atmosphere via a balloon and stirred at room temperature for 5 h. The catalyst was removed via filtration and the filtrate was concentrated in vacuo. Purification by flash chromatography failed to provide clean B so the 0.022 g (33%) of material thus isolated was used without further purification.

2-Morpholin-4-yl-N,N-dipropyl-1,3-benzothiazol-7-amine

To 0.022 g (0.094 mmol) of 2-morpholin-4-yl-1,3-benzothiazol-7-amine and 40 µL (0.56 mmol) of propionaldehyde in 2 mL of dichloroethane was added one drop of glacial acetic acid and 0.064 g (0.30 mmol) of sodium triacetoxyborohydride. The mixture was heated to 50° C. for 5 h and concentrated in vacuo. The crude solid was purified by flash chromatography eluting with a 17% ethyl acetate/hexanes mixture to give 0.009 g (30%) of the title compound as a light golden colored oil.

MS Calcd.: 319. Found: 320 (M+H).

Example 10

N-(7-(Dipropylamino)-1,3-benzothiazol-2-yl)-2,4,6-trimethylbenzamide

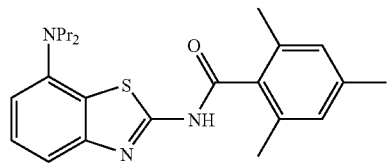

(3-Nitrophenyl)thiourea

To 7.20 g (40 mmol) of 3-nitrophenylisothiocyanate in 25 mL of methanol was added 28.5 mL (200 mmol) of 7 N ammonia in methanol. After 30 min., the slurry was concentrated to give 7.9 g (100%) of the title compound as a yellow-orange powder that did not require further purification.

MS Calcd.: 197. Found: 198 (M+H).

7-Nitro-1,3-benzothiazol-2-amine

To 0.60 g (3.0 mmol) of (3-nitrophenyl)thiourea in 25 mL of carbon tetrachloride was added 0.17 mL (3.4 mmol) of bromine in 10 mL of carbon tetrachloride dropwise over 1 h. The mixture was heated to reflux for 18 h, cooled to room temperature and the precipitate that formed was collected by filtration. The precipitate was slurried in glacial acetic acid and the solids were collected by filtration. The solids thus obtained were slurried in water and saturated potassium carbonate was added until the pH was about 9. The free base was collected by filtration to give 0.30 g (51%) of the title compound as a light orange solid.

MS Calcd.: 195. Found: 196 (M+H).

2,4,6-Trimethyl-N-(7-nitro-1,3-benzothiazol-2-yl)benzamide

To 0.089 g (0.46 mmol) of 7-nitro-1,3-benzothiazol-2-amine in 1 mL of pyridine was added 0.17 g (0.91 mmol) of 2,4,6-trimethylbenzoyl chloride. The mixture was heated to 75° C. for 18 h and the volatiles were removed in vacuo. The residue was washed with water and 1 N hydrochloric acid, dissolved in ethyl acetate, dried over sodium sulfate, filtered, concentrated in vacuo and the resulting crude solid was purified by flash chromatography eluting with 25% ethyl acetate/hexanes mixture to give 0.103 g (66%) of the title compound as a tan solid.

$^1$H NMR (DMSO-d$_6$) δ 2.21 (s, 6H), 2.26 (s, 3H), 6.95 (s, 2H), 7.72 (t, J=8.0 Hz, 1H), 8.20 (d, J=8.0 Hz, 1H), 8.31 (d, J=8.2 Hz, 1H), 12.98 (s, 1H).

MS Calcd.: 341. Found: 342 (M+H).

N-(7-Amino-1,3-benzothiazol-2-yl)-2,4,6-trimethylbenzamide

To 0.200 (0.586 mmol) of 2,4,6-trimethyl-N-(7-nitro-1,3-benzothiazol-2-yl)benzamide in 5 mL of THF was added a pipet tip of Raney nickel. The reaction was kept under a hydrogen atmosphere via a balloon and stirred at room temperature for 90 min. The catalyst was removed via filtration and the filtrate was concentrated in vacuo to give a burnt orange solid. The resulting crude solid was purified by flash chromatography eluting with 25% ethyl acetate/hexanes mixture to give 0.118 g (65%) of the title compound as a light yellow powder.

MS Calcd.: 311. Found: 312 (M+H).

N-(7-(Dipropylamino)-1,3-benzothiazol-2-yl)-2,4,6-trimethylbenzamide

To 0.118 g (0.379 mmol) of N-(7-amino-1,3-benzothiazol-2-yl)-2,4,6-trimethylbenzamide and 0.14 mL (1.9 mmol) of propionaldehyde in 5 mL of dichloroethane was added one drop of glacial acetic acid and 0.24 g (1.1 mmol) of sodium triacetoxyborohydride. The mixture was heated to 50° C. for 3 h and an additional 0.14 mL of propionaldehyde was added. The reaction was heated at 50° C. for 18 h and concentrated in vacuo. The crude solid was purified by flash chromatography eluting with a 13% ethyl acetate/hexanes mixture to give 0.080 g (53%) of the title compound as a cream colored powder.

MS Calcd.: 395. Found: 396 (M+H).

Example 11

2-(2,4-Dimethylphenoxy)-N,N-dipropyl-1,3-benzothiazol-7-amine

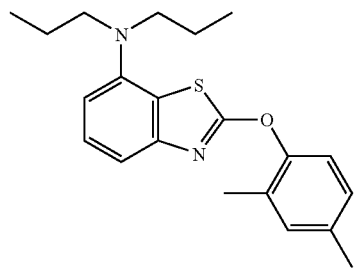

2-Bromo-7-nitro-1,3-benzothiazole

To a suspension of 7-nitro-1,3-benzothiazol-2-ylamine (1.80 g, 9.22 mmol) in acetic acid (AcOH) (20 ml) was added 48% hydrogen bromide in H$_2$O (10 ml) with ice-cooling. Bromine (0.157 ml) was added dropwise followed by sodium nitrite (177 mg, 23.9 mmol) in H$_2$O (1 ml). The temperature was kept at 0 to 5° C. The mixture was stirred for 2 h with ice-cooling and then was made alkaline by dropwise addition of 6N NaOH solution. The resulting precipitate was collected by filtration, washed with water and dried under vacuum to give 1.91 g of the title compound.

$^1$H-NMR (CDCl$_2$) δ 7.68 (1H, m), 8.33 (1H, m), 8.43 (1H, m).

MS Calcd: 257. Found: 258 (M+H), 260.

2-(2,4-Dimethylphenoxy)-7-nitro-1,3-benzothiazole

A mixture of 2-bromo-7-nitro-1,3-benzothiazole (200 mg, 0.772 mmol), 2,4-dimethylphenol (0.093 ml, 0.772 mmol) and potassium carbonate (128 mg, 0.772 mmol) in DMF (10 ml) was stirred at 80° C. for 15 h. The mixture was diluted with water and extracted with ethyl acetate (AcOEt). The extract was washed with saturated NaHCO$_3$ solution and brine, dried over Magnesium sulfate and concentrated under vacuum. The residue was purified by chromatography eluting with 10% AcOEt in n-hexane to afford 226 mg of the title compound.

$^1$H-NMR (CDCl$_3$) δ 2.26 (3H, s), 2.38 (3H, s), 7.10-7.20 (3H, m), 7.55 (1H, t, J=8.0 Hz), 8.02 (1H, dd, J=0.8, 8.0 Hz), 8.24 (1H, dd, J=0.8, 8.0 Hz).

MS Calcd: 300. Found: 301 (M+H).

2-(2,4-Dimethylphenoxy)-1,3-benzothiazol-7-amine

A mixture of 2-(2,4-dimethylphenoxy)-7-nitro-1,3-benzothiazole (220 mg, 0.733 mmol) and tin(II) chloride dihydrate (694 mg, 3.66 mmol) in DMF (10 ml) was stirred at 80° C. for 15 h and diluted with saturated NaHCO$_3$ solution. The aqueous solution was extracted with AcOEt. The extract was washed with brine, dried over Magnesium sulfate, and concentrated under vacuum. The residue was purified by chromatography eluting with 10% AcOEt in n-hexane to afford 226 mg of the title compound.

$^1$H-NMR (CDCl$_3$) δ 2.26 (3H, s), 2.36 (3H, s), 3.70 (2H, s), 6.61 (1H, dd, J=1.6, 8.0 Hz), 7.08 (1H, d, J=8.0 Hz), 7.11 (1H, m), 7.17 (1H, t, J=8.0 Hz), 7.22 (1H, d, J=8.0 Hz), 7.24 (1H, d, J=1.6 Hz).

MS Calcd: 270. Found: 271 (M+H).

2-(2,4-Dimethylphenoxy)-N,N-dipropyl-1,3-benzothiazol-7-amine

To a solution of 2-(2,4-dimethylphenoxy)-1,3-benzothiazol-7-amine (54 mg, 0.200 mmol) in dichloromethane (DCM) (3 ml) was added propionaldehyde (0.058 ml, 0.799 mmol) followed after 30 min by sodium triacetoxyborohydride (169 mg, 0.799 mmol) and AcOH (0.023 ml). The mixture was stirred at room temperature for 15 h. The reaction was quenched with saturated NaHCO$_3$ solution. The aqueous solution was extracted with dichloromethane. The extract was washed with brine, dried over magnesium sulfate and concentrated under vacuum. The residue was purified by chromatography eluting with 2% AcOEt in n-hexane to afford 57 mg of the title compound.

$^1$H-NMR (CDCl$_3$) δ 0.85 (6H, t, J=7.2 Hz), 1.40-1.55 (4H, m), 2.62 (3H, s), 3.25 (3H, s), 3.08 (4H, t, J=7.2 Hz), 6.87 (1H, d, J=8.0 Hz), 7.06 (1H, d, J=8.0 Hz), 7.10 (1H, s), 7.16 (1H, d, J=8.0 Hz), 7.27 (1H, t, J=8.0 Hz), 7.37 (1H, d, J=8.0 Hz).

MS Calcd: 354. Found: 355 (M+H).

Examples 12-14

Example 12

2-[(2,4-Dimethylphenyl)thio]-N,N-dipropyl-1,3-benzothiazol-7-amine (A)

Example 13

2-[(2,4-Dimethylphenyl)sulfinyl]-N,N-dipropyl-1,3-benzothiazol-7-amine (B)

Example 14

2-[(2,4-Dimethylphenyl)sulfonyl]-N,N-dipropyl-1,3-benzothiazol-7-amine (C)

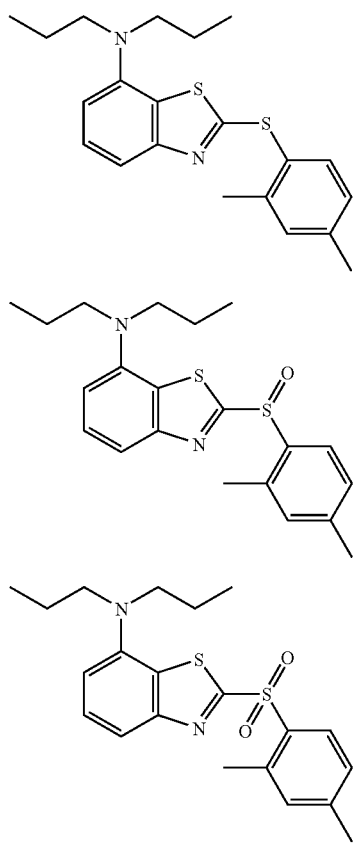

2-[(2,4-Dimethylphenyl)thio]-N,N-dipropyl-1,3-benzothiazol-7-amine (A)

Compound (A) was prepared in a manner similar to that described in example 11.

$^1$H-NMR (CDCl$_3$) δ 0.79 (6H, t, J=7.2 Hz), 1.35-1.50 (4H, m), 2.40 (3H, s), 2.48 (3H, s), 3.05 (4H, t, J=7.2 Hz), 6.82 (1H, d, J=8.0 Hz), 7.11 (1H, d, J=8.0 Hz), 7.21 (1H, s), 7.29 (1H, t, J=8.0 Hz), 7.48 (1H, d, J=8.0 Hz), 7.61 (1H, d, J=8.0 Hz).

MS Calcd: 370. Found: 371 (M+1).

2-[(2,4-Dimethylphenyl)sulfinyl]-N,N-dipropyl-1,3-benzothiazol-7-amine (B)

3-Chloroperoxybenzoic acid (MCPBA) (20 mg, 0.0810 mmol) was added to a solution of 2-[(2,4-dimethylphenyl)thio]-N,N-dipropyl-1,3-benzothiazol-7-amine (30 mg, 0.0810 mmol) in dichloromethane (2 ml). The mixture was stirred at room temperature for 18 h and diluted with saturated NaHCO$_3$. The organic layer was dried over magnesium sulfate and concentrated under vacuum. The residue was purified by chromatography eluting with 5% methanol in dichloromethane to afford 16 mg of the title compound.

$^1$H-NMR (CDCl$_3$) δ 0.81 (6H, t, J=7.2 Hz), 1.20-1.30 (2H, m), 1.85-2.00 (2H, m), 2.36 (3H, s), 2.49 (3H, s), 3.40-3.60 (4H, m), 6.98 (1H, d, J=8.0 Hz), 7.06 (1H, d, J=8.0 Hz), 7.16 (1H, s), 7.39 (1H, t, J=8.0 Hz), 7.60 (1H, d, J=8.0 Hz), 7.79 (1H, d, J=8.0 Hz).

MS Calcd: 386. Found: 387 (M+H).

2-[(2,4-Dimethylphenyl)sulfonyl]-N,N-dipropyl-1,3-benzothiazol-7-amine (C)

MCPBA (50 mg, 0.202 mmol) was added to a solution of 2-((2,4-dimethylphenyl)thio)-N,N-dipropyl-1,3-benzothiazol-7-amine (30 mg, 0.081 mmol) in dichloromethane (2 ml). The mixture was stirred at room temperature for 18 h and diluted with saturated NaHCO$_3$ solution. The organic layer was dried over magnesium sulfate and concentrated under vacuum. The residue was purified by chromatography eluting with 5% methanol in dichloromethane to afford 6.4 mg of the title compound.

$^1$H-NMR (CDCl$_3$) δ 0.83 (6H, t, J=7.6 Hz), 1.10-1.20 (2H, m), 1.95-2.05 (2H, m), 2.38 (3H, s), 2.70 (3H, s), 3.45-3.70 (4H, m), 7.11 (1H, s), 7.22 (1H, d, J=8.0 Hz), 7.27 (1H, d, J=8.0 Hz), 7.58 (1H, t, J=8.0 Hz), 8.12 (1H, d, J=8.0 Hz), 8.16 (1H, d, J=8.0 Hz).

MS Calcd: 402. Found: 403 (M+H).

Example 15

N$^2$-Mesityl-4-methyl-N$^7$,N$^7$-dipropyl-1,3-benzothiazole-2,7-diamine

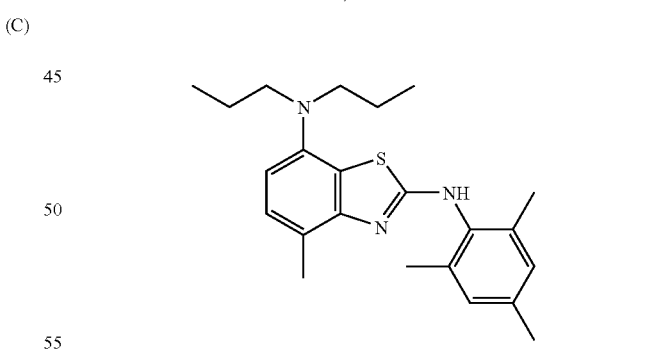

4-Methyl-3-nitro)-N,N-dipropylaniline

To a solution of 4-methyl-3-nitroaniline (2.00 g, 13.1 mmol) in dichloromethane (100 ml) was added propionaldehyde (3.79 ml, 52.6 mmol) followed after 30 min by sodium triacetoxyborohydride (11.1 g, 52.6 mmol) and AcOH (0.75 ml). The mixture was stirred at room temperature for 15 h. The reaction was quenched with saturated NaHCO$_3$ solution. The aqueous solution was extracted with dichloromethane. The extract was washed with brine, dried over magnesium sulfate and concentrated under vacuum. The residue was purified by chromatography eluting with 2% AcOEt in n-hexane to afford 2.50 g of the title compound.

$^1$H-NMR (CDCl$_3$) δ 0.93 (6H, t, J=7.6 Hz), 1.50-1.65 (4H, m), 2.44 (3H, s), 3.24 (4H, t, J=7.6 Hz), 6.74 (1H, dd, J=2.8, 8.8 Hz), 7.09 (1H, d, J=8.8 Hz), 7.18 (1H, d, J=2.8 Hz).

MS Calcd: 236. Found: 237 (M+H).

4-Methyl-N$^1$,N$^1$-dipropyl-benzene-1,3-diamine

A mixture of 4-methyl-3-nitro-N,N-dipropylaniline (2.49 g, 10.5 mmol) and 10% Pd on carbon (1.00 g) in AcOEt (50 ml) was hydrogenated for 18 h. The catalyst was removed by filtration through Celite. The filtrate was concentrated under vacuum. The residue was purified by chromatography eluting with 10% AcOEt in n-hexane to afford 689 mg of the title compound.

$^1$H-NMR (CDCl$_3$) δ 0.85-0.95 (6H, m), 1.45-1.60 (4H, m), 2.07 (3H, s), 3.16 (4H, t, J=7.6 Hz), 3.50 (2H, m), 6.01 (1H, d, J=2.8 Hz), 6.07 (1H, dd, J=28, 8.0 Hz), 6.85 (1H, d, J=8.0 Hz).

MS Calcd: 206. Found: 207 (M+H).

1-(5-Dipropylamino-2-methylphenyl)-3-mesityl thiourea

A mixture of 4-Methyl-N$^1$,N$^1$-dipropyl-benzene-1,3-diamine (200 mg, 0.970 mmol) and 2,4,6-trimethylphenyl-isothiocyanate (215 mg, 1.21 mmol) in methanol (2 ml) was refluxed for 18 h. The solvent was evaporated under vacuum. The residue was triturated with methanol. The solid was collected by filtration and washed with methanol to afford 261 mg of the title compound.

$^1$H-NMR (CDCl$_3$) δ 0.92 (6H, t, J=7.2 Hz), 1.56 (6H, s), 1.50-1.65 (4H, m), 2.22 (3H, s), 2.26, 2.27 (3H, s), 2.30-2.40 (4H, m), 6.57, 6.60 (1H, s), 6.80-6.90 (2H, m), 7.15, 7.26 (1H, s), 7.52 (1H, s).

MS Calcd: 383. Found: 384 (M+H).

N$^2$-Mesityl-4-methyl-N$^7$,N$^7$-dipropyl-1,3-benzothiazole-2,7-diamine

To a mixture of 1-(5-dipropylamino-2-methylphenyl)-3-mesitylthiourea (100 mg, 0.261 mmol) in carbon tetrachloride (10 ml) was added dropwise bromine (0.015 ml, 0.287 mmol) in carbon tetrachloride (5 ml) over 30 min. The mixture was refluxed for 18 h and diluted with water. The aqueous solution was extracted with dichloromethane. The extract was washed with water and brine and concentrated under vacuum. The residue was purified by chromatography eluting with 10% AcOEt in n-hexane to afford 39 mg of the title compound.

$^1$H-NMR (CDCl$_3$) δ 0.76-0.82 (6H, m), 1.25-1.45 (4H, m), 1.58 (3H, s), 2.29 (3H, s), 2.30 (3H, s), 2.52 (3H, s), 2.90-2.99 (4H, m), 6.71 (1H, d, J=8.0 Hz), 6.95 (1H, m), 6.98 (2H, s), 7.04 (1H, d, J=8.0 Hz).

MS Calcd: 381. Found: 382 (M+H).

Example 16

N$^2$-(2,4-Dimethylphenyl)-4-methyl-N$^7$,N$^7$-dipropyl-1,3-benzothiazole-2,7-diamine

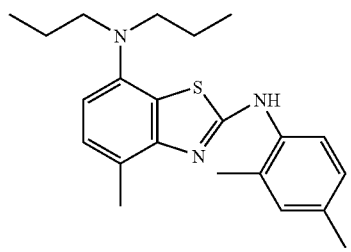

The compound of example 16 was prepared in a manner similar to that described in example 15.

MS Calcd: 367. Found: 368 (M+H).

Examples 17 and 18

Example 17

N$^2$-Mesityl-6-methyl-N$^7$,N$^7$-dipropyl-1,3-benzothiazole-2,7-diamine, and

Example 18

4-Ethoxy-N$^2$-mesityl-6-methyl-N$^7$,N$^7$-dipropyl-1,3-benzothiazole-2,7-diamine

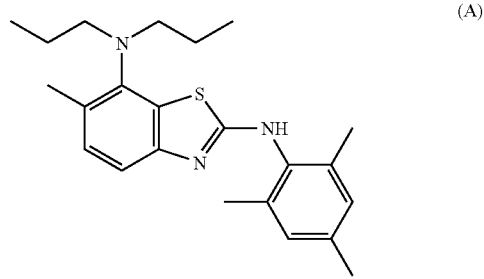

(A)

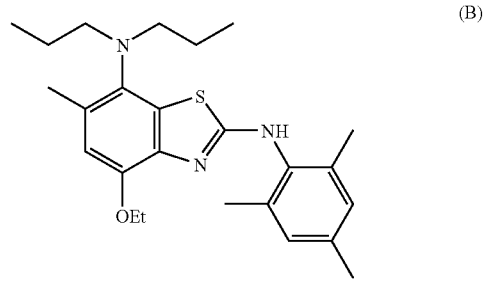

(B)

4-Isothiocyanato-1-methyl-2-nitrobenzene

To a mixture of 4-methyl-3-nitroaniline (1.00 g, 6.57 mmol) and triethylamine (2.75 ml, 19.7 mmol) in THF (150 ml) was added dropwise thiophosgene (0.55 ml) at 0° C. After addition, the reaction mixture was allowed to stir at room temperature for 15 h. The mixture was diluted with water and extracted with ether. The extract was washed with water and brine, dried over magnesium sulfate, and concentrated under vacuum to afford 1.04 g of the title compound.

$^1$H-NMR (CDCl$_3$) δ 2.60 (3H, s), 7.30-7.40 (2H, m), 7.83 (1H, m).

1-Mesityl-3-(4-methyl-3-nitrophenyl)thiourea

A mixture of 4-isothiocyanato-1-methyl-2-nitrobenzene (500 mg, 2.58 mmol) and 2,4,6-trimethylaniline (0.329 ml, 2.34 mmol) in methanol (10 ml) was refluxed for 4 h. The solvent was evaporated under vacuum. The residue was triturated with ether. The resulting solid was collected by filtration to afford 550 mg of the title compound.

$^1$H-NMR (CDCl$_3$) δ 2.31 (6H, s), 2.33 (3H, s), 2.58 (3H, s), 7.05 (1H, s), 7.30 (1H, d, J=8.0 Hz), 7.52 (1H, s), 7.79 (1H, d, J=8.0 Hz), 7.93 (1H, s).

MS Calcd: 329. Found: 330 (M+H).

N-Mesityl-6-methyl-7-nitro-1,3-benzothiazol-2-amine

To a mixture of 1-mesityl-3-(4-methyl-3-nitrophenyl)thiourea (500 mg, 1.52 mmol) in carbon tetrachloride (25 ml) was added dropwise bromine (0.097 ml, 1.90 mmol) in carbon tetrachloride (10 ml) over 1 h. The mixture was refluxed for 18 h and diluted with water. The aqueous solution was extracted with dichloromethane. The extract was washed with water and brine and concentrated under vacuum. The residue was triturated with ether. The resulting solid was collected by filtration to afford 225 mg of the title compound.

$^1$H-NMR (CDCl$_3$) δ 2.30 (6H, s), 2.35 (3H, s), 2.75 (3H, s), 7.01 (2H, s), 7.17 (1H, bs), 7.28 (1H, d, J=8.0 Hz), 7.62 (1H, d, J=8.0 Hz).

MS Calcd: 327. Found: 328 (M+H).

N$^2$-Mesityl-6-methyl-N$^7$,N$^7$-dipropyl-1,3-benzothiazole-2,7-diamine (A) and 4-Ethoxy-N$^2$-mesityl-6-methyl-N$^7$,N$^7$-dipropyl-1,3-benzothiazole-2,7-diamine (B)

To a solution of N-mesityl-6-methyl-7-nitro-1,3-benzothiazol-2-amine (210 mg, 0.641 mmol) in ethanol was added tin(II) chloride dihydrate (608 mg, 3.21 mmol). The mixture was refluxed for 15 h. The solvent was evaporated under vacuum. The residue was diluted with saturated NaHCO$_3$ solution. The aqueous solution was extracted with AcOEt. The extract was washed with brine dried over magnesium sulfate and concentrated under vacuum. The residue was dissolved in dichloromethane (10 ml). To this solution was added propionaldehyde (0.087 ml, 1.21 mmol) followed after 30 min by sodium triacetoxyborohydride (257 mg, 1.21 mmol) and AcOH (0.035 ml). The mixture was stirred at room temperature for 18 h. The reaction was quenched with saturated NaHCO$_3$ solution. The aqueous solution was extracted with dichloromethane. The extract was washed with brine, dried over magnesium sulfate and concentrated under vacuum. The residue was purified by chromatography eluting with 10% AcOEt in n-hexane to afford 7.1 mg of compound (A) and 11.9 mg of compound (B).

Compound (A):
$^1$H-NMR (CDCl$_3$) δ 0.75-0.85 (6H, m), 1.25-1.40 (4H, m), 2.31 (6H, s), 2.33 (3H, s), 2.34 (3H, s), 2.90 (4H, t, J=7.6 Hz), 6.99 (2H, s), 7.06 (1H, d, J=8.0 Hz), 7.15 (1H, d, J=8.0 Hz), 7.50 (1H, m).

MS Calcd: 381. Found: 382 (M+H).

Compound (B):
$^1$H-NMR (CDCl$_3$) δ 0.75-0.85 (6H, m), 1.25-1.35 (4H, m), 1.53 (3H, t, J=7.2 Hz), 2.29 (6H, s), 2.33 (6H, s), 2.84 (4H, t, J=7.6 Hz), 4.18 (2H, q, J=7.2 Hz), 6.60 (1H, s), 6.75 (1H, m), 6.98 (2H, s).

MS Calcd: 425. Found: 426 (M+H).

Example 19

N$^2$-Mesityl-5-methyl-N$^7$,N$^7$-dipropyl-1,3-benzothiazole-2,7-diamine

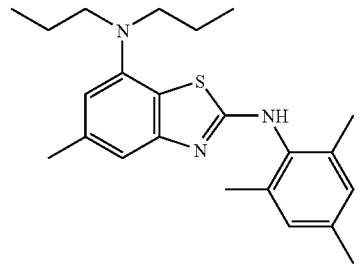

Methyl 2-mesitylamino-7-nitro-1,3-benzothiazole-5-carboxylate (A) and Methyl 2-mesitylamino-5-nitro-1,3-benzothiazole-7-carboxylate (B)

To a mixture of methyl 3-[[mesitylamino)carbonothioyl]amino]-5-nitrobenzoate (1.65 g, 4.42 mmol), which was prepared in a manner similar to that described in example 17, in carbon tetrachloride (50 ml) was added dropwise bromine (0.283 ml, 1.25 mmol) in carbon tetrachloride (20 ml) over 1 h. The mixture was refluxed for 18 h and diluted with water. The aqueous solution was extracted with dichloromethane. The extract was washed with water and brine and concentrated under vacuum. The residue was purified by chromatography eluting with 20% AcOEt in n-hexane to afford 707 mg of compound (A) and 450 mg of compound (B).

Compound (A):
$^1$H-NMR (CDCl$_3$) δ 2.30 (6H, s), 2.36 (3H, s), 3.99 (3H, s), 7.04 (2H, s), 8.41 (1H, d, J=1.6 Hz), 8.70 (1H, d, J=1.6 Hz).

MS Calcd: 371. Found: 372 (M+H).

Compound (B):
$^1$H-NMR (CDCl$_3$) δ 2.29 (6H, s), 2.35 (3H, s), 3.98 (3H, s), 7.01 (2H, s), 8.46 (1H, d, J=2.2 Hz), 8.62 (1H, d, J=2.2 Hz).

MS Calcd: 371. Found: 372 (M+H).

(2-Mesitylamino-7-nitro-1,3-benzothiazol-5-yl)methanol

To a solution of methyl 2-mesitylamino-7-nitro-1,3-benzothiazole-5-carboxylate (350 mg, 0.942 mmol) in ethyl ether (6 ml) was added 2.0 M solution of lithium borohydride in tetrahydrofuran (THF) (1.41 ml, 2.82 mmol). The mixture was stirred at room temperature for 15 h. The reaction was quenched with saturated NH$_4$Cl solution. The aqueous phase was extracted with ethyl ether. The extract was washed with brine, dried over magnesium sulfate, and concentrated under vacuum. The residue was purified by chromatography eluting with 20% AcOEt in n-hexane to afford 189 mg of the title compound.

$^1$H-NMR (CDCl$_3$) δ 2.28 (6H, s), 2.38 (3H, s), 4.94 (2H, s), 7.06 (2H, s), 8.25-8.35 (3H, m).

MS Calcd: 343. Found: 344 (M+H).

5-Chloromethyl-N-mesityl-7-nitro-1,3-benzothiazol-2-amine

Thionyl chloride (0.191 ml, 2.62 mmol) was added to a solution of (2-mesitylamino-7-nitro-1,3-benzothiazol-5-yl)methanol (180 mg, 0.524 mmol) in chloroform. The mixture was stirred at room temperature for 18 h and at 60° C. for 24h. The mixture was poured into water and neutralized with saturated NaHCO$_3$ solution. The aqueous solution was extracted with AcOEt. The extract was washed with brine, dried over magnesium sulfate and concentrated under vacuum. The residue was purified by chromatography eluting with 20% AcOEt in n-hexane to afford 122 mg of the title compound.
$^1$H-NMR (CDCl$_3$) δ 2.29 (6H, s), 2.36 (3H, s), 4.67 (2H, s), 7.03 (2H, s), 7.80 (1H, d, J=1.6 Hz), 8.08 (1H, d, J=1.6 Hz).
MS Calcd: 361. Found: 362 (M+H), 364.

N-Mesityl-5-methyl-7-nitro-1,3-benzothiazol-2-amine

To a solution of 5-chloromethyl-N-mesityl-7-nitro-1,3-benzothiazol-2-amine (120 mg, 0.332 mmol) in dimethyl sulfoxide (DMSO) (2 ml) was added sodium borohydride (25 mg, 0.663 mmol). The mixture was stirred at room temperature for 3 h and diluted with water and neutralized with 1N HCl solution. The aqueous solution was extracted with AcOEt.
The extract was washed with brine, dried over magnesium sulfate and concentrated under vacuum. The residue was purified by chromatography eluting with 2% AcOEt in n-hexane to afford 45 mg of the title compound.
$^1$H-NMR (CDCl$_3$) δ 2.28 (6H, s), 2.37 (3H, s), 2.60 (3H, s), 7.05 (2H, s), 8.01 (1H, s), 8.16 (1H, s), 8.28 (1H, s).
MS Calcd: 327. Found: 328 (M+H).

N$^2$-Mesityl-5-methyl-1,3-benzothiazole-2,7-diamine

A mixture of N-mesityl-5-methyl-7-nitro-1,3-benzothiazol-2-amine (45 mg, 0.137 mmol) and tin(II) chloride dihydrate (124 mg, 0.550 mmol) in DMF (2 ml) was heated at 80° C. for 1 h. The mixture was poured into ice and the pH was made slightly basic (pH 7-8) by addition of 1N NaOH solution. The aqueous solution was extracted with AcOEt. The extract was washed with brine, dried over magnesium sulfate and concentrated under vacuum. The residue was purified by chromatography eluting with 20% AcOEt in n-hexane to afford 10 mg of the title compound.
MS Calcd: 297. Found: 298 (M+H).

N$^2$-Mesityl-5-methyl-N$^7$,N$^7$-dipropyl-1,3-benzothiazole-2,7-diamine

To a solution of N$^2$-mesityl-5-methyl-1,3-benzothiazole-2,7-diamine (10 mg, 0.0336) in dichloromethane (1 ml) was added propionaldehyde (0.012 ml, 0.168 mmol) followed after 30 min by sodium triacetoxyborohydride (29 mg, 0.135 mmol) and AcOH (0.0039 ml). The mixture was stirred at room temperature for 18 h. The reaction was quenched with saturated NaHCO$_3$ solution. The aqueous solution was extracted with dichloromethane. The extract was washed with brine, dried over magnesium sulfate and concentrated under vacuum. The residue was triturated with n-hexane. The resulting solid was collected by filtration to afford 6.8 mg of the title compound.
$^1$H-NMR (CDCl$_3$) δ 0.80-1.00 (6H, m), 1.35-1.45 (4H, m), 2.29 (6H, s), 2.33 (3H, s), 2.37 (3H, s), 2.95-3.05 (4H, m), 6.55 (1H, s), 6.98 (2H, s), 7.02 (1H, s).
MS Calcd: 381. Found: 382 (M+H).

Example 20

2-(Mesitylamino)-5-nitro-N,N-dipropyl-1,3-benzothiazole-7-carboxamide

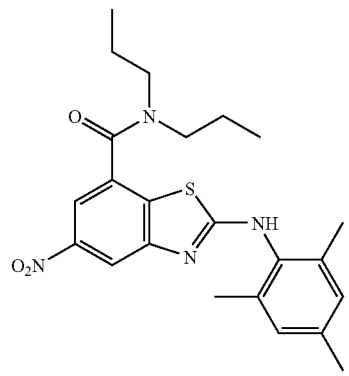

2-Mesitylamino-5-nitro-1,3-benzothiazole-7-carboxylic acid

To a mixture of methyl 2-mesitylamino-5-nitro-1,3-benzothiazole-7-carboxylate (230 mg, 0.619 mmol) (prepared in example 19) in methanol (5 ml) and THF (5 ml) was added 1 N NaOH solution (2.48 ml, 2.48 mmol). The mixture was stirred at 50° C. for 3 h. The solvent was evaporated under vacuum and the aqueous residue was neutralized with 1N HCl solution. The resulting precipitate was collected by filtration and dried under vacuum to afford 177 mg of the title compound.
$^1$H-NMR (DMSO-d$_6$) δ 2.15 (6H, s), 2.26 (3H, s), 7.01 (2H, s), 8.31 (2H, m), 10.00 (1H, m).

To a solution of 2-mesitylamino-5-nitro-1,3-benzothiazole-7-carboxylic acid (90 mg, 0.252 mmol) in DMF (2 ml) were added diethyl cyanophosphonate (0.042 ml, 0.277 mmol), dipropylamine (0.039 ml, 0.277 mmol) and triethylamine (0.74 ml, 0.277 mmol). The mixture was stirred at room temperature for 18 h and diluted with water. The aqueous solution was extracted with ether. The extract was washed with brine, dried over MgSO$_4$ and concentrated under vacuum. The residue was purified by chromatography eluting with 20% AcOEt in n-hexane to afford 70 mg of the title compound.
$^1$H-NMR (CDCl$_3$) δ 0.85-1.00 (6H, m), 1.60-1.65 (4H, m), 2.27 (6H, s), 2.33 (3H, s), 3.36 (4H, m), 6.99 (2H, s), 7.12 (1H, m), 7.96 (1H, d, J=1.6 Hz), 8.35 (1H, d, J=1.6 Hz).
MS Calcd: 440. Found: 441 (M+H).

Example 21

5-Amino-2-(mesitylamino)-N,N-dipropyl-1,3-benzothiazole-7-carboxamide

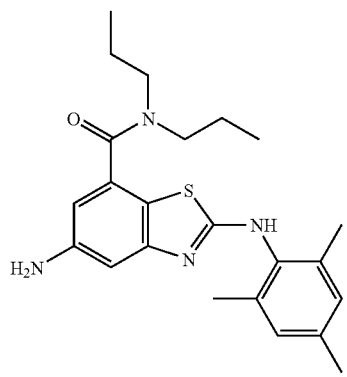

A mixture of 2-(mesitylamino)-5-nitro-N,N-dipropyl-1,3-benzothiazole-7-carboxamide (61 mg, 0.139 mmol) and 10% Pd on carbon (30 mg) in ethanol (10 ml) was hydrogenated for 4 h. The catalyst was removed by filtration through Celite. The filtrate was concentrated under vacuum. The residue was purified by chromatography eluting with 20% AcOEt in n-hexane to afford 40 mg of the title compound.

$^1$H-NMR (CDCl$_3$) δ 0.80-0.90 (6H, m), 1.59 (4H, m), 2.26 (6H, s), 2.31 (3H, s), 3.30 (4H, m), 3.71 (2H, m), 6.45 (1H, d, J=2.0 Hz), 6.88 (1H, d, J=2.0 Hz), 6.95 (2H, s).

MS Calcd: 410. Found: 411 (M+H).

Example 22

5-(Acetylamino)-2-(mesitylamino)-N,N-dipropyl-1,3-benzothiazole-7-carboxamide (A), and

Example 23

5-(Acetylamino)-2-[acetyl(mesityl)amino]-N,N-dipropyl-1,3-benzothiazole-7-carboxamide (B)

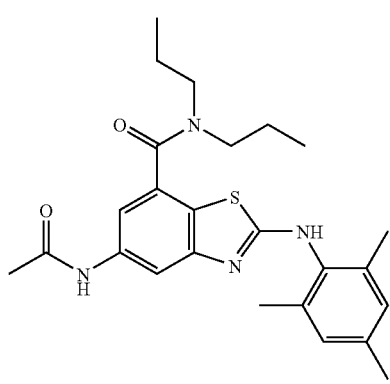

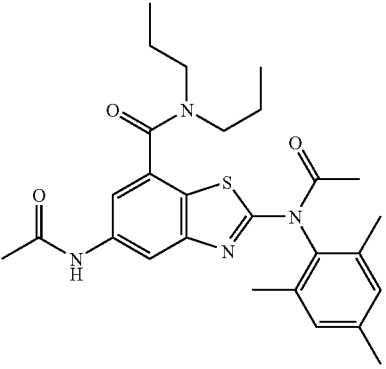

Acetyl chloride (0.0029 ml, 0.0402 mmol) was added to a mixture of 5-amino-2-(mesitylamino)-N,N-dipropyl-1,3-benzothiazole-7-carboxamide (15 mg, 0.0365 mmol) and triethylamine (0.0056 ml, 0.0402 mmol) in THF (1 ml). The mixture was stirred at room temperature for 3 h and diluted with H$_2$O. The aqueous solution was extracted with ether. The extract was washed with brine, dried over magnesium sulfate and concentrated under vacuum. The residue was purified by chromatography eluting with 20% AcOEt in n-hexane to afford 5.8 mg of compound (A) and 5.1 mg of compound (B).

Compound (A):
$^1$H-NMR (CDCl$_3$) δ 0.80-0.95 (6H, m), 1.50-1.80 (4H, m), 2.19 (3H, s), 2.25 (6H, s), 2.30 (3H, s), 3.34 (4H, m), 6.93 (2H, s), 7.51 (2H, s), 7.70 (1H, m).
MS Calcd: 452. Found: 453 (M+H).

Compound (B):
$^1$H-NMR (CDCl$_3$) δ 0.70-1.10 (6H, m), 1.50-1.80 (4H, m), 2.05 (3H, s), 2.07 (6H, s), 2.11 (3H, s), 2.38 (3H, s), 3.20-3.55 (4H, m), 7.04 (2H, s), 7.80 (1H, s), 7.97 (1H, s).
MS Calcd: 494. Found: 495 (M+H).

Example 24

7-((Dipropylamino)methyl)-N-mesityl-1,3-benzothiazol-2-amine

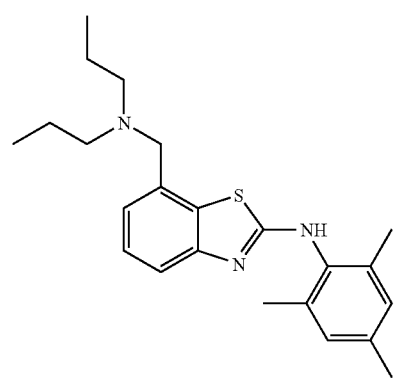

3-(tert-Butyldimethylsilyloxymethyl)aniline

To 1.00 g (8.1 mmol) of 3-hydroxymethylaniline in 25 mL of DMF was added 0.61 g (8.9 mmol) of imidazole and 1.35 g (8.9 mmol) of tert-butyldimethylsilyl chloride. The reaction was stirred at room temperature for 18 h and poured into 12 volumes of water. The product was extracted with ether and the combined organic layers were washed successively with water and brine, dried over sodium sulfate, filtered and concentrated to a golden oil. The oil was purified by flash chromatography eluting with a 20% ethyl acetate/hexanes mixture to give 1.2 g (62%) of the title compound as a colorless oil.

$^1$H NMR (CDCl$_3$) δ 0.00 (s, 6H), 0.84 (s, 9H), 4.48 (s, 2H), 4.93 (s, 2H), 6.36 (d, J=7.6 Hz, 2H), 6.45 (s, 1H), 6.89 (t, J=7.6 Hz, 1H).

1-[3-(tert-Butyldimethylsilyloxymethyl)phenyl]-3-mesitylthiourea

To 0.45 g (1.9 mmol) of 3-(tert-butyldimethylsilyloxymethyl)aniline in 3 mL of methanol was added 0.67 g (3.8 mmol) of mesitylisothiocyanate. The mixture was heated at reflux for 18 h. The mixture was concentrated and purified by flash chromatography eluting with a 16% ethyl acetate/hexanes mixture to give 0.56 (71%) of the title compound as a sticky white solid.

MS Calcd.: 414. Found: 415 (M+H).

1-(3-Hydroxymethylphenyl)-3-mesitylthiourea

To 0.56 g (0.1.4 mmol) of 1-[3-(tert-butyldimethylsilyloxymethyl)phenyl]-3-mesitylthiourea in 10 mL of ethanol was added 10 drops of concentrated hydrochloric acid. After 30 min, the reaction was diluted with water and the precipitate that formed was collected to give 0.35 g (86%) of the title compound as a white powder.

MS Calcd.: 300. Found: 301 (M+H).

7-(Hydroxymethyl)-N-mesityl-1,3-benzothiazol-2-amine

To 0.25 g (0.83 mmol) of 1-(3-hydroxymethylphenyl)-3-mesitylthiourea in 5 mL of glacial acetic acid was added 47 μL (0.91 mmol) of bromine. The reaction was stirred for 5 min and concentrated in vacuo to give the title compound and its regioisomer as their O-acetates. The mixture was stirred in methanol over potassium carbonate for 1 h. The mixture was concentrated in vacuo, slurried in dichloromethane and filtered. The filtrate was concentrated and purified by flash chromatography eluting with a 33-66% ethyl acetate/hexanes gradient mixture to give 0.070 g (28%) of the title compound as a white solid.

MS Calcd.: 298. Found: 299 (M+H).

7-(Bromomethyl)-N-mesityl-1,3-benzothiazol-2-amine

To 0.065 g (0.22 mmol) of 7-(hydroxymethyl)-N-mesityl-1,3-benzothiazol-2-amine in 2 mL of dichloromethane was added 58 μL (0.72 mmol) of pyridine and 0.24 mL (0.24 mmol) of phosphorous tribromide (1 M in dichloromethane). The reaction was stirred at room temperature for 8 h and quenched with saturated sodium bicarbonate. The organic layer was washed with brine, dried over sodium sulfate, filtered and concentrated to give 0.045 g (57%) of the title compound that was used without further purification.

MS Calcd.: 313. Found: 314 (M+H).

7-((Dipropylamino)methyl)-N-mesityl-1,3-benzothiazol-2-amine

To 0.045 g (0.12 mmol) of 7-(bromomethyl)-N-mesityl-1,3-benzothiazol-2-amine in 0.5 mL of acetonitrile and 2 mL of dichloromethane was added 0.086 g (0.62 mmol) of potassium carbonate and 85 μl, (0.62 mmol) of dipropylamine. The reaction was stirred for 40 min, diluted with dichloromethane and filtered. The filtrate was concentrated and purified by flash chromatography eluting with a 25% ethyl acetate/hexanes mixture to give 0.027 g (57%) of the title compound as a light yellow powder.

$^1$H NMR (CDCl$_3$) δ 0.76 (t, J=7.4 Hz, 6H), 1.40 (q, J=7.4 Hz, 4H), 2.30-2.34 (m, 13H), 3.58 (s, 2H), 6.95-7.01 (m, 3H), 7.18 (t, J=7.8 Hz, 1H), 7.23-7.33 (m, 1H), 8.12 (br s, 1H).

MS Calcd.: 381. Found: 382 (M+H).

Example 25

$N^2$-Mesityl-$N^7$,$N^7$-dipropyl-1,3-benzoxazole-2,7-diamine

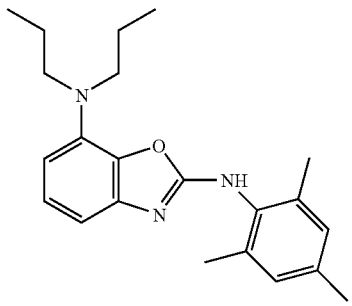

2-Amino-6-nitrophenol

A suspension of 2,6-dinitrophenol 5.0 g (27 mmol), ammonium hydroxide (3 ml) and ammonium chloride 14.3 g (270 mmol) in 30 ml of water was heated to 70° C. A solution of sodium sulfide nonahydrate (24.19 g, 100 mmol) in water was added and the resulting mixture stirred at 70° C. for 2 h. The reaction was cooled to room temperature, acidified (pH 3.2) with 2N HCl, and the brown precipitate separated by filtration. The filtrate was extracted with chloroform (6×75 ml), the organic extracts combined with the precipitate, and evaporated in-vacuo to yield 2.5 g (60%) of product as a dark brown solid.

$^1$H NMR (CDCl$_3$) δ 4.09 (s, 2H), 6.78 (t, 1H, J=8.2 Hz), 6.95 (d, 1H, J=7.8 Hz), 7.47 (d, 1H, J=8.6 Hz), 10.73 (s, 3H).

1-(2-Hydroxy-3-nitrophenyl)-3-mesitylthiourea

To a mixture containing 0.10 g (0.65 mmol) of 2-amino-6-nitrophenol and 0.14 g (1.3 mmol) of sodium carbonate in ethanol was added 0.14 g (0.78 mmol) of 2-isothiocyanato-1,3,5-trimethylbenzene. The reaction was heated at reflux overnight. The reaction was cooled to room temperature, filtered and concentrated under reduced pressure. Purification of the residue via Biotage chromatography eluting with 20% ethyl acetate/dichloromethane gave 0.17 g (80%) of product.

MS Calcd.: 331. Found: 332 (M+H).

N-Mesityl-7-nitro-1,3-benzoxazol-2-amine

To a solution containing 0.06 g (0.18 mmol) of 1-(2-hydroxy-3-nitrophenyl)-3-mesitylthiourea in acetonitrile was added 0.10 g (0.36 mmol) of mercury (II) chloride, and the mixture was then stirred for 1 h. The reaction mixture was diluted with ethyl acetate (2 ml) and filtered through a prepacked celite column. The filtrate was concentrated under reduced pressure and the residue was purified via Biotage chromatography eluting with 20% ethyl acetate/dichloromethane to afford 0.047 g (90%) of product.

$^1$H NMR (CDCl$_3$) δ 2.29 (s, 6H), 2.32 (s, 3H), 6.99 (s, 2H), 7.30 (t, 1H, J=8.2 Hz), 7.77 (d, 1H, J=8.1 Hz), 7.78 (d, 1H, J=8.6 Hz).

MS Calcd.: 297. Found: 298 (M+H).

N$^2$-Mesityl-N$^7$,N$^7$-dipropyl-1,3-benzoxazole-2,7-diamine

To a flask was added 0.10 g (0.34 mmol) of N-mesityl-7-nitro-1,3-benzoxazol-2-amine and 40 ml of methanol. The flask was purged with nitrogen followed by the addition of 0.01 g of 10% palladium on carbon. The flask was evacuated and pressurized to 2-3 psig hydrogen and stirred for 1 h. After completion as determined by HPLC, the reaction was filtered through GF/F filter paper. The filtrate was transferred to round bottom flask and 0.1 ml (1.7 mmol) of propionaldehyde, 0.1 g (1.7 mmol) of NaBH$_3$CN and 1 ml of acetic acid were added. The mixture was stirred overnight, then diluted with ethyl acetate and washed with water. The organic phase was dried over magnesium sulfate. Filtration, removal of solvent and purification of the residue via Biotage chromatography eluting with 5% methanol/dichloromethane gave 0.11 g (90% for 2 steps) of product.

$^1$H NMR (CDCl$_3$) δ 0.74 (t, 6H, J=7.2 Hz), 1.47-1.53 (m, 4H), 2.27 (s, 6H), 2.29 (s, 3H), 3.18 (t, 4H, J=7.8 Hz), 6.34 (d, 1H, J=8.1 Hz), 6.70 (d, 1H, J=7.0 Hz), 6.93 (s, 2H), 6.98 (t, 1H, J=8.1 Hz).

MS Calcd.: 351. Found: 352 (M+H).

Example 26

N$^2$-Mesityl-1-methyl-N$^7$,N$^7$-dipropyl-1H-benzimidazole-2,7-diamine

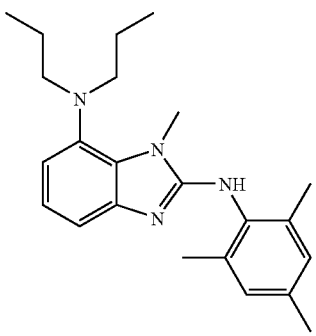

N-Methyl-2,6-dinitroaniline

Methylamine (4.5 ml of 2.0 M solution in THF) was added to a stirred solution of 2-chloro-1,3-dinitrobenzene (0.90 g, 4.4 mmol) in 40 ml of THF and the mixture was stirred for 30 min. The reaction was quenched by the addition of water and ether. The aqueous layer was separated and extracted twice with ether. The combined organic extracts were washed with saturated NaHCO$_3$, brine and dried over magnesium sulfate. Filtration, removal of solvent and purification of residue via Biotage chromatography eluting with 20% ethyl acetate/dichloromethane to gave 0.80 g (91%) of product.

$^1$H NMR (CDCl$_3$) δ 2.89 (d, 3H, J=5.6 Hz), 6.75 (t, 1H, J=8.1 Hz), 8.18 (d, 2H, J=8.3 Hz).

N$^2$-Methylbenzene-1,2,3-triamine

To a flask was added 0.30 g (1.5 mmol) of N-methyl-2,6-dinitroaniline and 40 ml of methanol. The flask was purged with nitrogen followed by the addition of 0.03 g of 10% palladium on carbon. The flask was evacuated and pressurized to 2-3 psig hydrogen and stirred for 1 h. After completion as determined by HPLC, the reaction was filtered through GF/F filter paper. The filtrate was evaporated to give 0.2 g (95%) of product.

MS Calcd.: 137. Found: 138 (M+H).

1-(3-Amino-2-methylaminophenyl) 3-mesitylthiourea

To a mixture containing 0.25 g (1.82 mmol) of N$^2$-methylbenzene-1,2,3-triamine and 0.40 g (3.7 mmol) of sodium carbonate in ethanol was added 0.32 g (1.86 mmol) of 2-isothiocyanato-1,3,5-trimethylbenzene. The reaction was heated at reflux and the solvent was removed under reduced pressure. Purification of the residue via Biotage chromatography eluting with 20% ethyl acetate/dichloromethane gave 0.34 g (60%) of product.

$^1$H NMR (CDCl$_3$) δ 2.19 (s, 6H), 2.26 (s, 3H), 3.68 (s, 3H), 3.85 (s, 4H), 6.20 (d, 2H, J=8.1 Hz), 6.87 (s, 2H), 6.95 (t, 1H, J=8.1 Hz), 7.07 (s, 1H).

MS Calcd.: 314. Found: 315 (M+H).

N$^2$-Mesityl-1-methyl-1H-benzimidazole-2,7-diamine

To a solution containing 0.25 g (0.79 mmol) of 1-(3-amino-2-methylaminophenyl)-3-mesitylthiourea in acetonitrile was added 0.52 g (1.6 mmol) of mercury (II) chloride, and the mixture stirred for 1 h. The reaction mixture was diluted with ethyl acetate (2 ml) and filtered through a prepacked celite column. The filtrate was concentrated under reduced pressure and the residue purified via Biotage chromatography eluting with 20% ethyl acetate/dichloromethane to afford 0.12 g (55%) of product.

$^1$H NMR (CD$_3$OD) δ 2.27 (s, 6H), 2.36 (s, 3H), 4.13 (s, 3H), 7.13 (s, 2H), 7.24-7.26 (m, 2H), 7.33 (t, 1H, J=8.1 Hz).

MS Calcd.: 280. Found: 281 (M+H).

N$^2$-Mesityl-1-methyl-N$^7$,N$^7$-dipropyl-1H-benzimidazole-2,7-diamine

To a solution containing 0.05 g (0.18 mmol) of N$^2$-mesityl-1-methyl-1H-benzimidazole-2,7-diamine in methanol (5 ml) was added 0.03 ml (0.54 mmol) of propionaldehyde, 0.03 g (0.54 mmol) of NaBH$_3$CN and 0.1 ml of acetic acid. The mixture was stirred overnight then diluted with ethyl acetate and washed with water. The organic phase was dried over magnesium sulfate. Filtration, removal of solvent and purification of the residue via Biotage chromatography eluting with 5% methanol/dichloromethane gave 0.04 g (70%) of product.

$^1$H NMR (CDCl$_3$) δ 0.85 (t, 6H, J=7.3 Hz), 1.46-1.53 (m, 4H), 2.22 (s, 6H), 2.28 (s, 3H), 2.98 (s, 4H), 3.94 (s, 3H), 6.86 (d, 1H, J=7.8 Hz), 6.92 (s, 2H), 6.99 (t, 1H, J=8.1 Hz), 7.20 (s, 1H).

MS Calcd.: 364. Found: 365 (M+H).

Compounds of Examples 27-30, shown in Table 2, were prepared in a manner similar to that described in Example 26.

TABLE 2

| Example | Structure | Name | Physical Data |
| --- | --- | --- | --- |
| 27 | 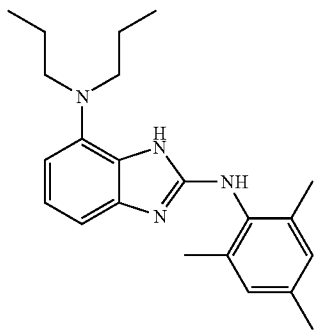 | $N^2$-Mesityl-$N^7$, $N^4$-dipropyl-1H-benzimidazole-2,7-diamine | MS Calcd.: 350; Found: 351 (M + H). |
| 28 | 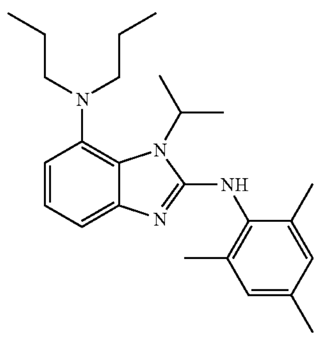 | 1-Isopropyl-$N^2$-mesityl-$N^7$, $N^7$-dipropyl-1H-benzimidazole-2,7-diamine | $^1$H NMR (CDCl$_3$) δ 0.86 (t, 6H, J = 7.4 Hz), 1.45-1.55 (m, 4H), 1.64 (d, 6H, J = 7.0 Hz), 2.24 (s, 6H), 2.28 (s, 3H), 2.90-3.05 (m, 4H), 6.57-6.65 (m, 1H), 6.89 (d, 1H, J = 7.8 Hz), 6.93 (s, 2H), 6.98 (t, 1H, J= 7.8 Hz), 7.23 (d, 1H, J = 7.8 Hz); MS Calcd.: 392; Found: 393 (M + H). |
| 29 | 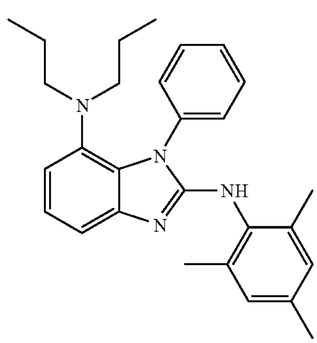 | $N^2$-Mesityl-1-phenyl-$N^7$, $N^7$-dipropyl-1H-benzimidazole-2,7-diamine | MS Calcd.: 426; Found: 427 (M + H). |

TABLE 2-continued

| Example | Structure | Name | Physical Data |
|---|---|---|---|
| 30 | 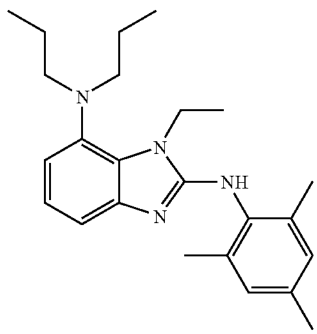 | 1-Ethyl-$N^2$-mesityl-$N^7$, $N^7$-dipropyl-1H-benzimidazole-2,7-diamine | $^1$H NMR (CDCl$_3$) δ 0.86 (t, 6H, J = 7.2 Hz), 1.36 (t, 3H, J = 7.0 Hz), 1.48-1.54 (m, 4H), 2.23 (s, 6H), 2.28 (s, 3H), 2.93-3.00 (m, 4H), 4.53-4.60 (m, 2H), 6.89 (d, 1H, J = 7.8 Hz), 6.93 (s, 2H), 7.00 (t, 1H, J = 7.8 Hz), 7.23 (d, 1H, J = 7.5 Hz); MS Calcd.: 378; Found: 379 (M + H). |

Example 31

$N^7$-Cyclopropylmethyl-$N^2$-mesityl-1-methyl-$N^7$-propyl-1H-benzoimidazole-2,7-diamine

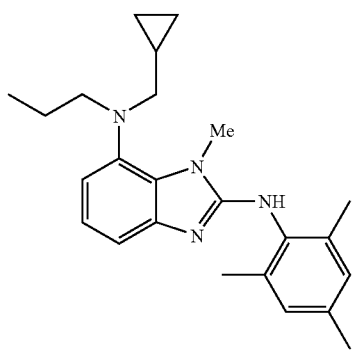

7-Amino-1-methyl-1,3-dihydro-2H-benzimidazol-2-one

To 9.6 g (70 mmol) of $N^2$-methylbenzene-1,2,3-triamine dissolved in 350 mL of THF was added 11.3 g (70 mmol) of N,N'-carbonyldiimidazole. The reaction mixture was stirred for 18 h and was concentrated in vacuo. The crude solid was triturated with dichloromethane and collected by filtration to give 6.94 g (61%) of the title compound as a brown powder.
$^1$H NMR (DMSO-d$_6$) δ 3.51 (s, 3H), 4.85 (s, 2H), 6.30 (d, J=7.6 Hz, 1H), 6.35 (d, J=8.0 Hz, 1H), 6.68 (t, J=8.0, 1H), 10.55 (s, 1H).

1-Methyl-7-(propylamino)-1,3-dihydro-2H-benzimidazol-2-one

To 0.87 g (5.3 mmol) of 7-amino-1-methyl-1,3-dihydro-2H-benzoimidazol-2-one in 50 mL of methanol was added 1.94 mL (26.7 mmol) of propionaldehyde and 1.0 g (16 mmol) of sodium cyanoborohydride. The mixture was stirred at room temperature for 5 h and concentrated in vacuo. The crude solid was partitioned between water and ethyl acetate, the biphasic mixture was filtered to remove particulates and the layers were separated. The organic layer was washed with brine, dried over sodium sulfate, filtered, concentrated and purified by flash chromatography eluting with a 50% ethyl acetate/hexanes mixture to give 0.69 g (63%) of the title compound as a cream colored powder.
MS Calcd.: 205. Found: 206 (M+H).

7-Benzyl(propyl)amino-1-methyl-1,3-dihydro-2H-benzimidazol-2-one

To 0.69 g (3.4 mmol) of 1-methyl-7-(propylamino)-1,3-dihydro-2H-benzimidazol-2-one in 20 mL of methanol was added 0.68 mL (6.7 mmol) of benzaldehyde, 10 drops of glacial acetic acid and 0.63 g (10 mmol) of sodium cyanoborohydride. The mixture was stirred at 50° C. for 18 h and an additional 0.68 mL of benzaldehyde, 10 drops of glacial acetic acid and 0.63 g of sodium cyanoborohydride were added. This mixture was heated for an additional 24 h before adding an additional 0.68 mL of benzaldehyde, 10 drops of glacial acetic acid and 0.63 g of sodium cyanoborohydride. The reaction was cooled to room temperature and the volatiles were removed in vacuo. The crude solid was partitioned between water and ethyl acetate, the organic layer was then washed with brine, dried over sodium sulfate, filtered, concentrated and purified by flash chromatography eluting with a 33% ethyl acetate/hexanes mixture to give 0.65 g (65%) of the title compound as a colorless sticky solid.
MS Calcd.: 295. Found: 296 (M+H).

$N^7$-Benzyl-2-chloro-1-methyl-$N^7$-propyl-1H-benzimidazol-7-amine

A solution of 0.65 g (2.2 mmol) of 7-benzyl(propyl)amino-1-methyl-1,3-dihydro-2H-benzimidazol-2-one in 10 mL of phosphorous oxychloride was heated to 100° C. After stirring for 24 h, the mixture was concentrated in vacuo and quenched with saturated sodium bicarbonate. The quenched reaction was extracted with ethyl acetate and the extracts were then washed with brine, dried over sodium sulfate, filtered and concentrated to give 0.56 g (81%) of the title compound as a viscous yellow oil. This crude oil was used without further purification in the preparation of E.

MS Calcd.: 313. Found: 314 (M+H).

$N^7$-Benzyl-$N^2$-mesityl-1-methyl-$N^7$-propyl-1H-benzimidazole-2,7-diamine A solution of 0.56 g (1.8 mmol) of $N^7$-benzyl-2-chloro-1-methyl-$N^7$-propyl-1H-benzimidazol-7-amine in 0.75 mL (5.4 mmol) of mesityl amine was heated to 130° C. After stirring for 24 h, the mixture was dissolved in ethyl acetate and washed with saturated sodium bicarbonate, brine, dried over sodium sulfate, filtered and concentrated to give a tan solid. The solid thus obtained was purified by flash chromatography eluting with a 1.3% methanol/dichloromethane mixture to give 0.59 g (80%) of the title compound as a cream colored solid.

MS Calcd.: 412. Found: 413 (M+H).

$N^2$-Mesityl-1-methyl-$N^7$-propyl-1H-benzimidazole-2,7-diamine

To a solution of 0.50 g (1.2 mmol) of $N^7$-benzyl-$N^2$-mesityl-1-methyl-$N^7$-propyl-1H-benzimidazole-2,7-diamine in 30 mL of methanol was added 0.43 g (10 mol % Pd) of 20% Pearlman's catalyst (50% wet). The reaction was kept under a hydrogen atmosphere via a balloon and stirred at room temperature for 48 h. The catalyst was removed via filtration and the filtrate was concentrated in vacuo. Purification by flash chromatography eluting with a 7% methanol/dichloromethane mixture gave 0.23 g (58%) of the title compound as a cream colored solid.

MS Calcd.: 322. Found: 323 (M+H).

$N^7$-Cyclopropylmethyl-$N^2$-mesityl-1-methyl-$N^7$-propyl-1H-benzimidazole-2,7-diamine To 0.041 g (0.13 mmol) of $N^2$-mesityl-1-methyl-$N^7$-propyl-1H-benzimidazole-2,7-diamine in 2 mL of methanol was added 95 µL (1.3 mmol) of cyclopropane carboxaldehyde, 200 µL of glacial acetic acid and 0.032 g (0.51 mmol) of sodium cyanoborohydride. The mixture was stirred at room temperature for 24 h. The reaction mixture was cooled to room temperature and the volatiles were removed in vacuo. The crude solid was partitioned between saturated sodium bicarbonate and dichloromethane, the organic layer was separated, dried over sodium sulfate, filtered, concentrated and purified by reverse-phase HPLC to give 0.026 g (42%) of the title compound as a colorless sticky solid.

MS Calcd.: 376. Found: 377 (M+H).

Compounds of Examples 32-60, shown in the Table 3, were prepared in a manner similar to that described in Example 31. Compounds 32-53 were purified by reverse phase HPLC ($CH_3CN$ containing 0.1% TFA/water containing 0.1% TFA) to obtain TFA salts.

TABLE 3

| Example | Structure | Name | Physical Data |
| --- | --- | --- | --- |
| 32 | 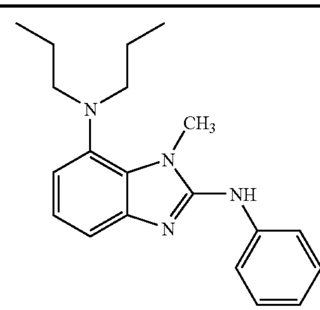 | 1-methyl-$N^2$-phenyl-$N^7$,$N^7$-dipropyl-1H-benzimidazole-2,7-diamine | MS Calcd.: 322<br>MS Found: 323<br>(M + H) |
| 33 | 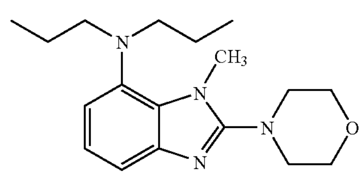 | 1-methyl-2-morpholin-4-yl-N,N-dipropyl-1H-benzimidazol-7-amine | MS Calcd.: 316<br>MS Found: 317<br>(M + H) |
| 34 | 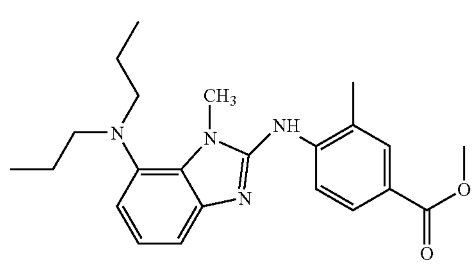 | methyl 4-{[7-(dipropylamino)-1-methyl-1H-benzimidazol-2-yl]amino}-3-methylbenzoate | MS Calcd.: 394<br>MS Found: 395<br>(M + H) |

TABLE 3-continued

| Example | Structure | Name | Physical Data |
|---|---|---|---|
| 35 | 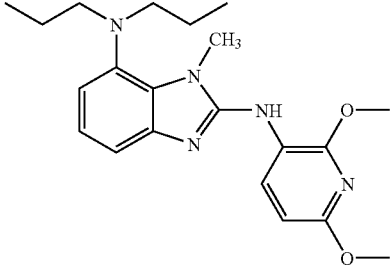 | $N^2$-(2,6-dimethoxypyridin-3-yl)-1-methyl-$N^7$,$N^7$-dipropyl-1H-benzimidazole-2,7-diamine | MS Calcd.: 383<br>MS Found: 384<br>(M + H) |
| 36 | 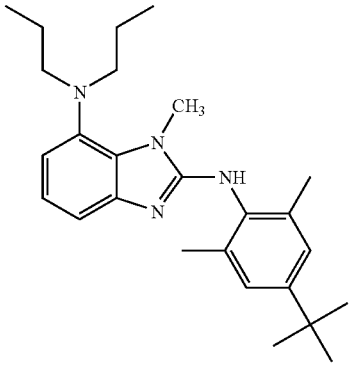 | $N^2$-(4-tert-butyl-2,6-dimethylphenyl)-1-methyl-$N^7$,$N^7$-dipropyl-1H-benzimidazole-2,7-diamine | MS Calcd.: 406<br>MS Found: 407<br>(M + H) |
| 37 | 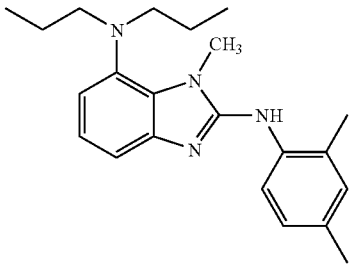 | $N^2$-(2,4-dimethylphenyl)-1-methyl-$N^7$,$N^7$-dipropyl-1H-benzimidazole-2,7-diamine | MS Calcd.: 350<br>MS Found: 351<br>(M + H) |
| 38 | 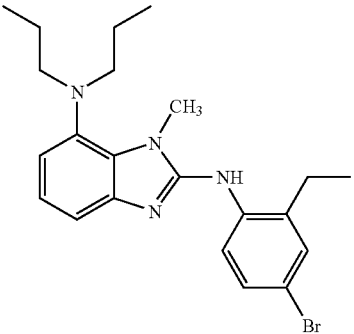 | $N^2$-(4-bromo-2-ethylphenyl)-1-methyl-$N^7$,$N^7$-dipropyl-1H-benzimidazole-2,7-diamine | MS Calcd.: 428<br>MS Found: 429<br>(M + H) |

TABLE 3-continued

| Example | Structure | Name | Physical Data |
|---|---|---|---|
| 39 | 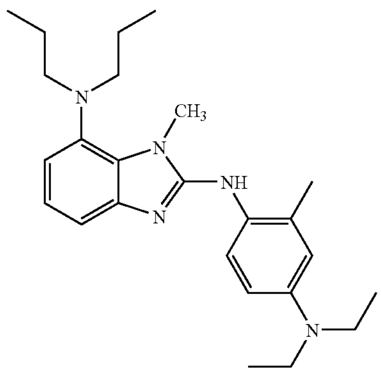 | $N^2$-[4-(diethylamino)-2-methylphenyl]-1-methyl-$N^7,N^7$-dipropyl-1H-benzimidazole-2,7-diamine | MS Calcd.: 407<br>MS Found: 408<br>(M + H) |
| 40 | 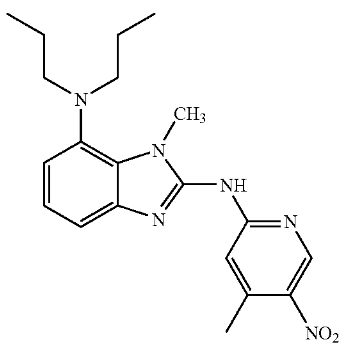 | 1-methyl-$N^2$-(4-methyl-5-nitropyridin-2-yl)-$N^7,N^7$-dipropyl-1H-benzimidazole-2,7-diamine | MS Calcd.: 382<br>MS Found: 383<br>(M + H) |
| 41 | 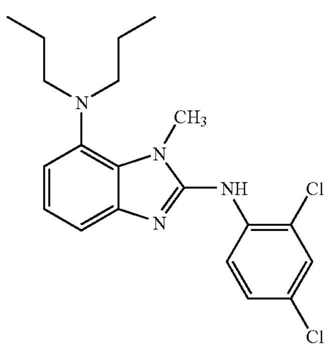 | $N^2$-(2,4-dichlorophenyl)-1-methyl-$N^7,N^7$-dipropyl-1H-benzimidazole-2,7-diamine | MS Calcd.: 390<br>MS Found: 391<br>(M + H) |
| 42 | 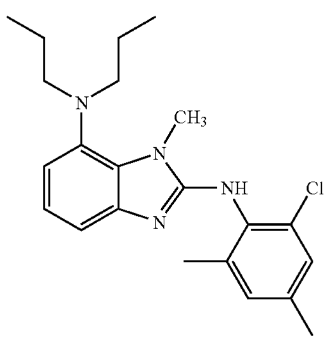 | $N^2$-(2-chloro-4,6-dimethylphenyl)-1-methyl-$N^7,N^7$-dipropyl-1H-benzimidazole-2,7-diamine | MS Calcd.: 384<br>MS Found: 385<br>(M + H) |

TABLE 3-continued

| Example | Structure | Name | Physical Data |
|---|---|---|---|
| 43 | 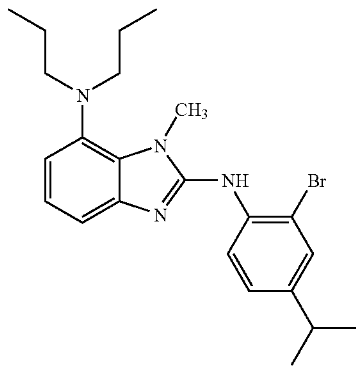 | $N^2$-(2-bromo-4-isopropylphenyl)-1-methyl-$N^7,N^7$-dipropyl-1H-benzimidazole-2,7-diamine | MS Calcd.: 442<br>MS Found: 443<br>(M + H) |
| 44 | 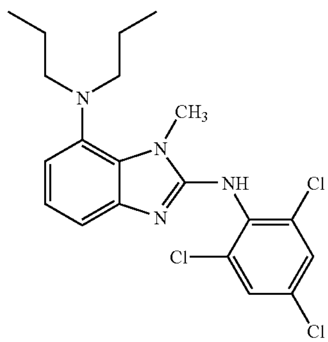 | 1-methyl-$N^7,N^7$-dipropyl-$N^2$-(2,4,6-trichlorophenyl)-1H-benzimidazole-2,7-diamine | MS Calcd.: 424<br>MS Found: 425<br>(M + H) |
| 45 | 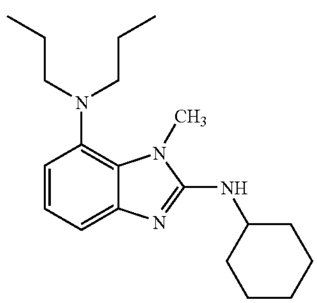 | $N^2$-cyclohexyl-1-methyl-$N^7,N^7$-dipropyl-1H-benzimidazole-2,7-diamine | MS Calcd.: 328<br>MS Found: 329<br>(M + H) |
| 46 | 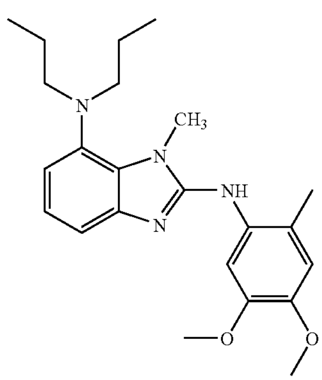 | $N^2$-(4,5-dimethoxy-2-methylphenyl)-1-methyl-$N^7,N^7$-dipropyl-1H-benzimidazole-2,7-diamine | MS Calcd.: 396<br>MS Found: 397<br>(M + H) |

TABLE 3-continued

| Example | Structure | Name | Physical Data |
|---------|-----------|------|---------------|
| 47 | 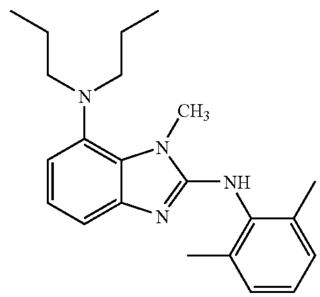 | $N^2$-(2,6-dimethylphenyl)-1-methyl-$N^7$,$N^7$-dipropyl-1H-2,7-diamine | MS Calcd.: 350<br>MS Found: 351<br>(M + H) |
| 48 | 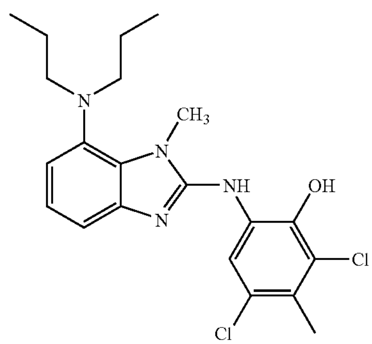 | 2,4-dichloro-6-{[7-(dipropylamino)-1-methyl-1H-benzimidazol-2-yl]amino}-3-methylphenol | MS Calcd.: 420<br>MS Found: 421<br>(M + H) |
| 49 | 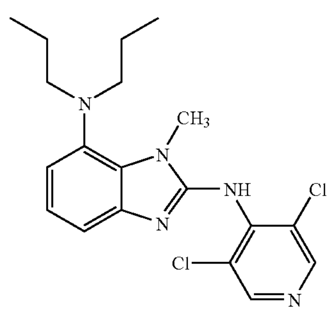 | $N^2$-(3,5-dichloropyridin-4-yl)-1-methyl-$N^7$,$N^7$-dipropyl-1H-benzimidazole-2,7-diamine | MS Calcd.: 391<br>MS Found: 391<br>(M + H) |
| 50 | 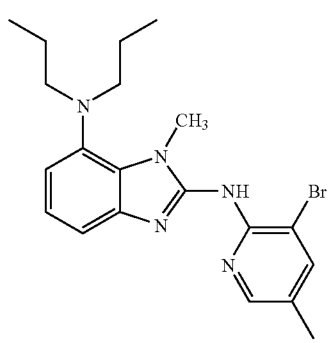 | $N^2$-(3-bromo-5-methylpyridin-2-yl)-1-methyl-$N^7$,$N^7$-dipropyl-1H-benzimidazole-2,7-diamine | MS Calcd.: 415<br>MS Found: 416<br>(M + H) |

TABLE 3-continued

| Example | Structure | Name | Physical Data |
|---|---|---|---|
| 51 | 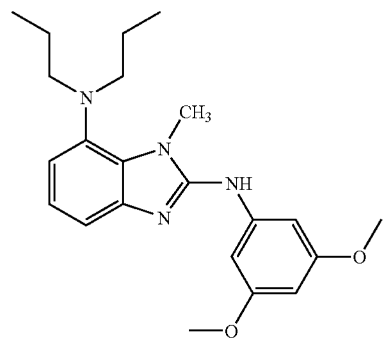 | $N^2$-(3,5-dimethoxyphenyl)-1-methyl-$N^7,N^7$-dipropyl-1H-benzimidazole-2,7-diamine | MS Calcd.: 382<br>MS Found: 383<br>(M + H) |
| 52 | 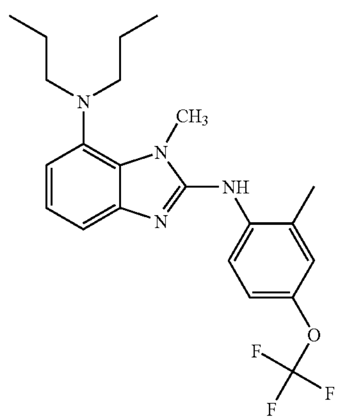 | 1-methyl-$N^2$-[2-methyl-4-(trifluoromethoxy)phenyl]-$N^7,N^7$-dipropyl-1H-benzimidazole-2,7-diamine | MS Calcd.: 420<br>MS Found: 421<br>(M + H) |
| 53 | 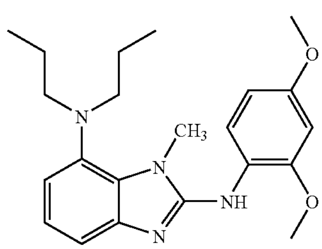 | $N^2$-(2,4-dimethoxyphenyl)-1-methyl-$N^7,N^7$-dipropyl-1H-benzimidazole-2,7-diamine | MS Calcd.: 382<br>MS Found: 383<br>(M + H) |
| 54 | 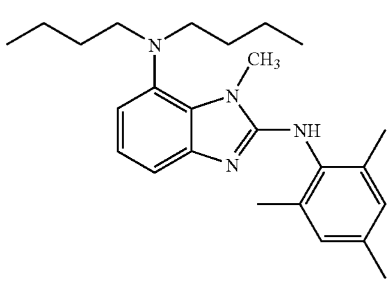 | $N^7, N^7$-dibutyl-$N^2$-mesityl-1-methyl-1H-benzimidazole-2,7-diamine | MS Calcd.: 392<br>MS Found: 393<br>(M + H) |

TABLE 3-continued

| Example | Structure | Name | Physical Data |
|---|---|---|---|
| 55 | 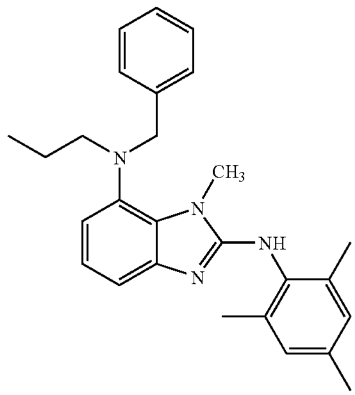 | $N^7$-benzyl-$N^2$-mesityl-1-methyl-$N^7$-propyl-1H-benzimidazole-2,7-diamine | MS Calcd.: 412<br>MS Found: 413<br>(M + H) |
| 56 | 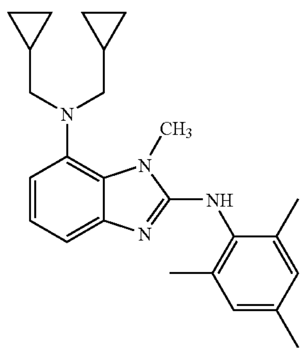 | $N^7,N^7$-bis(cyclopropylmethyl)-$N^2$-mesityl-1-methyl-1H-benzimidazole-2,7-diamine | MS Calcd.: 388<br>MS Found: 389<br>(M + H) |
| 57 | 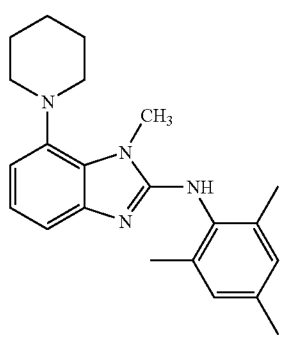 | N-mesityl-1-methyl-7-piperidin-1-yl-1H-benzimidazol-2-amine | MS Calcd.: 348<br>MS Found: 349<br>(M + H) |
| 58 | 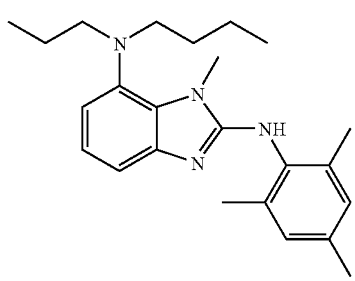 | $N^7$-butyl-$N^2$-mesityl-1-methyl-$N^7$-propyl-1H-benzimidazole-2,7-diamine | MS Calcd.: 378<br>MS Found: 379<br>(M + H) |

TABLE 3-continued

| Example | Structure | Name | Physical Data |
|---|---|---|---|
| 59 | 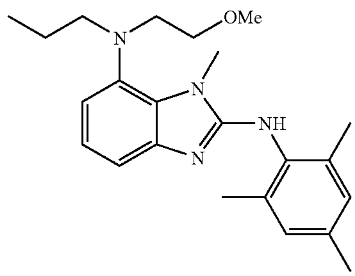 | $N^2$-mesityl-1-methyl-$N^7$-(2-methoxyethyl)-$N^7$-propyl-1H-benzimidazole-2,7-diamine | MS Calcd.: 380<br>MS Found: 381<br>(M + H) |
| 60 | 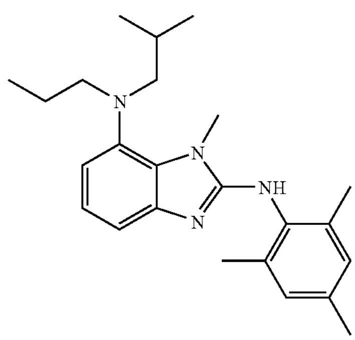 | $N^7$-isobutyl-$N^2$-mesityl-1-methyl-$N^7$-propyl-1H-benzimidazole-2,7-diamine | MS Calcd.: 378<br>MS Found: 379<br>(M + H) |

Example 61

$N^2$-(2,4-Dimethylphenyl)-$N^5$,$N^5$-dipropylimidazo[1,2-a]pyridine-2,5-diamine

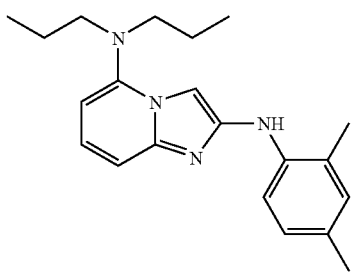

Imidazo[1,2-a]pyridin-5-amine 2,6-diaminopyridine (5.0 g, 46 mmol) and chloroacetaldehyde (50% wt. soln in water, 6.4 mL, 50 mmol) were dissolved in absolute EtOH (120 mL). The solution was heated at 75° C. for 1 hour. The mixture was cooled and concentrated via rotavap. The residue was taken up in saturated NaHCO₃ and EtOAc. The solution was extracted with EtOAc (3 times), dried over magnesium sulfate, and concentrated to give a brown solid. 4.85 g isolated (80% yield).

$^1$H NMR (CDCl₃) δ 4.48 (s, 2H), 6.10 (dd, J=7.2, 1.2 Hz, 1H), 7.10-7.20 (m, 2H), 7.42 (d, J=1.2 Hz, 1H), 7.65 (d, J=1.2 Hz, 1H).

MS Calcd.: 133. Found: 134 (M+H).

N,N-Dipropylimidazo[1,2-a]pyridin-5-amine

Imidazo[1,2-a]pyridin-5-amine (4.85 g, 36 mmol) was dissolved in DMF (72 mL). Sodium hydride (60% in mineral oil, 5.8 g, 146 mmol) was added carefully. The mixture stirred for 0.5 hr. at room temperature. 1-Bromopropane (13.2 mL, 145 mmol) was added. After 1 hour, the solution was quenched with water and extracted with ether (4 times). The combined organic layers were dried over magnesium sulfate, and concentrated. Flash chromatography (80-100% EtOAc/hexanes) gave the title compound as a brown oil. 7.92 g obtained (83% yield).

$^1$H NMR (CDCl₃) δ 0.88 (t, J=8.4 Hz, 6H), 1.51-1.57 (m, 4H), 3.06-3.10 (m, 4H), 6.34 (d, J=6.8 Hz, 1H), 7.14-7.18 (m, 1H), 7.36 (d, J=8.8 Hz, 1H), 7.63 (d, J=5.6 Hz, 2H).

MS Calcd.: 217. Found 218 (M+H).

2-Bromo-N,N-dipropylimidazo[1,2-a]pyridin-5-amine

N,N-Dipropylimidazo[1,2-a]pyridin-5-amine (1.0 g, 4.6 mmol) was diluted in DMF (25 mL). The solution was cooled to 0° C. N-bromosuccinamide (0.83 g, 4.7 mmol) was added. After 5 minutes, the reaction was quenched with water. The solution was extracted with ether, dried, and concentrated. Flash chromatography (40% EtOAc/hexanes) gave the title compound as a yellow oil which solidified upon overnight freezing at −20° C. 0.67 g obtained (49% yield).

$^1$H NMR (CDCl$_3$) δ 0.86 (t, J=7.6 Hz, 6H), 1.43-1.64 (m, 4H), 2.98-3.13 (m, 4H), 6.40 (d, J=8.0 Hz, 1H), 7.10-7.14 (m, 1H), 7.34 (d, J=8.8 Hz, 1H), 7.52 (s, 1H).

MS Calcd.: 296. Found: 296 (M) 298 (M+2H).

N$^2$-(2,4-Dimethylphenyl)-N$^5$,N$^5$-dipropylimidazo[1,2-a]pyridine-2,5-diamine 2-Bromo-N,N-dipropylimidazo[1,2-a]pyridin-5-amine (C) (0.127 g, 0.43 mmol) was diluted in 2,4-dimethylaniline (2 mL). The solution was heated to 75° C. in a sealed tube for hours. The solution was flash chromatographed (20% EtOAc/hexanes) using basic alumina to give the title compound as a brown residue. 0.029 g obtained (20% yield).

$^1$H NMR (CDCl$_3$) δ 0.88 (t, J=6.8 Hz, 6H), 1.49-1.56 (m, 4H), 2.28 (s, 3H), 2.29 (s, 3H), 3.04-3.07 (m, 4H), 6.12 (s, 1H), 6.30-6.32 (m, 1H), 7.02-7.04 (m, 2H), 7.10-7.12 (m, 2H), 7.22 (s, 1H), 7.35 (d, J=7.6 Hz, 1H).

MS Calcd.: 336. Found: 337 (M+H).

Compounds of examples 62-63, shown in table 4, were prepared in a manner similar to that described in Example 61.

2-Bromo-N,N-dipropylimidazo[1,2-a]pyridin-5-amine (prepared in example 61) (0.136 g, 0.46 mmol) was dissolved in THF (1 mL). The solution was cooled to −78° C. t-BuLi (1.7M, 0.57 mL, 0.96 mmol) was added dropwise and the solution stirred for 1 hr. at −78° C. 2,4-Dimethylbenzoyl chloride (0.097 g, 0.57 mmol) diluted in 0.5 mL THF was added to the reaction mixture. After 0.5 hr, the solution was quenched with water and warmed to room temperature. Extraction occurred with EtOAc and the organic layer was dried over magnesium sulfate and concentrated. Flash chromatography (30-40% EtOAc/hexanes) gave the title compound. 0.039 g obtained (24% yield).

$^1$H NMR (CDCl$_3$) δ 0.82 (t, J=7.6 Hz, 6H), 1.32-1.65 (m, 4H), 2.40 (s, 3H), 2.48 (s, 3H), 3.13-3.19 (m, 4H), 6.55 (d, J=7.6 Hz, 1H), 7.05 (d, J=8.0 Hz, 1H), 7.13 (s, 1H), 7.33 (d, J=8.0 Hz, 1H), 7.44 (t, J=8.4 Hz, 1H), 7.55 (d, J=7.6 Hz, 1H), 7.77 (s, 1H).

MS Calcd.: 349. Found: 350 (M+H).

TABLE 4

| Example | Structure | Name | Physical Data |
|---|---|---|---|
| 62 | 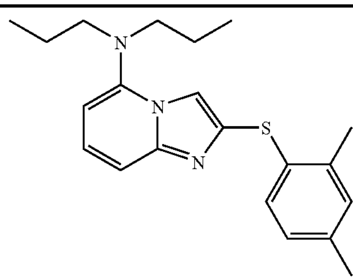 | 2-((2,4-dimethylpheny)thio)-N,N-dipropylimidazo[1,2-a]pyridin-5-amine | MS Calcd.: 353; Found: 354 (M + H). |
| 63 | 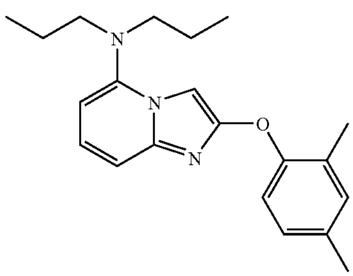 | 2-(2,4-dimethylphenoxy)-N,N-dipropylimidazo[1,2-a]pyridin-5-amine | MS Calcd.: 337; Found: 338 (M + H). |

Example 64

(2,4-Dimethylphenyl)(5-(dipropylamino)imidazo[1,2-a]pyridin-2-yl)methanone

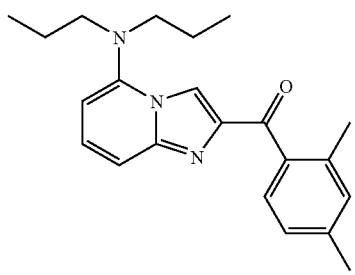

Example 65

2-(2,4-Dimethylphenyl)-N,N-dipropylimidazo[1,2-a]pyridin-5-amine

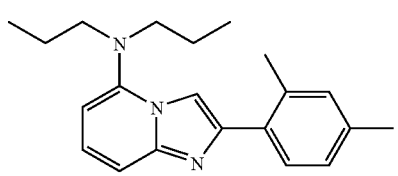

2-(2,4-Dimethylphenyl)-N,N-dipropylimidazo[1,2-a]pyridin-5-amine

2-Bromo-N,N-dipropylimidazo[1,2-a]pyridin-5-amine (prepared in example 61) (0.17 g, 0.57 mmol) was dissolved in 1,2-dimethoxyethane (DME) (1.5 mL). Pd(PPh$_3$)$_4$ (0.033 g, 0.028 mmol) was added and the reaction was stirred at 50° C. for 15 minutes. The solution was cooled and 2,4-dimethylphenylboronic acid (0.103 g, 0.69 mmol) in DME (1 mL) was added to the reaction mixture. KOtBu (0.128 g, 1.14 mmol) in tBuOH (1 mL) was also added to the reaction. The reaction was heated to 100° C. for 1 hr. The solution was filtered through paper and concentrated. Crude material was purified via reverse phase HPLC (acetonitrile containing 0.1% TFA/water containing 0.1% TFA) to obtain 3.1 mg of the title compound (2% yield).

MS Calcd.: 321. Found: 322 (M+H).

Example 66

5-Fluoro-N$^2$-mesityl-1-methyl-N$^7$,N$^7$-dipropyl-1H-benzimidazole-2,7-diamine

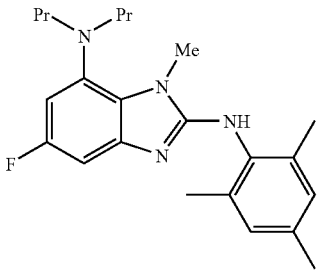

2-Chloro-5-fluoro-1,3-dinitrobenzene

To a solution of 0.65 g (2.2 mmol) of 4-fluoro-2,6-dinitrophenol in 30 mL dimethylformamide was added 1.4 mL (15 mmol) of phosphorous oxychloride. The mixture was heated to 70° C. overnight, cooled to room temperature and quenched with ice. The mixture was diluted with water and the precipitate was collected giving 1.35 g (82%) of the title compound as a cream colored solid.

$^1$H NMR (DMSO-d$_6$) δ 8.55 (d, J=1.5 Hz, 1H), 8.57 (d, J=1.3 Hz, 1H).

4-Fluoro-N-methyl-2,6-dinitroaniline

To 1.35 g (6.12 mmol) of 2-chloro-5-fluoro-1,3-dinitrobenzene in 20 mL of THF at 0° C. was added 6.1 mL (12 mmol) of 2N methylamine in THF. The cold bath was removed and the reaction was stirred at room temperature for 45 minutes. The solution was concentrated, diluted with ether and washed with saturated sodium bicarbonate solution. The resulting organic solution was dried over sodium sulfate, filtered and concentrated giving 1.30 g (99%) of the title compound as a bright orange powder.

$^1$H NMR (DMSO-d$_6$) δ 2.70 (d, J=5.5 Hz, 3H), 8.20 (br s, 1H) 8.29 (d, J=8.2 Hz, 2H).

1-[3-Amino-5-fluoro-2-(methylamino)phenyl]-3-mesitylthiourea

In 75 mL of ethanol was mixed 1.30 g (6.04 mmol) of 4-fluoro-N-methyl-2,6-dinitroaniline, 3.7 mL (36 mmol) of cyclohexene and 5.1 g (2.4 mmol, 40 mol %) of 10% palladium on carbon (50% water, Degussa type). The mixture was refluxed for 2.5 h and filtered into a flask containing 0.77 g (7.3 mmol) of sodium carbonate and 1.07 g (6.04 mmol) of 2-isothiocyanato-1,3,5-trimethylbenzene. The resulting slurry was refluxed for 4 h, concentrated and slurried in dichloromethane. The slurry was filtered, concentrated and purified by flash chromatography eluting with a 70% hexanes/ethyl acetate mixture to give 0.65 g (32%) of the title compound as an off-white solid.

$^1$H NMR (DMSO-d$_6$) δ 2.09 (s, 6H), 2.20 (s, 3H), 3.45 (s, 3H), 5.00 (br s, 4H), 5.78 (d, J=11.2 Hz, 2H), 6.79 (s, 2H), 7.93 (br s, 1H).

MS Calcd.: 332. Found: 299 (M+H-H$_2$S).

5-Fluoro-N$^2$-mesityl-1-methyl-N$^7$,N$^7$-dipropyl-1H-benzimidazole-2,7-diamine To 0.29 g (0.87 mmol) of 1-[3-amino-5-fluoro-2-(methylamino)phenyl]-3-mesitylthiourea in 15 mL of acetonitrile was added 1.09 mL (7.9 mmol) of triethylamine followed by 0.4 g (1.5 mmol) of mercuric chloride. After 2h at room temperature an additional 0.7 g (2.6 mmol) of mercuric chloride was added. After 2 h of additional reaction time, the mixture was diluted with water and the resulting crude 5-fluoro-N$^2$-mesityl-1-methyl-1H-benzoimidazole-2,7-diamine was collected as a brown precipitate via filtration. The crude product thus obtained was slurried in 50 mL of methanol and treated with 1.6 mL (22 mmol) of propionaldehyde, 3 mL of glacial acetic acid and 1.1 g (17 mmol) of sodium cyanoborohydride. The mixture was stirred at 50° C. for 24 h. The reaction mixture was cooled to room temperature and the volatiles were removed in vacuo. The crude solid was mixed with water and made basic with saturated potassium carbonate. The mixture was partioned with ethyl acetate and separated. The organic layer was washed with brine, dried over sodium sulfate, filtered, concentrated onto silica gel and purified by flash chromatography eluting with a 75% hexanes/ethyl acetate mixture to give impure title compound. The impure material was slurried in hexanes and 0.065 g (20%) of the title compound was collected as a white solid.

$^1$H NMR (DMSO-d$_6$) δ 0.83 (t, J=7.2 Hz, 6H), 1.43 (q, J=7.2 Hz, 4H), 2.11 (s, 6H), 2.26 (s, 3H), 2.94 (m, 4H), 3.92 (s, 3H), 6.60 (t, J=12.3 Hz, 2H), 6.91 (s, 2H), 8.01 (s, 1H).

$^{19}$F NMR (DMSO-d$_6$) δ -117.85 (s, 1F).

MS Calcd.: 382. Found: 383 (M+H).

Other Examples

TABLE 5

| Example | Structure | Name | Physical Data |
|---|---|---|---|
| 67 | 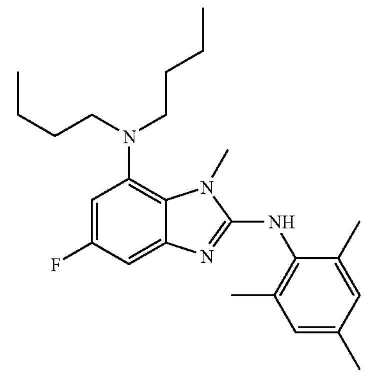 | $N^7,N^7$-dibutyl-5-fluoro-$N^2$-mesityl-1-methyl-1H-benzimidazole-2,7-diamine | $^1$H NMR (DMSO-$d_6$) δ (HCl salt) 0.86 (t, 6H, J = 7.3 Hz), 1.24-1.31 (m, 4H), 1.39-1.43 (m, 4H), 2.20 (s, 6H), 2.32 (s, 3H), 3.05 (br s, 4H), 4.06 (s, 3H), 6.80 (d, 1H, J = 7.6 Hz), 7.04 d 1H, J = 11.9 Hz), 7.10 (s, 2H), 10.46 (s, 1H); $^{19}$F NMR (DMSO-$d_6$) δ 117.7 (s, 1F); MS Calcd.: 410; MS Found: 411 (M + H). |
| 68 | 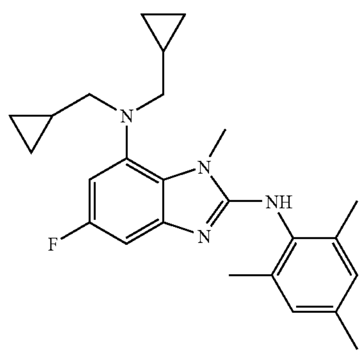 | $N^7,N^7$-bis(cyclopropylmethyl)-5-fluoro-$N^2$-mesityl-1-methyl-1H-benzimidazole-2,7-diamine | $^1$H NMR (DMSO-$d_6$) δ (HCl salt) 0.08 (d, 4H, J = 4.3 Hz), 0.40 (d, 4H, J = 7.8 Hz), 0.84-0.92 (m, 2H), 2.20 (s, 6H), 2.32 (s, 3H), 2.99 (br s, 4H), 4.16 (s, 3H), 6.84 (d, 1H, J = 7.8 Hz), 7.10-7.15 (m, 2H), 10.49 (s, 1H); $^{19}$F NMR (DMSO-$d_6$) δ −117.7 (s, 1F); MS Calcd.: 406; MS Found: 407 (M + H). |

Example 69

$N^7$-Butyl-$N^2$-mesityl-$N^7$-(4-methoxyphenyl)-1-methyl-1H-benzimidazole-2,7-diamine

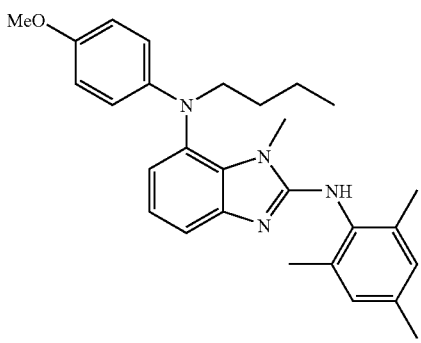

7-[(4-Methoxyphenyl)amino]-1-methyl-1,3-dihydro-2H-benzimidazol-2-one

A mixture of 0.183 g (1.12 mmol) of 7-amino-1-methyl-1,3-dihydrobenzimidazol-2-one, 0.037 g (0.11 mmol) of biphenyl-2-yl-dicyclohexylphosphane, 0.237 g (2.47 mmol) of sodium tert-butoxide and 0.041 g (0.045 mmol) of tris(dibenzylidineacetone)dipalladium in 6 mL of THF was treated with 0.14 mL (1.12 mmol) of 4-bromoanisole and heated to 60° C. for 18 h. The crude reaction mixture was diluted with ethyl acetate, filtered through a pad of celite and purified by flash chromatography eluting with a 97% dichloromethane/methanol mixture to give 0.126 g (42%) of the title compound as a tan powder.

$^1$H NMR (DMSO-$d_6$) δ 3.29 (s, 3H), 3.66 (s, 3H), 6.62 (d, J=8.8 Hz, 2H), 6.70-6.83 (m, 4H), 6.91 (t, J=7.8 Hz, 1H), 7.30 (s, 1H), 10.85 (s, 1H).

MS Calcd.: 269. Found: 270 (M+H).

7-[Butyl(4-methoxyphenyl)amino]-1-methyl-1,3-dihydro-2H-benzimidazol-2-one

A mixture of 0.100 g (0.37 mmol) of 7-[(4-methoxyphenyl)amino]-1-methyl-1,3-dihydro-2H-benzimidazol-2-one and 0.13 mL (1.5 mmol) of butyraldehyde in 15 mL of dichloroethane was treated with four drops of glacial acetic acid and 0.31 g (1.5 mmol) of sodium triacetoxyborohydride. The mixture was heated to 70° C. for five days. The mixture was diluted with ethyl acetate and was washed successively with saturated sodium bicarbonate and brine before being dried over sodium sulfate. The solution was filtered, concentrated in vacuo and the resulting crude oil was purified by flash chromatography eluting with a 97% dichloromethane/methanol mixture to give 0.70 g (45%) of the title compound as a yellow sticky semi-solid that was used without further purification.

N-Butyl-2-chloro-N-(methoxyphenyl)-1-methyl-1H-benzimidazol-7-amine

A solution of 0.070 g (0.22 mmol) of 7-[butyl(4-methoxyphenyl)amino]-1-methyl-1,3-dihydro-2H-benzimidazol-2-one in 2 mL of phosphorous oxychloride was heated to 100° C. After stirring for 2 h, the mixture was concentrated in vacuo and quenched with saturated sodium bicarbonate. The quenched reaction was extracted with ethyl acetate and the extracts were then washed with brine, dried over sodium sulfate, filtered and concentrated onto silica gel and purified by flash chromatography eluting with a 85% hexanes/ethyl acetate mixture to give 0.018 g (36%) of the title compound as a colorless oil.

MS Calcd.: 343. Found: 310 (M+H-Cl).

$N^7$-Butyl-$N^2$-mesityl-$N^7$-(4-methoxyphenyl)-1-methyl-1H-benzimidazole-2,7-diamine A solution of 0.018 g (0.05 mmol) of N-butyl-2-chloro-N-(methoxyphenyl)-1-methyl-1H-benzimidazol-7-amine in 0.10 mL (0.73 mmol) of mesityl amine was heated to 130° C. After stirring for 18 h, the mixture was dissolved in dichloromethane, loaded onto silica gel and purified by flash chromatography eluting with a 96% dichloromethane/methanol mixture to give 0.015 g (65%) of the title compound as a reddish-brown solid.

$^1$H NMR (DMSO-d$_6$) δ 0.90 (t, J=7.2 Hz, 3H), 1.34 (q, J=7.4 Hz, 2H), 1.62 (m, 2H), 2.10 (s, 6H), 2.26 (s, 3H), 3.45-3.55 (m, 2H), 3.52 (, 3H), 3.65 (s, 3H), 6.48 (d, J=9.0 Hz, 2H), 6.70 (d, J=7.4 Hz, 1H), 6.77 (d, J=8.2 Hz, 2H), 6.95-7.04 (m, 2H), 7.93 (s, 1H).

MS Calcd.: 442. Found: 443 (M+H).

The following examples were prepared according to the procedures described in Example 26 or 31.

TABLE 6

| Example | Structure | Name | Physical Data |
| --- | --- | --- | --- |
| 70 | 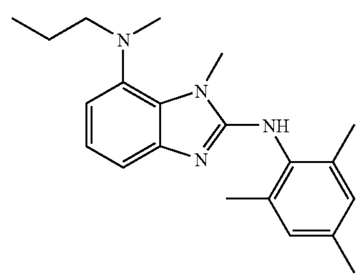 | $N^2$-mesityl-$N^7$,1-dimethyl-N-propyl-1H-benzimidazole-2,7-diamine | MS Calcd.: 336; MS Found: 337 (M + H) |
| 71 | 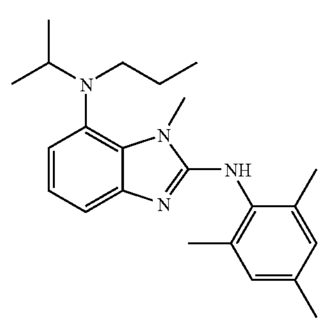 | $N^7$-isopropyl-$N^2$-mesityl-1-propyl-1H-benzimidazole-2,7-diamine | MS Calcd.: 364; MS Found: 365 (M + H) |

TABLE 6-continued

| Example | Structure | Name | Physical Data |
|---|---|---|---|
| 72 | 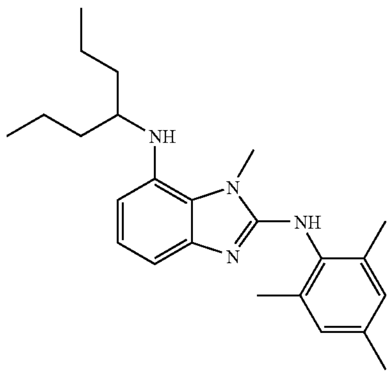 | $N^2$-mesityl-1-methyl-$N^7$-(1-propylbutyl)-1H-benzimidazole-2,7-diamine | $^1$H NMR (DMSO-$d_6$) δ 0.91 (t, J = 7.2 Hz, 6H), 1.37-1.56 (m, 8H), 2.19 (s, 6H), 2.33 (s, 3H), 4.06 (s, 3H), 4.88 (br s, 1H), 6.59 (dd, J = 4.7, 7.8 Hz, 2H), 7.05 (t, J = 8.0 Hz, 1H), 7.10 (s, 1H), 12.25 (s, 1H); MS Calcd.: 378; MS Found: 379 (M + H). |
| 73 | 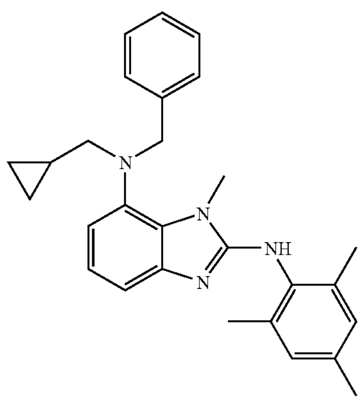 | $N^7$-benzyl-$N^7$-(cyclopropylmethyl)-$N^2$-mesityl-1-methyl-1H-benzimidazole-2,7-diamine | $^1$H NMR (DMSO-$d_6$) δ 0.02 (s, 2H), 0.37 (d, J = 7.6 Hz, 2H), 0.86 (t, J = 7.0 Hz, 2H), 2.11 (s, 6H), 2.26 (s, 3H), 2.85 (d, J = 5.7 Hz, 2H), 4.02 (s, 3H), 4.32 (s, 2H), 6.80-6.87 (m, 3H), 6.91 (s, 2H), 7.19 (t, J = 7.3 Hz, 1H), 7.28 (t, J = 7.6 Hz, 2H), 7.33 (d, J = 7.0 Hz, 2H), 7.88 (s, 1H); MS Calcd.: 424; MS Found: 425 (M + H). |
| 74 | 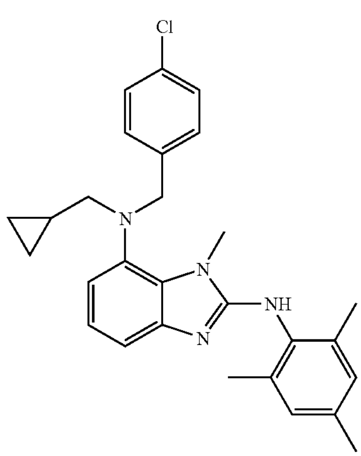 | $N^7$-(4-chlorobenzyl)-$N^7$-(cyclopropylmethyl)-$N^2$-mesityl-1-methyl-1H-benzimidazole-2,7-diamine | $^1$H NMR (DMSO-$d_6$) δ -0.01 (s, 2H), 0.38 (d, J = 7.6 Hz, 2H), 0.84-0.90 (m, 1H), 2.11 (s, 6H), 2.26 (s, 3H), 2.85 (br s, 2H), 4.90 (s, 3H), 4.30 (s, 2H), 6.81-6.84 (m, 3H), 6.91 (s, 2H), 7.32 (s, 4H), 7.88 (s, 1H); MS Calcd.: 458; MS Found: 459 (M + H). |

TABLE 6-continued

| Example | Structure | Name | Physical Data |
|---------|-----------|------|---------------|
| 75 | 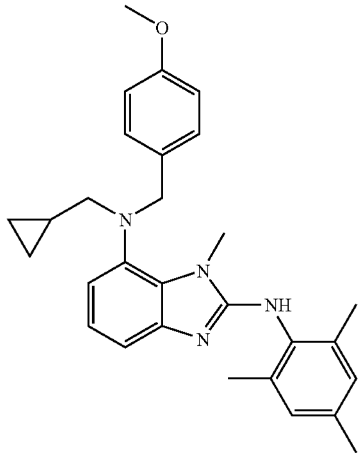 | $N^7$-(cyclopropylmethyl)-$N^2$-mesityl-$N^7$-(4-methoxybenzyl)-1-methyl-1H-benzimidazole-2,7-diamine | $^1$H NMR (DMSO-$d_6$) δ 0.00 (s, 2H), 0.38 (d, J = 6.6 Hz, 2H), 0.87 (br s, 1H), 2.12 (s, 6H), 2.27 (s, 3H), 2.84 (br s, 2H), 3.72 (s, 3H), 4.02 (s, 3H), 4.25 (br s, 2H), 6.84 (br s, 5H), 6.93 (s, 2H), 7.23 (d, J = 8.2 Hz, 2H), 7.88 (s, 1H); MS Calcd.: 454; MS Found: 455 (M + H). |
| 76 | 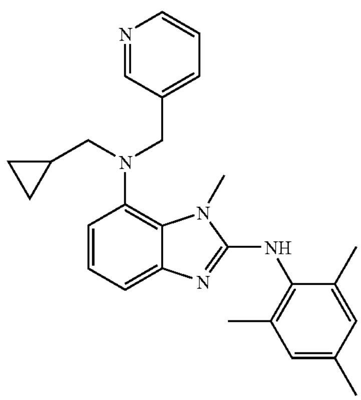 | $N^7$-(cyclopropylmethyl)-$N^2$-mesityl-1-methyl-$N^7$-(pyridin-3-ylmethyl)-1H-benzimidazole-2,7-diamine | $^1$H NMR (DMSO-$d_6$) δ 0.00 (s, 2H), 0.40 (d, J = 7.4 Hz, 2H), 0.90 (br s, 1H), 2.12 (s, 6H), 2.27 (s, 3H), 2.90 (br s, 2H), 4.04 (s, 3H), 4.36 (s, 2H), 6.87 (br s, 2H), 6.96 (br s, 3H), 7.29 (t, J = 5.1 Hz, 1H), 7.68 (d, J = 7.8 Hz, 1H); 8.39 (s, 1H), 8.50 (s, 1H); MS Calcd.: 425; MS Found: 426 (M + H). |
| 77 | 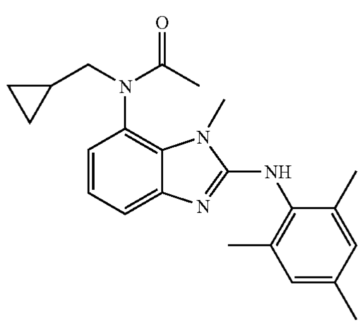 | $N^7$-(cyclopropylmethyl)-$N^2$-[2-(mesitylamino)-1-methyl-1H-benzimidazol-7-yl]acetamide | $^1$H NMR (DMSO-$d_6$) δ 0.08-0.14 (m, 2H), 0.37-0.44 (m, 2H), 0.97-1.00 (m, 1H), 1.77 (s, 3H), 2.12 (s, 6H), 2.26 (s, 3H), 3.17 (dd, J = 7.7, 13.7 Hz, 1H), 3.66 (s, 3H), 3.87 (dd, J = 6.9, 13.6 Hz, 1H), 6.83 (d, J = 7.6 Hz, 1H), 6.92 (s, 2H), 6.98 (t, J = 7.8 Hz, 1H), 7.11 (d, J = 7.8 Hz, 1H); 8.09 (s, 1H); MS Calcd.: 376; MS Found: 377 (M + H). |

TABLE 6-continued

| Example | Structure | Name | Physical Data |
|---|---|---|---|
| 78 | 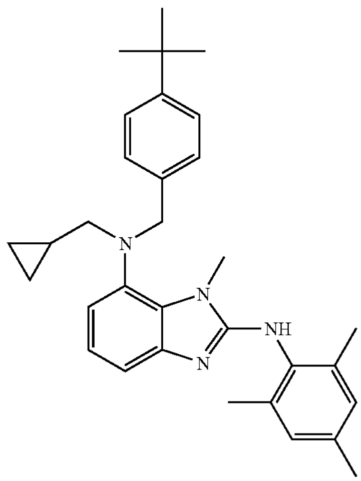 | N[7]-(4-tert-butylbenzyl)-N[7]-(cyclopropylmethyl)-N[2]-mesityl-1-methyl-1H-benzimidazole-2,7-diamine | $^1$H NMR (DMSO-$d_6$) δ 0.03 (br s, 2H), 0.36 (d, J = 7.4 Hz, 2H), 0.85 (br s, 1H), 1.24 (s, 9H), 2.11 (s, 6H), 2.26 (s, 3H), 2.84 (d, J = 6.4 Hz, 2H), 4.01 (s, 3H), 4.28 (br s, 2H), 6.81-6.85 (m, 3H), 6.91 (s, 2H), 7.25-7.32 (m, 4H), 7.88 (s, 1H); MS Calcd.: 480; MS Found: 481 (M + H). |
| 79 | 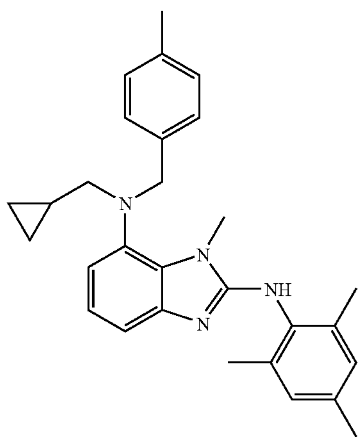 | N[7]-(cyclopropylmethyl)-N[2]-mesityl-1-methyl-N[7]-(4-methylbenzyl)-1H-benzimidazole-2,7-diamine | $^1$H NMR (DMSO-$d_6$) δ −0.01 (br s, 2H), 0.36 (d, J = 7.8 Hz, 2H), 0.84-0.87 (m, 1H), 2.11 (s, 6H), 2.24 (s, 3H), 2.26 (s, 3H), 2.83 (d, J = 5.4 Hz, 2H), 4.01 (s, 3H), 4.26 (br s, 2H), 6.80-6.84 (m, 3H), 6.91 (s, 2H), 7.07 (d, J = 7.8 Hz, 2H), 7.19 (d, J = 7.8 Hz, 2H), 7.86 (s, 1H); MS Calcd.: 438; MS Found: 439 (M + H). |
| 80 | 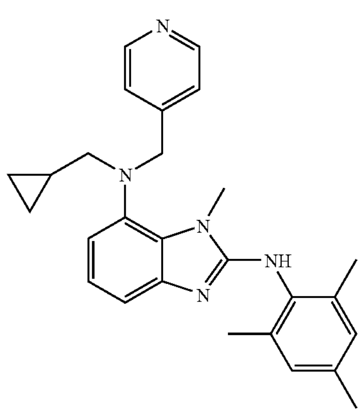 | N[7]-(cyclopropylmethyl)-N[2]-mesityl-1-methyl-N[7]-(pyridin-4-ylmethyl)-1H-benzimidazole-2,7-diamine | $^1$H NMR (DMSO-$d_6$) δ 0.00 (br s, 2H), 0.39 (d, J = 7.6 Hz, 2H), 0.86-0.88 (m, 1H), 2.12 (s, 6H), 2.26 (s, 3H), 2.88 (br s, 2H), 4.04 (s, 3H), 4.38 (br s, 2H), 6.82 (s, 3H), 6.92 (s, 2H), 7.36 (d, J = 4.5 Hz, 2H), 7.91 (s, 1H), 8.45 (d, J = 4.3 Hz, 2H); MS Calcd.: 425; MS Found: 426 (M + H). |

TABLE 6-continued

| Example | Structure | Name | Physical Data |
|---|---|---|---|
| 81 | 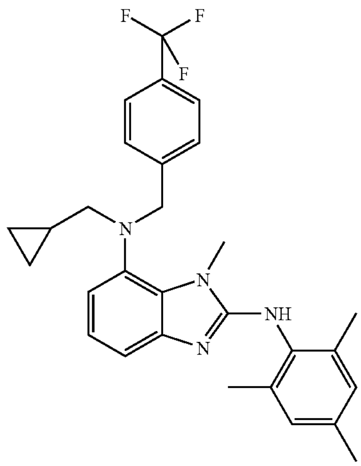 | N$^7$-(cyclopropylmethyl)-N$^2$-mesityl-1-methyl-N$^7$-[4-(trifluoromethyl)benzyl]-1H-benzimidazole-2,7-diamine | $^1$H NMR (DMSO-d$_6$) δ 0.00 (br s, 2H), 0.39 (d, J = 6.1 Hz, 2H), 0.88 (br s, 1H), 2.10 (s, 6H), 2.25 (s, 3H), 2.88 (br s, 2H), 4.01 (s, 3H), 4.42 (br s, 2H), 6.82-6.86 (m, 3H), 6.91 (s, 2H(, 7.54 (d, J = 7.2 Hz, 2H), 1H); $^{19}$F NMR (DMSO-d$_6$)-61.23 (s, 3F); MS Calcd.: 492; MS Found: 493 (M + H). |
| 82 | 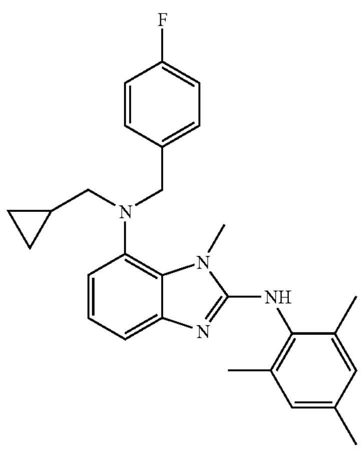 | N$^7$-(cyclopropylmethyl)-N$^7$-(4-fluorobenzyl)-N$^2$-mesityl-1-methyl-1H-benzimidazole-2,7-diamine | $^1$H NMR (DMSO-d$_6$) δ 0.00 (br s, 2H), 0.38 (d, J = 7.2 Hz, 2H), 0.87 (br s, 1H), 2.11 (s, 6H), 2.26 (s, 3H), 2.85 (br s, 2H), 4.01 (s, 3H), 4.29 (br s, 2H), 6.83 (br s, 3H), 6.92 (s, 2H), 7.07-7.11 (m, 2H), 7.32-7.36 (m, 2H), 7.88 (br s, 1H); $^{19}$F NMR (DMSO-d$_6$) δ −116.51 (s, 1F); MS Calcd.: 442; MS Found: 443 (M + H). |
| 83 | 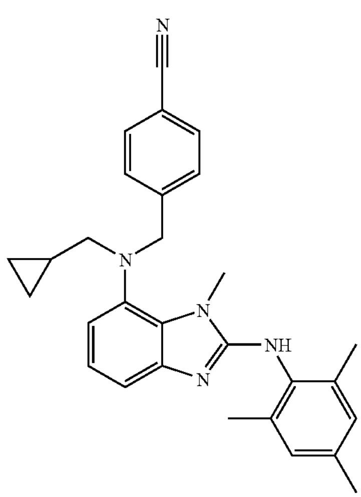 | 4-({(cyclopropylmethyl) [2-(mesitylamino)-1-methyl-1H-benzimidazol-7-yl]amino}methyl)benzonitrile | $^1$H NMR (DMSO-d$_6$) δ 0.00 (br s, 2H), 0.39 (d, J = 6.9 Hz, 2H), 0.88 (br s, 1H), 2.11 (s, 6H), 2.26 (s, 3H), 2.88 (br s, 2H), 4.01 (s, 3H), 4.42 (s, 2H), 6.83 (br s, 3H), 6.92 (s, 2H), 7.52 (d, J = 8.0 Hz, 2H), 7.74 (d, J = 8.2 Hz, 2H), 7.89 (s, 1H); MS Calcd.: 449; MS Found: 450 (M + H). |

TABLE 6-continued

| Example | Structure | Name | Physical Data |
|---|---|---|---|
| 84 | 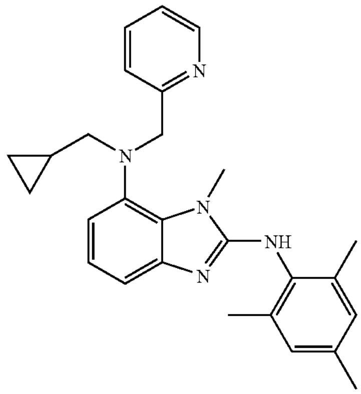 | N$^7$-(cyclopropylmethyl)-N$^2$-mesityl-1-methyl-N$^7$-(pyridin-2-ylmethyl)-1H-benzimidazole-2,7-diamine | $^1$H NMR (DMSO-d$_6$) δ 0.00 (s, 2H), 0.37 (d, J = 7.6 Hz, 2H), 0.86 (br s, 1H), 2.12 (s, 6H), 2.26 (s, 3H), 2.90 (d, J = 5.8 Hz, 2H), 4.05 (s, 3H), 4.44 (s, 2H), 6.81 (s, 3H), 6.91 (s, 2H), 7.21 (t, J = 6.2 Hz, 1H), 7.34 (d, J = 6.8 Hz, 1H); 7.69 (t, J = 7.6 Hz, 1H), 7.89 (s, 1H), 8.48 (d, J = 4.7 Hz, 1H); MS Calcd.: 425; MS Found: 426 (M + H). |
| 85 | 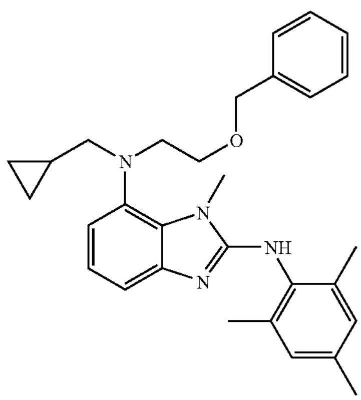 | N$^7$-[2-(benzyloxy)ethyl]-N$^7$-(cyclopropylmethyl)-N$^2$-mesityl-1-methyl-1H-benzimidazole-2,7-diamine | $^1$H NMR (DMSO-d$_6$) δ 0.03 (d, J = 4.3 Hz, 2H), 0.36 (d, J = 7.8 Hz, 2H), 0.85 (br s, 1H), 2.11 (s, 6H), 2.26 (s, 3H), 2.88 (br s, 2H), 3.32 (d, J = 6.6 Hz, 2H), 3.49 (br s, 2H), 3.98 (s, 3H), 4.41 (s, 2H), 6.80-6.86 (m, 3H), 6.91 (s, 2H), 7.23-7.32 (m, 5H), 7.86 (s, 1H); MS Calcd.: 468; MS Found: 469 (M + H). |
| 86 | 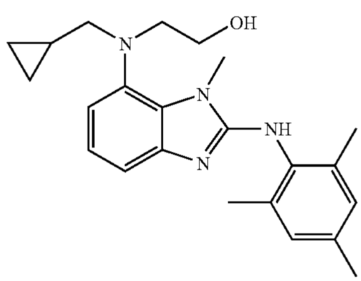 | 2-{(cyclopropylmethyl)[2-(mesitylamino)-1-methyl-1H-benzimidazol-7-yl]amino}ethanol | $^1$H NMR (DMSO-d$_6$) δ 0.04 (d, J = 4.7 Hz, 2H), 0.36 (d, J = 8.0 Hz, 2H), 0.84 (br s, 1H), 2.12 (s, 6H), 2.26 (s, 3H), 2.88 (br s, 2H), 3.19 (t, J = 6.5 Hz, 2H), 3.31 (d, J = 1.6 Hz, 2H), 3.46 (q, J = 6.1 Hz, 2H), 4.01 (s, 3H), 4.45 (t, J = 5.1 Hz, 1H), 6.85 (br s, 3H), 6.92 (s, 2H), 7.87 (s, 1H); MS Calcd.: 378; MS Found: 379 (M + H). |

TABLE 6-continued

| Example | Structure | Name | Physical Data |
|---|---|---|---|
| 87 | 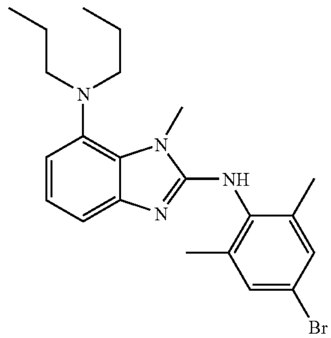 | $N^2$-(4-bromo-2,6-dimethylphenyl)-1-methyl-$N^7,N^7$-dipropyl-1H-benzimidazole-2,7-diamine | MS Calcd.: 428; MS Found: 429 (M + H) |
| 88 | 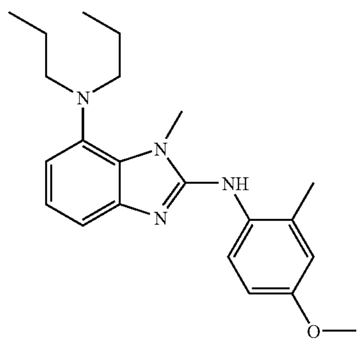 | $N^2$-(4-methoxy-2-methylphenyl)-1-methyl-$N^7,N^7$-dipropyl-1H-benzimidazole-2,7-diamine | MS Calcd.: 366; MS Found: 367 (M + H) |
| 89 | 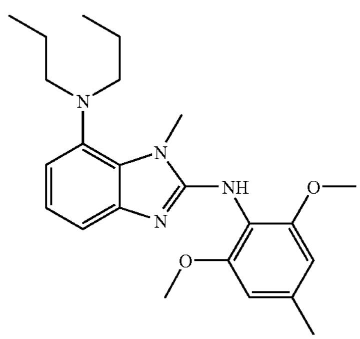 | $N^2$-(2,6-dimethoxy-4-methylphenyl)-1-methyl-$N^7,N^7$-dipropyl-1H-benzimidazole-2,7-diamine | MS Calcd.: 396; MS Found: 397 (M + H) |
| 90 | 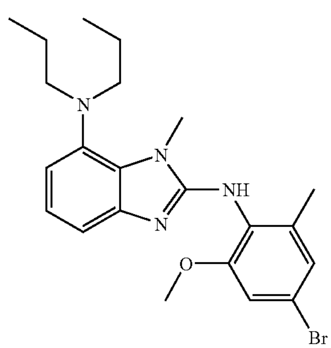 | $N^2$-(4-bromo-2-methoxy-6-methylphenyl)-1-methyl-$N^7,N^7$-dipropyl-1H-benzimidazole-2,7-diamine | MS Calcd.: 444; MS Found: 445 (M + H) |

TABLE 6-continued

| Example | Structure | Name | Physical Data |
|---|---|---|---|
| 91 | 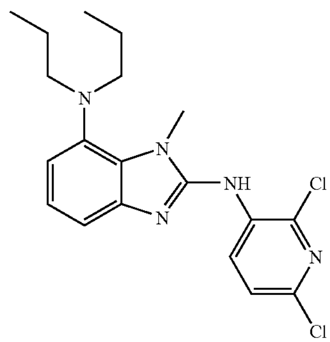 | $N^2$-(2,6-dichloropyridin-3-yl)-1-methyl-$N^7$,$N^7$-dipropyl-1H-benzimidazole-2,7-diamine | MS Calcd.: 391; MS Found: 392 (M + H) |
| 92 | 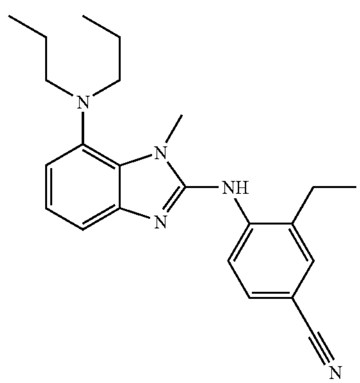 | 4-{[7-(dipropylamino)-1-methyl-1H-benzimidazol-2-yl]amino}-3-ethylbenzonitrile | MS Calcd.: 375; MS Found: 376 (M + H) |
| 93 | 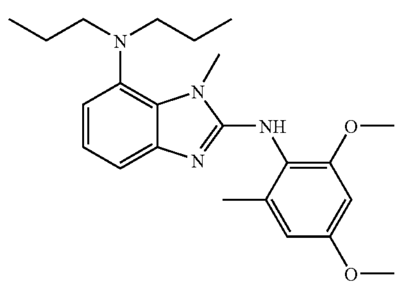 | $N^2$-(2,4-dimethoxy-6-methylphenyl)-1-methyl-$N^7$,$N^7$-dipropyl-1H-benzimidazole-2,7-diamine | $^1$H NMR (CD$_3$OD) δ (HCl salt) 0.91 (br s, 6H), 1.53 (br s, 4H), 2.32 (s, 3H), 3.12 (br s, 4H), 3.82 (s, 3H), 3.86 (s, 3H), 4.21 (s, 3H), 6.60 (br s, 2H), 7.07 (br s, 1H), 7.24 (br s, 2H); MS Calcd.: 396; MS Found: 397 (M + H). |
| 94 | 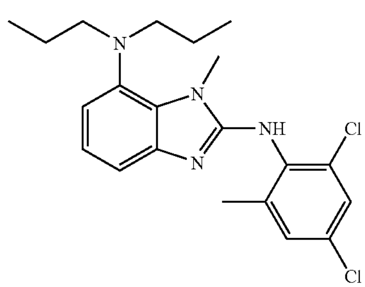 | $N^2$-(2,4-dichloro-6-methylphenyl)-1-methyl-$N^7$,$N^7$-dipropyl-1H-benzimidazole-2,7-diamine | $^1$H NMR (CD$_3$OD) δ (HCl salt) 0.91 (br s, 6H), 1.53 (br s, 4H), 2.42 (s, 3H), 3.10 (br s, 4H), 4.28 (s, 3H), 7.09 (d, 1H, J = 5.5 Hz), 7.27 (br s, 2H), 7.52 (br s, 1H), 7.63 (br s, 1H); MS Calcd.: 404; MS Found: 405 (M + H). |

TABLE 6-continued

| Example | Structure | Name | Physical Data |
|---|---|---|---|
| 95 | 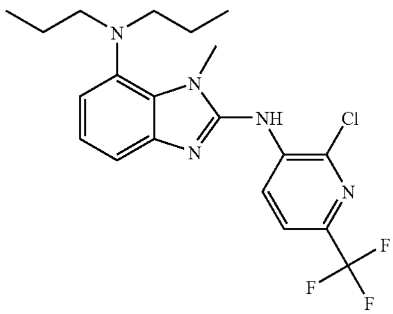 | $N^2$-[2-chloro-6-(trifluoromethyl)pyridin-3-yl]-1-methyl-$N^7$,$N^7$-dipropyl-1H-benzimidazole-2,7-diamine | $^1$H NMR (CD$_3$OD) δ (HCl salt) 0.91 (br s, 6H), 1.54 (br s, 4H), 3.12 (br s, 4H), 4.31 (s, 3H), 7.17 (br s, 1H), 7.32 (br s, 2H), 8.03 (br s, 1H), 8.33 (br s, 1H); MS Calcd.: 425; MS Found: 426 (M + H). |
| 96 | 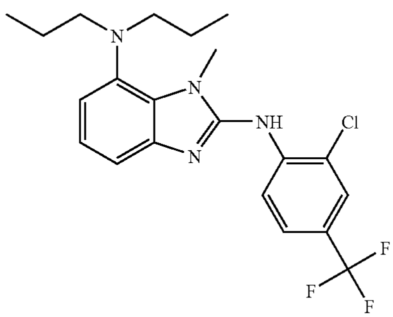 | $N^2$-[2-chloro-4-(trifluoromethyl)phenyl]-1-methyl-$N^7$,$N^7$-dipropyl-1H-benzimidazole-2,7-diamine | $^1$H NMR (CD$_3$OD) δ (HCl salt) 0.92 (br s, 6H), 1.54 (br s, 4H), 3.14 (br s, 4H), 4.29 (s, 3H), 7.17 (d, 1H, 4.7 Hz), 7.32 (br s, 2H), 7.87 (br s, 2H), 8.06 (s, 1H); MS Calcd.: 424; MS Found: 425 (M + H). |
| 97 | 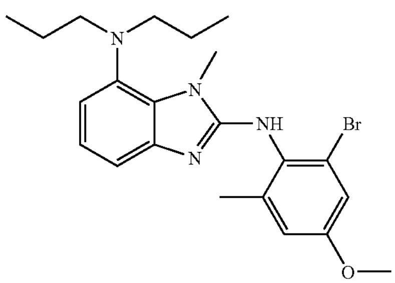 | $N^2$-(2-bromo-4-methoxy-6-methylphenyl)-1-methyl-$N^7$,$N^7$-dipropyl-1H-benzimidazole-2,7-diamine | $^1$H NMR (CD$_3$OD) δ (HCl salt) 0.90 (br s, 6H), 1.53 (br s, 4H), 2.39 (s, 3H), 3.10 (br s, 4H), 3.87 (s, 3H), 4.26 (s, 3H), 7.04 (s, 1H), 7.08 (d, 1H, J = 5.2 Hz), 7.25 (br s, 3H); MS Calcd.: 444; MS Found: 445 (M + H); |
| 98 | 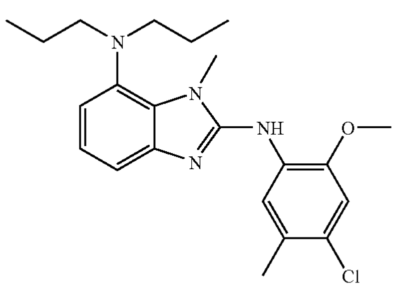 | $N^2$-(4-chloro-2-methoxy-5-methylphenyl)-1-methyl-$N^7$,$N^7$-dipropyl-1H-benzimidazole-2,7-diamine | $^1$H NMR (CD$_3$OD) δ (HCl salt) 0.91 (br s, 6H), 1.53 (br s, 4H), 2.37 (s, 3H), 3.22 (br s, 4H), 3.87 (s, 3H), 4.21 (s, 3H), 7.19 (br s, 1H), 7.28 (s, 1H), 7.33 (br s, 2H), 7.41 (br s, 1H); MS Calcd.: 400; MS. Found: 401 (M + H). |

TABLE 6-continued

| Example | Structure | Name | Physical Data |
|---|---|---|---|
| 99 | 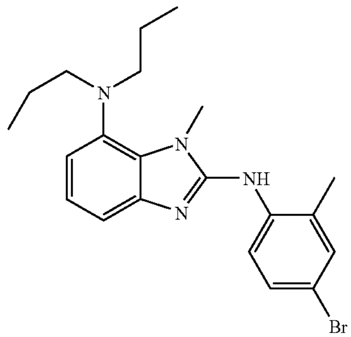 | $N^2$-(4-bromo-2-methylphenyl)-1-methyl-$N^7$,$N^7$-dipropyl-1H-benzimidazole-2,7-diamine | $^1$H NMR (CDCl$_3$) δ (HCl salt) 0.83 (br s, 6H), 1.44-1.50 (m, 4H), 2.32 (s, 3H), 2.98 (br s, 4H), 4.00 (br s, 3H), 5.89 (s, 1H), 6.95 (d, 1H, J = 7.8 Hz), 7.08 (br s, 1H), 7.33 (br s, 3H), 7.73 (br s, 1H); MS Calcd.: 414; MS Found: 415 (M + H). |
| 100 | 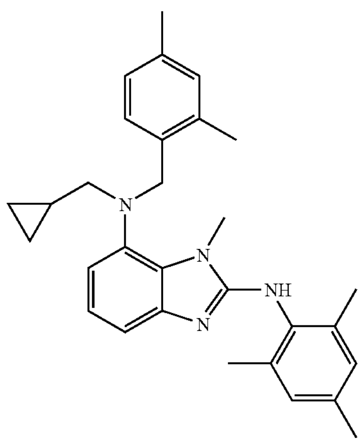 | $N^7$-(cyclopropylmethyl)-$N^7$-(2,4-dimethylbenzyl)-$N^2$-mesityl-1-methyl-1H-benzimidazole-2,7-diamine | $^1$H NMR (DMSO-d$_6$) δ (HCl salt) 0.04 (s, 2H), 0.43 (d, 2H, J = 7.4 Hz), 0.97 (br s, 1H), 2.16 (s, 6H), 2.20 (s, 3H), 2.31 (s, 3H), 2.32 (s, 3H), 2.97 (br s, 2H), 4.02 (br s, 3H), 4.27 (br s, 2H), 6.84 (d, 1H, J = 7.8 Hz), 6.97-7.02 (m, 3H), 7.10 (s, 2H), 7.21 (t, 1H, J = 7.9 Hz), 7.38 (d, 1H, J = 8.0 Hz), 10.23 (s, 1H); MS Calcd.: 452; MS Found: 453 (M + H). |
| 101 | 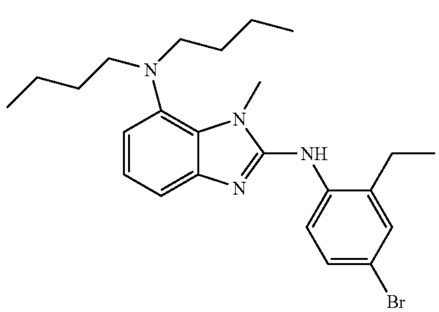 | $N^2$-(4-bromo-2-ethylphenyl)-$N^7$,$N^7$-dibutyl-1-methyl-1H-benzimidazole-2,7-diamine | $^1$H NMR (CDCl$_3$) δ (HCl salt) 0.85-0.88 (m, 6H), 1.22-1.34 (m, 7H), 1.40-1.47 (m, 4H), 2.68 (q, 2H, J = 7.5 Hz), 3.01 (br s, 4H), 3.96 (s, 3H), 6.01 (s, 1H), 6.81 (d, 1H, J = 7.8 Hz), 7.09 (t, 1H, J = 7.0 Hz), 7.32-7.34 (m, 3H), 7.66 (s, 1H); MS Calcd.: 456; MS Found: 457 (M + H). |

TABLE 6-continued

| Example | Structure | Name | Physical Data |
|---|---|---|---|
| 102 | 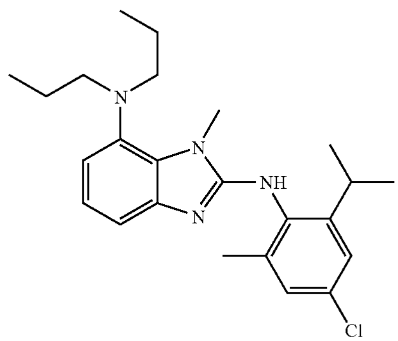 | $N^2$-(4-chloro-2-isopropyl-6-methylphenyl)-1-methyl-$N^7,N^7$-dipropyl-1H-benzimidazole-2,7-diamine | $^1$H NMR (DMSO-$d_6$) δ (HCl salt) 0.85 (t, 6H, J = 7.3 Hz), 1.07-1.14 (m, 4H), 1.19 (d, 3H, J = 6.6 Hz), 1.40-1.50 (m, 4H), 2.23 (s, 3H), 3.02 (br s, 4H), 4.15 (s, 3H), 7.01 (d, 1H, J = 7.2 Hz), 7.15-7.19 (m, 2H), 7.42 (s, 2H), 10.49 (s, 1H); MS Calcd.: 412; MS Found: 413 (M + H). |
| 103 | 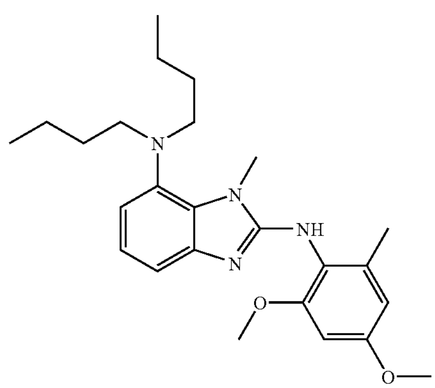 | $N^7,N^7$-dibutyl-$N^2$-(2,4-dimethoxy-6-methylphenyl)-1-methyl-1H-benzimidazole-2,7-diamine | $^1$H NMR (DMSO-$d_6$) δ (HCl salt) 0.80-0.87 (m, 6H), 1.21-1.30 (m, 4H), 1.34-1.41 (m, 4H), 2.25 (s, 3H), 3.04 (s, 4H), 3.76 (s, 3H), 3.83 (s, 3H), 4.07 (s, 3H), 6.62 (s, 1H), 6.65 (s, 1H), 7.01 (d, 1H, J = 7.4 Hz), 7.14-7.21 (m, 2H), 9.99 (s, 1H); MS Calcd.: 424; MS Found: 425 (M + H). |
| 104 | 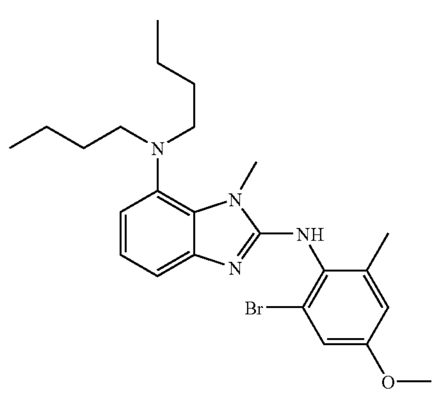 | $N^2$-(2-bromo-4-methoxy-6-methylphenyl)-$N^7,N^7$-dibutyl-1-methyl-1H-benzimidazole-2,7-diamine | $^1$H NMR (DMSO-$d_6$) δ (HCl salt) 0.85 (t, 6H, J =7.3 Hz), 1.21-1.30 (m, 4H), 1.41 (br s, 4H), 2.34 (s, 3H), 3.05 (br s, 4H), 3.84 (s, 3H), 4.13 (s, 3H), 7.05 (d, 1H, J = 7.4 Hz), 7.09 (s, 1H), 7.16-7.24 (m, 2H), 7.29 (s, 1H), 10.76 (s, 1H); MS Calcd.: 472; MS Found: 473 (M + H). |

TABLE 6-continued

| Example | Structure | Name | Physical Data |
|---|---|---|---|
| 105 | 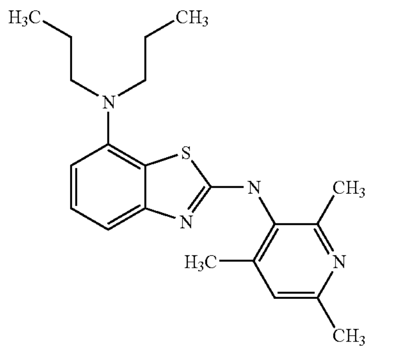 | N[7],N[7]-dipropyl-N[2]-(2,4,6-trimethylpyridin-3-yl)-1,3-benzothiazole-2,7-diamine | $^1$H NMR (CDCl$_3$) δ 0.81 (t, 6H, J = 7.5 Hz), 1.36-1.47 (m, 4H), 2.34 (s, 3H), 2.56 (s, 3H), 2.58 (s, 3H), 3.01-3.05 (m, 4H), 6.74 (d, 1H, J = 7.2 Hz), 6.98 (d, 1H, J = 7.2 Hz), 7.02 (s, 1H), 7.17 (t, 1H, J = 8.0 Hz); MS Calcd.: 368; Found: 369 (M + H). |
| 106 | 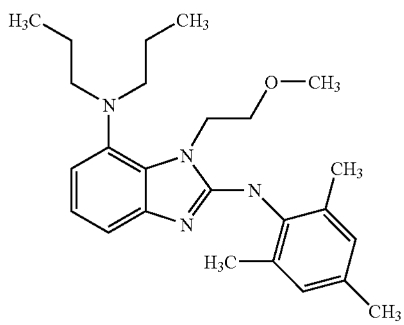 | N[2]-mesityl-1-(2-methoxyethyl)-N[7],N[7]-dipropyl-1H-benzimidazole-2,7-diamine | $^1$H NMR (CDCl$_3$) δ 0.85 (t, 6H, J = 7.5 Hz), 1.43-1.55 (m, 4H), 2.19 (s, 6H), 2.27 (s, 3H), 2.90-2.96 (m, 4H), 3.43 (s, 3H), 3.83 (t, 2H, J =4.3 Hz), 4.83 (t, 2H, J = 4.3 Hz), 6.89-6.92 (m, 3H), 6.99 (t, 1H, J = 7.8 Hz), 7.28 (d, 1H, J = 8.0 Hz); MS Calcd.: 408; Found: 409 (M + H). |
| 107 | 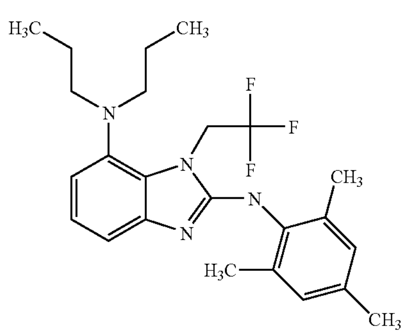 | N[2]-mesityl-N[7],N[7]-dipropyl-1-(2,2,2-trifluoroethyl)-1H-benzimidazole-2,7-diamine | $^1$H NMR (CDCl$_3$) δ 0.85 (t, 6H, J = 7.2 Hz), 1.42-1.55 (m, 4H), 2.18 (s, 6H), 2.28 (s, 3H), 2.85-2.98 (m, 4H), 5.36-5.45 (m, 2H), 6.92 (s, 2H), 6.99 (d, 1H, J = 7.8 Hz), 7.07 (t, 1H, J = 7.8 Hz), 7.29 (d, 1H, J = 7.5 Hz); MS Calcd.: 432; Found: 433 (M + H). |

TABLE 6-continued

| Example | Structure | Name | Physical Data |
|---|---|---|---|
| 108 | 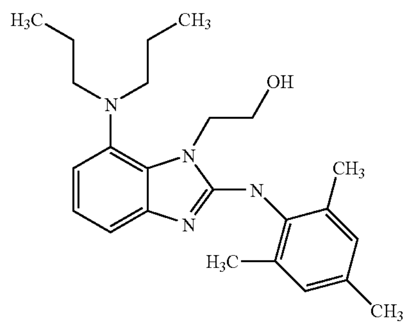 | 2-[7-(dipropylamino)-2-(mesitylamino)-1H-benzimidazol-1-yl]ethanol | $^1$H NMR (CDCl$_3$) δ 0.85 (t, 6H, J = 7.5 Hz), 1.42-1.54 (m, 4H), 2.18 (s, 6H), 2.25 (s, 3H), 2.88-2.96 (m, 4H), 4.03 (t, 2H, J = 4.0 Hz), 4.73 (br. s, 2H), 6.86-6.92 (m, 3H), 6.94-7.00 (m, 1H), 7.22-7.32 (m, 1H),; MS Calcd.: 394; Found: 395 (M + H). |
| 109 | 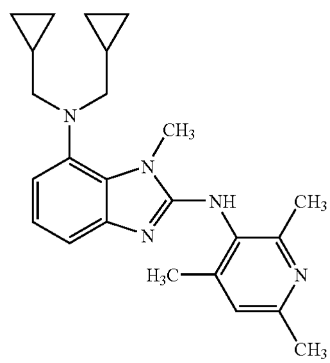 | N$^7$,N$^7$-bis(cyclopropylmethyl)-1-methyl-N$^2$-(2,4,6-trimethylpyridin-3-yl)-1H-benzimidazole-2,7-diamine | $^1$H NMR (CDCl$_3$) δ 0.04-0.07 (m, 4H), 0.38-0.42 (m, 4H), 0.84-0.88 (m, 2H), 2.27 (s, 3H), 2.39 (s, 3H), 2.43 (s, 3H), 2.82-3.08 (m, 4H), 3.99 (s, 3H), 6.92 (s, 1H), 6.98-7.09 (m, 3H),; MS Calcd.: 389; Found: 390 (M + H). |
| 110 | 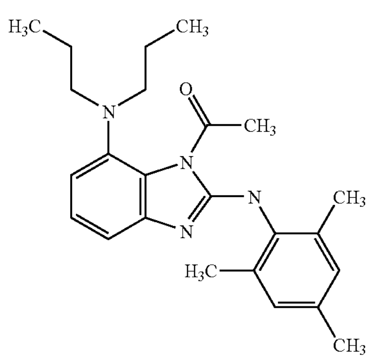 | 1-acetyl-N$^2$-mesityl-N$^7$,N$^7$-dipropyl-1H-benzimidazole-2,7-diamine | $^1$H NMR (CDCl$_3$) δ[ 0.63 (t, J = 7.5 Hz), 0.97 (t, J = 7.5 Hz), 6H, rotamer], [1.44-1.53 (m), 1.58-1.64 (m), 4H, rotamer], 1.95 (s, 3H), [2.09 (s), 2.14(s), 6H, rotamer], [2.35 (s), 2.33 (s), 3H, rotamer], [3.13-3.18 (m), 3.28-3.34 (m), 4H, rotamer], [6.26 (d, J = 8.0 Hz), 6.76 (d, J = 8.0 Hz), 1H, rotamer], 6.97-7.09 (m, 3H), [6.72 (d, J = 7.8 Hz), 7.22 (d, J = 7.8 Hz), 1H, rotamer]; MS Calcd.: 392; Found: 393 (M + H). |

TABLE 6-continued

| Example | Structure | Name | Physical Data |
|---|---|---|---|
| 111 | 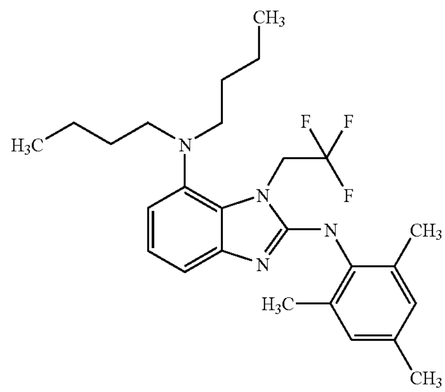 | $N^7,N^7$-dibutyl-$N^2$-mesityl-1-(2,2,2-trifluoroethyl)-1H-benzimidazole-2,7-diamine | $^1$H NMR (CDCl$_3$) δ 0.89 (t, 6H, J = 7.2 Hz), 1.21-1.30 (m, 4H), 1.37-1.50 (m, 4H), 2.19 (s, 6H), 2.28 (s, 3H), 2.88-2.99 (m, 4H), 5.35-5.43 (m, 2H), 6.93 (s, 2H), 6.99 (d, 1H, J = 7.5 Hz), 7.07 (t, 1H, J = 7.8 Hz), 7.29 (d, 1H, J = 7.2 Hz); MS Calcd.: 460; Found: 461 (M + H). |
| 112 | 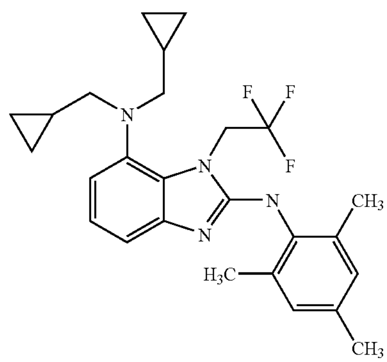 | $N^7,N^7$-bis(cyclopropylmethyl)-$N^2$-mesityl-1-(2,2,2-trifluoroethyl)-1H-benzimidazole-2,7-diamine | $^1$H NMR (CDCl$_3$) δ 0.02-0.14 (m, 4H), 0.33-0.48 (m, 4H), 0.80-0.85 (m, 2H), 2.17 (s, 6H), 2.27 (s, 3H), 2.74-2.82 (m, 2H), 3.00-3.05 (m, 2H), 5.52-5.62 (m, 2H), 6.91 (s, 2H), 7.01-7.06 (m, 2H), 7.29 (br, s, 1H); MS Calcd.: 456; Found: 457 (M + H). |

Example 113

4-Bromo-$N^2$-mesityl-1-methyl-$N^7,N^7$-dipropyl-1H-benzimidazole-2,7-diamine

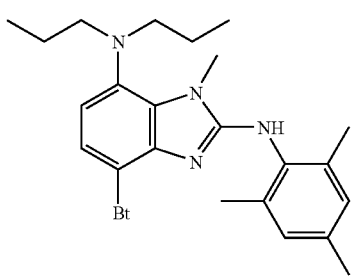

4-Bromo-7-dipropylamino-1-methyl-1,3-dihydro-2H-benzimidazol-2-one

A mixture of 7-dipropylamino-1-methyl-1,3-dihydro-2H-benzimidazol-2-one (200 mg, 0.809 mmol), N-bromosuccinimide (216 mg, 1.21 mmol) and catalytic amount of benzoylperoxide in carbon tetrachloride (20 ml) was refluxed for 60 h and diluted with water. The aqueous solution was extracted with dichloromethane. The extract was washed with brine, dried over magnesium sulfate and concentrated under vacuum. The residue was purified by column chromatography eluting 30% ethyl acetate/n-hexane to afford 73 mg (28%) of the title compound.

$^1$H-NMR (CDCl$_3$) δ 0.84 (6H, t, J=7.2 Hz), 1.35-1.48 (4H, m), 2.85-2.95 (4H, m), 3.71 (3H, s), 6.81 (1H, d, J=8.4 Hz), 7.09 (1H, d, J=8.4 Hz), 7.82 (1H, s).

MS Calcd.: 325. Found: 326 (M+H), 328.

4-Bromo-2-chloro-1-methyl-N,N-dipropyl-1H-benzimidazol-7-amine

A mixture of 4-bromo-7-dipropylamino-1-methyl-1,3-dihydro-2H-benzimidazol-2-one (210 mg, 0.644 mmol) and phosphorus oxychloride (3.0, 32 mol) was refluxed for 18 h with stirring and concentrated to dryness under vacuum. The residue was diluted with water. The aqueous solution was extracted with dichloromethane. The extract was washed with water, dried over magnesium sulfate and concentrated under vacuum to afford 220 mg (99%) of the title compound. The residue was used for the next reaction without further purification.

¹H-NMR (DMSO-d₆) δ 0.80 (6H, t, J=7.2 Hz), 1.35-1.45 (4H, m), 2.97 (4H, m), 4.08 (3H, s), 7.05 (1H, d, J=8.0 Hz), 7.38 (1H, d, J=8.0 Hz).

MS Calcd.: 343. Found: 344 (M+H), 346.

4-Bromo-N²-mesityl-1-methyl-N⁷,N⁷-dipropyl-1H-benzimidazole-2,7-diamine

A mixture of 4-bromo-2-chloro-1-methyl-N,N-dipropyl-1H-benzimidazol-7-amine (220 mg, 0.638 mmol) and mesityl amine (1.79 ml, 12.8 mmol) was heated at 120° C. for 60 h. The mixture was dissolved in ethyl acetate and washed with saturated sodium bicarbonate in water, dried over magnesium sulfate and concentrated under vacuum. The residue was purified by column chromatography eluting 5% n-hexane/ethyl acetate to afford the title compound.

¹H-NMR (CDCl₃) δ 0.80 (6H, t, J=7.2 Hz), 1.42 (4H, q, J=7.2 Hz), 2.20 (6H, s), 2.30 (3H, s), 2.91 (4H, m), 3.53 (3H, s), 6.05 (1H, s), 6.71 (1H, d, J=8.4 Hz), 6.91 (2H, s), 7.19 (1H, d, J=8.4 Hz).

MS Calcd.: 442. Found: 443 (M+H), 445.

Compounds of Examples 114-117 shown in Table 7 were prepared in a similar manner to that described previously in Example 1.

TABLE 7

| Example | Structure | Name | Physical Data |
|---|---|---|---|
| 114 | 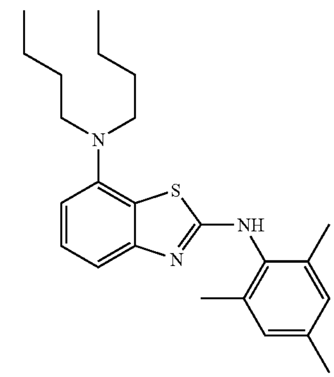 | N⁷,N⁷-dibutyl-N²-mesityl-1,3-benzothiazole-2,7-diamine | MS Calcd.: 395; MS Found: 396 (M + H) |
| 115 | 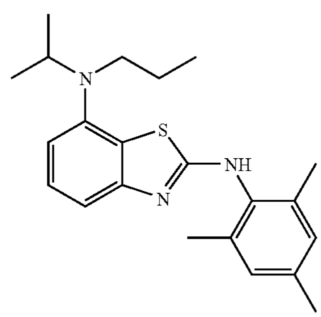 | N⁷-isopropyl-N²-mesityl-N⁷-propyl-1,3-benzothiazole-2,7-diamine | MS Calcd.: 367; MS Found: 368 (M + H) |
| 116 | 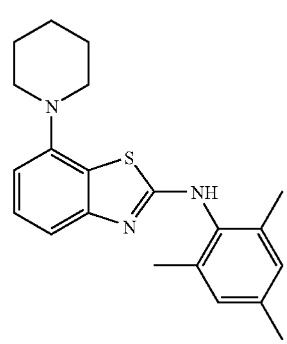 | N-mesityl-7-(1-piperidinyl)-1,3-benzothiazol-2-amine | MS Calcd.: 351; MS Found: 352 (M + H). |

TABLE 7-continued

| Example | Structure | Name | Physical Data |
|---|---|---|---|
| 117 | 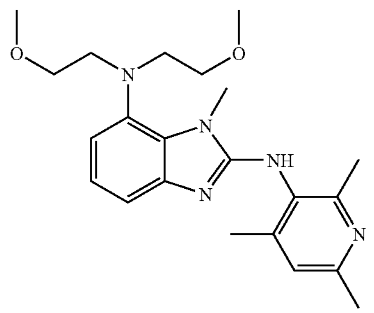 | $N^2$-(2,4,6-trimethylpyridin-3-yl)-1-methyl-$N^7$, $N^7$-di(2-methoxyethyl)-1H-benzimidazole-2,7-diamine hydrochloride | $^1$H NMR (CDCl$_3$) δ 2.27 (s, 4H), 2.61 (s, 4H), 3.13 (br s, 3H), 3.17 (br s, 3H), 3.28 (br d, J = 31 Hz, 9H), 3.60 (br s, 3H), 7.17 (br s, 3H), 7.55 (br s, 1H); MS Calcd.: 397; Found: 398 (M + H) |

Compounds of Examples 118-122, shown in Table 8, were prepared in a manner similar to that described in Example 1.

TABLE 8

| Example | Structure | Name | Physical Data |
|---|---|---|---|
| 118 | 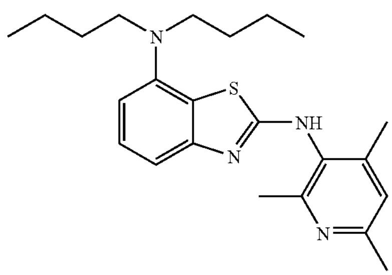 | $N^7,N^7$-dibutyl-$N^2$-(2,4,6-trimethylpyridin-3-yl)-1,3-benzothiazole-2,7-diamine | $^1$H-NMR (CDCl$_3$) δ 0.82 (6H, t, J=7.24 Hz), 1.20-1.27 (4H, m), 1.34-1.42 (4H, m), 2.33 (3H, s), 2.55 (3H, s), 2.57 (3H, s), 3.04-3.08 (4H, m), 6.73 (1H, d, J=7.78 Hz), 7.00-7.03 (2H, m), 7.18 (1H, t, J=8.05 Hz); S Calcd.: 396; Found: 397 (M + H). |
| 119 | 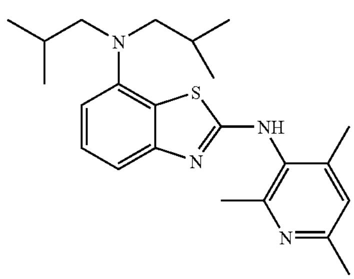 | $N^7,N^7$-diisobutyl-$N^2$-(2,4,6-trimethylpyridin-3-yl)-1,3-benzothiazole-2,7-diamine | $^1$H-NMR (CDCl$_3$) δ 0.81 (12H, t, J=6.76 Hz), 1.69-1.77 (2H, m), 2.33 (3H, s), 2.56 (3H, s), 2.58 (3H, s), 2.88 (4H, d, J=7.24 Hz), 6.76 (1H, d, J=7.78 Hz), 6.92-7.01 (2H, m), 7.6 (1H, t, J=7.78 Hz); MS Calcd.:396; Found: 397 (M + H). |

TABLE 8-continued

| Example | Structure | Name | Physical Data |
|---|---|---|---|
| 120 | 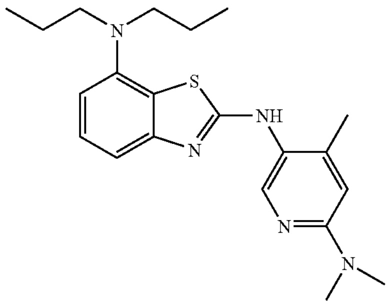 | $N^2$-[6-(dimethylamino)-4-methylpyridin-3-yl]-$N^7,N^7$-dipropyl-1,3-benzothiazole-2,7-diamine | $^1$H-NMR (CDCl$_3$)δ 0.88 (6H, t, J=7.24 Hz), 1.37-1.46 (4H, m), 2.29 (3H, s), 3.01-3.05 (4H, m), 3.13 (6H, s), 6.44 (1H, s), 6.73 (18, d, J=8.05 Hz), 7.06 (1H, d, J=8.05 Hz), 7.17, (1H, t, J=7.78 Hz) 8.22 (1H, s); MS Calcd.: 383; Found: 384 (M + H). |
| 121 | 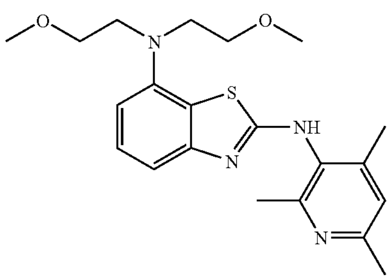 | $N^7,N^7$-bis(2-methoxyethyl)-$N^2$-(2,4,6-trimethylpyridin-3-yl)-1,3-benzothiazole-2,7-diamine | $^1$H-NMR (CDCl$_3$)δ 2.31 (3H, s), 2.54 (6H, s), 3.24 (6H, s), 3.38 (8H, s), 6.85 (1H, d, J=7.78 Hz), 6.99 (1H, s), 7.14 (1H, d, J=8.05 Hz), 7.23 (1H, t, J=7.78 Hz); MS Calcd.: 400; Found: 401 (M + H). |
| 122 | 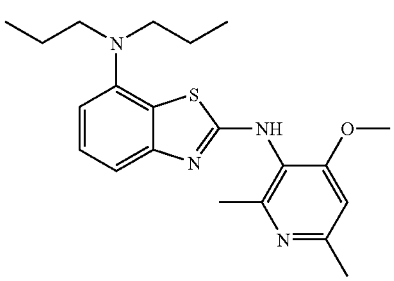 | $N^7$-(4-methoxy-2,6-dimethylpyridin-3-yl)-$N^7,N^7$-dipropyl-1,3-benzothiazole-2,7-diamine | $^1$H-NMR (CDCl$_3$)δ 0.82 (6H, t, J=7.24 Hz), 1.38-1.48 (4H, m), 2.55 (3H, s), 2.56 (3H, s), 3.03 (4H, t, J=7.24 Hz), 3.81 (3H, s), 6.65 (1H, s), 6.74 (1H, d, J=7.78 Hz), 7.13 (1H, d, J=8.05 Hz), 7.19 (1H, t, J=7.78 Hz); MS Calcd.: 384; Found: 385 (M + H). |

Example 123

N²-(4-Bromo-2-methoxy-6-methylphenyl)-N⁷,N⁷-bis(2-methoxyethyl)-1-methyl-1H-benzimidazole-2,7-diamine

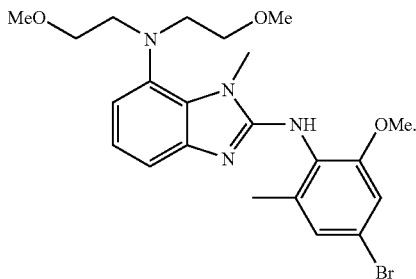

To a solution of 200 mg (1.66 mmol) of 1,1,3-trimethoxypropane in 25 mL of chloroform was added 5 g (1.66 mmol) of iron (II) chloride on silica (5% by weight) and the slurry was stirred at room temperature for several hours. The slurry was filtered, concentrated in vacuo to about 5 mL and added to a slurry of 200 mg (0.55 mmol) of N²-(4-bromo-2-methoxy-6-methylphenyl)-1-methyl-1H-benzimidazole-2,7-diamine, 1 mL of acetic acid and 2.5 g (5.08 mmol) of MP-CNBH$_3$ in 10 mL of methanol and was stirred overnight. The above aldehyde preparation was repeated each day for 7 days and added to the reaction. The reaction was filtered and concentrated in vacuo to a residue. The residue was purified by flash chromatography eluting with a solution of 40% ethyl acetate/hexanes containing 2% ammonium hydroxide to give 47 mg (18%) of the title compound.

$^1$H NMR (CDCl$_3$) δ 2.19 (s, 3H), 3.28 (s, 6H), 3.33 (br s, 4H), 3.41 (br s, 4H), 3.82 (s, 3H), 4.06 (s, 3H), 5.85 (s, 1H), 6.92-6.97 (m, 2H), 7.02-7.04 (m, 2H), 7.30 (d, J=7.7 Hz, 1H); MS Calcd.: 476. Found: 477 (M+H).

Compounds described below were prepared in a similar method.

TABLE 9

| Example | Structure | Name | Physical Data |
|---|---|---|---|
| 124 | 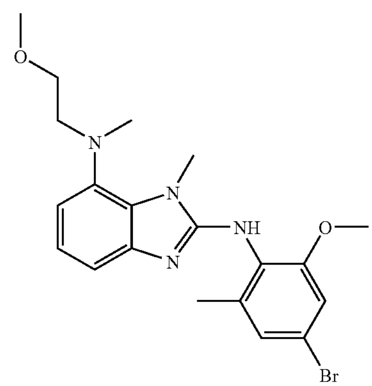 | N²-(4-bromo-2-methoxy-6-methylphenyl)-N⁷-(2-methoxyethyl)-N⁷,1-dimethyl-1H-benzimidazole-2,7-diamine | $^1$H NMR (CDCl$_3$) δ 2.18 (s, 3H), 2.80 (s, 3H), 3.23 (br s, 2H), 3.33 (s, 3H), 3.51 (t, J = 5.8 Hz, 2H), 3.82 (s, 3H), 4.05 (s, 3H), 5.88 (s, 1H), 6.90-6.92 (m, 2H), 7.01-7.04 (m, 2H), 7.26 (br s, 1H); MS Calcd.: 432; MS Found: 433 (M + H). |
| 125 | 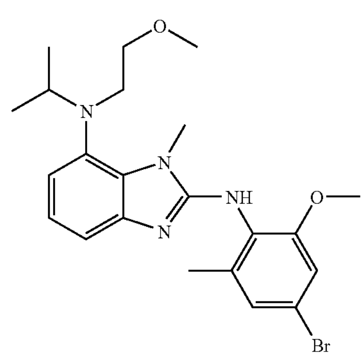 | N²-(4-bromo-2-methoxy-6-methylphenyl)-N⁷-isopropyl-N⁷-(2-methoxyethyl)-1-methyl-1H-benzimidazole-2,7-diamine | MS Calcd.: 460; MS Found: 461 (M + H). |

Example 126

4-[[2-[(4-Bromo-2-methoxy-6-methylphenylamino)-1-methyl-1H-benzimidazol-7-yl](isopropyl)amino]butanoic acid

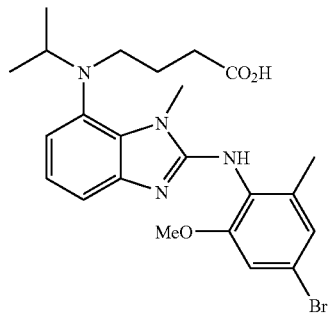

To a solution of 100 mg (0.20 mmol) of methyl 4-[[2-(4-bromo-2-methoxy-6-methylphenyl)amino]-1-methyl-1H-benzimidazol-7-yl](isopropyl)amino/butanoate in 5 mL of tetrahydrofuran and 2.5 mL of water was added 83 mg (2.0 mmol) of lithium hydroxide monohydrate. The reaction was stirred at room temperature overnight. The solvent was removed in vacuo and the residue was diluted with water and carefully adjusted to pH 7 using 1N aqueous hydrochloric acid and the resulting slurry was filtered. The solids were washed with water, and dried under high vacuum to give 95 mg (98%) of the title compound.

MS Calcd.: 488. MS Found: 489 (M+H).

Example 127

4-[[2-[(4-Bromo-2-methoxy-6-methylphenyl)amino]-1-methyl-1H-benzimidazol-7-yl](isopropyl)amino]-N-methylbutanamide

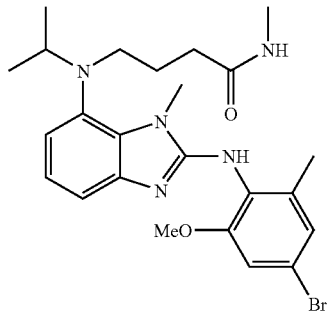

To a solution of 25 mg (0.050 mmol) of 4-[[2-[(4-bromo-2-methoxy-6-methylphenylamino)-1-methyl-1H-benzimidazol-7-yl](isopropyl)amino]butanoic acid, 0.044 mL (0.26 mmol) of diisopropylethylamine, and 58 mg (0.15 mmol) of O-(7-azabenzotriazol-1-yl)-N,N,N',N',-tetramethyluronium hexafluorophosphate (HATU) was added 0.128 mL (0.26 mmol) of methylamine (2M solution in tetrahydrofuran). The reaction was stirred overnight at room temperature and concentrated in vacuo. The residue thus obtained was purified by flash chromatography eluting with a solution of 8% methanol/dichloromethane to give 42 mg (82%) of the title compound.

MS Calcd.: 501. MS Found: 502 (M+H).

Compounds described below were prepared in a similar method.

TABLE 10

| Example | Structure | Name | Physical Data |
|---|---|---|---|
| 128 | 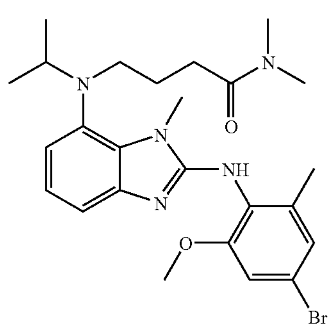 | 4-[[2-[(4-bromo-2-methoxy-6-methylphenyl)amino]-1-methyl-1H-benzimidazol-7-yl](isopropyl)amino]-N,N-dimethylbutanamide | MS Calcd.: 515; MS Found: 516 (M + H). |

TABLE 10-continued

| Example | Structure | Name | Physical Data |
|---|---|---|---|
| 129 | 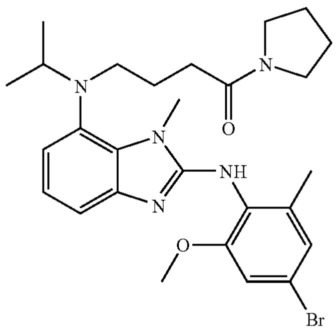 | $N^2$-(4-bromo-2-methoxy-6-methylphenyl)-$N^7$-isopropyl-1-methyl-$N^7$-(4-oxo-4-pyrrolidin-1-ylbutyl)-1H-benzimidazole-2,7-diamine | $^1$H NMR (CDCl$_3$) δ 1.06 (d, J = 5.8 Hz, 3H), 1.17 (d, J = 6.3 Hz, 3H), 1.76-1.89 (m, 6H), 2.19 (br s, 5H), 3.06-3.10 (m, 1H), 3.18-3.21 (m, 3H), 3.31-3.37 (m, 1H), 3.41 (t, J = 6.7 Hz, 2H), 3.82 (s, 3H), 4.08 (s, 3H), 5.86 (s, 1H), 6.92-6.95 (m, 2H), 6.99-7.04 (m, 2H), 7.26 (b s, 1H); MS Calcd.: 541; MS Found: 542 (M + H). |
| 130 | 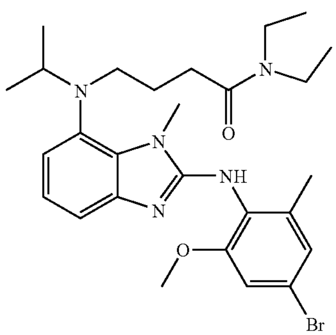 | 4-[[2-[(4-bromo-2-methoxy-6-methylphenyl)amino]-1-methyl-1H-benzimidazol-7-yl](isopropyl)amino]-N,N-diethylbutanamide | $^1$H NMR (CDCl$_3$) δ 1.01-1.08 (m, 9H), 1.18 (d, J = 5.8 Hz, 3H), 1.76-1.80 (m, 2H), 2.19 (s, 3H), 2.21-2.25 (m, 2H), 3.02-3.24 (m, 4H), 3.29-3.82 (s, 3H), 4.08 (s, 3H), 5.83 (br s, 1H), 6.92 6.94 (m, 2H), 6.99-7.04 (m, 2H), 7.26 (br s, 1H); MS Calcd.: 543; MS Found: 544 (M + H). |
| 131 | 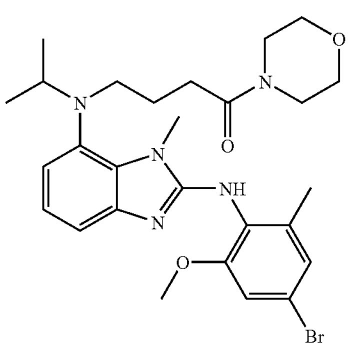 | $N^2$-(4-bromo-2-methoxy-6-methylphenyl)-$N^7$-isopropyl-1-methyl-$N^7$-(4-morpholin-4-yl-4-oxobutyl)-1H-benzimidazole-2,7-diamine | $^1$H NMR (CDCl$_3$) δ 1.07 (d, J = 5.8 Hz, 3H), 1.18 (d, J = 5.8 Hz, 3H), 1.58 (s, 3H), 1.73-1.79 (m, 2H), 2.20 (s, 3H), 2.23-2.33 (m, 2H), 3.01-3.08 (m, 1H), 3.14-3.21 (m, 3H), 3.31-3.38 (m, 1H), 3.46-3.53 (m, 3H), 3.83 (s, 3H), 4.08 (s, 3H), 5.84 (br s, 1H), 6.91-6.93 (m, 2H), 7.01 (t, J = 5.8 Hz, 1H), 7.05 (s, 1H), 7.26 (br s, 1H); MS Calcd.: 557; MS Found: 558 (M + H). |

TABLE 10-continued

| Example | Structure | Name | Physical Data |
|---|---|---|---|
| 132 | 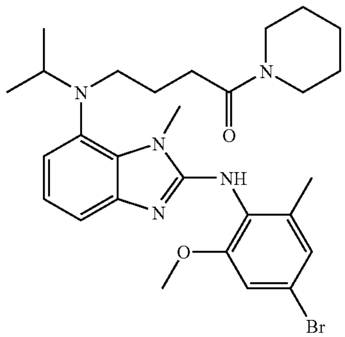 | $N^2$-(4-bromo-2-methoxy-6-methylphenyl)-$N^7$-isopropyl-1-methyl-$N^7$-(4-oxo-4-piperidin-1-ylbutyl)-1H-benzimidazole-2,7-diamine | MS Calcd.: 555; MS Found: 556 (M + H). |
| 133 | 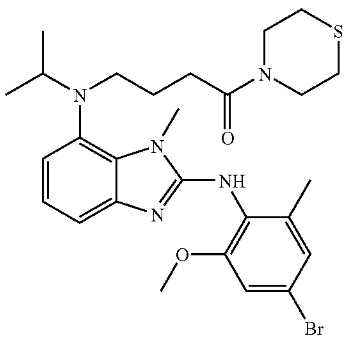 | $N^2$-(4-bromo-2-methoxy-6-methylphenyl)-$N^7$-isopropyl-1-methyl-$N^7$-(4-oxo-4-thiomorpholin-4-ylbutyl)-1H-benzimidazole-2,7-diamine | MS Calcd.: 573; MS Found: 574 (M + H) |
| 134 | 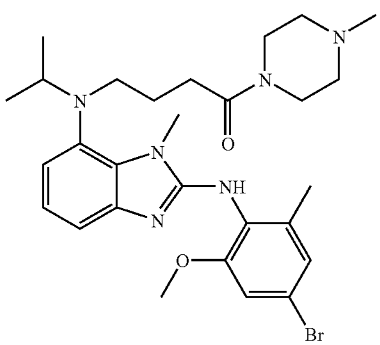 | $N^2$-(4-bromo-2-methoxy-6-methylphenyl)-$N^7$-isopropyl-1-methyl-$N^7$-[4-(4-methylpiperazin-1-yl)-4-oxobutyl]-1H-benzimidazole-2,7-diamine | MS Calcd.: 570 MS Found: 571 (M + H). |
| 135 | 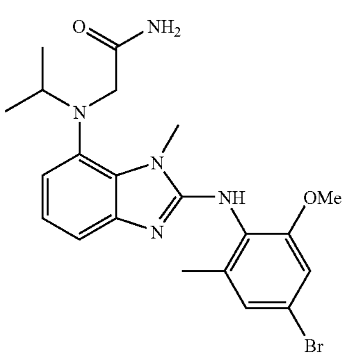 | $N^2$-[2-[(4-Bromo-2-methoxy-6-methylphenyl)amino]-1-methyl-1H-benzimidazol-7-yl]-$N^2$-isopropylglycinamide | MS Calcd.: 459; MS Found: 460 (M + H). |

Example 136

N[7]-(2-Aminoethyl)-N[2]-(4-bromo-2-methoxy-6-methylphenyl)-N[7]-isopropyl-1-methyl-1H-benzimidazole-2,7-diamine Hydrochloride

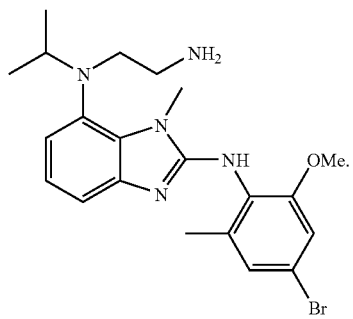

To a solution of 100 mg (0.25 mmol) of W-(4-bromo-2-methoxy-6-methylphenyl)—N[7]-isopropyl-1-methyl-1H-benzimidazole-2,7-diamine in 2 mL of 1,2-dichloroethane containing 2 drops of acetic acid was added a solution of 79 mg (0.50 mmol) of (2-oxoethyl)carbamic acid tert-butyl ester in 1 mL of 1,2-dichloroethane. To the reaction mixture was then added 158 mg (0.74 mmol) of sodium triacetoxyborohydride. The reaction was stirred for several hours and then another two equivalents of the aldehyde were added to the reaction. The reaction was stirred overnight at room temperature and another two equivalents of the aldehyde were added and the reaction was stirred several hours. The reaction was then heated at 80° C. overnight. The reaction was cooled to room temperature and concentrated in vacuo, dissolved in dichloroethane and 1 ml (13 mmol) of trifluoroacetic acid was added. This mixture was stirred at room temperature for several hours and concentrated in vacuo. This residue thus obtained was purified by preparative HPLC to give the title compound as the trifluoroacetic acid salt. The salt was dissolved in methanol and treated with hydrochloric acid (1N solution in diethyl ether). The solution was concentrated in vacuo to give 20 mg (18%) of the title compound as the hydrochloric salt.

MS Calcd.: 445. MS Found: 446 (M+H).

Example 137

N[2]-(4-Bromo-2-methoxy-6-methylphenyl)-N[7]-[2-(dimethylamino)ethyl]-/N[7]-isopropyl-1-methyl-1H-benzimidazole-2,7-diamine Hydrochloride

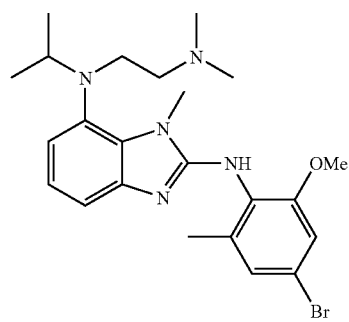

To a solution of 10 mg (0.022 mmol) of N[7]-(2-aminoethyl)-N[2]-(4-bromo-2-methoxy-6-methylphenyl)isopropyl-1-methyl-1H-benzimidazole-2,7-diamine was added 0.02 mL (0.22 mmol) of formaldehyde (37% by weight aqueous solution) and 24 mg (0.11 mmol) of sodium triacetoxyborohydride. The reaction was stirred for 2 h at room temperature and diluted with dichloromethane. The organics were washed with aqueous sodium bicarbonate, dried over sodium sulfate, filtered, and concentrated in vacuo. This residue thus obtained was purified by preparative HPLC to give the title compound as the trifluoroacetic acid salt. The salt was dissolved in methanol and treated with hydrochloric acid (1N solution in diethyl ether). The solution was concentrated in vacuo to give the 4 mg (38%) of the title compound as the hydrochloric salt MS Calcd.: 473. MS Found: 474 (M+H).

Example 138

N[2]-(4-Chloro-2-methoxy-6-methylphenyl)-N[7]-(4-chlorophenyl)-N[7]-isopropyl-1-methyl-1H-benzimidazole-2,7-diamine Hydrochloride

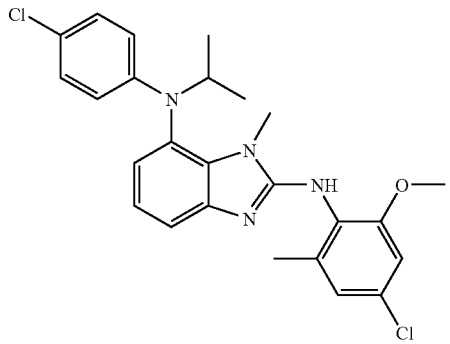

7-[(4-Chlorophenyl)amino]-1-methyl-1,3-dihydro-2H-benzimidazol-2-one

A mixture of 7-amino-1-methyl-1,3-dihydrobenzimidazol-2-one (5.0 g, 30.6 mmol), biphenyl-2-yl-dicyclohexylphosphine (0.537 g, 1.53 mmol), sodium tert-butoxide (7.4 g, 2.5 mmol) and tris(dibenzylidineacetone)dipalladium (0.56 g, 0.61 mmol) and dioxane (80 ml) was treated with 4-bromoanisole (6.16 g, 32.2 mmol) and refluxed for 22 h. The crude reaction mixture was cooled, poured into water (200 ml) and neutralized to pH8 by saturated aqueous ammonium chloride. The precipitate was filtered, washed with water and dried. Recrystallization from ethanol gave 3.69 g (44%) of the title compound as a tan powder.

MS Calcd.: 273. Found: 274 (M+H).

7-[(4-Chlorophenyl)amino]-3-(4-methoxybenzyl)-1-methyl-1,3-dihydro-2H-benzimidazol-2-one A mixture of 7-[(4-chlorophenyl)amino]-1-methyl-1,3-dihydro-2H-benzimidazol-2-one (0.27 g, 1.0 mmol), 4-methoxybenzyl chloride (0.17 ml, 1.20 mmol), potassium carbonate (0.21 g, 1.50 mmol) and N,N-dimethylformamide (1 ml) was stirred at 70° C. for 100 min. The mixture was diluted with water (20 ml) and extracted with ethyl acetate (30 ml). The extract was washed with water, dried over magnesium sulfate and evaporated in vacuo. The residue was flash chromatographed eluting with a 15% ethyl acetate/hexanes to give 0.39 g (quant.) of the title compound as a powder.

MS Calcd.: 393. Found: 394 (M+H).

$^1$H NMR (CDCl$_3$) δ 3.49 (3H, s), 3.78 (3H, s), 5.02 (2H, s), 5.30 (1H, s), 6.56 (2H, d, J=8.4 Hz), 6.80-6.95 (4H, m), 6.97 (1H, t, J=8.0 Hz), 7.13 (2H, d, J=8.4 Hz), 7.30 (2H, d, J=8.0 Hz).

7-[(4-Chlorophenyl)(isopropyl)amino]-3-(4-methoxy-benzyl)-1-methyl-1,3-dihydro-2H-benzimidazol-2-one To a mixture of 7-[(4-chlorophenyl)amino]-3-(4-methoxy-benzyl)-1-methyl-1,3-dihydro-2H-benzimidazol-2-one (0.118 g, 0.30 mmol), 2-bromopropane (0.056 ml, 0.60 mmol), tetrabutylammonium iodide (small amounts) and N,N-dimethylformamide (2 ml) was added sodium hydride (16 mg, 0.60 mmol, 90% dry). The mixture was stirred at 60° C. for 6 h. The mixture was diluted with water (20 ml) and extracted with ethyl acetate (40 ml). The extract was washed with water, dried over magnesium sulfate and evaporated in vacuo. The residue was flash chromatographed with 20-33% ethyl acetate/hexanes to give 80.6 mg (62%) of the title compound as an oil.

MS Calcd.: 435. Found: 436 (M+H).

$^1$H NMR (CDCl$_3$) δ 0.96 (3H, d, J=6.0 Hz), 1.33 (3H, d, J=6.0 Hz), 3.30 (3H, s), 3.79 (3H, s), 4.20-4.35 (1H, m), 5.02 (2H, s), 6.40 (2H, d, J=9.2 Hz), 6.77 (1H, d, J=8.0 Hz), 6.87 (2H, d, J=8.4 Hz), 6.92 (1H, d, J=8.0 Hz), 7.05 (1H, d, J=8.0 Hz), 7.09 (2H, d, J=9.2 Hz), 7.32 (2H, d, J=8.4 Hz).

7-[(4-Chlorophenyl)(isopropyl)amino]-1-methyl-1,3-dihydro-2H-benzimidazol-2-one

To a mixture of 7-[(4-chlorophenyl)(isopropyl)amino]-3-(4-methoxybenzyl)-1-methyl-1,3-dihydro-2H-benzimidazol-2-one (80 mg, 0.18 mmol) and trifluoroacetic acid (3 ml) was stirred at 65° C. for 19 h. The mixture was concentrated in vacuo, diluted with saturated aqueous sodium bicarbonate (20 ml) and extracted with ethyl acetate (30 ml). The extract was washed with water, dried over magnesium sulfate and evaporated. The residue was flash chromatographed eluting with a 33% ethyl acetate/hexanes to give 26.8 mg (34%) of the title compound as an oil.

MS Calcd.: 315. Found: 316 (M+H).

$^1$H NMR (CDCl$_3$) δ 0.98 (3H, d, J=6.4 Hz), 1.36 (3H, d, J=6.4 Hz), 3.28 (3H, s), 4.20-4.35 (1H, m), 6.43 (2H, d, J=8.8 Hz), 6.78-6.85 (1H, m), 7.05-7.20 (4H, m), 9.09 (1H, s).

2-Chloro-N-(4-chlorophenyl)-N-isopropyl-1-methyl-1H-benzimidazol-7-amine

A mixture of 7-[(4-chlorophenyl)(isopropyl)amino]-1-methyl-1,3-dihydro-2H-benzimidazol-2-one (42 mg, 0.13 mmol) and phosphorous oxychloride (1.5 ml) was stirred at 80° C. for 1.5 h. The mixture was concentrated in vacuo and quenched with saturated aqueous sodium bicarbonate (10 ml) and extracted with ethyl acetate (20 ml). The extract was washed with water, dried over magnesium sulfate and evaporated. The residue was flash chromatographed eluting with a 17% ethyl acetate/hexanes to give 31.9 mg (72%) of the title compound as an oil.

MS Calcd.: 333. Found: 334 (M+H)

$^1$H NMR (CDCl$_3$) δ 0.95 (3H, d, J=6.0 Hz), 1.39 (3H, d, J=6.0 Hz), 3.63 (3H, s), 4.30-4.40 (1H, m), 6.40 (2H, d, J=8.8 Hz), 7.03 (1H, d, J=8.0 Hz), 7.09 (2H, d, J=8.8 Hz), 7.30 (1H, t, J=8.0 Hz), 7.70 (1H, d, J=8.0 Hz).

$N^2$-(4-Chloro-2-methoxy-6-methylphenyl)-$N^7$-(4-chlorophenyl)-$N^7$-isopropyl-1-methyl-1H-benzimidazole-2,7-diamine Hydrochloride A mixture of 2-chloro-N-(4-chlorophenyl)-N-isopropyl-1-methyl-1H-benzimidazol-7-amine (30 mg, 0.90 mmol) and 4-chloro-2-methoxy-6-methylaniline (46 mg, 0.27 mmol) was stirred at 120° C. for 19 h. The mixture was dissolved in ethyl acetate (30 ml), washed with saturated aqueous sodium bicarbonate (15 ml) and water (10 ml), dried over magnesium sulfate and evaporated in vacuo. The residue was purified by reverse phase HPLC (acetonitrile containing 0.1 trifluoroacetic acid/water containing 0.1% trifluoroacetic acid). The fraction was concentrated to dryness, dissolved in methanol (10 ml) and treated with 2 M hydrogen chloride in diethyl ether (2 ml) and evaporated in vacuo to give 7.8 mg (19%) of the title compound as a powder.

MS Calcd.: 468. Found: 469 (M+H).

$^1$H NMR (CDCl$_3$) δ 0.96 (3H, m), 1.35 (3H, m), 2.39 (3H, s), 3.08 (3H, s), 3.63 (3H, s), 4.20-4.35 (1H, m), 6.39 (2H, d, J=8.8 Hz), 6.74 (1H, s), 6.89 (1H, s), 7.04 (1H, d, J=8.0 Hz), 7.10 (2H, d, J=8.8 Hz), 7.40 (1H, t, J=8.0 Hz), 7.56 (1H, d, J=8.0 Hz), 10.64 (1H, brs).

Compounds described below were prepared in a similar method.

TABLE 11

| Example | Structure | Name | Physical Data |
|---|---|---|---|
| 139 | 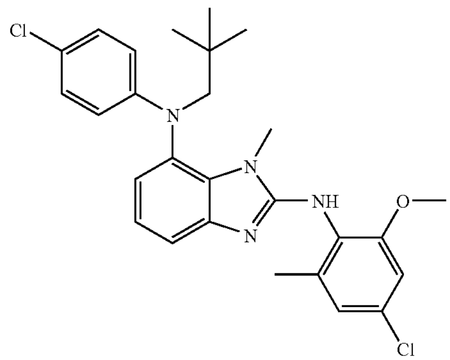 | $N^2$-(4-chloro-2-methoxy-6-methylphenyl)-$N^7$-(4-chlorophenyl)-1-methyl-$N^7$-neopentyl-1H-benzimidazole-2,7-diamine | MS Calcd: 496; Found: 497 (M + H). $^1$H NMR (CDCl$_3$)δ (HCl salt) 0.93 (9H, s), 2.38 (3H, s), 3.10 (3H, s), 3.42 (1H, d, J = 14.8 Hz), 3.62 (3H, s), 3.90 (1H, d, J = 14.8 Hz), 6.51 (2H, d, J = 8.0 Hz), 6.73 (1H, s), 6.87 (1H, 7.10 (2H, d, J = 8.0 Hz), 7.20 7.40 (1H, m), 7.42 (1H, s), 10.47 (1H, s), 13.35 (1H, s). |
| 140 | 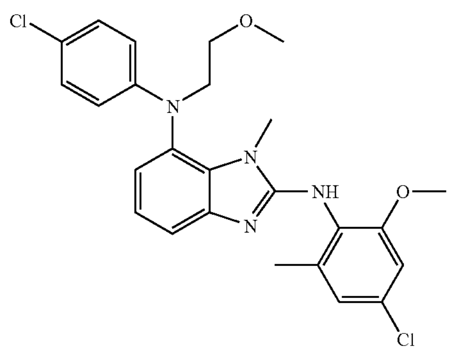 | $N^2$-(4-chloro-2-methoxy-6-methylphenyl)-$N^7$-(2-chlorophenyl)-$N^7$-(2-methoxyethyl)-1-methyl-1H-benzimidazole-2,7-diamine | MS Calcd: 484; Found: 485 (M + H). $^1$H NMR (CDCl$_3$)δ (HCl salt) 2.38 (3H, s), 3.07 (3H, s), 3.25 (3H, s), 3.56 (2H, m), 3.61 (3H, s), 3.80-4.00 (2H, m), 6.49 (2H, d, J = 8.0 Hz), 6.71 (1H, s), 6.86 (1H, s), 7.12 (2H, d, J = 8.0 Hz), 7.14 (1H, d, J = 8.0 Hz), 7.35 7.50 (2H, m), 10.59 (1H, s). |
| 141 | 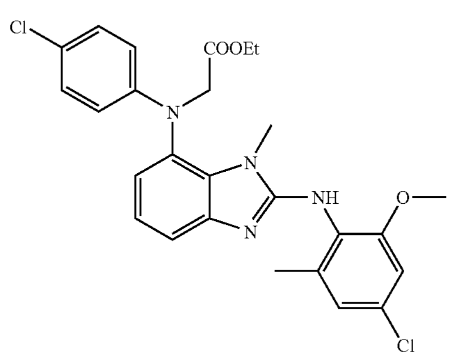 | ethyl N-{2-[(4-chloro-2-methoxy-6-methylphenyl)amino]-1-methyl-1H-benzimidazol-7-yl}-N-(4-chlorophenyl)glycinate | MS Calcd: 513; Found: 514 (M + H). $^1$H NMR (CDCl$_3$)δ (HCl salt) 1.23 (3H, t, J = 6.8 Hz), 2.36 (3H, s), 3.20 (3H, s), 3.66 (3H, s), 4.23 (2H, q, J = 6.8 Hz), 4.30 4.50 (1H, m), 4.50-4.70 (1H, m), 6.39 (2H, d, J = 8.0 Hz), 6.73 (1H, s), 6.87 (1H, s), 7.14 (2H, d, J = 8.0 Hz), 7.20-7.30 (1H, m), 7.30-7.60 (2H, m), 10.36 (1H, s). |

TABLE 11-continued

| Example | Structure | Name | Physical Data |
|---------|-----------|------|---------------|
| 142 | 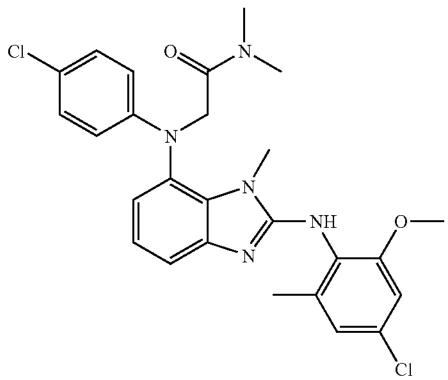 | N²-[2-[(4-chloro-2-methoxy-6-methylphenyl)amino]-1-methyl-1H-benzimidazol-7-yl]-N²-(4-chlorophenyl)-N¹,N¹-dimethylglycinamide | MS Calcd:.511; Found: 512 (M + H). ¹H NMR (CDCl₃)δ (HCl salt) 2.35 (3H, s), 2.97 (3H, s), 3.06 (3H, s), 3.29 (3H, s), 3.63 (3H, s), 4.40-4.60 (1H, m), 4.65-4.90 (1H, m), 6.37 (2H, d, J = 8.8 Hz), 6.69 (1H, s), 6.85 (1H, s), 7.11 (2H, d, J = 8.8 Hz), 7.21 (1H, d, J = 8.0 Hz), 7.35-7.50 (2H, m), 10.45 (1H, s). |
| 143 | 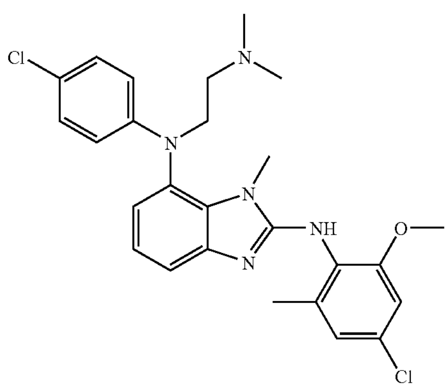 | N²-(4-chloro-2-methoxy-6-methylphenyl)-N⁷-(4-chlorophenyl)-N⁷-(2-(dimethylamino)ethyl)-1-methyl)-1H-benzimidazole-2,7-diamine | MS Calcd: 497; Found: 498 (M + H). ¹H NMR (CD₃OD)δ (2HCl salt) 2.34 (3H, s), 2.97 (6H, s), 3.55-3.65 (3H, s), 3.84 (3H, s), 4.00-4.20 (1H, m), 4.30-4.50 (1H, m), 6.74 (2H, d, J = 8.8 Hz), 7.10 (1H, s), 7.25 (1H, s), 7.25-7.35 (4H, m), 7.35 (1H, d, J = 8.0 Hz), 7.45 (1H, t, J = 8.0 Hz). |
| 144 | 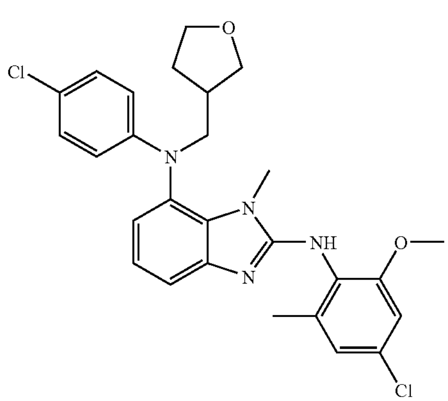 | N²-(4-chloro-2-methoxy-6-methylphenyl)-N⁷-(4-chlorophenyl)-1-methyl-N⁷-(tetrahydrofuran-3-ylmethyl)-1H-benzimidazole-2,7-diamine | MS Calcd: 510; Found: 511 (M + H). ¹H NMR (CDCl₃)δ 1.50-1.70 (1H, m), 2.00-2.15 (1H, m), 2.18 (3H, s), 2.65-2.80 (1H, m), 3.51 (3H, s), 3.50-3.70 (2H, m), 3.81 (3H, s), 3.65-4.00 (4H, m), 5.81 (1H, s), 6.56 (2H, d, J = 8.0 Hz), 6.79 (1H, s), 6.85-7.00 (2H, m), 7.13 (2H, d, J = 8.0 Hz), 7.10-7.20 (1H, m), 7.47 (1H d, J = 6.8 Hz). |

TABLE 11-continued

| Example | Structure | Name | Physical Data |
|---|---|---|---|
| 145 | 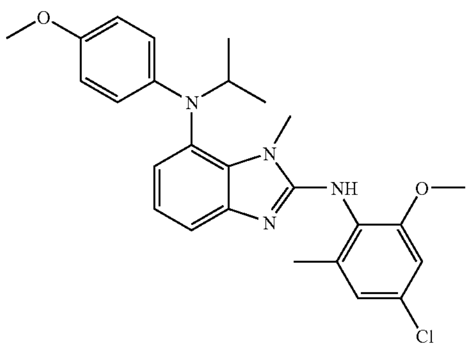 | N²-(4-chloro-2-methoxy-6-methylphenyl)-N⁷-isopropyl-N⁷-(4-methoxyphenyl)-1-methyl-1H-benzimidazole-2,7-diamine | MS Calcd: 464; Found: 465 (M + H). ¹H NMR (CDCl₃) δ 1.00-1.45 (6H, m), 2.24 (3H, s), 3.48 (3H, s), 3.74 (6H, s), 4.25-4.40 (1H, m), 6.50 (2H, d, J = 8.8 Hz), 6.75 (1H, s), 6.76 (2H, d, J = 8.8 Hz), 6.88 (1H, s), 6.91 (1H, d, J = 8.0 Hz), 7.18 (1H, d, J = 8.0 Hz), 7.45 (1H, d, J = 8.0 Hz). |
| 146 | 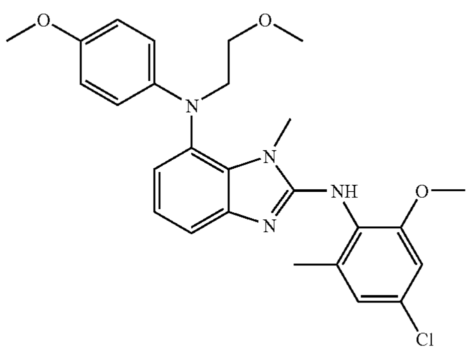 | N²-(4-chloro-2-methoxy-6-methylphenyl)-N⁷-(2-methoxyethyl)-N⁷-(4-methoxyphenyl)-2-methyl-1H-benzimidazole-2,7-diamine | MS Calcd: 480; Found: 481 (M + H). ¹H NMR (CDCl₃) δ 2.18 (3H, s), 3.31 (3H, s), 3.70 (2H, m), 3.75 (3H, s), 3.80 (3H, s), 3.85-4.00 (2H, m), 5.80 (1H, s), 6.61 (2H, d, J = 8.0 Hz), 6.77 (2H, d, J = 8.0 Hz), 6.78 (1H, s), 6.89 (1H, s), 6.91 (1H, d, J = 8.0 Hz), 7.12 (1H, t, J = 8.0 Hz), 7.42 (1H, d, J = 8.0 Hz). |
| 147 | 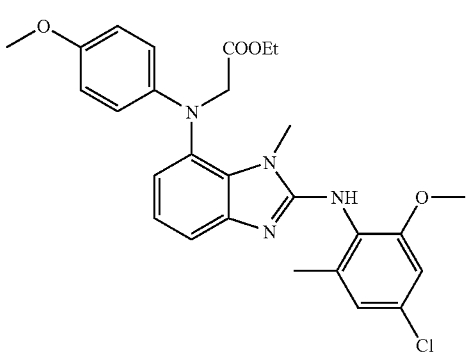 | ethyl N-{2-[(4-chloro-2-methoxy-6-methylphenyl)amino]-1-methyl-1H-benzimidazol-7-yl}-N-(4-methoxyphenyl)glycinate | MS Calcd: 508; Found: 509 (M + H). ¹H NMR (CDCl₃) δ 1.28 (3H, t, J = 7.2 Hz), 2.19 (3H, s), 3.69 (3H, s), 3.75 (3H, s), 3.81 (3H, s), 4.23 (2H, q, J = 7.2 Hz), 4.4H (2H, s), 5.80 (1H, s), 6.50 (2H, d, J = 8.8 Hz), 6.77 (2H, d, J = 8.8 Hz), 6.78 (1H, s), 6.89 (1H, s), 7.01 (1H, d, J = 8.0 Hz), 7.12 (1H, t, J = 8.0 Hz), 7.43 (1H, d, J = 8.0 Hz). |

TABLE 11-continued

| Example | Structure | Name | Physical Data |
|---------|-----------|------|---------------|
| 148 | 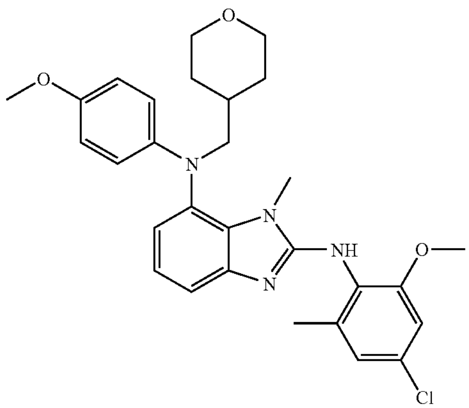 | N²-(4-chloro-2-methoxy-6-methylphenyl)-N⁷-(4-methoxyphenyl)-1-methyl-N⁷-(tetrahydro-2H-pyran-4-ylmethyl)-1H-benzimidazole-2,7-diamine | MS Calcd: 520; Found: 521 (M + H). ¹H NMR (CDCl₃)δ 1.30-1.50 (2H, m), 1.70-1.80 (2H, m), 2.00-2.20 (1H, m), 2.16 (3H, s), 3.35 (2H, t, J = 7.6 Hz), 3.49 (3H, s), 3.75 (3H, s), 3.80 (3H, s), 3.70-3.90 (2H, m), 3.97 (2H, d, J = 8.8 Hz), 5.77 (1H, s), 6.57 (2H, d, J = 8.8 Hz), 6.76 (2H, d, J = 8.8 Hz), 6.78 (1H, s), 6.88 (1H, s), 6.97 (1H, d, J = 8.0 Hz), 7.13 (1H, t, J = 8.0 Hz), 7.42 (1H, d, J = 8.0 Hz). |
| 149 | 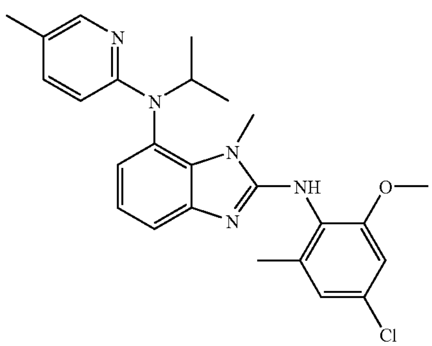 | N²-(4-chloro-2-methoxy-6-methylphenyl)-N⁷-isopropyl-1-methyl-N⁷-(5-methylpyridin-2-yl)-1H-benzimidazole-2,7-diamine | MS Calcd: 449; Found: 450 (M + H). ¹H NMR (CDCl₃)δ 1.00 (3H, d, J = 6.8 Hz), 1.39 (3H, d, J = 6.8 Hz), 2.18 (6H, s), 3.53 (3H, s), 3.80 (3H, s), 5.10-5.20 (1H, m), 5.91 (1H, d, J = 8.8 Hz), 5.80-6.00 (1H, br), 6.78 (1H, s), 6.87 (1H, d, J = 8.0 Hz), 6.89 (1H, s), 7.11 (1H, d, J = 8.0 Hz), 7.16 (1H, t, J = 8.0 Hz), 7.51 (1H, d, J = 8.0 Hz), 8.07 (1H, s). |

TABLE 11-continued

| Example | Structure | Name | Physical Data |
|---|---|---|---|
| 150 | 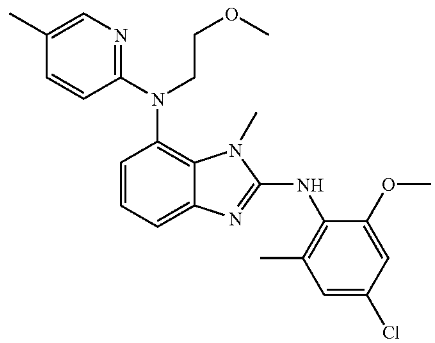 | $N^2$-(4-chloro-2-methoxy-6-methylphenyl)-$N^7$-(2-methoxyethyl)-1-methyl-$N^7$-(5-methylpyridin-2-yl)-1H-benzimidazole-2,7-diamine | MS Calcd: 465; Found: 466 (M + H). $^1$H NMR (CDCl$_3$)δ 2.19 (6H, s), 3.29 (3H, s), 3.61 (3H, s), 3.60-3.70 (1H, m), 3.70-3.80 (1H, m), 3.81 (3H, s), 4.00-4.15 (1H, m), 4.30-4.40 (1H, m), 5.83 (1H, s), 6.06 (1H, d, J = 8.0 Hz), 6.78 (1H, s), 6.89 (1H, s), 6.93 (1H, d, J = 8.0 Hz), 7.05-7.20 (2H, m), 7.40-7.50 (1H, m), 8.06 (1H, s). |

Example 151

$N^2$-[2-[(4-Chloro-2-methoxy-6-methylphenyl)amino]-1-methyl-1H-benzimidazol-7-yl]-$N^1$,$N^1$-diethyl-$N^2$-(4-methoxyphenyl)glycinamide Hydrochloride

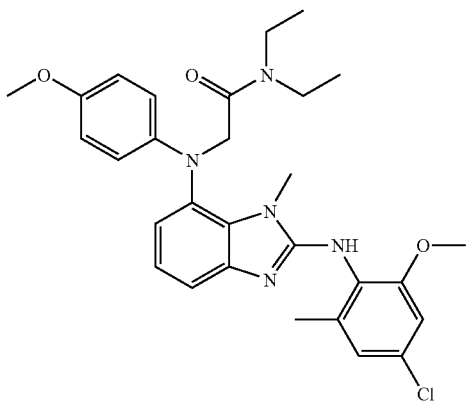

To a solution of ethyl N-[2-[(4-chloro-2-methoxy-6-methylphenyl)amino]-1-methyl-1H-benzimidazol-7-yl]-N-(4-methoxyphenyl)glycinate (20 mg, 0.039 mmol) in methanol (0.5 ml) was added 1N sodium hydroxide (0.5 ml). The mixture was stirred at room temperature for 1.5 h, then neutralized with 1N hydrochloric acid (0.5 ml) and concentrated to dryness. To a mixture of the residue, diethylamine (0.0081 ml, 0.079 mmol) and N,N-dimethylformamide (3 ml) were added triethylamine (0.011 ml, 0.079 mmol) and O-benzotriazol-1-yl-N,N,N',N'-tetramethyluronium hexafluorophosphate (22.4 mg, 0.079 mmol). The mixture was stirred at room temperature for 1.5 h. The mixture was diluted with water (20 ml) and extracted with ethyl acetate (30 ml). The extract was washed with water, dried over magnesium sulfate and evaporated in vacuo. The residue was flash chromatographed eluting with a 20% acetone/hexanes) to give the crude product. The crude product was purified by reverse phase HPLC (acetonitrile containing 0.1 trifluoroacetic acid/water containing 0.1% trifluoroacetic acid). The eluent was concentrated in vacuo and the residue was dissolved in methanol (2 ml) before 2M hydrogen chloride in diethylether (2 ml) was added. The mixture was concentrated in vacuo to give 9.6 mg (46%) of the title as a powder.

MS Calcd: 535. Found: 536 (M+H).

$^1$H NMR (CDCl$_3$) δ 1.20-1.40 (6H, m), 2.34 (3H, s), 3.25-3.40 (7H, m), 3.59 (3H, s), 3.74 (3H, s), 4.50-4.70 (2H, m), 6.41 (2H, d, J=8.8 Hz), 6.65 (1H, s), 6.73 (2H, d, J=8.8 Hz), 6.83 (1H, s), 7.15-7.45 (3H, m).

Example 152

N-(2-[(4-Chloro-2-methoxy-6-methylphenyl)amino]-1-methyl-1H-benzimidazol-7-yl]-N-(4-chlorophenyl)acetamide Hydrochloride

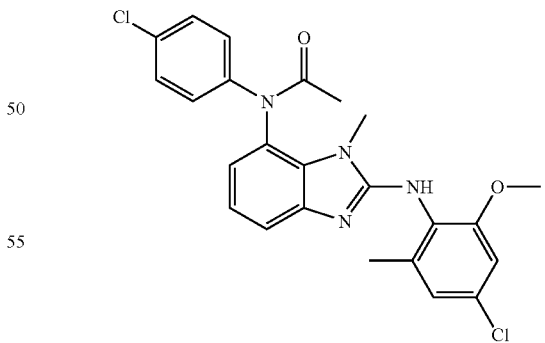

A mixture of 4-[(4-chlorophenyl)amino]-1-(4-methoxybenzyl)-3-methyl-1,3-dihydro-2H-benzimidazol-2-one (0.393 g, 1.0 mmol), pyridine (0.1 ml) and acetic anhydride (10 ml) was heated at 120° C. for 4 days. The mixture was evaporated in vacuo. The residue was diluted with ethyl acetate (50 ml), washed with saturated sodium bicarbonate, dried over magnesium sulfate and evaporated in vacuo. The residue was flash chromatographed eluting with 40-50% ethyl acetate/hexanes to give N-(4-chlorophenyl)-N-[1-(4-methoxybenzyl)-3-methyl-2-oxo-2,3-dihydro-1H-benzimidazol-4-yl]acetamide (0.388 g, quant.) as an oil.

MS Calcd: 435. Found: 436 (M+H).

$^1$H NMR (CDCl$_3$) δ 2.05 (3H, s), 3.47 (3H, s), 3.79 (3H, s), 4.99 (1H, d, J=15.6 Hz), 5.05 (1H, d, J=15.6 Hz), 6.87 (2H, d, J=8.4 Hz), 6.80-6.90 (1H, m), 6.90-7.10 (2H, m), 7.31 (2H, d, J=8.4 Hz), 7.20-7.40 (4H, m).

From this compound, the title compound was prepared in a similar manner as described in Example 138.

MS Calcd: 468. Found: 469 (M+H).

$^1$H NMR (CDCl$_3$) δ 2.11 (3H, s), 2.37 (3H, s), 3.48 (3H, s), 3.65 (3H, s), 6.76 (1H, s), 6.82 (1H, s), 7.00-7.20 (1H, m), 7.20-7.30 (2H, m), 7.30-7.45 (3H, m), 7.50-7.65 (1H, m), 10.80 (1H, s).

Compound described below were prepared in a similar method.

7-[(4-Methylsulfonyl)phenylamino]-1-methyl-1,3-dihydro-2H-benzimidazol-2-one

A mixture of 7-amino-1-methyl-1,3-dihydrobenzimidazol-2-one (0.500 g, 3.06 mmol), 2-(dicyclohexylphosphino)-2',6'-dimethoxy-1,1'-biphenyl (0.0629 g, 0.153 mmol), sodium tert-butoxide (0.590 g, 6.10 mmol), tris(dibenzylideneacetone)dipalladium (0.280 g, 0.310 mmol) and dioxane (5 ml) was treated with 4-bromophenylmethylsulfone (0.860 g, 3.70 mmol) and refluxed for 3 h. The crude reaction mixture was cooled, poured into water, and extracted with ethyl acetate (X2) and ethyl acetate-tetrahydrofuran (X2). The extract was dried over sodium sulfate and concentrated in vacuo. The residual solids were washed with ethyl acetate to give 525 mg of the title compound as crystals.

TABLE 12

| Example | Structure | Name | Physical Data |
|---|---|---|---|
| 153 | 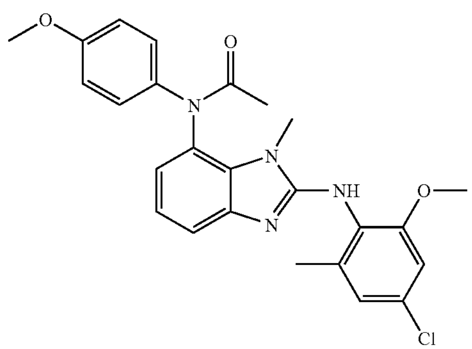 | N-{2-[(4-chloro-2-methoxy-6-methylphenyl)amino]-1-methyl-1H-benzimidazol-7-yl}-N-(4-methoxyphenyl)acetamide | MS Calcd: 464; Found: 465 (M + H). $^1$H NMR (CDCl$_3$) δ 2.06 (3H×2/3, s), 2.20 (3H, s), 2.20 (3H×1/3, s), 3.71 (3H×2/3, s), 3.79 (3H×1/3, s), 3.80 (6H, s), 5.90-6.10 (1H, brs), 6.79 (1H, s), 6.90 (1H, s), 6.80-7.00 (3H, m), 7.05-7.20 (1H, m), 7.20-7.40 (2H, m), 7.40-7.60 (1H, m). |

Example 154

N$^2$-(4-Bromo-2-methoxy-6-methylphenyl)-N$^7$-isopropyl-1-methyl-N$^7$-[4-(methylsulfonyl)phenyl]-1H-benzimidazole-2,7-diamine

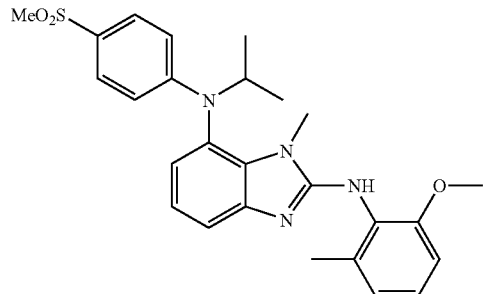

$^1$H NMR (CDCl$_3$) δ 3.09 (3H, s), 3.25 (3H, s), 6.70 (2H, d, J=8.6 Hz), 6.83 (1H, d, J=8.0 Hz), 6.93 (1H, d, J=8.0 Hz), 7.02 (1H, t, J=8.0 Hz), 7.64 (2H, d, J=8.6 Hz), 8.53 (1H, s), 11.01 (1H, s).

From this compound, the title compound was prepared in a similar manner as described in Example 138.

MS Calcd: 556. Found: 557 (M+H).

$^1$H NMR (CDCl$_3$) δ 1.04 (3H, d, J=6.4 Hz), 1.44 (3H, d, J=6.4 Hz), 2.19 (3H, s), 3.01 (3H, s), 3.49 (3H, s), 3.81 (3H, s), 4.38-4.46 (1H, m), 5.83 (1H, s), 6.61 (2H, d, J=8.8 Hz), 6.80 (1H, d, J=8.0 Hz), 6.93 (1H, s), 7.06 (1H, s), 7.17 (1H, t, J=8.0 Hz), 7.55 (1H, d, J=8.0 Hz), 7.69 (2H, d, J=8.8 Hz).

Compound described below were prepared in a similar method.

TABLE 13

| Example | Structure | Name | Physical Data |
|---|---|---|---|
| 155 | 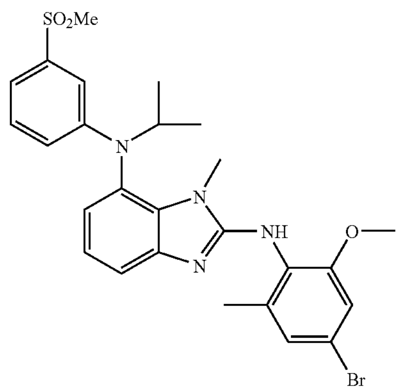 | $N^2$-(4-bromo-2-methoxy-6-methylphenyl)-$N^7$-isopropyl-1-methyl-$N^7$-[3-(methylsulfonyl)phenyl]-1H-benzimidazole-2,7-diamine | MS Calcd: 556, 558; Found: 557, 559 (M + H). $^1$H NMR (CDCl$_3$) δ 1.03 (3H, d, J = 6.2 Hz), 1.42 (3H, d, J = 6.2 Hz), 2.18 (3H, s), 3.05 (3H, s), 3.53 (3H, s), 3.81 (3H, s), 4.39-4.45 (1H, m), 5.83 (1H, s), 6.58 (1H, d, J = 7.8 Hz), 6.80 (1H, d, J = 7.8 Hz), 6.81 (1H, d, J = 7.8 Hz), 6.92 (1H, s), 7.05 (1H, s), 7.16 (1H, t, J = 7.8 Hz), 7.22-7.29 (3H, m), 7.53 (1H, d, J = 7.8 Hz). |

Compounds of Examples 156-182, shown in the Table 14, were prepared in a manner similar to that described in Example 31.

TABLE 14

| Example | Structure | Name | Physical Data |
|---|---|---|---|
| 156 | 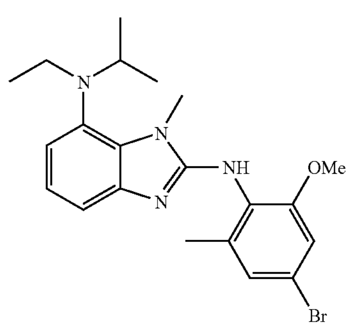 | $N^2$-(4-bromo-2-methoxy-6-methylphenyl)-$N^7$-ethyl-$N^7$-isopropyl-1-methyl-1H-benzimidazole-2,7-diamine | $^1$H NMR (DMSO-d$_6$) δ (HCl salt) 0.92 (t, 3H, J = 7.0 Hz), 1.03 (br s, 3H); 1.13 (br s, 3H); 2.29 (s, 3H); 3.10-3.14 (m, 2H); 3.32-3.39 (m, 1H); 3.80 (s, 3H); 4.12 (s, 3H); 7.06 1H, J = 7.2. Hz); 7.18-7.25 (m, 2H); 7.29 (s, 1H); 7.33 (s, 1H); 10.21 (s, 1H); 12.61 (s, 1H); MS Calcd.: 430; MS Found: 431 (M + H). |

TABLE 14-continued

| Example | Structure | Name | Physical Data |
|---------|-----------|------|---------------|
| 157 | 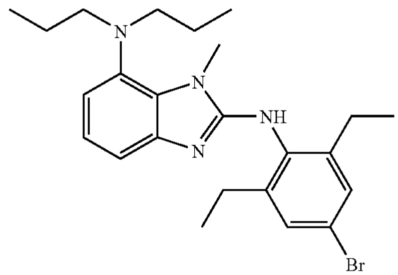 | N²-(4-bromo-2,6-diethylphenyl)-1-methyl-N⁷1N⁷-dipropyl-1H-benzimidazole-2,7-diamine | MS Calcd.: 457; MS Found: 458 (M + H). |
| 158 | 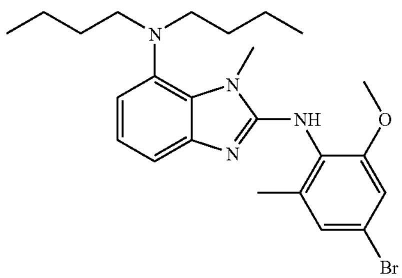 | N²-(4-bromo-2-methoxy-6-methylphenyl)-N⁷,N⁷-dibutyl-1-methyl-1H-benzimidazole-2,7-diamine | ¹H NMR (CDCl₃) δ 0.88 (t, J = 7.2 Hz, 6H), 1.27 (q, J = 7.4 Hz, 4H), 1.45 (t, J = 7.2 Hz, 4H), 2.19 (3H, s), 3.01 (br s, 4H), 3.83 (s, 3H), 4.04 (s, 3H), 6.89-6.92 (m, 2H), 7.00 7.05 (m, 2H), 7.26 (br, s, 1H); MS Calcd.: 472; MS Found: 473 (M + H). |
| 159 | 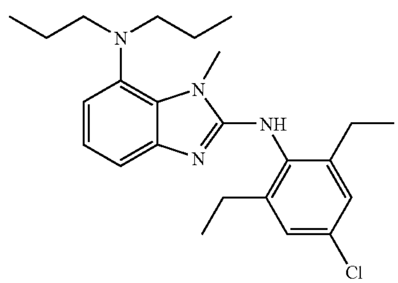 | N²-(4-chloro-2,6-diethylphenyl)-1-methyl-N⁷,N⁷-dipropyl-1H-benzimidazole-2,7-diamine | ¹H NMR (CDCl₃) δ 0.86 (t, J = 7.2 Hz, 6H), 1.18 (t, J = 7.2 Hz, 6H), 1.50 (q, J = 7.2 Hz, 4H), 2.61 (d, J = 7.1 Hz, 4H), 2.98 (br s, 4H), 4.01 (s, 3H), 6.88 (d, J = 7.3 Hz, 1H), 7.01 (br s, 1H), 7.15 (s, 2H), 7.22 (d, J = 6.7 Hz, 1H); MS Calcd.: 413; MS Found: 414 (M + H). |
| 160 | 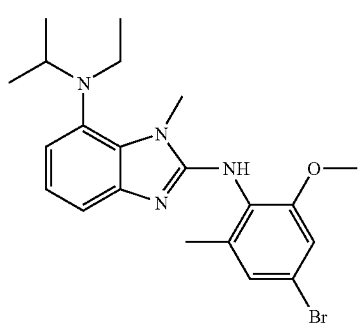 | N²-(4-bromo-2-methoxy-6-methylphenyl)-N⁷-ethyl-N⁷-isopropyl-1-methyl-1H-benzimidazole-2,7-diamine | MS Calcd.: 430; MS Found: 431 (M + H). |

TABLE 14-continued

| Example | Structure | Name | Physical Data |
|---------|-----------|------|---------------|
| 161 | 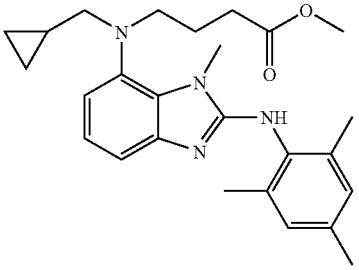 | methyl 4-[(cyclopropylmethyl)[2-(mesitylamino)-1-methyl-1H-benzimidazol-7-yl]amino]butanoate | MS Calcd.: 434; MS Found: 435 (M + H). |
| 162 | 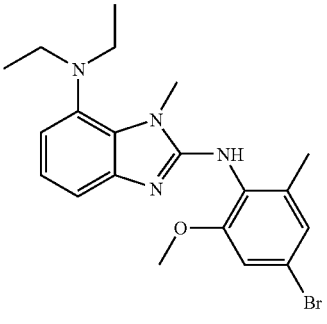 | $N^2$-(4-bromo-2-methoxy-6-methylphenyl)-$N^7,N^7$-diethyl-1-methyl-1H-benzimidazole-2,7-diamine | MS Calcd.: 416; MS Found: 417 (M + H). |
| 163 | 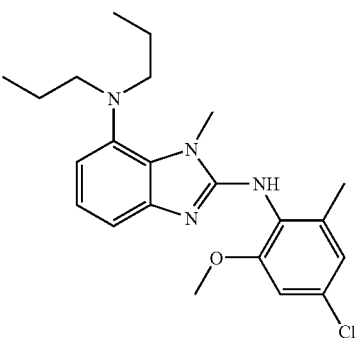 | $N^2$-(4-chloro-2-methoxy-6-methylphenyl)-1-methyl-$N^7,N^7$-dipropyl-1H-benzimidazole-2,7-diamine | MS Calcd.: 400; MS Found: 401 (M + H). |
| 164 | 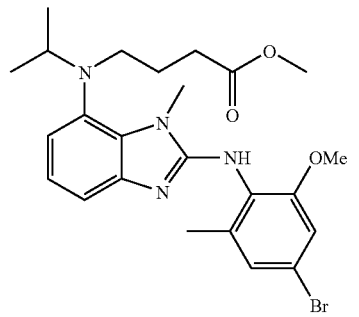 | methyl 4-[[2-[(4-bromo-2-methoxy-6-methylphenyl)amino]-1-methyl-1H-benzimidazol-7-yl](isopropyl)amino]butanoate | $^1$H NMR (CDCl$_3$) δ 1.02 (d, J = 5.9 Hz, 3H), 1.19 (d, J = 5.9 Hz, 3H), 1.73-1.79 (m, 2H), 2.19 (s, 3H), 2.28-2.32 (m, 2H), 2.97-3.02 (m, 1H), 3.18-3.22 (m, 1H), 3.29-3.35 (m, 1H), 3.64 (s, 3H), 3.82 (s, 3H), 4.05 (s, 3H), 6.90-6.92 (m, 2H), 6.96-7.06 (m, 2H), 7.25-7.28 (m, 1H); MS Calcd.: 502; MS Found: 503 (M + H). |

TABLE 14-continued

| Example | Structure | Name | Physical Data |
|---|---|---|---|
| 165 | 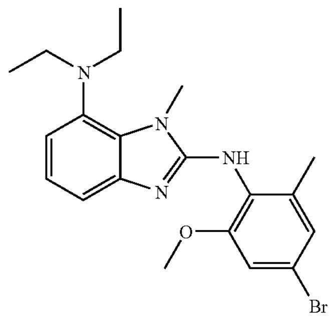 | $N^2$-(4-bromo-2-methoxy-6-methylphenyl)-$N^7$,$N^7$-diethyl-1-methyl-1H-benzimidazole-2,7-diamine | $^1$H NMR (DMSO-$d_6$) δ 0.95 (t, J = 7.0 Hz, 6H), 2.09 (s, 3H), 3.00-3.08 (m, 4H), 3.74 (s, 3H), 3.95 (s, 3H), 6.77-6.80 (m, 1H), 6.86-6.89 (m, 2H), 7.09 (d, J = 8.6 Hz, 2H), 7.84 (s, 1H); MS Calcd.: 416; MS Found: 417 (M + H). |
| 166 | 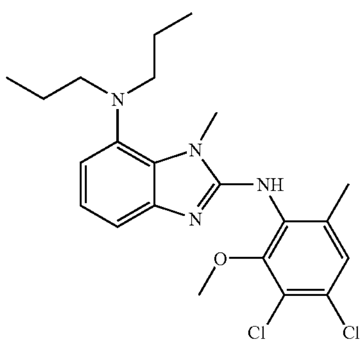 | $N^2$-(3,4-dichloro-2-methoxy-6-methylphenyl)-1-methyl-$N^7$,$N^7$-dipropyl-1H-2,7-diamine | MS Calcd.: 434; MS Found: 435 (M + H). |
| 167 | 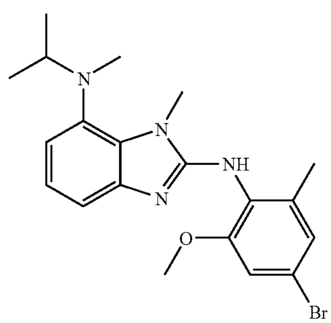 | $N^2$-(4-bromo-2-methoxy-6-methylphenyl)-$N^7$-isopropyl-$N^7$,1-dimethyl-1H-benzimidazole-2,7-diamine | $^1$H NMR (CDCl$_3$) δ 1.11 (d, J = 5.5 Hz, 6H), 2.17 (s, 3H), 2.71 (s, 3H), 3.33-3.41 (m, 1H), 3.81 (s, 3H), 4.03 (s, 3H), 6.87-6.93 (m, 2H), 6.99-7.04 (m, 2H), 7.23-7.24 (m, 1H); MS Calcd.: 416; MS Found: 417 (M + H). |
| 168 | 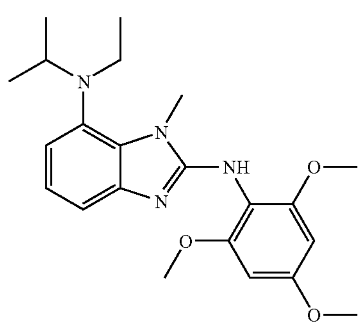 | $N^7$-ethyl-$N^7$-isopropyl-1-ethyl-$N^2$-(2,4,6-trimethoxyphenyl)-1H-benzimidazole-2,7-diamine | $^1$H NMR (CDCl$_3$) δ 0.95 (t, J = 7.0 Hz, 3H), 1.09 (d, J = 5.5 Hz, 6H), 3.07-3.12 (m, 2H), 3.28-3.33 (m, 1H), 3.78 (s, 6H), 3.82 (s, 3H), 4.02 (s, 3H), 6.21 (s, 2H), 6.88 (d, J = 7.8 Hz, 1H), 6.98 (t, J = 7.8 Hz, 1H), 7.26-7.27 (m, 1H); MS Calcd.: 398; MS Found: 399 (M + H). |

TABLE 14-continued

| Example | Structure | Name | Physical Data |
| --- | --- | --- | --- |
| 169 | 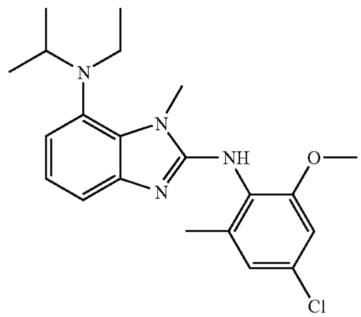 | N²-(4-chloro-2-methoxy-6-methylphenyl)-N⁷-ethyl-N⁷-isopropyl-1-methyl-1H-benzimidazole-2,7-diamine | ¹H NMR (CDCl₃) δ 0.97 (t, J = 7.0 Hz, 3H), 1.10 (br s, 6H), 2.20 (s, 3H), 3.02-3.16 (m, 2H), 3.31-3.36 (m, 1H), 3.82 (s, 3H), 4.07 (s, 3H), 6.78 (s, 1H), 6.89-6.94 (m, 2H), 7.01 (t, J = 7.8 Hz, 1H), 7.26-7.29 (m, 1H); MS Calcd.: 386; MS Found: 387 (M + H). |
| 170 | 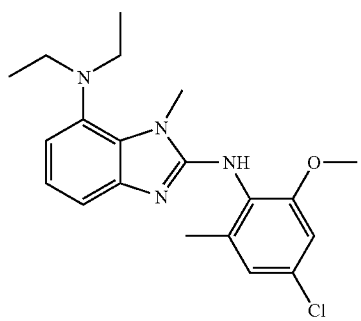 | N²-(4-chloro-2-methoxy-6-methylphenyl)-N⁷,N⁷-diethyl-1-methyl-1H-benzimidazole-2,7-diamine | ¹H NMR (CDCl₃) δ 1.02 (t, J = 7.0 Hz, 6H), 2.19 (s, 3H), 3.06-3.11 (m, 4H), 3.81 (s, 3H), 4.06 (s, 3H), 6.78 (s, 1H), 6.87-6.90 (m, 2H), 7.02 (t, J = 7.8 Hz, 1H), 7.23-7.26 (m, 1H); MS Calcd.: 372; MS Found: 373 (M + H). |
| 171 | 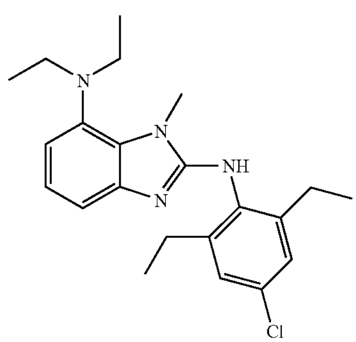 | N²-(4-chloro-2,6-diethylphenyl)-N⁷,N⁷-diethyl-1-methyl-1H-benzimidazole-2,7-diamine | MS Calcd.: 484; MS Found: 485 (M + H). |
| 172 | 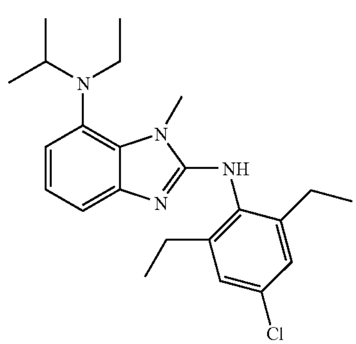 | N²-(4-chloro-2,6-diethylphenyl)-N⁷-ethyl-N⁷-isopropyl-1-methyl-1H-benzimidazole-2,7-diamine | MS Calcd.: 398; MS Found: 399 (M + H). |

TABLE 14-continued

| Example | Structure | Name | Physical Data |
|---|---|---|---|
| 173 | 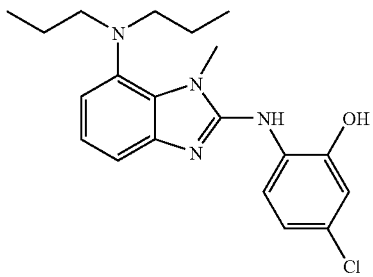 | 5-chloro-2-[[7-(dipropylamino)-1-methyl-1H-benzimidazol-2-yl]amino]phenol | $^1$H NMR (CDCl$_3$) δ 0.84 (t, J = 7.4 Hz, 6H) 1.41-1.48 (m, 4H), 2.97 (br s, 4H), 4.10 (s, 3H), 6.81-6.84 (m, 1H), 6.90 (d, J = 8.6 Hz, 1H), 6.96 (d, J = 7.8 Hz, 1H), 7.06-7.09 (m, 2H), 7.21 (d, J = 7.8 Hz, 1H); MS Calcd.: 372; MS Found: 373 (M + H). |
| 174 | 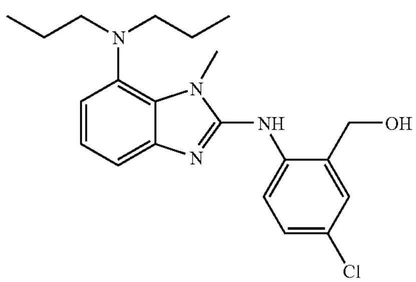 | [5-chloro-2-[[7-(dipropylamino)-1-methyl-1H-benzimidazol-2-yl]amino]phenyl]methanol | MS Calcd.: 386; MS Found: 387 (M + H). |
| 175 | 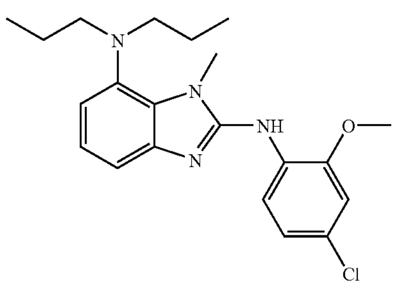 | $N^2$-(4-chloro-2-methoxyphenyl)-1-methyl-$N^7$,$N^7$-benzimidazole-2,7-diamine | MS Calcd.: 386; MS Found: 387 (M + H). |
| 176 | 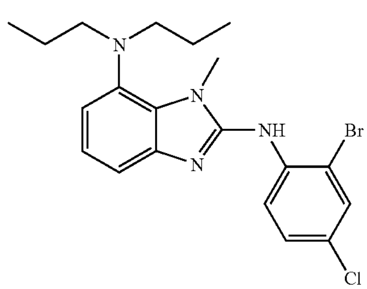 | $N^2$-(2-bromo-4-chlorophenyl)-dipropyl-1H-1-methyl-$N^7$,$N^7$-benzimidazole-2,7-diamine | $^1$H NMR (CDCl$_3$) δ 0.84 (t, J = 7.2 Hz, 6H), 1.47 (q, J = 7.5 Hz, 4H), 2.99 (br s, 4H), 4.12 (s, 3H), 6.87 (br s, 1H), 6.98 Hz, 1H), 7.10 (d, J = 7.8 (t, J = 7.8 Hz, 1H), 7.33-7.37 (m, 2H), 7.5 (d, J = 2.4 Hz, 1H), 8.58 (d, J = 8.2 Hz, 1H); MS Calcd.: 434; MS Found: 435 (M + H). |

TABLE 14-continued

| Example | Structure | Name | Physical Data |
|---|---|---|---|
| 177 | 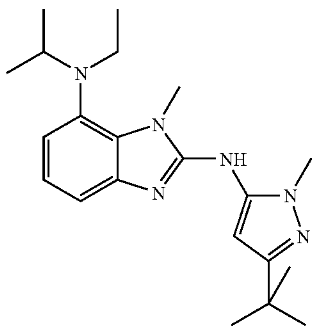 | $N^2$-(3-tert-butyl-1-methyl-1H-pyrazol-5-yl)-$N^7$-ethyl-$N^7$-isopropyl-1-methyl-1H-benzimidazole-2,7-diamine | $^1$H NMR (CDCl$_3$) δ 0.95 (t, J = 7.1 Hz, 3H), 1.09 (d, J = 6.5 Hz, 6H), 1.33 (s, 9H), 3.80 (q, J = 7.0 Hz, 2H), 3.25-3.30 (m, 1H), 3.48 (s, 1H), 3.74 (s, 3H), 3.86 (s, 3H), 4.71 (s, 1H), 6.83 (s, 1H), 6.95 (s, 2H); MS Calcd.: 368; MS Found: 369 (M + H). |
| 178 | 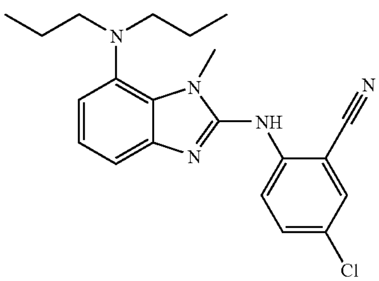 | 5-chloro-2-[[7-(dipropylamino)-1-methyl-1H-benzimidazol-2-yl]amino]benzonitrile | MS Calcd.: 382; MS Found: 383 (M + H). |
| 179 | 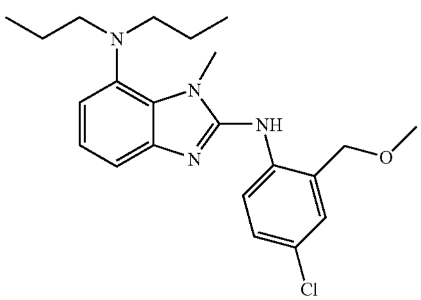 | $N^2$-[4-chloro-2-(methoxymethyl)-phenyl]-1-methyl-$N^7$1$N^7$-dipropyl-1H-benzimidazole-2,7-diamine | MS Calcd.: 400; MS Found: 401 (M + H). |
| 180 | 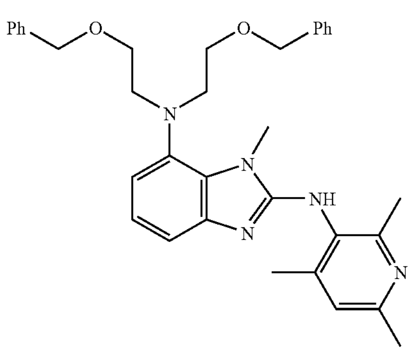 | $N^7$,$N^7$-bis[2-(benzyloxy)ethyl]-1-methyl-$N^2$-(2,4,6-trimethylpyridin-3-yl)-1H-benzimidazole-2,7-diamine | $^1$H NMR (DMSO-d$_6$) δ 2.20 (s, 3H); 2.45 (s, 6H); 3.39 (s, 4H); 3.55-3.62 (m, 4H); 3.93 (s, 3H); 4.43 (s, 4H); 6.91 (s, 2H); 7.00 (br s, 1H); 7.24-7.35 (m, 12H); MS Calcd.: 549; MS Found: 550 (M + H). |

TABLE 14-continued

| Example | Structure | Name | Physical Data |
|---|---|---|---|
| 181 | 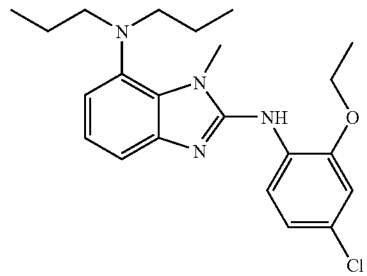 | $N^2$-(4-chloro-2-methoxyphenyl)-3-methyl-$N^7,N^7$-dipropyl-1H-benzimidazole-2,7-diamine | MS Calcd.: 400; MS Found: 401 (M + H). |
| 182 | 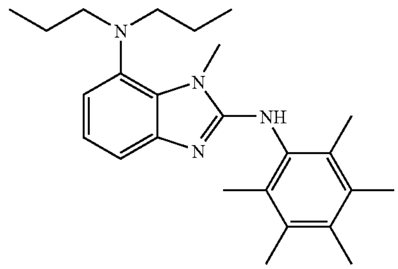 | 1-methyl-$N^2$-(pentamethylphenyl)-$N^7,N^7$-dipropyl-1H-benzimidazole-2,7-diamine | $^1$H NMR (CDCl$_3$) δ 0.84 (t, 6H, J = 7.5 Hz), 1.38-1.48 (m, 4H), 2.03 (s, 6H), 2.18 (s, 6H), 2.19 (s, 3H), 2.90-2.95 (t, 4H, J = 7.5 Hz), 3.90 (s, 3H), 6.89 (d, 1H, J = 7.8 Hz), 6.92 (s, 1H), 6.98 (t, 1H, J = 7.8 Hz) 7.23 (d, 1H, J = 7.8 Hz) MS Calcd.: 392 MS Found: 393 (M + H) |

Example 183

N-(4-Bromo-2-methoxy-6-methylphenyl)-7-(2-ethyl-1-piperidinyl)-1-methyl-1H-benzimidazol-2-amine

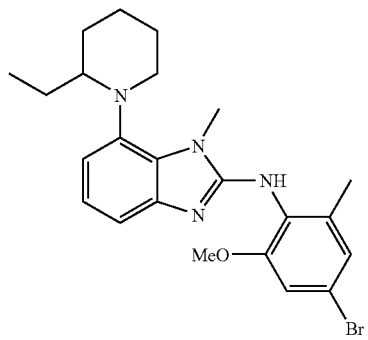

7-(2-Ethyl-1-piperidinyl)-1-methyl-1,3-dihydro-2H-benzimidazol-2-one

A mixture of 1-ethylcyclopentene (1.0 g, 10.4 mmol) and sodium bicarbonate (0.1 g, 1.19 mmol) in methanol (150 ml) was ozonized at −78° C. until TLC analysis indicated complete consumption of 1-ethylcyclopentene. The crude ozonide was transferred directly to a mixture of 7-amino-1-methyl-1,3-dihydro-2H-benzimidazol-2-one (0.5 g, 3.07 mmol) and 10% palladium on carbon (0.05 g, Degussa type; 50% wet). The flask was fitted with a balloon of hydrogen and allowed to stir for 12 h. The reaction was filtered through GF/F paper and the filtrate concentrated under reduced pressure. The residue was purified by column chromatography eluting with a 10% acetone/hexanes mixture to afford 597 mg (75%) of the title compound.

$^1$H-NMR (CDCl$_3$) δ 0.73 (3H, t, J=7.5 Hz), 1.15-1.21 (1H, m), 1.29-1.44 (3H, m), 1.62-1.68 (2H, m), 1.86-1.91 (2H, m), 2.63-2.69 (1H, m), 2.77-2.82 (1H, m), 3.01-3.04 (1H, m), 3.77 (3H, s), 6.89-7.01 (3H, m), 10.08 (1H, s); MS Calcd.: 259. Found: 260 (M+H).

2-Chloro-7-(2-ethyl-1-piperidinyl)-1-methyl-1H-benzimidazole

A mixture of 7-(2-ethyl-1-piperidinyl)-1-methyl-1,3-dihydro-2H-benzimidazol-2-one (200 mg, 0.77 mmol) and phosphorus oxychloride (3.55 g, 23.1 mol) was refluxed for 12 h with stirring and concentrated to dryness under vacuum. The residue was purified by column chromatography eluting with a 10% acetone/hexanes mixture to afford 192 mg (90%) of the title compound.

$^1$H-NMR (CD$_3$OD) δ 0.77 (3H, t, J=7.5 Hz), 1.21-1.57 (4H, m), 1.67-1.81 (2H, m), 1.83-2.02 (2H, m), 2.74 (1H, t, J=11.27 Hz), 3.03 (1H, t, J=6.4 Hz), 3.15 (1H, d, J=12.1 Hz), 4.41 (3H, s), 7.51-7.61 (3H, m); MS Calcd.: 277. Found: 278 (M+H).

N-(4-Bromo-2-methoxy-6-methylphenyl)-7-(2-ethyl-1-piperidinyl)-1-methyl-1H-benzimidazol-2-amine

A mixture of 2-chloro-7-(2-ethyl-1-piperidinyl)-1-methyl-1H-benzimidazole (100 mg, 0.36 mmol) and 4-bromo-2-methoxy-6-methylaniline (390 mg, 1.8 mmol) was heated at 110° C. for 12 h. The mixture was dissolved in ethyl acetate and washed with saturated sodium bicarbonate in water, dried over magnesium sulfate and concentrated under vacuum. The residue was purified by column chromatography eluting with a 15% acetone/hexanes mixture to afford 49.3 mg (30%) of the title compound.

$^1$H-NMR (CDCl$_3$) δ 0.73 (3H, t, J=7.5 Hz), 1.16-1.26 (2H, m), 1.34-1.48 (2H, m), 1.62-1.65 (2H, m), 1.87-1.95 (2H, m), 2.18 (3H, s), 2.67-2.74 (1H, m), 2.83-2.87 (1H, m), 3.09-3.12 (1H, m), 3.81 (3H, s), 4.10 (3H, s), 6.91 (1H, s), 6.95-7.04 (3H, m), 7.29 (1H, d, J=7.5 Hz); MS Calcd.: 456. Found: 457 (M+H), 459.

Compounds described below were prepared in a similar method.

TABLE 15

| Example | Structure | Name | Physical Data |
|---|---|---|---|
| 184 | 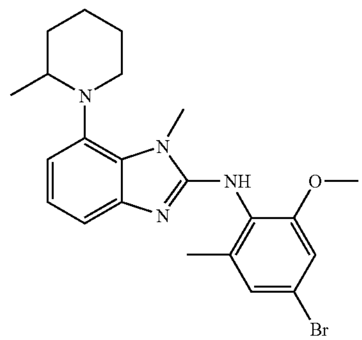 | N-(4-bromo-2-methoxy-6-methylphenyl)-1-methyl-7-(2-methylpiperidin-1-yl)-1H-benzimidazol-2-amine | $^1$H-NMR (CDCl$_3$) δ 0.90 (3H, d, J=6.17 Hz), 1.38-1.48 (2H, m), 1.67-1.73(2H, m), 1.81-1.82(2H, m), 2.18(3H, s), 2.69-2.76 (1H, m), 2.96-3.08(1H, m), 3.02-3.15(1H, m), 3.81(3H, s), 4.11(3H, s), 6.91(1H, s), 6.95-7.04 (3H, m), 7.26-7.29(1H, m); MS Calcd.: 442; Found: 443(M+H), 445. |
| 185 | 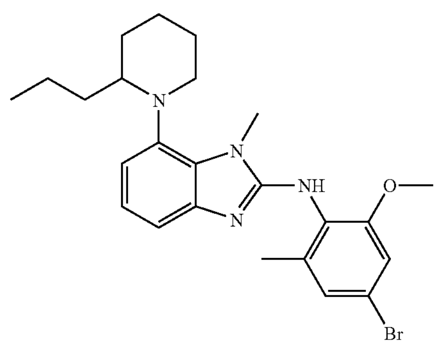 | N-(4-bromo-2-methoxy-6-methylphenyl)-7-(2-ethyl-1-pyrolidinyl)-1-methyl-1H-benzimidazol-2-amine | $^1$H-NMR (CDCl$_3$) δ 0.85 (3H, t, J=7.25 Hz), 1.29-1.38(1H, m), 1.56-1.67(2H, m), 1.81-1.97 (2H, m), 2.10-2.16(1H, m), 2.19(3H, s), 2.78-2.85(1H, m), 3.32-3.41 (2H, m), 3.81 (3H, s), 4.01 (3H, s), 6.91-6.98(2H, m), 7.01-7.05(2H, m), 7.25(1H, m); MS Calcd.: 442; Found: 443(M+H), 445. |
| 186 | 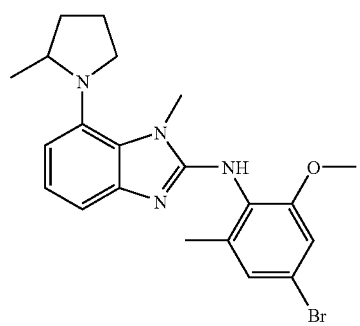 | N-(4-bromo-2-methoxy-6-methylphenyl)-1-methyl-7-(2-methyl-1-pyrolidin-1-yl)-1H-benzimidazol-2-amine | $^1$H-NMR (CDCl$_3$) δ 1.07 (3H, d, J=5.9 Hz), 1.54-1.63 (2H, m), 1.83-1.99(2H, m), 2.19(3H, s), 2.77-2.85(1H, m), 3.39-3.49 (2H, m), 3.81 (3H, s), 4.02 (3H, s), 6.88-6.92(2H, m), 7.00-7.05 (2H, m), 7.25(1H, m); MS Calcd.: 428; Found: 429(M+H), 431. |

TABLE 15-continued

| Example | Structure | Name | Physical Data |
|---|---|---|---|
| 187 | 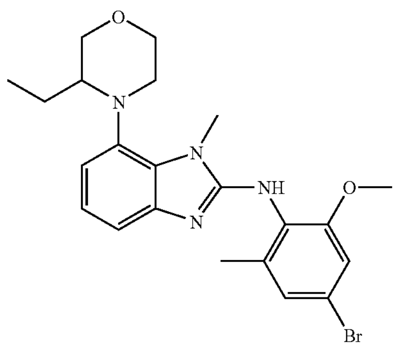 | N-(4-bromo-2-methoxy-6-methylphenyl)-7-(3-ethyl-4-morpholinyl)-1-methyl-1H-benzimidazol-2-amine | $^1$H-NMR (CDCl$_3$) δ 0.77 (3H, t, J=7.5 Hz), 1.13-1.20 (1H, m), 1.33-1.49(1H, m), 1.54-1.63(1H, m), 2.18(3H, s), 2.92-3.16 (3H, m), 3.40-3.46(1H, m), 3.77-3.81(1H, m), 3.82(3H, s), 3.91-3.94 (1H, m), 4.09 (3H, s), 6.92 (1H, s), 6.98-7.08(3H, m), 7.31-7.34(1H, m); MS Calcd.: 458; Found: 459(M + H), 461. |
| 188 | 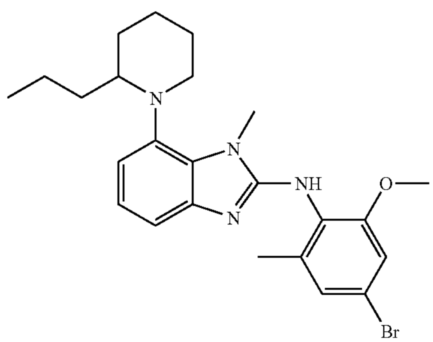 | N-(4-bromo-2-mthoxy-6-methylphenyl)-1-methyl-7-(2-propyl-1-piperidinyl)-1H-benzimidazol-2-amine | $^1$H-NMR (CDCl$_3$) δ 0.73 (3H, t, J=6.9 Hz), 1.10-1.68 (8H, m), 1.83-1.88(1H, m), 1.95-1.98(1H, m), 2.19(3H, s), 2.66 2.72 (1H, m), 2.88-2.92(1H, m), 23.08-3.12 (1H, m), 3.81(3H, s), 4.08(3H, s), 6.92-7.04 (4H, m), 7.28-7.30(1H, m); MS Calcd.: 470; Found: 471(M+H), 473. |
| 189 | 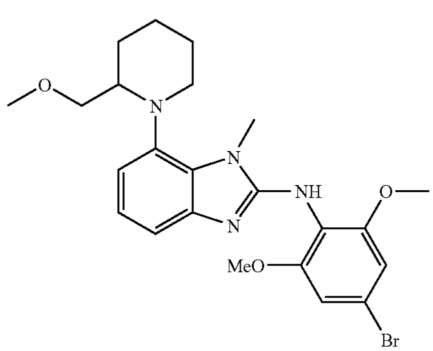 | N-(4-bromo-2-methoxy-6-methylphenyl)-1-methyl-7-(2-methoxymethyl-1-piperidinyl)-1H-benzimidazol-2-amine | $^1$H-NMR (CDCl$_3$) δ 1.24-1.28(1H, m), 1.46-1.57(3H, m), 1.67-1.71 (2H, m), 1.84-1.91(1H, m), 22.02-2.05(1H, m), 2.21(3H, s), 2.73-2.80 (1H, m), 3.09 (3H, s), 3.23-3.25(1H, m), 3.65-3.73(1H, m), 3.80(3H, s), 4.03(3H, s), 6.92(1H, s), 6.98-7.12 (3H, m),7.25-7.31(1H, m); MS Calcd.: 472; Found: 473(M+H), 475. |

TABLE 15-continued

| Example | Structure | Name | Physical Data |
|---|---|---|---|
| 190 | 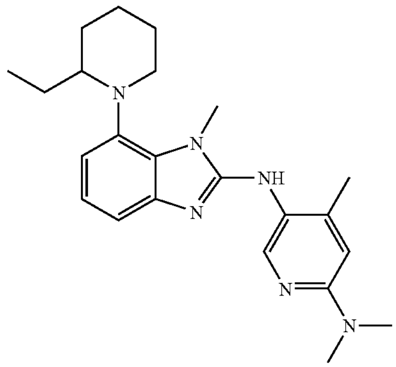 | N⁵-(7-(2-ethyl-1-piperidinyl)-1-methyl-1H-benzimidazol-2-yl)-N²,N²,4-trimethyl-2,5-pyridiamine | ¹H NMR (CDCl₃) δ. 0.74(t, J= 7.4 Hz, 3H), 1.18-1.23(m, 1H), 1.32-1.45 (m, 4H), 1.68 (br s, 1H), 1.91(m, 2H), 2.23(s, 3H), 2.70-2.73(m, 1H), 2.82-2.86 (m, 1H), 3.07 (br s, 6H), 4.03(s, 3H), 4.69(s, 2H), 6.42(s, 1H), 6.93-6.94(m, 1H), 7.02(t, J=7.7 Hz, 1H), 7.24-7.26 (m, 1H(), 8.10 (s, 1H); MS Calcd.: 392; MS Found: 393 (M+H). |
| 191 | 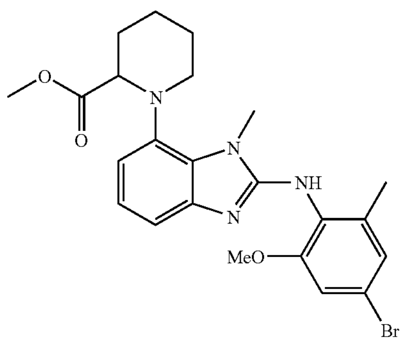 | methyl 1-[2-[(4-bromo-2-methoxy-6-methylphenyl)amino]--1-methyl-1H-benzimidazole-7-yl]piperidine-2-carboxylate | ¹H-NMR (CDCl₃) δ 1.56-1.85(4H, m), 1.94-1.98 (1H, m), 2.05-22.08(1H, m), 2.18(3H, s), 2.65-2.71(1H, m), 3.17-3.20(1H, m), 3.45(3H, s), 3.81(3H, s), 3.86-3.89(1H, m), 4.15(3H, s), 6.88-6.91(2H, m), 6.98(1H, t, J=8.05 Hz), 7.03(1H, s), 7.25-7.31 (1H, m); MS Calcd.: 486; Found: 487(M+H); 489. |

Example 192

N²-(4-Bromo-2-methoxy-6-methylphenyl)-3-methyl-N⁴,N⁴-dipropyl-3H-imidazo[4,5-c]pyridine-2,4-diamine trifluoroacetate

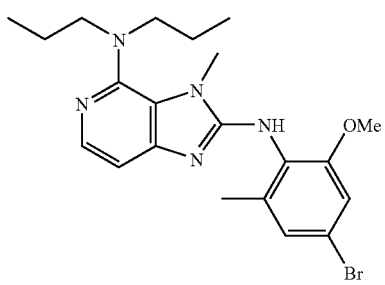

N³-Methyl-1-oxypyridine-3,4-diamine

To a slurry of 5.00 g (22.8 mmol) of 3-bromo-4-nitropyridine-1-oxide in 50 mL of tetrahydrofuran (THF) was slowly added 68.5 mL (137 mmol) of methylamine (2.0 M solution in THF). The reaction mixture was stirred overnight at room temperature and concentrated in vacuo. The thus obtained residue was dissolved in 250 mL of dichloromethane and washed with 100 mL of saturated aqueous sodium bicarbonate and 100 mL of water. The combined aqueous layers were extracted with 100 mL of dichloromethane. The combined organic layers were dried over sodium sulfate, filtered, and concentrated in vacuo to give 3.78 g (98%) of the title compound.

¹H NMR (CDCl₃) δ 3.03 (d, J=5.3 Hz, 3H), 7.48 (d, J=7.2 Hz, 1H), 7.94 (s, 1H), 8.02 (d, J=7.2 Hz, 1H); MS Calcd.: 169. Found: 170 (M+H).

N³-Methylpyridine-3,4-diamine

To a nitrogen inerted slurry of 3.78 g (22.3 mmol) of N³-methyl-1-oxypyridine-3,4-diamine in 150 mL of methanol was added 2 mL of Raney nickel (50% slurry in water). The reaction mixture was purged with hydrogen and then stirred under balloon pressure hydrogen overnight. The catalyst was removed by filtration through GFF paper and the filtrate was concentrated in vacuo to a pink residue that solidified under high vacuum to give 2.90 g (100%) of the title compound.

¹H NMR (CDCl₃) δ 2.89 (s, 3H), 3.48 (s, 1H), 3.99 (br s, 2H), 6.55 (d, J=5.1 Hz, 1H), 7.87 (s, 1H), 7.89 (d, J=5.3 Hz, 1H); MS Calcd.: 123. Found: 124 (M+H).

3-Methyl-1,3-dihydroimidazo[4,5-c]pyridin-2-one

To a solution of 2.80 g (22.7 mmol) of N³-methylpyridine-3,4-diamine in 125 mL of THF was added 4.42 g (27.3 mmol) of 1,1'-carbonyldiimidazole and the reaction was stirred overnight at room temperature. The reaction slurry was concentrated in vacuo to a volume of about 65 mL and cooled in a −10° C. bath, filtered, and the solids washed with 25 mL of THF. The solids were dried under high vacuum to give 2.35 g (69%) of the title compound.

¹H NMR (DMSO-d₆) δ 3.29 (d, J=1.2 Hz, 3H), 6.99 (d, J=5.1 Hz, 1H), 8.12 (d, J=5.1 Hz, 1H), 8.28 (s, 1H), 11.27 (br s, 1H); MS Calcd.: 149. Found: 150 (M+H).

3-Methyl-4-nitro-1,3-dihydroimidazo[4,5-c]pyridin-2-one

To a solution of 1.73 g (11.6 mmol) of 3-methyl-1,3-dihydroimidazo[4,5-c]pyridin-2-one in 6.3 mL of concentrated sulfuric acid, cooled in an 0° C. ice bath, was slowly added a solution of 1.50 mL (36.0 mmol) of fuming nitric acid in 1.5 mL of concentrated sulfuric acid. The reaction was removed from the ice bath and stirred for 0.5 h at room temperature and then heated at 100° C. for 2 h. The reaction was quenched over 300 mL of ice and solid ammonium carbonate was added to adjust the pH to 9. The resulting slurry was filtered and the collected solids washed with water and dried under high vacuum to give 1.94 g (86%) of the title compound.

¹H NMR (DMSO-d₆) δ 2.47 (s, 3H), 7.33-7.37 (m, 1H), 8.07 (d, J=5.1 Hz, 1H), 11.27 (br s, 1H); MS Calcd.: 194. Found: 195 (M+H).

4-Amino-3-methyl-1,3-dihydroimidazo[4,5-c]pyridin-2-one

To a nitrogen inerted slurry of 2.24 g (11.5 mmol) of 3-methyl-4-nitro-1,3-dihydroimidazo[4,5-c]pyridin-2-one in 25 mL of methanol was added 0.5 mL of Raney nickel (50% slurry in water). The reaction slurry was purged with hydrogen and then stirred under balloon pressure hydrogen for 1 h. To the reaction slurry was added 20 mL of methanol and the reaction slurry was purged with hydrogen and then stirred under balloon pressure hydrogen for 2 h.

The catalyst was removed by filtration through GFF paper and the filtrate was concentrated in vacuo. The residue thus obtained (1.54 g, 81%) was used in the next reaction without further purification.

MS Calcd.: 164. Found: 165 (M+H).

4-Dipropylamino-3-methyl-1,3-dihydroimidazo[4,5-c]pyridin-2-one

To a slurry of 750 mg (4.57 mmol) of 4-amino-3-methyl-1,3-dihydroimidazo[4,5-c]pyridin-2-one in 15 mL of dichloroethane was added 3.30 mL (45.7 mmol) of propionaldehyde, 1.0 mL of acetic acid, and 2.90 g (13.7 mmol) of sodium triacetoxyborohydride and the reaction was heated at 45° C. for 7.5 h. The reaction was diluted with 15 mL of dichloromethane and 15 mL of water and the aqueous layer was extracted with 15 mL of dichloromethane. The combined organic layers were dried over sodium sulfate, filtered, and concentrated in vacuo. The residue thus obtained (0.91 g, 80%) was used in the next reaction without further purification.

MS Calcd.: 248. Found: 249 (M+H).

(2-Chloro-3-methyl-3H-imidazo[4,5-c]pyridin-4-yl)-dipropylamine

A solution of 0.91 g (3.66 mmol) of 4-dipropylamino-3-methyl-1,3-dihydroimidazo[4,5-c]pyridin-2-one in 30 mL of phosphorous oxychloride was heated at 100° C. overnight and concentrated in vacuo. The thus obtained residue was quenched with water, adjusted with aqueous sodium bicarbonate to pH 5, and extracted with ethyl acetate. The organics were dried over sodium sulfate, filtered and concentrated in vacuo. The thus obtained residue was triturated with acetonitrile, filtered, and the filtrate, which contained the desired product, was concentrated in vacuo. The residue thus obtained (0.18 g, 18%) was used in the next reaction without further purification.

MS Calcd.: 266. Found: 267 (M+H).

N²-(4-Bromo-2-methoxy-6-methylphenyl)-3-methyl-N⁴,N⁴-dipropyl-3H-imidazo[4,5-c]pyridine-2,4-diamine trifluoroacetate A neat mixture of 180 mg (0.67 mmol) of (2-chloro-3-methyl-3H-imidazo[4,5-c]pyridin-4-yl)-dipropylamine and 157 mg (0.73 mmol) of 4-bromo-2-methoxy-6-methylaniline was heated at 100° C. for 1 h. The reaction was cooled to room temperature and the residue was dissolved in 10 mL of dichloromethane, washed with water and saturated aqueous sodium bicarbonate, dried over sodium sulfate, filtered, and concentrated in vacuo. This residue thus obtained was purified by preparative HPLC to give 4.5 mg (2% for 3 steps) of the title compound as the trifluoroacetic acid salt.

¹H NMR (CDCl₃) δ 0.87 (t, J=7.4 Hz, 6H), 1.47-1.56 (m, 4H), 2.22 (s, 3H), 3.17 (t, J=7.6 Hz, 4H), 3.83 (s, 3H), 3.99 (s, 3H), 4.72 (br s, 1H), 6.94 (s, 1H), 7.07 (s, 1H), 7.12 (d, J=5.4 Hz, 1H), 8.00 (d, J=5.4 Hz, 1H); MS Calcd.: 445. Found: 446 (M+H).

Example 193

N²-[2-(3-Bromopropoxy)-4-chlorophenyl]-1-methyl-N⁷,N⁷-dipropyl-1H-benzimidazole-2,7-diamine

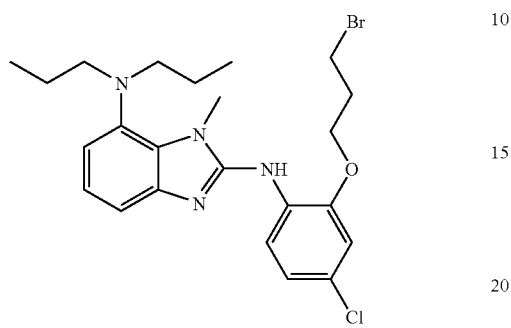

To a solution of 100 mg (0.27 mmol) of 5-chloro-2-(7-dipropylamino-1-methyl-1H-benzimidazol-2-ylamino)phenol in 4 mL of tetrahydrofuran was added 77 mg (0.30 mmol) of triphenylphosphine and 51 mg (0.30 mmol) of diethylazodicarboxylate and the reaction mixture was stirred for 90 minutes at room temperature. To the reaction mixture was added 41 mg (0.30 mmol) of 3-bromopropan-1-ol and the reaction was stirred overnight. The reaction was concentrated in vacuo and the resulting residue was purified by flash chromatography eluting with 20% ethyl acetate/hexanes to give 100 mg (76%) of the title compound.

¹H NMR (CDCl₃) δ 0.84 (t, J=7.2 Hz, 6H), 1.47 (q, J=7.2 Hz, 4H), 2.40-2.47 (m, 2H), 2.98 (br s, 4H), 3.61 (t, J=6.3 Hz, 2H), 4.07 (s, 3H), 4.28 (t, J=6.0 Hz, 2H), 6.85 (s, 1H), 6.91 (s, 1H), 6.95 (d, J=7.0 Hz, 1H), 7.03 (d, J=8.8 Hz, 1H), 7.08 (t, J=7.8, 1H), 7.36 (d, J=7.8 Hz, 1H), 8.47 (d, J=8.8 Hz, 1H); MS Calcd.: 492. MS Found: 493 (M+H).

Example 194

4-[(5-Chloro-2-[[7-(dipropylamino)-1-methyl-1H-benzimidazol-2-yl]amino]phenoxy)butanenitrile

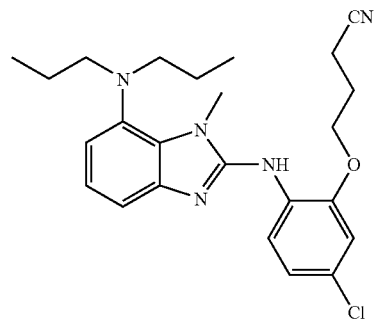

To a solution of 80 mg (0.16 mmol) of N²-[2-(3-bromopropoxy)-4-chlorophenyl]-1-methyl-N⁷,N⁷-dipropyl-1H-benzimidazole-2,7-diamine in 2 mL of dimethylsulfoxide was added 13 mg (0.19 mmol) of potassium cyanide. The reaction was stirred at room temperature for several hours, diluted with 10 mL water, and extracted twice with 10 mL ethyl acetate. The organics were washed with water, dried over sodium sulfate, filtered, concentrated in vacuo, and purified by flash chromatography eluting with a solution of 20% acetone/hexanes to give 75 mg (100%) of the title compound.

¹H NMR (CDCl₃) δ 0.84 (t, J=7.3 Hz, 6H), 1.42-1.51 (m, 4H), 2.22-2.28 (m, 2H), 2.59 (t, J=6.8 Hz, 2H), 2.98 (br s, 4H), 4.07 (s, 3H), 4.23 (t, J=5.5 Hz, 2H), 6.86 (d, J=8.6 Hz, 1H), 6.94 (d, J=7.8 Hz, 1H), 7.02-7.09 (m, 2H), 7.34 (d, J=7.8 Hz, 1H), 8.40 (d, J=8.6 Hz, 1H); MS Calcd.: 439. MS Found: 440 (M+H).

A compound described below was prepared in a similar method described in Example 193.

TABLE 16

| Example | Structure | Name | Physical Data |
| --- | --- | --- | --- |
| 195 | 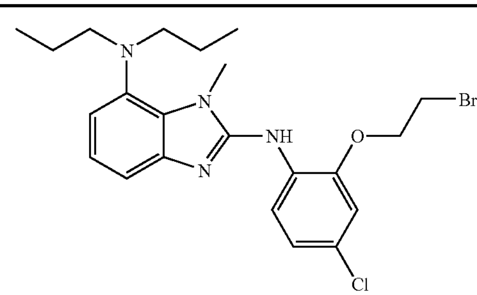 | N²-[2-(2-bromoethoxy)-4-chlorophenyl]-1-methyl-N⁷,N⁷-dipropyl-1H-benzimidazole-2,7-diamine | MS Calcd.: 478; MS Found: 479 (M+H). |

Example 196

[5-Chloro-2-[[7-(dipropylamino)-1-methyl-1H-benzimidazol-2-yl]amino]phenoxy]acetonitrile (A')

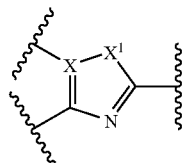

To a solution of 48 mg (0.40 mmol) of 5-chloro-2-(7-dipropylamino-1-methyl-1H-benzimidazol-2-ylamino)phenol in 5 mL of tetrahydrofuran was added 114 mg (0.59 mmol) of cesium bicarbonate and 50 mg (0.41 mmol) of bromoacetonitrile and the reaction was stirred overnight at room temperature. Bromoacetonitrile, 200 mg (1.64 mmol), was added to the reaction and the mixture was stirred several hours at room temperature. Then 50 mg (0.36 mmol) of potassium carbonate was added to the reaction and it was stirred at room temperature overnight. The reaction was concentrated in vacuo to a residue that was dissolved in dichloromethane, washed with water, dried over sodium sulfate, filtered and concentrated in vacuo. The resulting residue was purified by flash chromatography eluting with a solution of 20% ethyl acetate/hexanes to give 64 mg (58%) of the title compound.

$^1$H NMR (CDCl$_3$) δ 0.84 (t, J=7.3 Hz, 6H), 1.42-1.52 (m, 4H), 2.99 (br s, 4H), 4.09 (s, 3H), 4.88 (s, 2H), 6.68 (s, 1H), 6.93-6.98 (m, 2H), 7.09 (t, J=7.8 Hz, 1H), 7.12-7.15 (m, 1H), 7.35 (d, J=7.8 Hz, 1H), 8.51 (d, J=8.0 Hz, 1H); MS Calcd.: 411. MS Found: 412 (M+H).

A compound of Example 197, shown in the Table 17, was prepared in a manner similar to that described in Example 193.

TABLE 17

| Example | Structure | Name | Physical Data |
|---------|-----------|------|---------------|
| 197 | 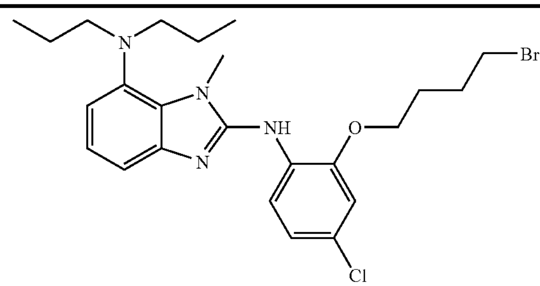 | N$^2$-[2-(4-bromobutoxy)-4-chlorophenyl]-1-methyl-N$^7$,N$^7$-dipropyl-1H-benzimidazole-2,7-diamine | MS Calcd.: 506; MS Found: 507 (M+H). |

A compound of Example 198, shown in the Table 18, was prepared in a manner similar to that described in Example 194.

TABLE 18

| Example | Structure | Name | Physical Data |
|---------|-----------|------|---------------|
| 198 | 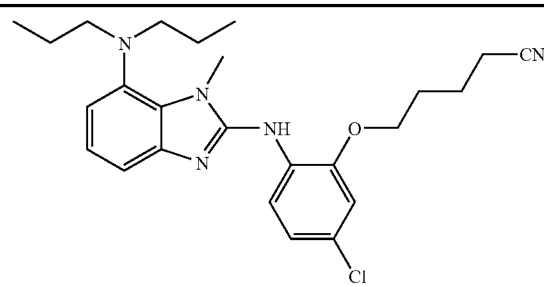 | 5-(5-cchloro-2-[[7-(dipropylamino)-1-methyl-1H-benzimidazol-2-yl]amino]phenoxxy)-pentanenitrile | $^1$H NMR (CDCl$_3$) δ 0.84(t, J= 7.2 Hz, 6H), 1.42-1.51(m, 4H), 1.88-1.95(m, 2H), 2.06-2.13(m, 2H), 2.49(t, J= 6.8 Hz, 2H), 2.98(br s, 4H), 4.08(s, 3H), 4.15(t, J=6.0 Hz, 2H), 4.72(s, 1H), 6.87(s, 1H), 6.95(d, J=7.8 Hz, 1H), 7.03(d, J=9.6 Hz, 1H), 7.08(t, J=8.0 Hz, 1H), 7.35(d, J=7.8 Hz, 1H), 8.44(d, J=8.8 Hz, 1H). MS Calcd.: 453; MS Found: 454 (M+H) |

Example 199

4-[5-Chloro-2-[[7-(dipropylamino)-1-methyl-1H-benzimidazol-2-yl]amino]phenoxy]butyric acid

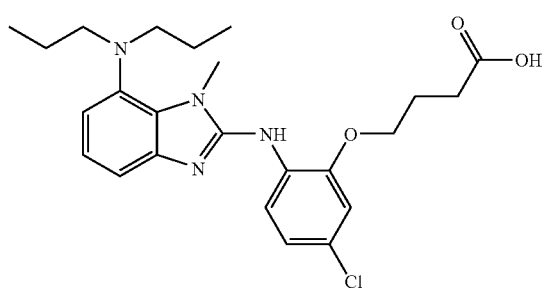

To a solution of 63 mg (0.14 mmol) of 4-[(5-chloro-2-[[7-(dipropylamino)-1-methyl-1H-benzimidazol-2-yl]amino]phenoxy]butanenitrile in 3 mL of EtOH and 1 mL of water was added 29 mg (0.72 mmol) of sodium hydroxide pellets and the reaction was stirred at 75° C. for 48 h. To the reaction mixture was added 75 mg (1.87 mmol) of sodium hydroxide pellets and the reaction heated at 75° C. for 24 h and concentrated in vacuo to a residue. The thus obtained residue was dissolved in 5 mL of water and the pH was adjusted to 4-5 using hydrochloric acid (1N aqueous solution). The resulting slurry was filtered, and the solids were washed with water and dried under high vacuum to give 46 mg (70%) of the title compound as white solids.

MS Calcd.: 458. MS Found: 459 (M+H).

Example 200

4-[5-Chloro-2-[[7-(dipropylamino)-1-methyl-1H-benzimidazol-2-yl]amino]phenoxy]-N-methylbutanamide Hydrochloride To a slurry of 20 mg (0.044 mmol) of 4-[5-chloro-2-[[7-(dipropylamino)-1-methyl-1H-benzimidazol-2-yl]amino]phenoxy]butyric acid in 2 mL of tetrahydrofuran was added 25 mg (0.065 mmol) of O-(7-azabenzotriazol-1-yl)-N,N,N',N'-tetramethyluronium hexafluorophosphate (HATU), 19 µL (0.11 mmol) of diisopropylethylamine, and 54 µL (0.11 mmol) of methylamine (2M solution in tetrahydrofuran). The reaction was stirred at room temperature for 3 h, diluted with water and extracted with dichloromethane. The organics were dried over sodium sulfate, filtered, and concentrated in vacuo. The thus obtained residue was purified via preparative TLC eluting with a 75% ethyl acetate/hexanes solution. The isolated product was washed off the silica with 100% ethyl acetate and concentrated in vacuo. The thus obtained residue was dissolved in methanol and hydrochloric acid (1N solution in diethyl ether) was added. The resulting slurry was concentrated in vacuo to give 9.0 mg (44%) of the title compound as the hydrochloric salt.

$^1$H NMR (CDCl$_3$) δ (free form) 0.84 (t, J=7.2 Hz, 6H), 1.43-1.52 (m, 4H), 2.23-2.28 (m, 2H), 2.31-2.34 (m, 2H), 2.66 (d, J=4.9 Hz, 3H), 2.99 (br s, 4H), 4.08 (t, J=5.6 Hz, 2H), 4.16 (s, 3H), 5.54 (br s, 1H), 6.82 (s, 1H), 6.95 (t, J=8.0 Hz, 2H), 7.07 (t, J=7.8 Hz, 2H), 7.29 (d, J=7.4 Hz, 1H), 8.31 (d, J=8.6 Hz, 1H). MS Calcd.: 471. MS Found: 472 (M+H).

A compound described below was prepared in a similar method.

TABLE 19

| Example | Structure | Name | Physical Data |
|---|---|---|---|
| 201 | 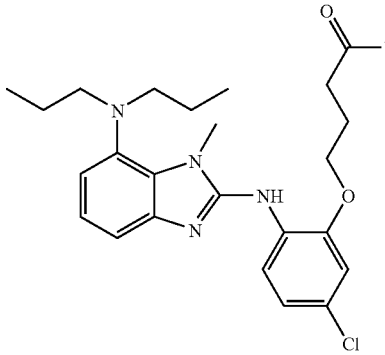 | 4-[5-chloro-2-[[7-(dipropylamino)-1-methyl-1H-benzimidazol-2-yl]amino]phenoxy]-N,N-dimthylbutanamide | $^1$H NMR (CDCl$_3$) δ 0.84(t, J= 7.2 Hz, 6H), 1.42-1.51(m, 4H), 2.24-2.30(m, 2H), 2.52(t, J= 6.6 Hz, 2H), 2.89(s, 3H), 2.97(br s, 7H), 4.12-4.15(m, 5H), 6.86(s, 1H), 6.93(d, J= 7.8 Hz, 1H), 6.98-7.00(m, 1H), 7.05-7.09(m, 2H), 7.34(d, J= 7.8 Hz,1H), 8.41(d, J= 8.8 Hz, 1H). MS Calcd.: 485; MS Found: 486 (M+H). |

Example 202

2-[(4-Bromo-2-methoxy-6-methylphenyl)amino]-N,N-diethyl-1-methyl-1H-benzimidazole-7-carboxamide Hydrochloride

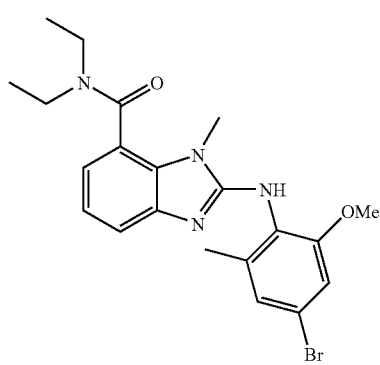

Methyl 2-chloro-1-methyl-1H-benzimidazole-7-carboxylate

A solution of 2.00 g (9.70 mmol) of methyl 1-methyl-2-oxo-1,3-dihydro-2H-benzimidazole-7-carboxylate in 20 mL of phosphorous oxychloride was heated at 100° C. for 6 h. The reaction was concentrated in vacuo and the thus obtained residue was quenched with water and extracted with ethyl acetate. The organics were dried over sodium sulfate, filtered, and concentrated in vacuo. The thus obtained residue was purified via flash chromatography eluting with a solution of 20% ethyl acetate/hexanes to give 1.77 g (81%) of the title compound as white solids.

$^1$H NMR (CDCl$_3$) δ 3.98 (s, 3H), 4.00 (s, 3H), 7.26-7.31 (m, 1H), 7.82 (d, J=7.8 Hz, 1H), 7.86 (d, J=8.0 Hz, 1H). MS Calcd.: 224. MS Found: 225 (M+H).

Methyl 2-[(4-bromo-2-methoxy-6-methylphenyl)amino]-1-methyl-1H-benzimidazole-7-carboxylate A mixture of 1.50 g (6.68 mmol) of methyl 2-chloro-1-methyl-1H-benzimidazole-7-carboxylate and 2.89 g (13.4 mmol) of 4-bromo-2-methoxy-6-methylphenylamine was heated at 100° C. for five days. The cooled reaction was dissolved in dichloromethane and washed with saturated aqueous sodium bicarbonate, water and brine. The organics were dried over sodium sulfate, filtered, and concentrated in vacuo. The thus obtained residue was purified via flash chromatography eluting with 100% dichloromethane to elute the residual 4-bromo-2-methoxy-6-methylphenylamine and 30% ethyl acetate/hexanes to give 356 mg (13%) of the title compound.

$^1$H NMR (CDCl$_3$) δ 2.17 (s, 3H), 3.82 (s, 3H), 3.86 (s, 3H), 3.97 (s, 3H), 5.96 (s, 1H), 6.94 (s, 1H), 7.05 (s, 1H), 7.12 (t, J=7.8 Hz, 1H), 7.61-7.67 (m, 2H). MS Calcd.: 403. MS Found: 404 (M+H).

2-[(4-Bromo-2-methoxy-6-methylphenyl)amino]-1-methyl-1H-benzimidazole-7-carboxylic acid To a solution of 150 mg (0.371 mmol) of methyl 2-[(4-bromo-2-methoxy-6-methylphenyl)amino]-1-methyl-1H-benzimidazole-7-carboxylate in 5 mL of tetrahydrofuran and 2.5 mL of water was added 156 mg (3.71 mmol) of lithium hydroxide monohydrate and the reaction was stirred at room temperature overnight and concentrated in vacuo. The thus obtained residue was diluted with water and carefully adjusted to pH 4-5 using 1 N aqueous hydrochloric acid. The resulting solids were filtered, washed with water and dried under high vacuum to give 112 mg (77%) of the title compound as white solids.

MS Calcd.: 389. MS Found: 390 (M+H).

2-[(4-Bromo-2-methoxy-6-methylphenyl)amino]-N,N-diethyl-1-methyl-1H-benzimidazole-7-carboxamide Hydrochloride To a slurry of 22 mg (0.056 mmol) of 2-[(4-bromo-2-methoxy-6-methylphenyl)amino]-1-methyl-1H-benzimidazole-7-carboxylic acid in 4 mL of tetrahydrofuran was added 32 mg (0.085 mmol) of HATU, 25 μL (0.14 mmol) of diisopropylethylamine, and 15 μL (0.14 mmol) of diethylamine and the reaction was stirred at room temperature for 4 h and concentrated in vacuo. The thus obtained residue was diluted with water and extracted with dichloromethane containing 5% methanol. The organics were dried over sodium sulfate, filtered, concentrated in vacuo and the thus obtained residue was purified via preparative TLC eluting with 10% methanol/dichloromethane. The isolated product was washed off the silica with 5% methanol/ethyl acetate and concentrated in vacuo. To a solution of the purified title compound in methanol was added hydrochloric acid (1N solution in diethyl ether) and the thus obtained slurry was concentrated in vacuo to give 14 mg (58%) of the title compound as the hydrochloric salt.

$^1$H NMR (CDCl$_3$) δ (free form) $^1$H NMR (CDCl$_3$) δ 1.11 (t, J=7.0 Hz, 3H), 1.32 (t, J=7.0 Hz, 3H), 2.17 (s, 3H), 3.31 (q, J=7.0 Hz, 2H), 3.55 (br s, 2H), 3.67 (s, 3H), 3.82 (s, 3H), 4.72 (s, 1H), 6.93-6.96 (m, 2H), 7.05 (s, 1H), 7.10 (t, J=7.7 Hz, 1H), 7.50 (d, J=8.0 Hz, 1H). MS Calcd.: 444. MS Found: 445 (M+H).

Compounds described below were prepared in a similar method.

TABLE 20

| Example | Structure | Name | Physical Data |
|---|---|---|---|
| 203 | 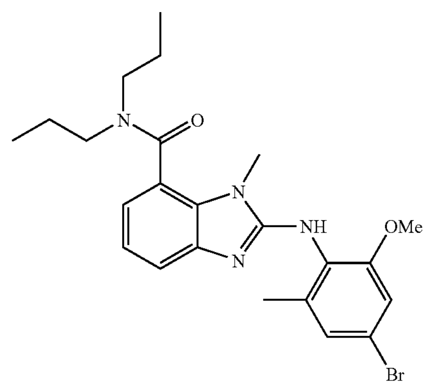 | 2-[[4-bromo-2-methoxy-6-methylphenyl)-amino]-N,N-dipropyl-1-methyl-1H-benzimidazole-7-carboxamide | MS Calcd.: 472; MS Found: 473 (M+H). |
| 204 | 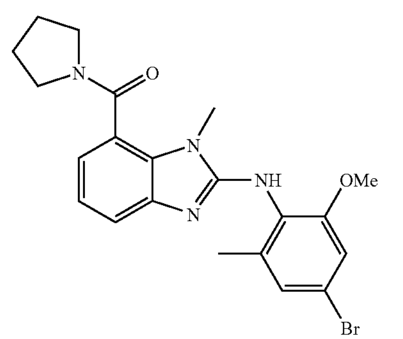 | N-(4-bromo-2-methoxy-6-methylphenyl)-1-methyl-7-(pyrolidin-1-ylcarbonyl)-1H-benzimidazol-2-amine | $^1$H NMR (CDCl$_3$) δ 1.90-1.95 (m, 2H), 1.99-2.04(m, 2H), 2.18(s, 3H), 3.35(t, J=6.7 Hz, 2H), 3.68(s, 3H), 3.73(t, J=6.7 Hz, 2H), 3.82(s, 3H), 4.72(s, 1H), 6.93(s, 1H), 7.01-7.05(m, 2H), 7.10(t, J=7.6 Hz, 1H), 7.51(d, J=8.0 Hz, 1H). MS Calcd.: 442; MS Found:443 (M+H). |

| Example | Structure | Name | Physical Data |
|---|---|---|---|
| 205 | 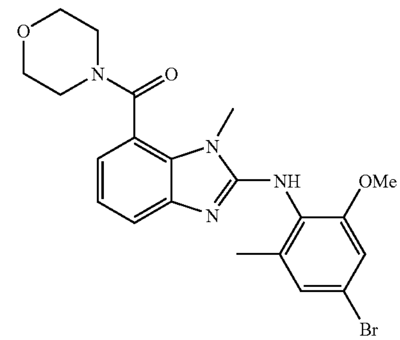 | N-(4-bromo-2-methoxy-6-methylphenyl)-1-methyl-7-(morpholin-4-ylcarbonyl)-1H-benzimidazol-2-amine | $^1$H NMR (CDCl$_3$) δ 2.19(s, 3H), 3.44-3.49(m, 2H), 3.61(br s, 1H), 3.70(br s, 4H), 3.82 (br s, 5H), 3.91(br s, 2H), 4.72(s, 1H), 6.94(br s, 2H), 7.06 (s, 1H), 7.11 (t, J=7.7 Hz, 1H), 7.52 (d, J=8.0 Hz, 1H). MS Calcd.: 458; MS Found: 459 (M+H). |

Example 206

N$^2$-(4-Bromo-2-methoxy-6-methylphenyl)-N$^7$-propyl-1-methyl-N$^7$-[2-(methylsulfonyl) phenyl]-1H-benzimidazole-2,7-diamine

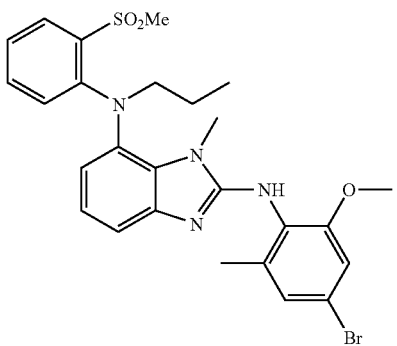

3-(4-Methoxybenzyl)-1-methyl-7-[[2-(methylsulfonyl)phenyl](propyl)amino]-1,3-dihydro-2H-benzimidazol-2-one A mixture of 1-(4-methoxybenzyl)-3-methyl-4-[[(2-methylthio)phenyl](propyl)amino]-1,3-dihydro-2H-benzimidazol-2-one (630 mg, 1.41 mmol), prepared in a similar manner as described in Example 15, m-chloroperbenzoic acid (730 mg, 4.22 mmol) and acetonitrile (5 ml) was stirred at room temperature for 3 hr. The reaction mixture was diluted with water and extracted with ethyl acetate. The extract was washed with brine, dried over sodium sulfate and concentrated in vacuo. The residue was chromatographed on silica gel eluting with a solution of 50% hexane/ethyl acetate to give 500 mg (74%) of the title compound as an oil.

MS Calcd: 479. Found: 480 (M+H).

$^1$H NMR (CDCl$_3$) δ 0.91 (3H, t, J=7.4 Hz), 1.68-1.74 (2H, m), 2.35 (3H, s), 3.50-3.54 (2H, m), 3.77 (3H, s), 3.89 (3H, s), 5.02 (2H, s), 6.20 (1H, d, J=8.0 Hz), 6.67 (1H, t, J=8.0 Hz), 6.74 (1H, d, J=8.0 Hz), 6.84 (2H, d, J=8.8 Hz), 7.26-7.31 (3H, m), 7.48 (1H, d, J=8.0 Hz), 7.64-7.69 (1H, m), 8.07 (1H, dd, J=8.0, 1.6 Hz).

From this compound, the title compound was prepared in a similar manner as described in Example 138.

MS Calcd: 556. Found: 557 (M+H).

$^1$H NMR (CDCl$_3$) δ 0.95 (3H, t, J=7.4 Hz), 1.73-1.79 (2H, m), 2.04 (3H, s), 2.22 (3H, s), 3.58 (2H, t, J=8.0 Hz), 3.85 (3H, s), 4.13 (3H, s), 5.95 (1H, s), 6.24 (1H, d, J=7.8 Hz), 6.83 (1H, t, J=7.8 Hz), 6.94 (1H, s), 7.06 (1H, s), 7.21-7.32 (2H, m), 7.49 (1H, d, J=7.8 Hz), 7.67 (1H, t, J=7.8 Hz), 8.07 (1H, d, J=7.8 Hz).

Example 207

4-[[2-[(4-Bromo-2-methoxy-6-methylphenyl) amino]-1-methyl-1H-benzimidazol-7-yl](isopropyl) amino]benzonitrile 4-[(2-Chloro-1-methyl-1H-benzimidazol-7-yl) amino]benzonitrile A mixture of 4-[(1-methyl-2-oxo-1,3-dihydro-2H-benzimidazol-7-yl)amino]benzonitrile (137 mg, 0.518 mmol), prepared in a similar manner as described in Example 154, and phosphorous oxychloride (1.5 ml) was refluxed for 3 h.

The mixture was concentrated in vacuo and quenched with saturated aqueous sodium bicarbonate and extracted with ethyl acetate. The extract was washed with brine, dried over magnesium sulfate and evaporated. The residue was flash chromatographed eluting with a solution of 25% ethyl acetate/hexane to give 66 mg (45%) of the title compound.

MS Calcd.: 282. Found: 283 (M+H)

$^1$H NMR (CDCl$_3$) δ3.79 (3H, s), 5.97 (1H, s), 6.62 (2H, d, J=8.6 Hz), 7.09 (1H, d, J=7.8 Hz), 7.28 (1H, t, J=7.8 Hz), 7.46 (2H, d, J=8.6 Hz), 7.66 (1H, d, J=7.8 Hz).

solution of 33% ethyl acetate/hexane. The desired fractions were concentrated in vacuo, and the residual solids were washed with diethyl ether-hexane to give 7.4 mg (9.5%) of the title compound.

MS Calcd.: 503, 505. Found: 504, 506 (M+H).

$^1$H NMR (CDCl$_3$) δ 1.03 (3H, d, J=6.6 Hz), 1.42 (3H, d, J=6.6 Hz), 2.18 (3H, s), 3.49 (3H, s), 3.81 (3H, s), 4.34-4.40 (1H, m), 5.82 (1H, s), 6.55 (2H, d, J=8.6 Hz), 6.80 (1H, d, J=7.8 Hz), 6.93 (1H, s), 7.06 (1H, s), 7.16 (1H, t, J=7.8 Hz), 7.42 (2H, d, J=8.6 Hz), 7.55 (1H, d, J=7.8 Hz).

A compounds described below was prepared in a similar method.

TABLE 21

| 208 | Structure | Name | $^1$H NMR (CDCl$_3$) δ |
|---|---|---|---|
| | (4-methoxy-NC-phenyl)(isopropyl)N- linked to 1-methyl-benzimidazole-2-NH- linked to 2-methyl-4-bromo-6-O-methoxyphenyl | 4-[[2-[(4-bromo-2-methoxy-6-methylphenyl)-amino]-1-methyl-1H-benzimidazol-7-yl](isopropyl)-amino]-2-methoxybenzonitrile | 1.03(3H, d, J=4.8 Hz), 1.37 (3H, d, J=4.8 Hz), 2.20(3H, s), 3.57(3H, s), 3.82(3H, s), 3.84(3H, s), 4.22-4.29 (1H, m), 5.84 (1H, s), 6.66-6.68(1H, m), 6.78-6.80(3H, m), 6.93(1H, s), 7.06(1H, s), 7.14(1H, d, J=7.8Hz), 7.51(1H, d, J=7.8 Hz). MS Calcd.: 533, 535; Found: 534, 536(M+H). |

4-[(2-Chloro-1-methyl-1H-benzimidazol-7-yl)(isopropyl)amino]benzonitrile

To a suspension of 4-[(2-chloro-1-methyl-1H-benzimidazol-7-yl)amino]benzonitrile (64 mg, 0.226 mmol), tetrabutylammonium iodide (8.4 mg, 0.023 mmol) and sodium hydride (18.1 mg, 0.679 mmol, 90% dry) was added 2-bromopropane (0.07231 ml, 0.679 mmol), and the mixture was stirred at room temperature for 12 hr. The reaction mixture was diluted with water and extracted with ethyl acetate. The extract was washed with brine, dried over sodium sulfate and concentrated in vacuo. The residue was chromatographed on silica gel eluting with a solution of 50% hexane/ethyl acetate to give 64 mg (84%) of the title compound.

MS Calcd.: 324. Found: 325 (M+H)

1H NMR (CDCl$_3$) δ0.96 (3H, d, J=6.6 Hz), 1.43 (3H, d, J=6.6 Hz), 3.58 (3H, s), 4.30-4.43 (1H, m), 6.49 (2H, d, J=8.2 Hz), 7.02 (1H, d, J=8.0 Hz), 7.34 (1H, t, J=8.0 Hz), 7.42 (2H, d, J=8.2 Hz), 7.75 (1H, d, J=8.0 Hz).

4-[[2-[(4-Bromo-2-methoxy-6-methylphenyl)amino]-1-methyl-1H-benzimidazol-7-yl](isopropyl)amino]benzonitrile A mixture of 4-[(2-chloro-1-methyl-1H-benzimidazol-7-yl)(isopropyl)amino]benzonitrile (50 mg, 0.154 mmol) and 4-bromo-6-methylaniline (100 mg, 0.46 mmol) was stirred at 120° C. for 3 days. The mixture was dissolved in ethyl acetate, washed with saturated aqueous sodium bicarbonate and water, dried over magnesium sulfate and evaporated in vacuo. The residue was chromatographed on silica gel eluting with a Experiment 1

Measurement of Corticotropin-Releasing Factor (CRF) Binding Inhibitory Rate

A receptor binding experiment was carried out using a human CRF receptor expressing CHO cellular membrane fraction and sheep CRF, [$^{125}$I]-tyr$^0$($^{125}$I-CRF). 1000 nM of a test compound was incubated with 1 µg of human CRF receptor expressing CHO cellular membrane fraction and 50 pM of $^{125}$I-CRF in a binding assay buffer (50 mM Tris-HCl, 5 mM EDTA, 10 mM MgCl$_2$, 0.05% CHAPS, 0.1% BSA, 0.5 mM PMSF, 0.1 g/ml pepstatin, 20 µg/ml leupeptin, pH 7.5). In addition, for measuring nonspecific binding (NSB), 0.1 µM unlabelled human Urocortin was incubated with 1 µg of human CRF receptor expressing CHO cellular membrane fraction and 50 pM of $^{125}$I-CRF in a binding assay buffer. After a binding reaction was carried out at room temperature for 1 hour, the membrane was entrapped on a glass filter (UniFilter plate GF-C/Perkin Elmer) by suction filtration using a cell harvester (Perkin Elmer), and washed with ice-cooled 50 mM Tris-HCl (pH 7.5). After drying the glass filter, a liquid scintillation cocktail (Microscinti 0, Perkin Elmer) was added, and the radioactivity of $^{125}$I-CRF remaining on a glass filter was measured using Topcount (Perkin Elmer).

(TB−SB)/(TB−NSB)×100 (SB: radioactivity when a compound is added, TB: maximum binding radioactivity, NSB: nonspecific binding radioactivity) was calculated to obtain a binding inhibitory rate under the presence of 1,000 nM or 100 nM of each test substances.

Binding inhibitory rates of respective compounds measured by the aforementioned method are shown in Table 22.

TABLE 22

| Example No. | Binding inhibitory rate (%) 1000 nM |
|---|---|
| 26 | >80 |
| 42 | >80 |
| 46 | >80 |
| 145 | >80 |
| 183 | >80 |

Experiment 2

CRF Antagonistic Activity

The CRF antagonistic activity was obtained by measuring inhibition of Adenylate Cyclase activity induced by CRF. Measurement of intracellular cyclic AMP (cAMP) concentration was carried out using Alpha Screen Reagent (Perkin Elmer) according to the method described in the protocol attached to the reagent. Specifically, a human CRF receptor expressing CHO cell was inoculated on a 96-well plate at 40000 cells/well, cultured for 24 hours, the culture medium was sucked, and 1 μM of test compound and 100 μl of assay buffer (20 mM HEPES, Hanks' Balanced Salt Solution, 0.1% BSA, 100 μM IBMX, pH 7.2) containing 1 nM of human CRF were added. In addition, in order to measure the intracellular cAMP concentration at stationary state, a compound and a buffer containing no CRF were added. After reacting at room temperature for 30 minutes, a buffer containing 1.5 μg of Anti-cAMP acceptor beads was added thereto, 2 μg of Biotin-cAMP/streptoavidin beads and a buffer containing 0.15% Tween 20 were added, the mixture were reacted at room temperature for 3 hours, and light emission was measured with Fusion (Perkin Elmer).

INDUSTRIAL APPLICABILITY

Compound (I) or (Ia) of the present invention has an excellent CRF antagonistic activity, and therefore useful as drugs for treating or preventing affective disorder, depression, anxiety, and the like.

The invention claimed is:

1. A compound represented by the formula (I):

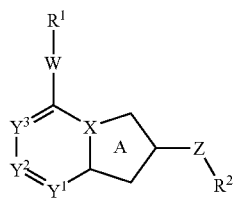

wherein, ring A is a 5-membered ring represented by the formula (A'):

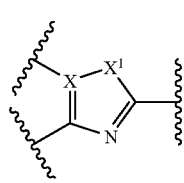

wherein X is a carbon and $X^1$ is $—NR^5—$ (wherein $R^5$ is a $C_{1-4}$ alkyl);
$R^1$ is (1) an amino substituted by two substituents selected from an optionally substituted $C_{1-4}$ alkyl, an optionally substituted phenyl and an optionally substituted pyridyl, or (2) an optionally substituted cyclic amino, provided that the amino nitrogen of said cyclic amino has no carbonyl adjacent to the nitrogen;
$R^2$ is an optionally substituted phenyl or an optionally substituted pyridyl;
$Y^1, Y^2$ and $Y^3$ are each methyne optionally substituted by a halogen;
W is a bond; and
or a salt thereof.

2. The compound according to claim 1 wherein $R^1$ is an amino substituted by two $C_{1-4}$ alkyls.

3. The compound according to claim 1 wherein $R^1$ is an amino substituted by an optionally substituted $C_{1-4}$ alkyl and an optionally substituted phenyl or an optionally substituted pyridyl.

4. The compound according to claim 1 wherein $R^1$ is a 5- or 6-membered cyclic amino which may be substituted with one or more substituents.

5. A method for treating a disease wherein a CRF receptor is implicated wherein the disease to be treated is selected from affective disorder, depression, and anxiety, which comprises administering to a subject in need thereof an effective amount of a compound represented by the formula (Ia):

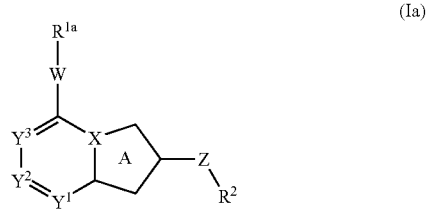

wherein ring A is a 5-membered ring represented by the formula (A'):

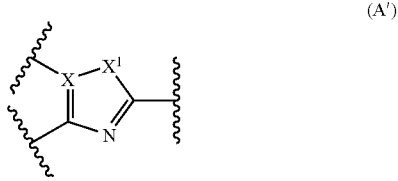

wherein X is a carbon and $X^1$ is $—NR^5—$ (wherein $R^5$ is $C_{1-4}$ alkyl;
$R^{1a}$ is (1) an amino substituted by two substituents selected from an optionally substituted $C_{1-4}$ alkyl, an optionally substituted phenyl and an optionally substituted pyridyl, or (2) an optionally substituted cyclic amino;
$R^2$ is an optionally substituted phenyl or an optionally substituted pyridyl;
$Y^1, Y^2$ and $Y^3$ are each a methyne optionally substituted by a halogen;
W is a bond; and
Z is a —NH;
or a salt thereof.

6. A method for manufacturing a medicament for treating a disease wherein a CRF receptor is implicated wherein the disease to be treated is selected from affective disorder, depression, and anxiety, comprising combining a compound represented by the formula (Ia):

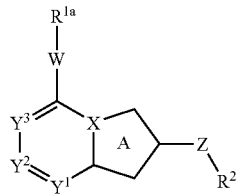

wherein ring A is a 5-membered ring represented by the formula (A'):

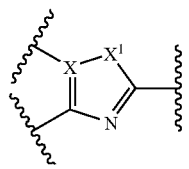

wherein X is a carbon and $X^1$ is —$NR^5$— (wherein $R^5$ is a $C_{1-4}$ alkyl);
$R^{1a}$ is (1) an amino substituted by two substituents selected from an optionally substituted $C_{1-4}$ alkyl, an optionally substituted phenyl and an optionally substituted pyridyl, or (2) an optionally substituted cyclic amino;
$R^2$ is an optionally substituted phenyl or an optionally substituted pyridyl;
$Y^1, Y^2$ and $Y^3$ are each a methyne optionally substituted by a halogen;
W is a bond; and
Z is —NH—; or a salt thereof, with a pharmaceutically acceptable carrier.

7. An agent for treating affective disorder, depression or anxiety which comprises a compound represented by the formula (Ia):

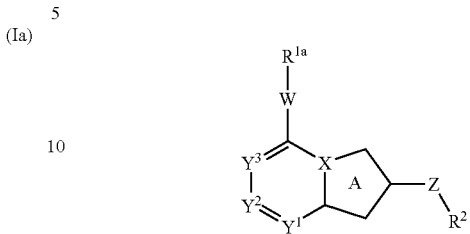

wherein ring A is a 5-membered ring represented by the formula (A'):

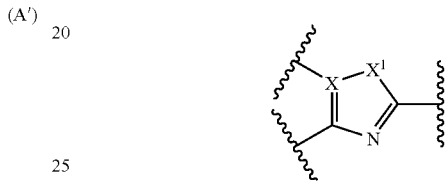

wherein X is a carbon and $X^1$ is —$NR^5$— (wherein $R^5$ is a $C_{1-4}$ alkyl);
$R^{1a}$ is (1) an amino substituted by two substituents selected from an optionally substituted $C_{1-4}$ alkyl, an optionally substituted phenyl and an optionally substituted pyridyl, or (2) an optionally substituted cyclic amino;
$R^2$ is an optionally substituted phenyl or an optionally substituted pyridyl;
$Y^1, Y^2$ and $Y^3$ are each a methyne optionally substituted by a halogen;
W is a bond; and
Z is —NH—; or a salt thereof.

* * * * *